(12) United States Patent
Koenen et al.

(10) Patent No.: US 9,853,228 B2
(45) Date of Patent: Dec. 26, 2017

(54) METAL COMPLEXES

(71) Applicant: Merck Patent GmbH, Darmstadt (DE)

(72) Inventors: Nils Koenen, Darmstadt (DE); Philipp Stoessel, Frankfurt am Main (DE); Anna Hayer, Darmstadt (DE); Holger Heil, Frankfurt am Main (DE); Philipp Harbach, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/500,082

(22) PCT Filed: Jul. 3, 2015

(86) PCT No.: PCT/EP2015/001358
§ 371 (c)(1),
(2) Date: Jan. 30, 2017

(87) PCT Pub. No.: WO2016/015815
PCT Pub. Date: Feb. 4, 2016

(65) Prior Publication Data
US 2017/0250353 A1 Aug. 31, 2017

(30) Foreign Application Priority Data
Jul. 28, 2014 (EP) .................................... 14002623

(51) Int. Cl.
*C07F 15/00* (2006.01)
*C09K 11/00* (2006.01)
*H01L 51/00* (2006.01)
*H05B 33/10* (2006.01)
*C09K 11/06* (2006.01)
*H01L 51/50* (2006.01)

(52) U.S. Cl.
CPC ...... *H01L 51/0085* (2013.01); *C07F 15/0033* (2013.01); *C09K 11/06* (2013.01); *C09K 2211/1007* (2013.01); *C09K 2211/1011* (2013.01); *C09K 2211/1014* (2013.01); *C09K 2211/1066* (2013.01); *C09K 2211/1074* (2013.01); *C09K 2211/1077* (2013.01); *C09K 2211/1088* (2013.01); *C09K 2211/185* (2013.01); *H01L 51/5016* (2013.01); *H01L 51/5072* (2013.01); *H01L 51/5096* (2013.01)

(58) Field of Classification Search
CPC ......... C07F 15/00; C09K 11/00; H01L 51/00; H05B 33/10
See application file for complete search history.

(56) References Cited

FOREIGN PATENT DOCUMENTS

| EP | 2128168 A1 | 12/2009 | |
|---|---|---|---|
| WO | WO 2014/023377 | * 2/2014 | ............. C07F 15/00 |
| WO | WO-2014/023377 A2 | 2/2014 | |

* cited by examiner

*Primary Examiner* — Erich A Leeser
(74) *Attorney, Agent, or Firm* — RatnerPrestia

(57) ABSTRACT

The present invention relates to metal complexes and to electronic devices, in particular organic electroluminescent devices, comprising these metal complexes.

16 Claims, No Drawings

METAL COMPLEXES

RELATED APPLICATIONS

This application is a national stage entry, filed pursuant to 35 U.S.C. §371, of PCT/EP2015/001358, filed Jul. 3, 2015, which claims the benefit of European Patent Application No. 14002623.8, filed Jul. 28, 2014, which is incorporated herein by reference in its entirety.

The present invention relates to metal complexes and to electronic devices, in particular organic electroluminescent devices, comprising these metal complexes.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 96/27136. The emitting materials employed here are increasingly organometallic complexes which exhibit phosphorescence instead of fluorescence. For quantum-mechanical reasons, an up to four-fold increase in the energy and power efficiency is possible using organometallic compounds as phosphorescence emitters. In general, however, there is still a need for improvement in OLED which exhibit triplet emission, in particular with respect to efficiency, operating voltage and lifetime.

accordance with the prior art, the triplet emitters employed in phosphorescent OLEDs are, in particular, iridium complexes, such as, for example, iridium complexes which contain phenylpyridin derivatives as ligands. WO 2008/78800 discloses phenylpyridine-iridium complexes which are substituted on the pyridine ring by a triazine or pyrimidine group. Yellow to red emission can be achieved using complexes of this type. However, further improvements, in particular with respect to photoluminescence quantum efficiency, EQE, in the electroluminescent device, solubility of the complexes and/or the emission colour and the width of the emission band, are still desirable.

The object of the present invention is therefore the provision of novel metal complexes which are suitable as emitters for use in OLEDs and result in improved properties of the OLED, in particular with respect to quantum efficiency, solubility of the complexes and/or the emission colour and the width of the emission band.

Surprisingly, it has been found that certain metal chelate complexes described in greater detail below achieve this object and exhibit improved properties in organic electroluminescent devices. In particular, these metal complexes exhibit higher photo- and electroluminescence quantum efficiencies, better solubility and a narrower emission band and thus a purer emission colour compared with the analogous metal complexes which do not contain a condensed-on aliphatic ring. The present invention therefore relates to these metal complexes and to electronic devices, in particular organic devices, which comprise these complexes.

The invention thus relates to a compound of the formula (1), $$[Ir(L)_n(L')_m] \quad \text{formula (1)}$$

where the compound of the general formula (1) contains a moiety $Ir(L)_n$ of the formula (2):

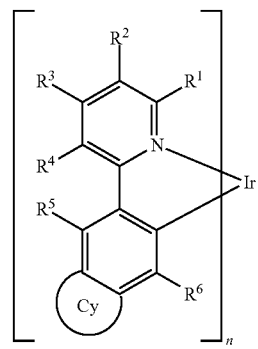

formula (2)

where the following apples to the symbols and indices used:

one of the radicals $R^2$ and $R^3$ is a group of the formula $-(Ar)_p$-HetAr and the other of the radicals $R^2$ and $R^3$ has the same meaning as defined for R, $R^1$, $R^4$, $R^5$ and $R^6$;

HetAr is a group of the following formula (3),

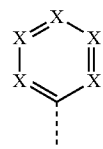

formula (3)

where the dashed bond indicates the bond to Ar or, for p=0, the bond to the pyridine group of the ligand;

X is on each occurrence, identically or differently, CR or N, with the proviso that at least one and at most three groups X in formula (3) stand for N;

Ar is on each occurrence, identically or differently, an aromatic or heteroaromatic ring system having 5 to 30 aromatic ring atoms, which may be substituted by one or more radicals R;

p is on each occurrence, identically or differently, 0 or 1;

Cy stands on each occurrence, identically or differently, for a group of the following formulae (4), (5), (6), (7), (8), (9) and (10),

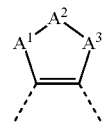

formula (4)

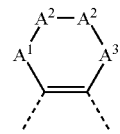

formula (5)

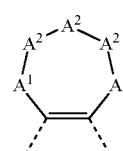

formula (6)

-continued

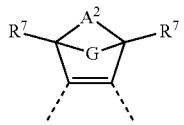

formula (7)

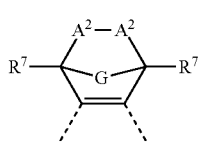

formula (8)

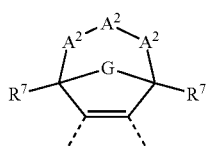

formula (9)

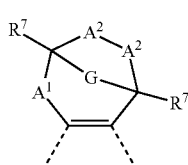

formula (10)

where the dashed bonds indicate the linking of the two carbon atoms in the ligand and furthermore:

$A^1$, $A^3$ are, identically or differently on each occurrence, $C(R^8)_2$, O, S, $NR^8$ or C(=O);

$A^2$ is $C(R^7)_2$, O, S, $NR^8$ or C(=O);

G is an alkylene group having 1, 2 or 3 C atoms, which may be substituted by one or more radicals $R^9$, —$CR^9$=$CR^9$— or an ortho linked arylene or heteroarylene group having 5 to 14 aromatic ring atoms, which may be substituted by one or more radicals $R^9$; with the proviso that no two heteroatoms in these groups are bonded directly to one another and no two groups C=O are bonded directly to one another;

R, $R^1$, $R^4$, $R^5$, $R^6$, $R^7$ are on each occurrence, identically or differently, H, D, F, Cl, Br, I, $N(R^9)_2$, CN, $Si(R^9)_3$, $B(OR^9)_2$, C(=O)$R^9$, a straight-chain alkyl, alkoxy or thioalkoxy group having 1 to 40 C atoms or a straight-chain alkenyl or alynyl group having 2 to 40 C atoms or a branched or cyclic alkyl, alkenyl, alkynyl, alkoxy or thioalkoxy group having 3 to 40 C atoms, each of which may be substituted by one or more radicals $R^9$, where one or more non-adjacent $CH_2$ groups may be replaced by $R^9$C=$CR^9$, $Si(R^9)_2$, C=O, $NR^9$, O, S or $CONR^9$ and where one or more H atom may be replaced by D, F or CN, or an aromatic or heteroaromatic ring system having 5 to 60 aromatic ring atoms, which may in each case be substituted by one or more radicals $R^9$, or an aryloxy or heteroaryloxy group having 5 to 60 aromatic ring atoms, which may be substituted by one or more radicals $R^9$, or a diarylamino group, diheteroarylamino group or arylheteroarylamino group having 10 to 40 aromatic ring atoms, which may be substituted by one or more radicals $R^9$; two adjacent radicals R here may also form an aliphatic, aromatic or heteroaromatic ring system with one another; furthermore, the radicals $R^4$ and $R^5$ may also form an aliphatic, aromatic or heteroaromatic ring system with one another; furthermore, the radicals $R^3$ and $R^4$ may form an aliphatic, aromatic or heteroaromatic ring system with one another if the group $R^2$ stands for a group of the formula —(Ar)$_p$-HetAr;

$R^8$ is, identically or differently on each occurrence, F, a straight-chain alkyl or alkoxy group having 1 to 10 C atoms, a branched or cyclic alkyl or alkoxy group having 3 to 10 C atoms, each of which may be substituted by one or more radicals R, where one or more non-adjacent $CH_2$ groups may be replaced by $R^9$C=$CR^9$, C≡C, $S(R^9)_2$, C=O, $NR^9$, O, S or $CONR^9$ and where one or more H atoms may be replaced by D or F, or an aromatic or heteroaromatic ring system having 5 to 24 aromatic ring atoms, which may in each case be substituted by one or more radicals $R^9$, or an aryloxy or heteroaryloxy group having 5 to 24 aromatic ring atoms, which may be substituted by one or more radicals $R^9$, or an aralkyl or heteroaralkyl group having 5 to 24 aromatic ring atoms, which may be substituted by one or more radicals $R^9$; two radicals $R^8$ here which are bonded to the same carbon atom may form an aliphatic or aromatic ring system with one another and thus form a spiro system; furthermore, $R^8$ may form an aliphatic ring system with an adjacent radical $R^7$;

$R^9$ is on each occurrence, identically or differently, H, D, F or an aliphatic, aromatic and/or heteroaromatic organic radical having 1 to 20 C atoms, in particular a hydrocarbon radical, in which, in addition, one or more H atoms may be replaced by D or F; two or more substituents $R^9$ here may also form an aliphatic or aromatic ring system with one another;

L' is, identically or differently on each occurrence, a mono- or bidentate ligand;

n is 1, 2 or 3;

m is 0, 1, 2, 3 or 4.

The indices n and m here are selected so that the coordination number at the iridium corresponds in total to 6. This is dependent, in particular, on how many ligands L are present and whether the ligands L' are mono- or bidentate ligands.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteoaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, N or O atom or a carbonyl group. Thus, for example, systems such as 9,9-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkylene group or by a silylene group.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, n-butyl, i-butyl, s-butyl, t-butyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, cyclohexyl, 2-methylpentyl, neohexyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo-[2.2.2]octyl, 2-(2,6-dimethyl)octyl, 3-(3,7-dimethyl)octyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cycloocta-dienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, 1-propoxy, n-butoxy, i-butoxy, s-butoxy, t-butoxy or 2-methylbutoxy. An aromatic or heteroaromatic ring system having 5-60 aromatic ring atoms, which may also in each case be substituted by the above-mentioned radicals R and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthalene, pentacene, benzopyrene, biphenyl, biphenylene, terphenyl, terphenylene, fluorene, spirobifluorene, dihydro-phenanthrene, dihydropyrene, tetrahydropyrene, cis- or trans-indenofluorene, cis- or trans-monobenzoindenofluorene, cis- or trans-dibenzoindeno-fluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimdine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraaza-perylene, pyrazin, phenazin, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-triazine, purine, pteridine, indolizine and benzothiadazole.

The complexes according to the invention may be facial or pseudofacial, or they may be meridional or pseudomeridional.

In a preferred embodiment, the Index n=3, i.e. it is a homoleptic metal complex and the index m=0.

In a further preferred embodiment, the index n=2 and m=1, the complex according to the invention contains two ligands L and one bidentate ligand L'. It is preferred here for the ligand L' to be a ligand which coordinates to the iridium via one carbon atom and one nitrogen atom, one carbon atom and one oxygen atom, two oxygen atoms, two nitrogen atoms or one oxygen atom and one nitrogen atom.

In a further preferred embodiment, the index n=1 and m=2, and the complex according to the invention contains one ligand L and two bidentate ligands L'. This is preferred, in particular, if the ligand L' is an ortho-metallated ligand which coordinates to the iridium via one carbon atom and one nitrogen atom or one carbon atom and one oxygen atom.

Particular preference is given to homoleptic metal complexes.

The compounds according to the invention are compounds which contain a moiety of the following formula (2a) or (2b),

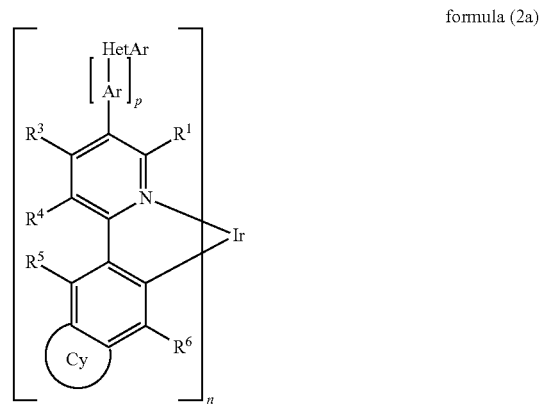

formula (2a)

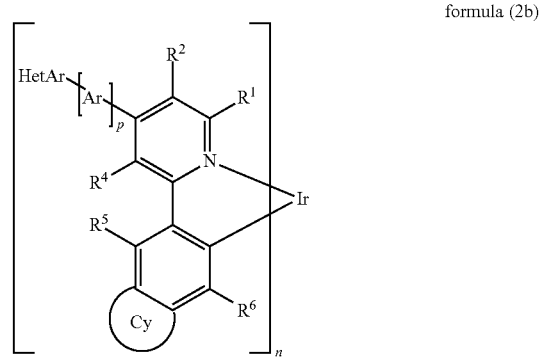

formula (2b)

where the symbols and indices used have the meanings given above.

Preference is given to the moiety of the formula (2a) which contains the group —(Ar)$_p$-HetAr bonded in the meta-position to the coordinating nitrogen atom of the pyridine ring.

If p=1 and the compound according to the invention contains a group Ar, this group Ar is preferably selected, identically or differently on each occurrence, from an aromatic or heteroaromatic ring system having 5 to 24 aromatic ring atoms, preferably having 6 to 18 aromatic ring atoms, particularly preferably phenyl or biphenyl, where Ar may in each case be substituted by one or more radicals R, but is preferably unsubstituted.

Preferably, the index p=0, and the group HetAr is bonded directly to the pyridine ring.

Preferred groups HetAr are described below.

Preferred embodiments of the group HetAr are the groups of the following formulae (3-1) to (3-10),

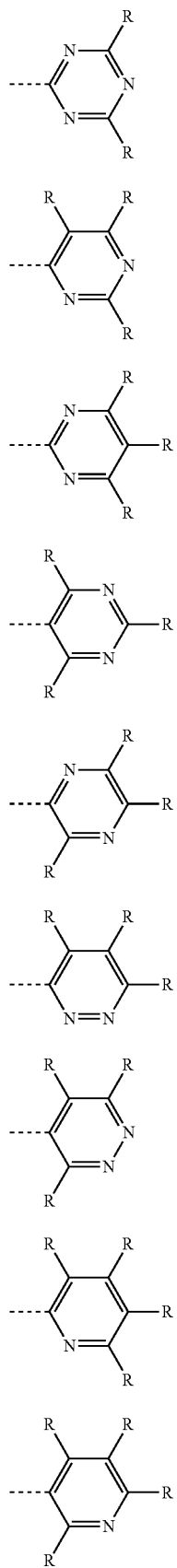

formula (3-1)

formula (3-2)

formula (3-3)

formula (3-4)

formula (3-5)

formula (3-6)

formula (3-7)

formula (3-8)

formula (3-9)

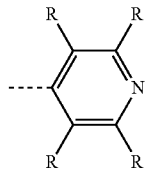

formula (3-10)

where the dashed bond represents the bond from these groups to Ar or, for p=0, to the pyridine ring and R has the meanings given above.

Preference is given to the groups of the formulae (3-1) to (3-3) and particular preference given to the group of the formula (3-1).

Preferred embodiments of the groups indicated above are the groups of the following formulae (3-1a) to (3-10a),

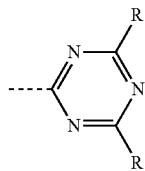

formula (3-1a)

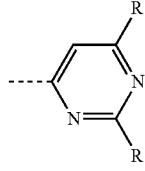

formula (3-2a)

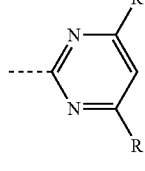

formula (3-3a)

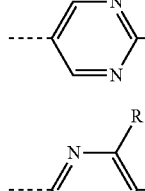

formula (3-4a)

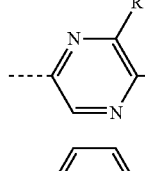

formula (3-5a)

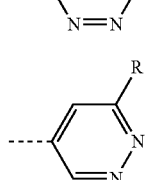

formula (3-6a)

formula (3-7a)

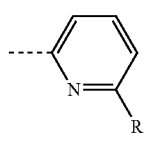

formula (3-8a)

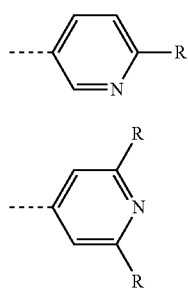

formula (3-9a)

formula (3-10a)

where the dashed bond represents the bond from these groups to Ar or, for p=0, to the pyridine ring and R represents a substituent in accordance with the definition given above other than hydrogen.

The substituent R on the group HetAr is preferably, identically or differently on each occurrence, H or an aromatic or heteroaromatic ring system having 6 to 24 aromatic ring atoms, which may be substituted by one or more radicals $R^9$. R in the groups of the formulae (3-1a) to (3-10a) is not equal to hydrogen. The aromatic or heteroaromatic ring system preferably has 6 to 18 aromatic ring atoms. It is particularly preferably an aromatic ring system having 6 to 12 aromatic ring atoms or a heteroaromatic ring system having 6 to 13 aromatic ring atoms, which may in each case be substituted by one or more radicals $R^9$, but is preferably unsubstituted. Examples of suitable groups R are selected from the group consisting of phenyl, biphenyl, in particular ortho-, meta- or para-biphenyl, terphenyl, in particular branched terphenyl, quaterphenyl, in particular branched quaterphenyl, 1-, 2-, 3- or 4-fluorenyl, 1-, 2-, 3- or 4-spiro-bifluorenyl, pyridyl, pyrimdinyl, 1-, 2-, 3- or 4-dibenzofuranyl, 1-, 2-, 3- or 4-dibenzothienyl and 1-, 2-, 3- or 4-carbazolyl, each of which may be substituted by one or more radicals $R^9$, but are preferably unsubstituted.

Examples of suitable groups R are the structures R-1 to R-15 shown below,

R-1
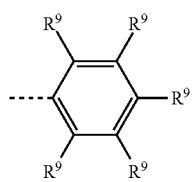

R-2
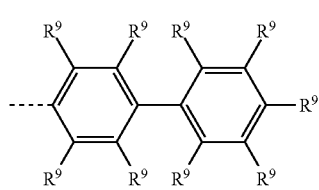

R-3
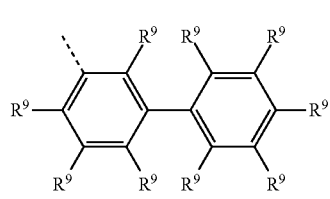

R-4
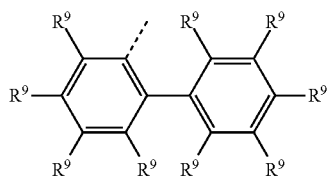

R-5
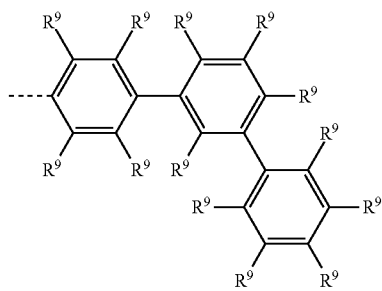

R-6
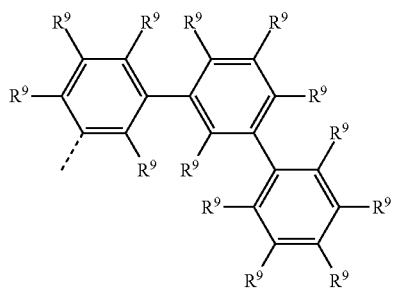

R-7
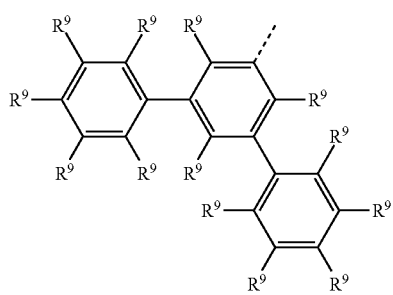

R-8
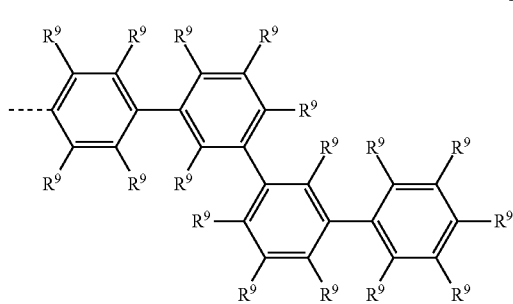

-continued

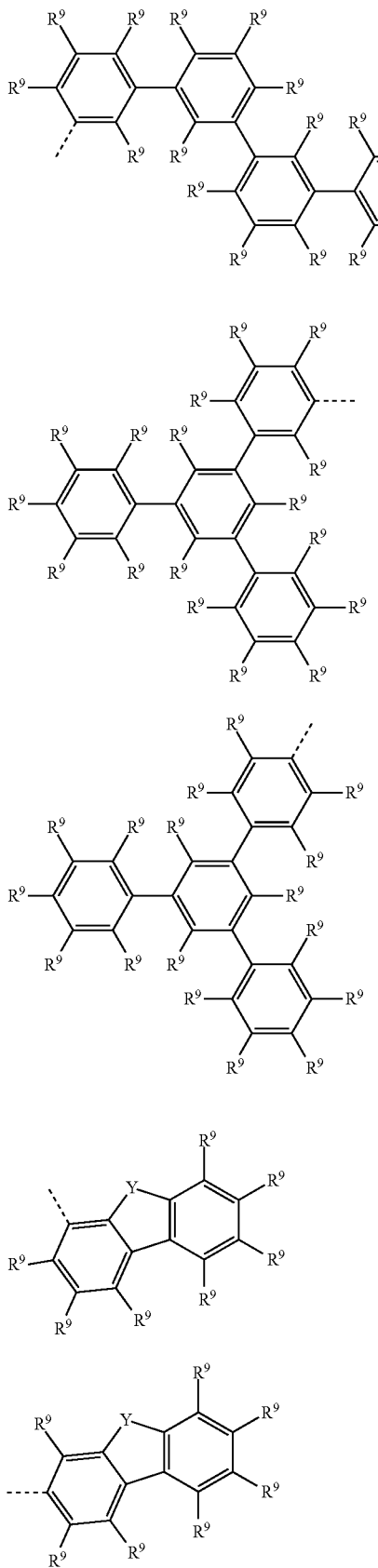

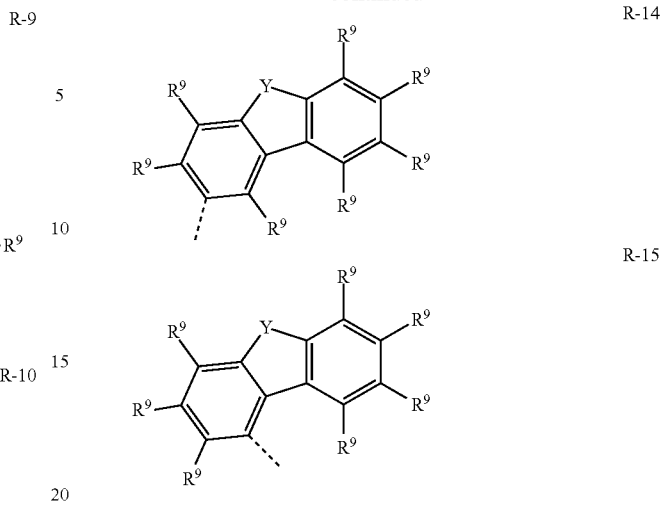

where Y stands for $C(R^9)_2$, $NR^9$, O or S, $R^9$ has the meanings given above and the dashed bond represents the bond to HetAr.

Preferred embodiments of the group Cy are described below. As described above, the group Cy represents a group of one of the formulae (4) to (10). In the structures of the formulae (4) to (10) depicted above and the further embodiments of these structures mentioned as preferred, a double bond is formally shown between the two carbon atoms. This represents a simplification of the chemical structure since these two carbon atoms are bonded into an aromatic system and the bond between these two carbon atoms is thus formally between the bond order of a single bond and that of a double bond. The drawing-in of the formal double bond should thus not be interpreted a limiting for the structure, but instead it is apparent to the person skilled in the art that this is an aromatic bond.

It is essential in the groups of the formulae (4) to (10) that these do not contain any acidic benzylic protons. Benzylic protons are taken to mean protons which are bonded to a carbon atom which is bonded directly to the ligand. The absence of acidic benzylic protons is achieved in the formulae (4) to (6) through $A^1$ and $A^3$, if they stand for $C(R^8)_2$, being defined in such a way that $R^8$ is not equal to hydrogen. The absence of acidic benzylic protons is achieved in formulae (7) to (10) through it being a bicyclic structure. Owing to the rigid spatial arrangement, $R^7$, if it stands for H, is significantly less acidic than benzyl protons, since the corresponding anion of the bicyclic structure is not mesomerism-stabilised. Even if $R^7$ in formulae (7) to (10) stands for H, this is therefore a non-acidic proton in the sense of the present application.

In a preferred embodiment of the structure of the formulae (4) to (10), a maximum of one of the groups $A^1$, $A^2$ and $A^3$ stands for a heteroatom, in particular for O or $NR^8$, and the other groups stand for $C(R^8)_2$ or $C(R^7)_2$, or $A^1$ and $A^3$ stand, identically or differently on each occurrence, for O or $NR^8$ and $A^2$ stands for $C(R^7)_2$. In a particularly preferred embodiment of the invention, $A^1$ and $A^3$ stand, identically or differently on each occurrence, for $C(R^8)_2$ and $A^2$ stands for $C(R^7)_2$, and particularly preferably for $C(R^8)_2$ or $CH_2$.

Preferred embodiments of the formula (4) are thus the structures of the formulae (4-A), (4-B), (4-C) and (4-D), ands particularly preferred embodiment of the formula (4-A) are the structures of the formulae (4-E) and (4-F),

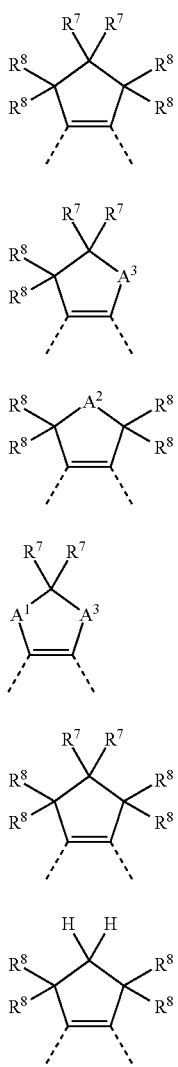

formula (4-A)

formula (4-B)

formula (4-C)

formula (4-D)

formula (4-E)

formula (4-F)

where R$^7$ and R$^8$ have the meanings given above, and A$^1$, A$^2$ and A$^3$ stand, identically or differently on each occurrence, for O or NR$^8$.

Preferred embodiments of the formula (5) are the structures of the following formulae (5-A) to (5-F),

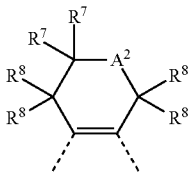

formula (5-A)

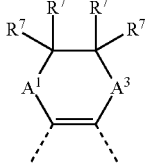

formula (5-B)

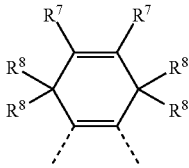

formula (5-C)

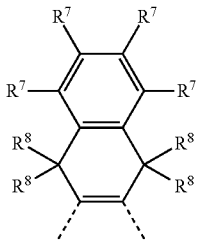

formula (5-D)

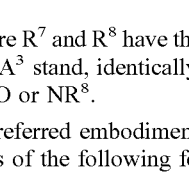

formula (5-E)

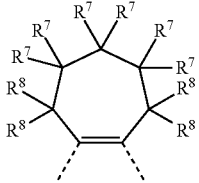

formula (5-F)

where R$^7$ and R$^8$ have the meanings given above, and A$^1$, A$^2$ and A$^3$ stand, identically or differently on each occurrence, for O or NR$^8$.

Preferred embodiments of the formula (6) are the structures of the following formulae (6-A) to (6-E),

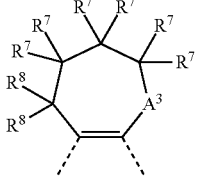

formula (6-A)

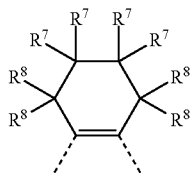

formula (6-B)

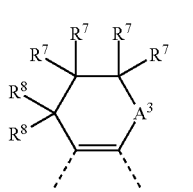

formula (6-C)

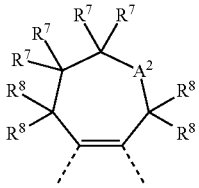

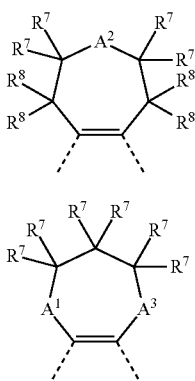

formula (6-D)

formula (6-E)

where $R^7$ and $R^8$ have the meanings given above, and $A^1$, $A^2$ and $A^3$ stand, identically or differently on each occurrence, for O or $NR^8$.

In a preferred embodiment of the structure of the formula (7), the radicals $R^7$ which are bonded to the bridgehead stand for H, D, F or $CH_3$. $A^2$ furthermore preferably stands for $C(R^7)_2$ or O, and particularly preferably for $C(R^8)_2$. Preferred embodiments of the formula (7) are thus the structures of the formulae (7-A) and (7-8), and a particularly preferred embodiment of the formula (7-A) is a structure of the formula (7-C),

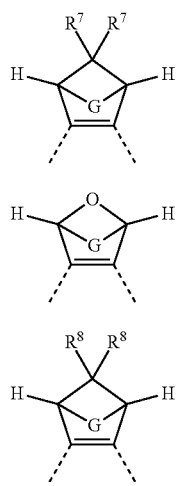

formula (7-A)

formula (7-B)

formula (7-C)

where the symbols used have the meanings given above.

In a preferred embodiment of the structure of the formulae (8), (9) and (10), the radicals $R^7$ which are bonded to the bridgehead stand for H, D, F or $CH_3$. $A^2$ furthermore preferably stands for $C(R^7)_2$. Preferred embodiments of the formulae (8), (9) and (10) are thus the structures of the formulae (8-A), (9-A) and (10-A),

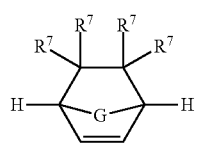

formula (8-A)

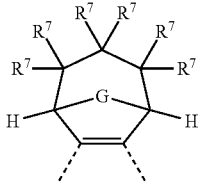

formula (9-A)

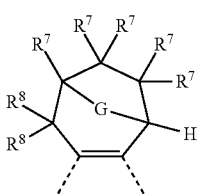

formula (10-A)

where the symbols used have the meanings given above.

The group G in the formulae (7), 7-A), (7-B), (7-C), (8), (8-A), (9), (9-A), (10) and (10-A) furthermore preferably stands for a 1,2-ethylene group, which may be substituted by one or more radicals $R^9$, where $R^9$ preferably stands, identically or differently on each occurrence, for H or an alkyl group having 1 to 4 C atoms, or an ortho-arylene group having 6 to 10 C atoms, which may be substituted by one or more radicals $R^9$, but is preferably unsubstituted, in particular an ortho-phenylene group, which may be substituted by one or more radicals $R^9$, but is preferably unsubstituted.

In a further preferred embodiment of the invention, $R^8$ in the groups of the formulae (4) to (10) and in the preferred embodiments stands, identically or differently on each occurrence, for F, a straight-chain alkyl group having 1 to 10 C atoms or a branched or cyclic alkyl group having 3 to 10 C atoms, where in each case one or more non-adjacent $CH_2$ groups may be replaced by $R^9C\!=\!CR^9$ and one or more H atoms may be replaced by D or F, or an aromatic or heteroaromatic ring system having 5 to 14 aromatic ring atoms, which may in each case be substituted by one or more radicals $R^9$; two radicals $R^8$ here which are bonded to the same carbon atom may form an aliphatic or aromatic ring system with one another and thus form a spiro system; furthermore, $R^8$ may form an aliphatic ring system with an adjacent radical $R^7$.

In a particularly preferred embodiment of the invention, $R^8$ in the groups of the formulae (4) to (10) and in the preferred embodiments stands, identically or differently on each occurrence, for F, a straight-chain alkyl group having 1 to 3 C atoms, in particular methyl, or an aromatic or heteroaromatic ring system having 5 to 12 aromatic ring atoms, each of which may be substituted by one or more radicals $R^9$, but is preferably unsubstituted; two radicals $R^8$ here which are bonded to the same carbon atom may form an aliphatic or aromatic ring system with one another and thus form a spiro system; furthermore, $R^8$ may form an aliphatic ring system with an adjacent radical $R^7$.

Examples of particularly suitable groups of the formula (4) are the groups (4-1) to (4-70) shown below

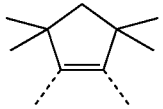

(4-1)

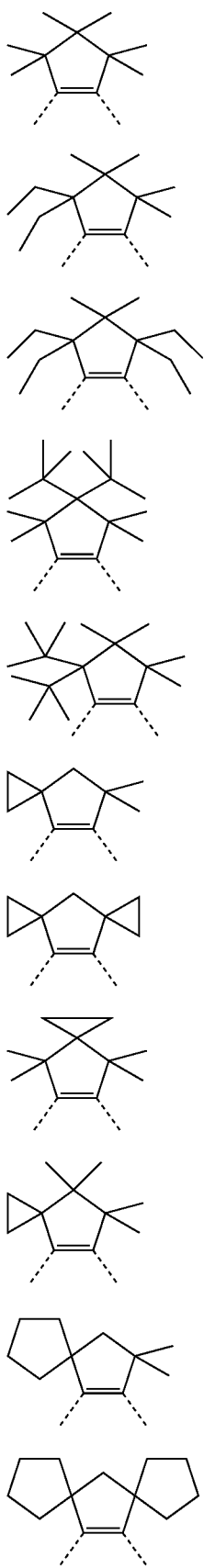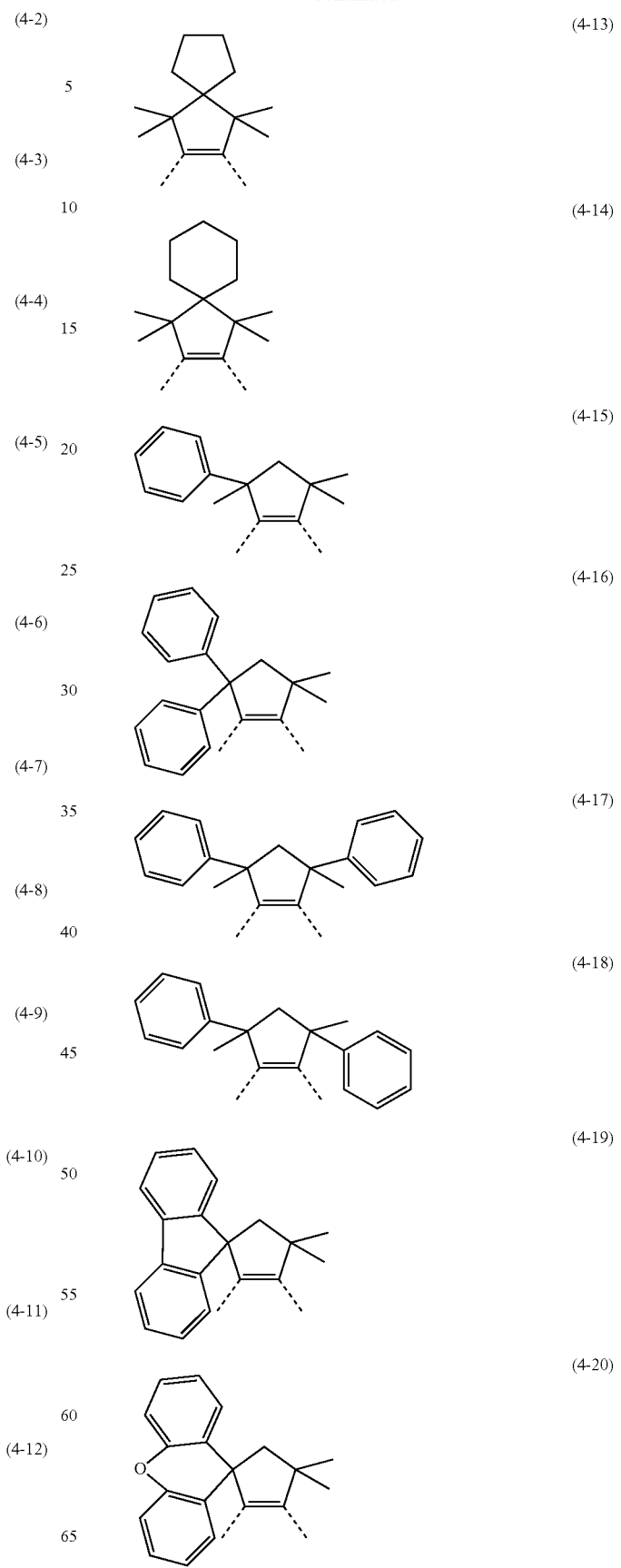

(4-21) 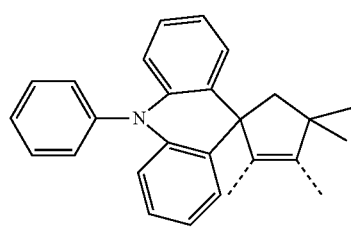
(4-22) 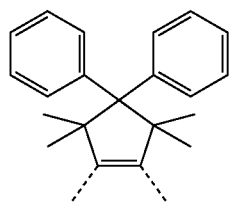
(4-23) 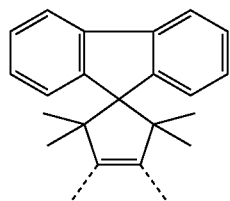
(4-24) 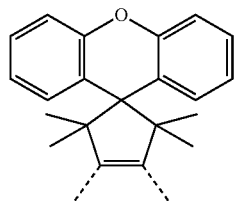
(4-25) 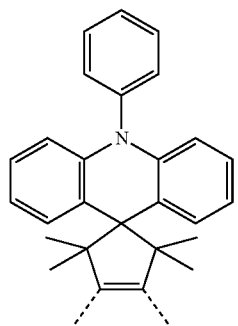
(4-26) 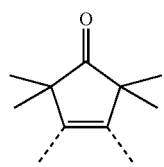
(4-27) 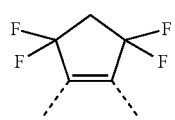
(4-28) 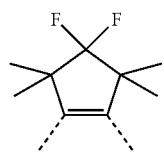
(4-29) 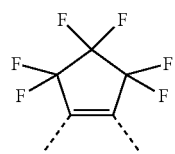
(4-30) 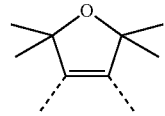
(4-31) 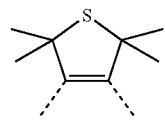
(4-32) 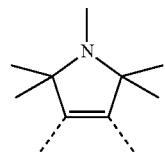
(4-33) 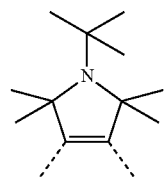
(4-34) 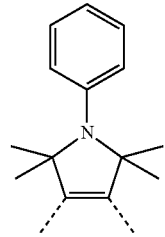
(4-35) 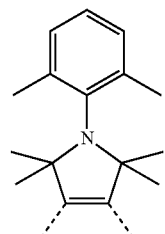
(4-36) 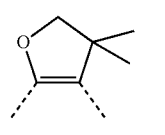
(4-37)

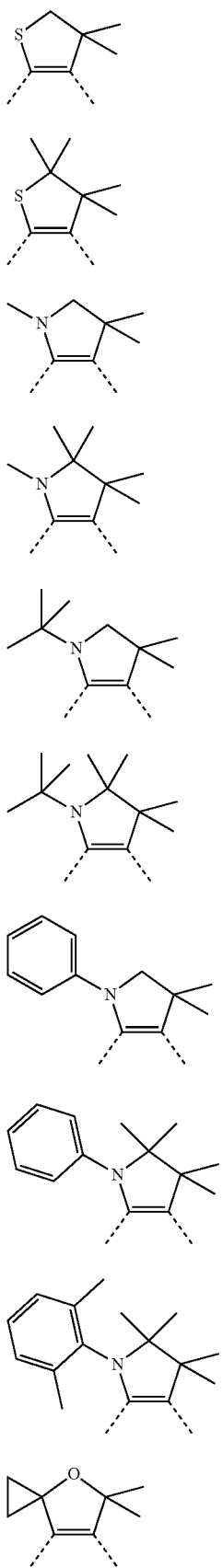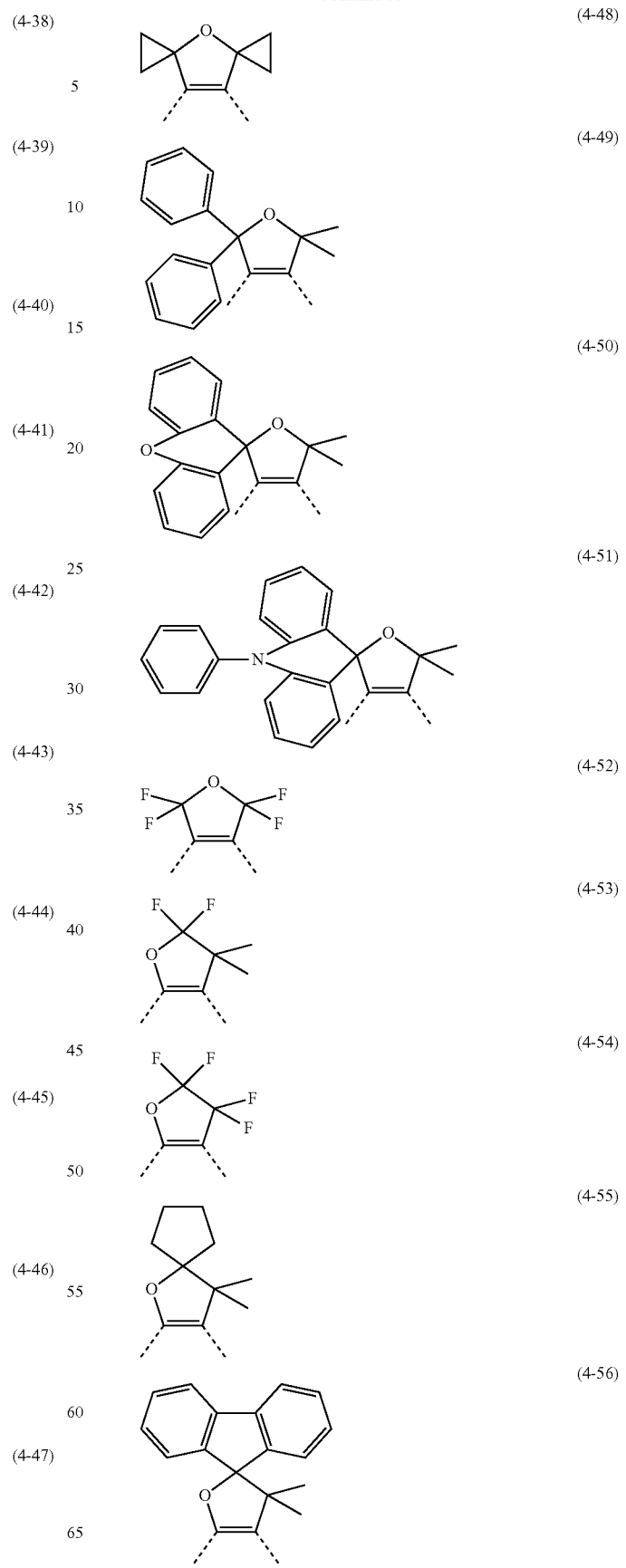

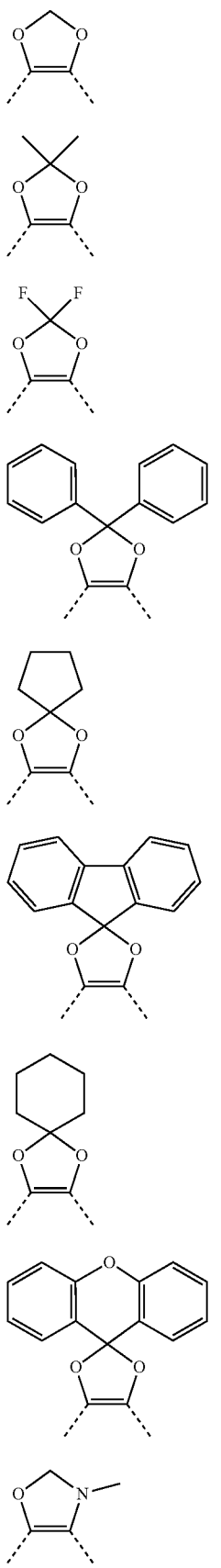
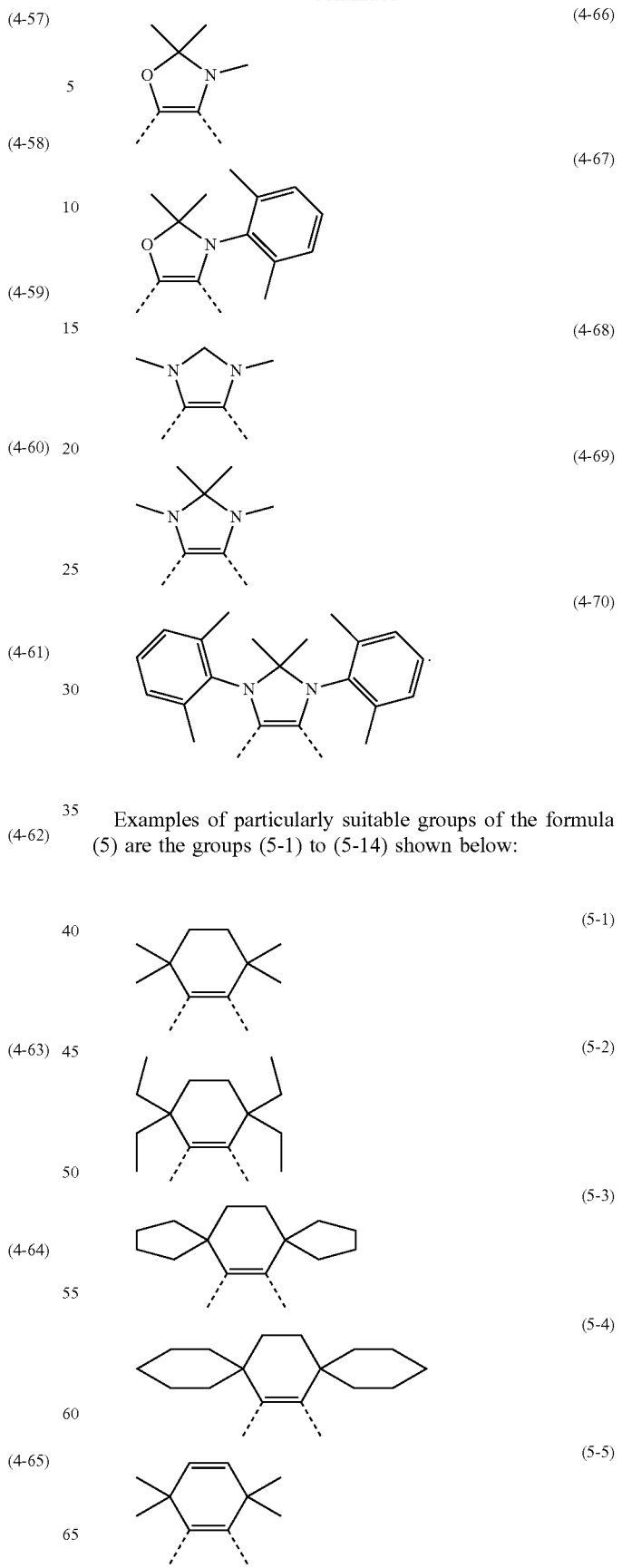
Examples of particularly suitable groups of the formula (5) are the groups (5-1) to (5-14) shown below:

-continued
(5-6)
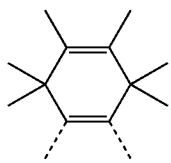
(5-7)
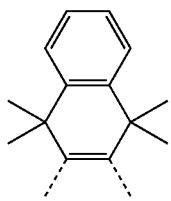
(5-8)
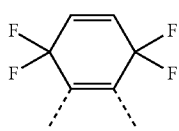
(5-9)
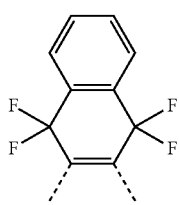
(5-10)
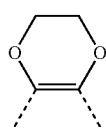
(5-11)
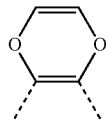
(5-12)
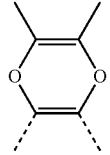
(5-13)
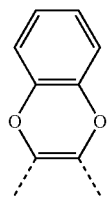
(5-14)
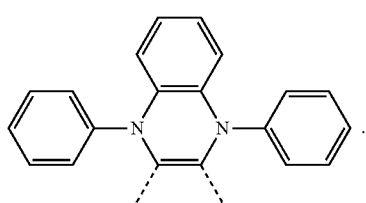
Examples of particularly suitable groups of the formulae (6), (9) and (10) are the groups (6-1), (9-1) and (10-1) shown below.
(6-1)
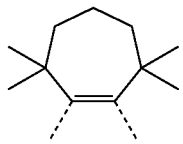
(9-1)
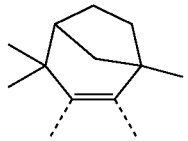
(10-1)
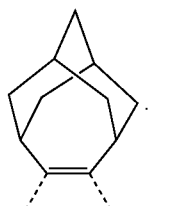
Examples of particularly suitable groups of the formula (7) are the groups (7-1) to (7-22) shown below.
(7-1)
(7-2)
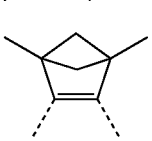
(7-3)
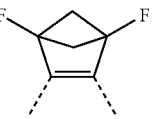
(7-4)
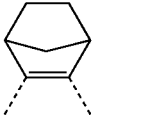
(7-5)
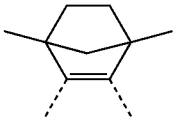
(7-6)
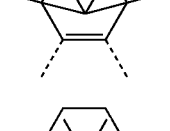
(7-7)

(7-8) 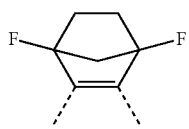
(7-9) 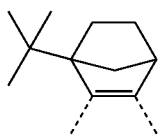
(7-10) 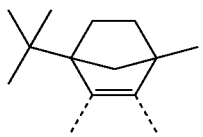
(7-11) 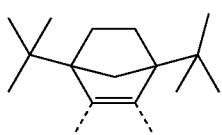
(7-12) 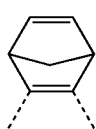
(7-13) 
(7-14) 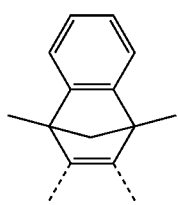
(7-15) 
(7-16) 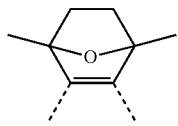
(7-17) 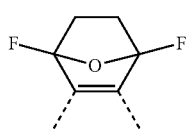
(7-18) 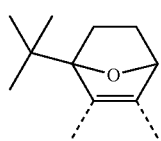
(7-19) 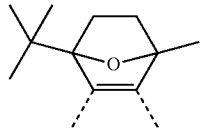
(7-20) 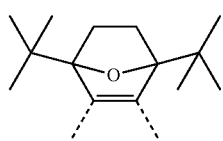
(7-21) 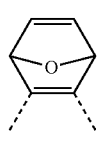
(7-22) 
Examples of particularly suitable groups of the formula (8) are the groups (8-1) to (8-6) shown below.
(8-1) 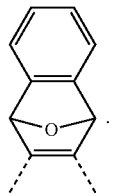
(8-2) 
(8-3) 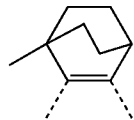
(8-4) 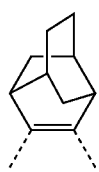

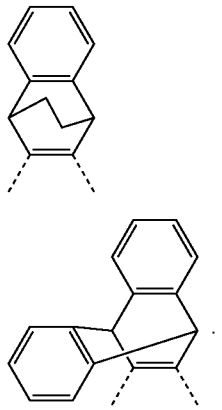

(8-5)

(8-6)

In particular, the use of condensed-on bicyclic structures of this type may also result in chiral ligands L owing to the chirality of the structures. Both the use of enantiomerically pure ligands and also the use of the racemate may be suitable here. It may also be suitable, in particular, to use not only one enantiomer of a ligand in the metal complex according to the invention, but intentionally both enantiomers, so that, for example, a complex (+L)$_2$(−L)M or a complex (+L)(−L)$_2$M forms, where +L or −L in each case denotes the corresponding + or − enantiomer of the ligand. This may have advantages with respect to the solubility of the corresponding complex compared with complexes which contain only +L or only −L as ligand.

If radicals $R^1$ to $R^6$ are also bonded in the moiety of the formula (2), these radicals R are preferably selected on each occurrence, identically or differently, from the group consisting of H, D, F, $N(R^9)_2$, CN, $Si(R^9)_3$, C(=O)$R^9$, a straight-chain alkyl group having 1 to 10 C atoms or an alkenyl group having 2 to 10 C atoms or a branched or cyclic alkyl group having 3 to 10 C atoms, each of which may be substituted by one or more radicals $R^9$, where one or more H atoms may be replaced by D or F, or an aromatic or heteroaromatic ring system having 5 to 24 aromatic ring atoms, which may in each case be substituted by one or more radicals $R^9$; the radicals $R^4$ and $R^5$ here may also form an aliphatic or aromatic ring system with one another. These radicals $R^1$ to $R^6$ are particularly preferably selected on each occurrence, identically or differently, from the group consisting of H, D, F, a straight-chain alkyl group having 1 to 6 C atoms or a branched or cyclic alkyl group having 3 to 10 C atoms, where one or more H atoms may be replaced by F, or an aromatic or heteroaromatic ring system having 5 to 18 aromatic ring atoms, which may in each case be substituted by one or more radicals $R^9$; the radicals $R^4$ and $R^5$ here may also form an aliphatic or aromatic ring system with one another. If the radicals $R^1$ to $R^6$ are an aromatic or heteroaromatic ring system, it is preferred for this to have not more than two aromatic 6-membered rings condensed directly onto one another, in particular absolutely no aromatic 6-membered rings condensed directly onto one another.

In a preferred embodiment of the invention, the substituents $R^1$ and $R^6$ stand, identically or differently on each occurrence, for H, D, F or methyl, in particular for H. This applies, in particular, in the case of facial, homoleptic complexes, while other radicals $R^1$ or $R^6$ may also be preferred in the case of meridional or heteroleptic complexes.

In a particularly preferred embodiment of the invention, all substituents $R^1$ to $R^6$ in formula (2) which do not stand for a group —(Ar)$_p$-HetAr stand for H.

Preferred ligands L', as can occur in compounds of the formula (1), are described below. The ligands L' are by definition mono- or bidentate ligands. The ligands L' are preferably neutral, monoanionic, dianionic or trianionic ligands, particularly preferably neutral or monoanionic ligands. Preference is given to bidentate monoanionic ligands L'.

Preferred neutral, monodentate ligands L' are selected from carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines. In particular halophosphines, trialkylphosphines, triarylphosphines or alkylarylphosphines, such as, for example, trifluorophosphine, trimethylphosphine, tricyclohexylphosphine, tri-tert-butylphosphine triphenylphosphine, tris(pentafluorophenyl)phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidin, triazine, and carbenes, in particular Arduengo carbenes.

Preferred monoanionic, monodentate ligands L' are selected from hydride, deuteride, the halides F$^-$, Cl$^-$, Br$^-$ and I$^-$, alkylacetylides, such as, for example, methy-C≡C$^-$, tert-butyl-C≡C$^-$, arylacetylides, such as, for example, phenyl-C≡C$^-$, cyanide, cyanate, isocyanate, thiocyanate, isothiocyanate, aliphatic or aromatic alcoholates, such as, for example, methanolate, ethanolate, propanolate, Isopropanolate, tert-butylate, phenolate, aliphatic or aromatic thioalcoholates, such as, for example, methanethiolate, ethanethiolate, propanethiolate, isopropanethiolate, tert-thiobutylate, thiophenolate, amides, such as, for example, dimethylamide, diethylamide, diisopropylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Preferred di- or trianionic ligands are O$^{2-}$, S$^{2-}$, carbides, which result in coordination in the form R—C≡M, and nitrenes, which result in coordination in the form R—N=M, where R generally stands for a substituent and N$^{3-}$.

Preferred neutral or mono- or dianionic, bidentate or polydentate ligands L' are selected from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-diisopropylphenylimino)ethyl]pyridine, 2-[1-(methylimino) ethyl]-pyridine, 2-[1-(ethylimino)ethyl]pyridine, 2-[1-(isopropylimino)ethyl]pyridine, 2-[1-(tert-butylimino)ethyl] pyridine, diimines, such as, for example, 1,2-bis (methylimino)ethane, 1,2-bis(ethylimino)ethane, 1,2-bis(isopropylimino)ethane, 1,2-bis(tert-butylimino)ethane, 2,3-bis(methylimino)butane, 2,3-bis(ethylimino)butane, 2,3-bis(isopropylimino)butane, 2,3-bis(tert-butylimino)butane, 1,2-bis(phenylimino)ethane, 1,2-bis(2-methylphenylimino) ethane, 1,2-bis(2,6-diisopropylphenylimino)ethane, 1,2-bis(2,6-di-tert-butylphenylimino)ethane, 2,3-bis(phenylimino) butane, 2,3-bis(2-methylphenylimino)butane, 2,3-bis(2,6-diisopropylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis (diphenylphosphino)methane, bis(diphenylphosphino)ethane, bis(diphenylphosphino)propane, bis(diphenylphosphino)butane, bis(dimethylphosphino)methane, bis (dimethylphosphino)ethane, bis(dimethylphosphino) propane, bis(diethylphosphino)methane, bis (diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1-trifluoroacetyl)methane 2,2,6,6-tetramethyl-3,5-heptanedione, 3-ketonates derived from 3-ketoesters, such as, for example, acetyl acetate, carboxylates derived from aminocarboxylic acids, such as, for example pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol.

In a further preferred embodiment of the invention, the ligands L' are bidentate monoanionic ligands L' which, with the iridium, form a cyclometallated five- or six-membered ring with at least one iridium-carbon bond, in particular a cyclometallated five-membered ring. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals R. A multiplicity of ligands of this type known to the person skilled in the art in the are of phosphorescent electroluminescent devices, and he will be able, without inventive step, to select further ligands of this type as ligand L' for compounds of the formula (1). The combination of two groups, as represented by the following formulae (11) to (38), where one group is bonded via a neutral atom and the other group is bonded via a negatively charged atom, is generally particularly suitable for this purpose. The neutral atom here is, in particular, a neutral nitrogen atom or a carbene carbon atom and the negatively charged atom is, in particular, a negatively charged carbon atom, a negatively charged nitrogen atom or a negatively charged oxygen atom. The ligand L' can then be formed from the groups of the formulae (11) to (38) by these groups bonding to one another in each case at the position denoted by #. The position at which the groups coordinate to the metal is denoted by *. Furthermore, two adjacent radicals R which are each bonded to the two groups of the formulae (11) to (38) form an aliphatic or aromatic ring system with one another.

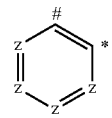 formula (11)

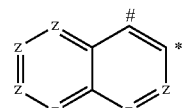 formula (12)

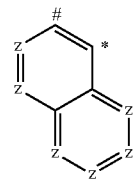 formula (13)

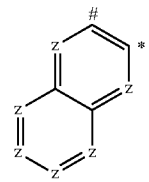 formula (14)

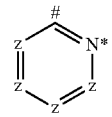 formula (15)

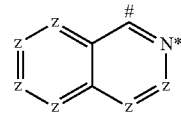 formula (16)

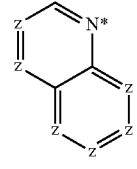 formula (17)

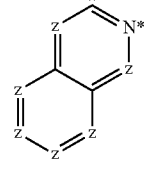 formula (18)

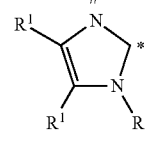 formula (19)

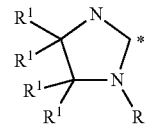 formula (20)

-continued

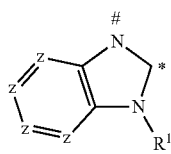
formula (21)

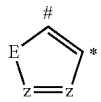
formula (22)

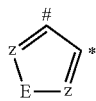
formula (23)

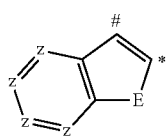
formula (24)

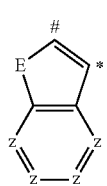
formula (25)

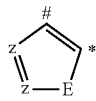
formula (26)

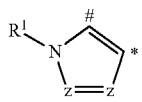
formula (27)

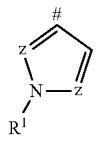
formula (28)

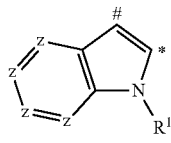
formula (29)

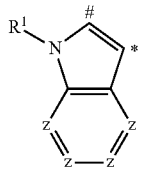
formula (30)

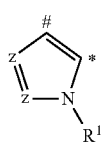
formula (31)

-continued

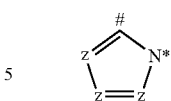
formula (32)

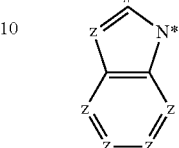
formula (33)

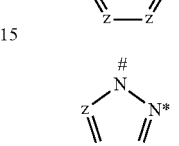
formula (34)

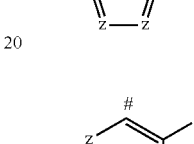
formula (35)

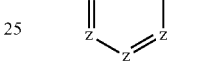
formula (36)

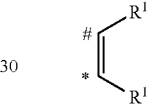
formula (37)

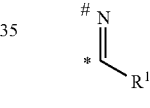
formula (38)

R' here has the same meaning a described above, Z stands, identically or differently on each occurrence, for $CR^1$ or N, E stands for O, S or $CR_2$, and preferably a maximum of two symbols Z in each group stand for N, particularly preferably a maximum of one symbol Z in each group stands for N. Very particularly preferably, all symbols Z stand, identically or differently on each occurrence, for $CR^1$.

In a very particularly preferred embodiment of the invention, the ligand L' is a monoanionic bidentate ligand formed from two of the groups of the formulae (11) to (38), where one of these groups is coordinated to the iridium via a negatively charged carbon atom and the other of these groups is coordinated to the iridium via a neutral nitrogen atom.

It may likewise be preferred if two adjacent symbols Z in these ligands stand for a group of the above-mentioned formulae (9) to (15).

The further preferred radicals $R^1$ in the structures shown above are defined like the radicals $R^1$ to $R^6$ of the ligand L.

Examples of suitable co-ligands are depicted in the following table:

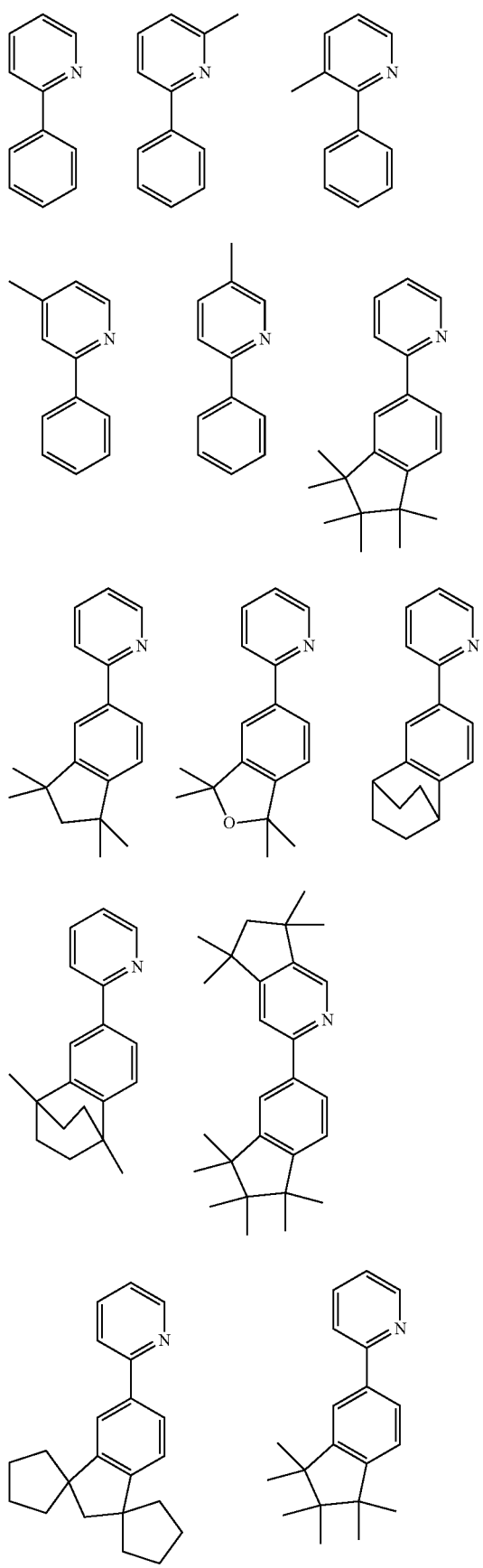
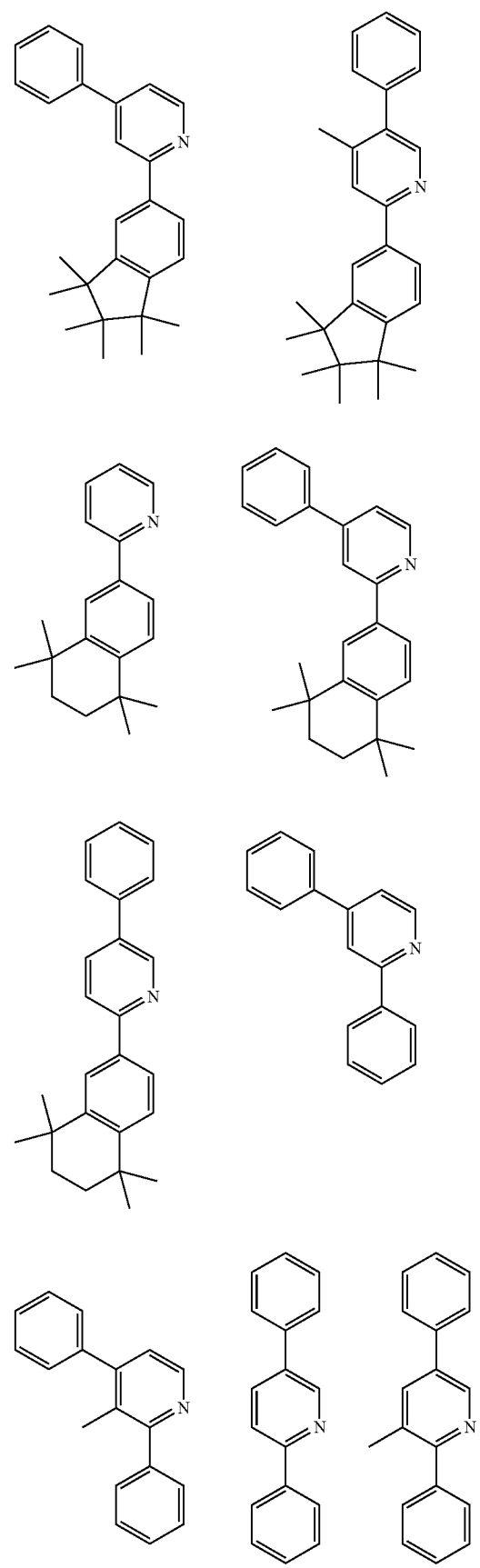

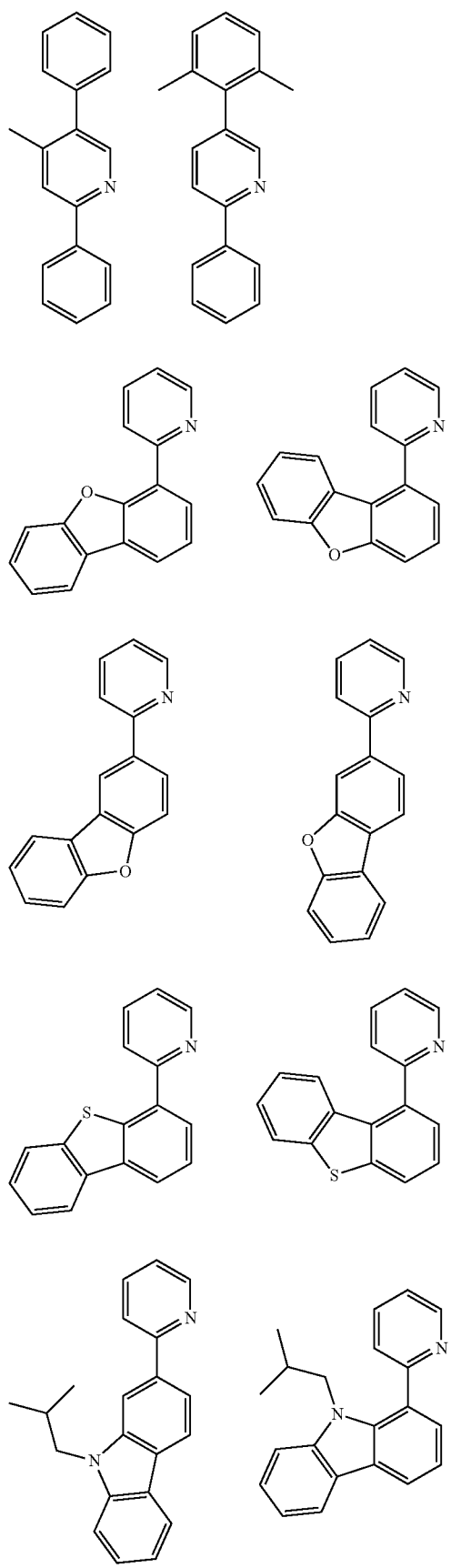
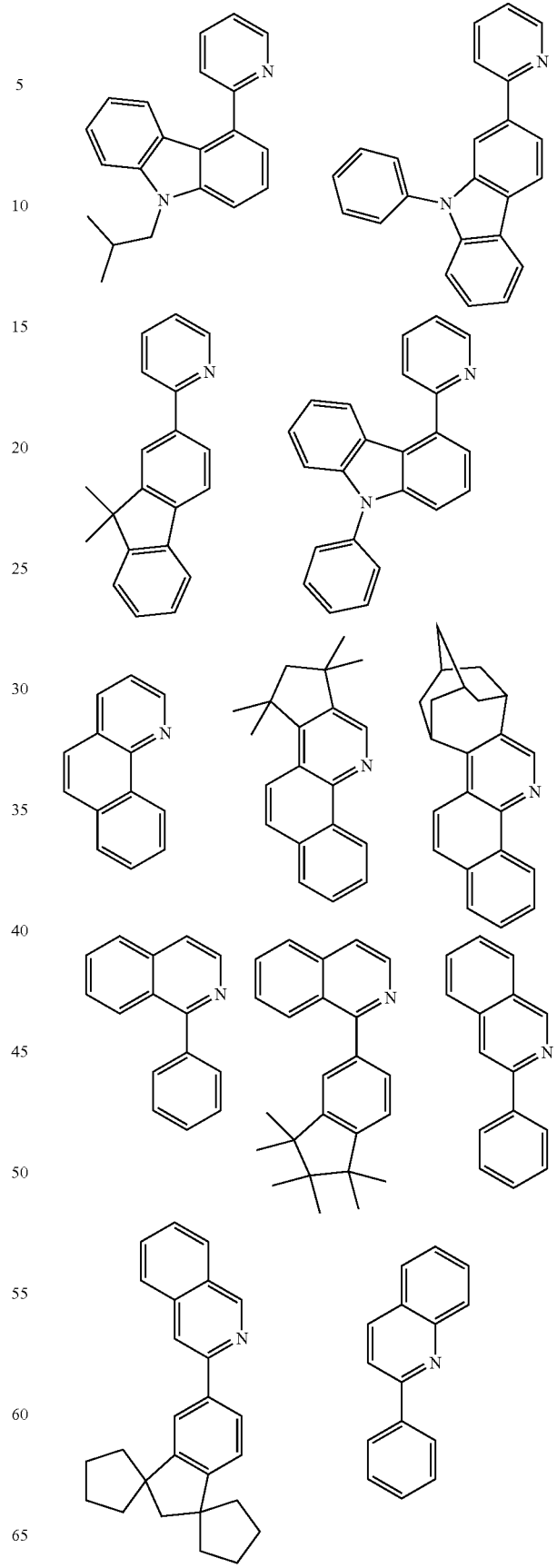

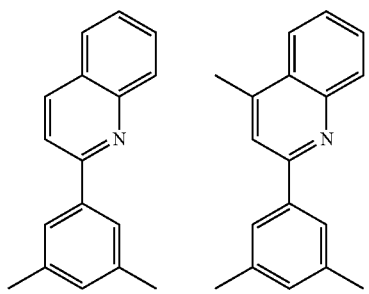
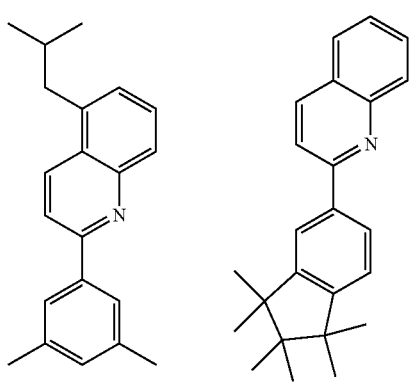
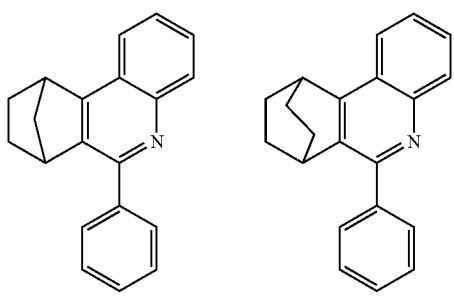
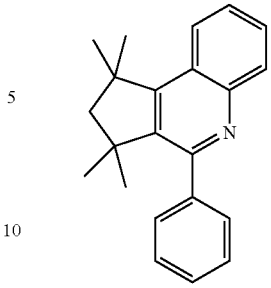

The ligands L and L' may also be chiral, depending on the structure. This is the case, in particular, if they contain a bicyclic group of the formulae (7) to (10) or if they contain substituents, for example alkyl, alkoxy, diallylamino or aralkyl groups, which have one or more stereocentres. Since the basic structure of the complex may also be a chiral structure, the formation of diastereomers and a plurality of enantiomer pairs is possible. The complexes according to the invention then encompass both the mixtures of the various diastereomers or the corresponding racemates and also the individual isolated diastereomers or enantiomers.

The compounds according to the invention may also be rendered soluble by suitable substitution, for example by relatively long alkyl groups (about 4 to 20 C atoms), in particular branched alkyl groups, or optionally substituted aryl groups, for example xylyl, mesityl or branched terphenyl or quaterphenyl groups. Compounds of this type are then soluble in adequate concentration in common organic solvents at room temperature in order to enable the complexes to be processed from solution, for example by printing processes.

The preferred embodiments mentioned above can be combined with one another as desired. In a particularly preferred embodiment of the invention, the preferred embodiments mentioned above apply simultaneously.

The compounds can also be employed as chiral, enantiomerically pure complexes which are able to emit circular-polarised light. This may have advantages, since the polarising filter on the device can thus be omitted. In addition, complexes of this type are also suitable for use in security labels, since, besides the emission, they also have the polarisation of the light as an easily readable feature.

Examples of suitable compounds according to the invention are the structures shown in the following table.

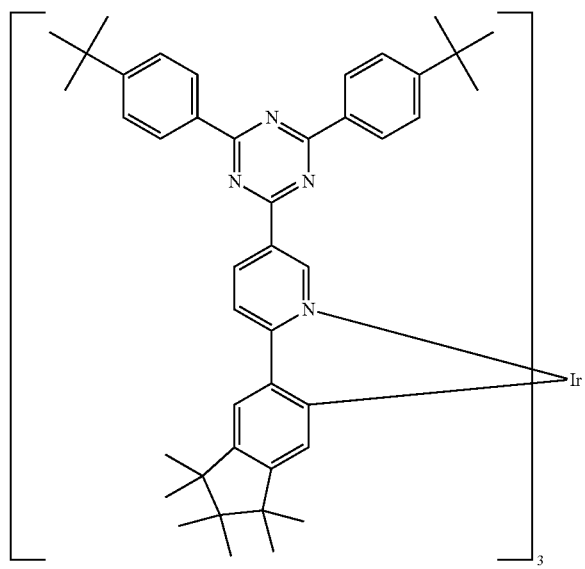

41    42
-continued
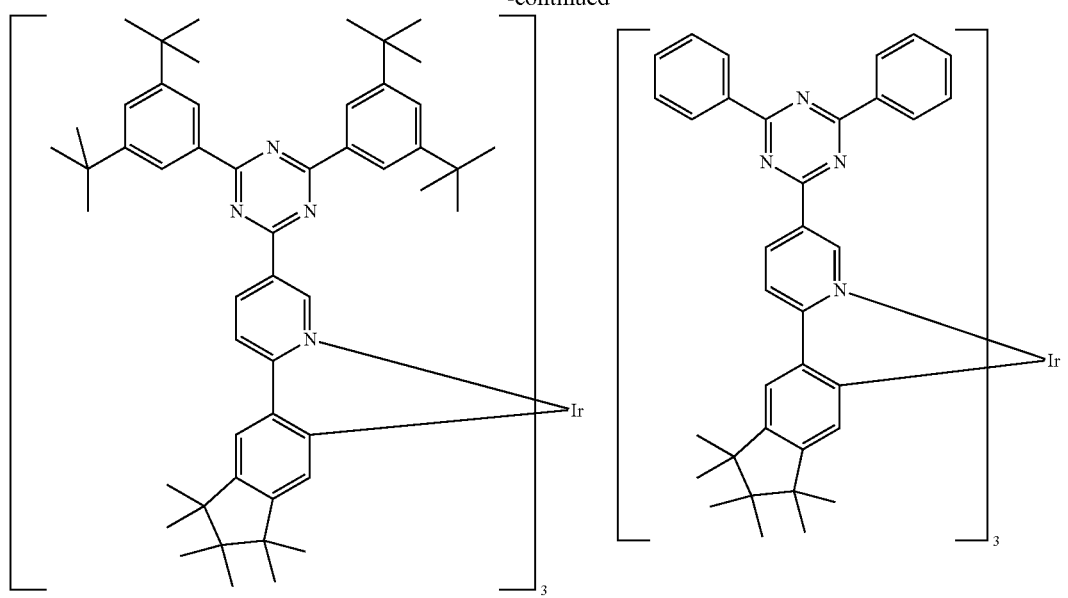
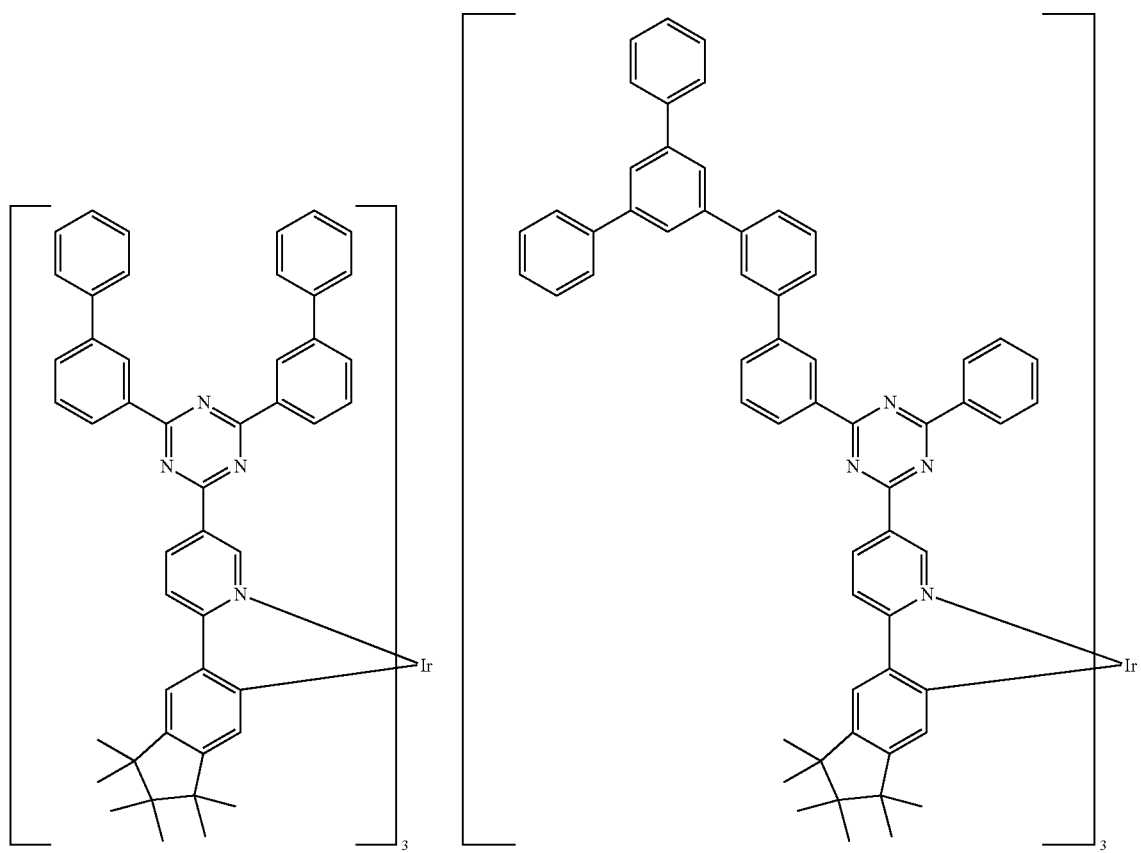

43
44
-continued
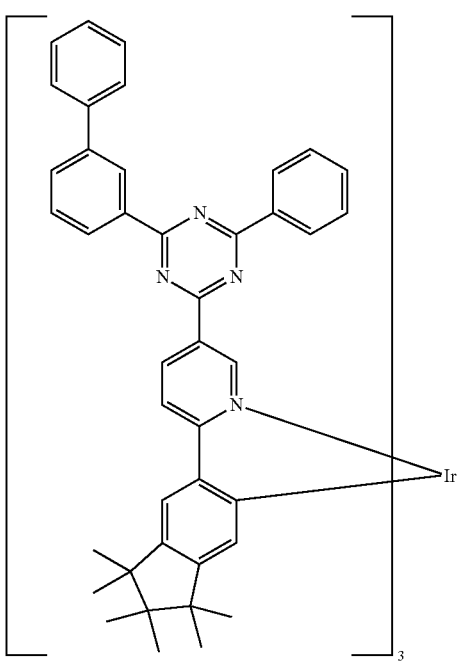
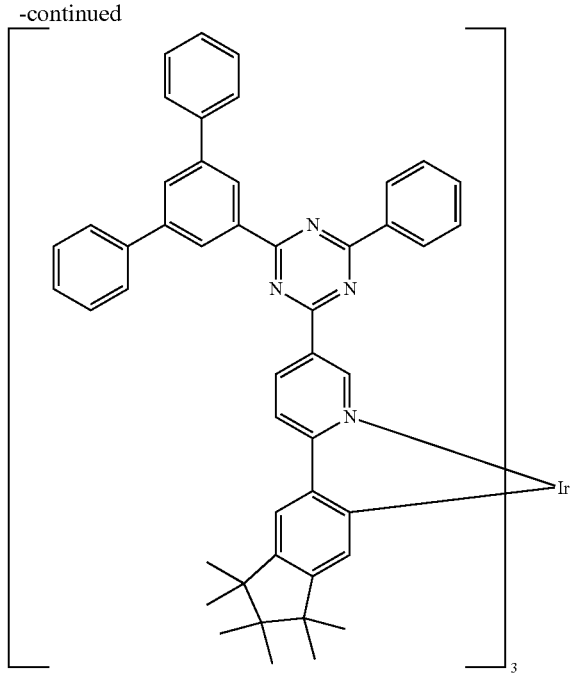
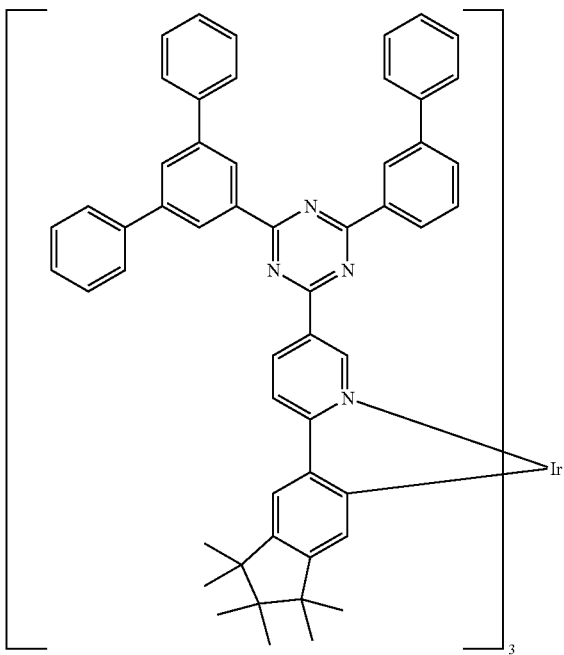
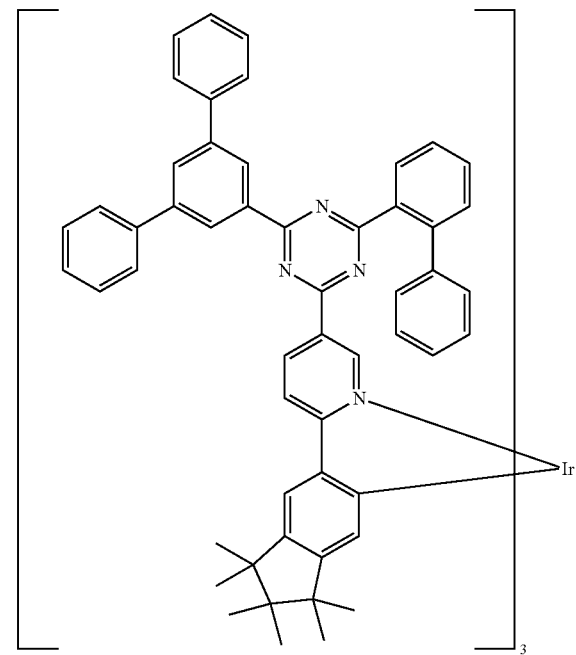

-continued
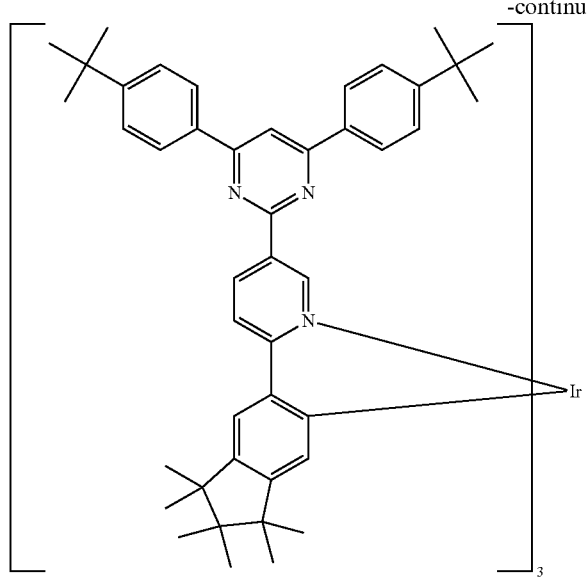
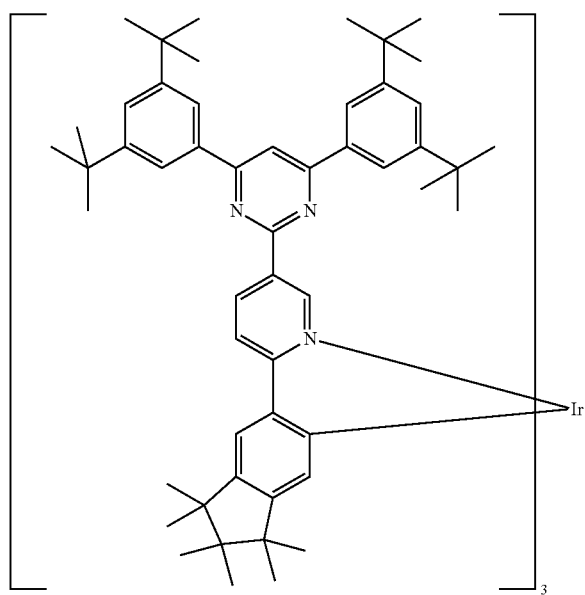
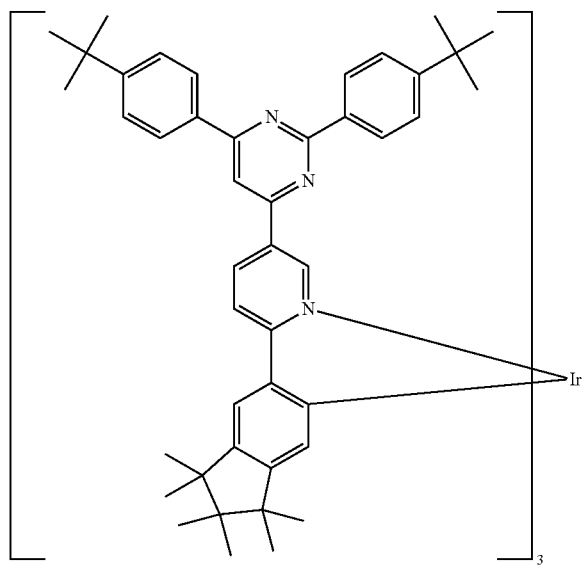
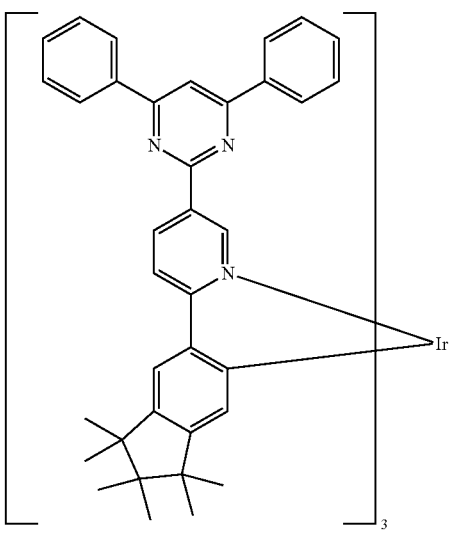

-continued
47
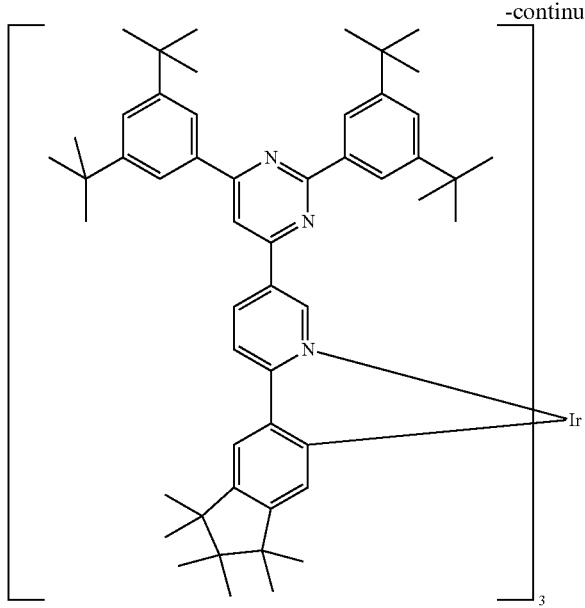
48
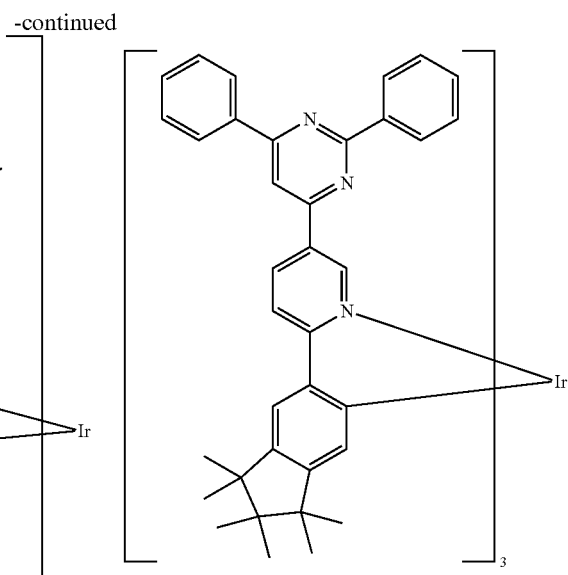
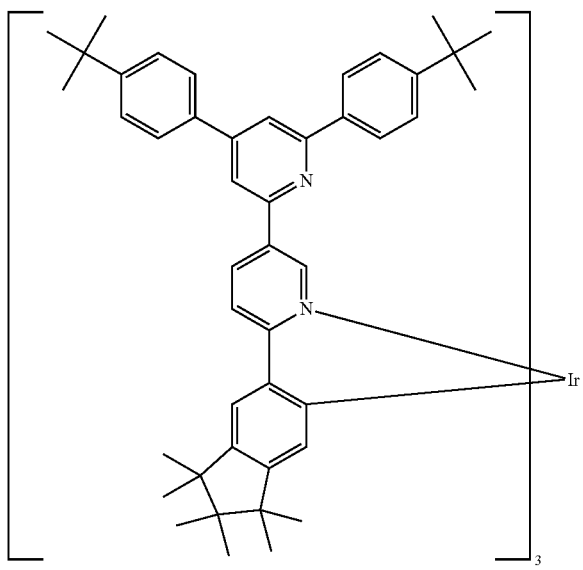

-continued
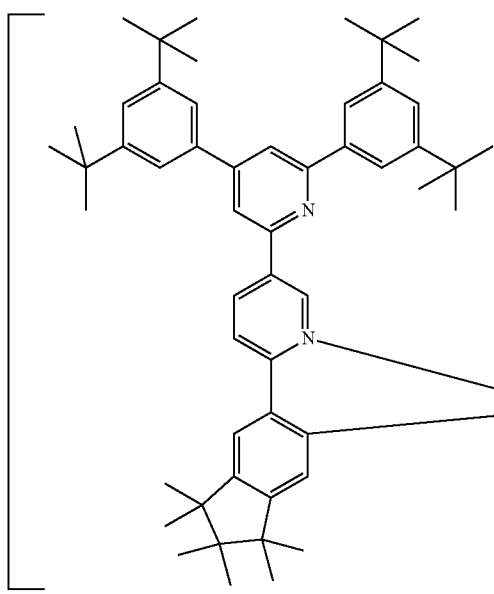
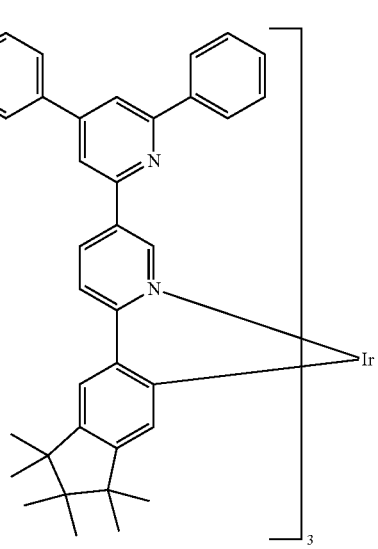
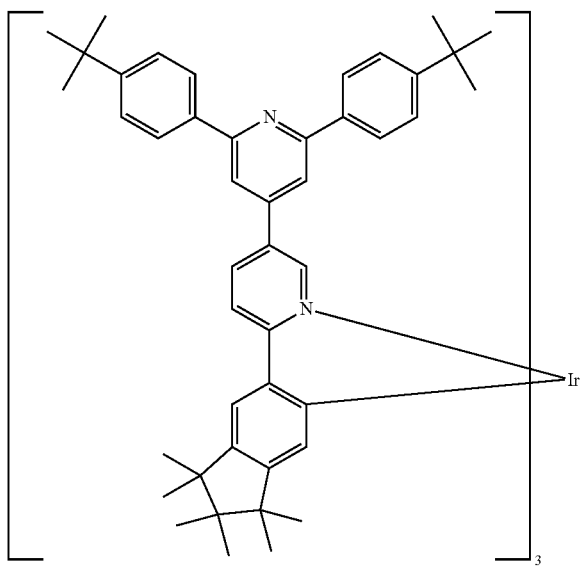

-continued
51 52
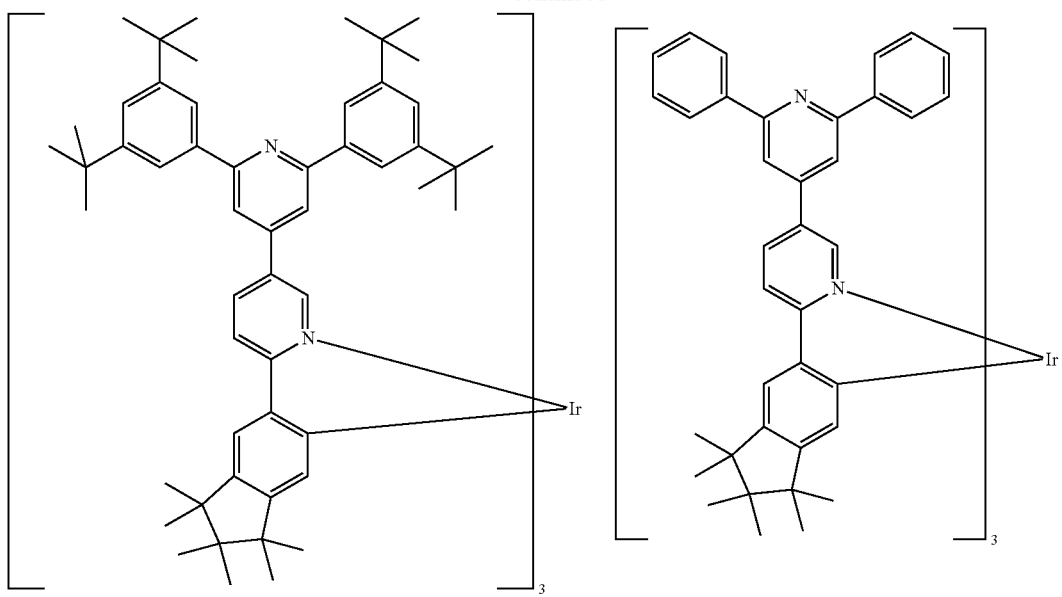
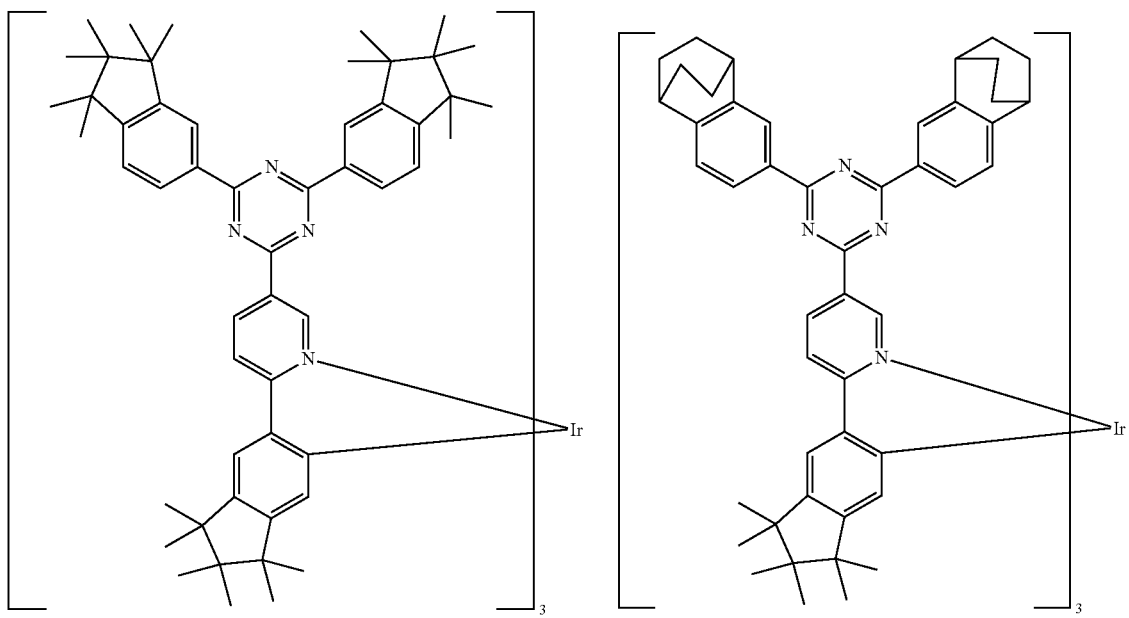

-continued
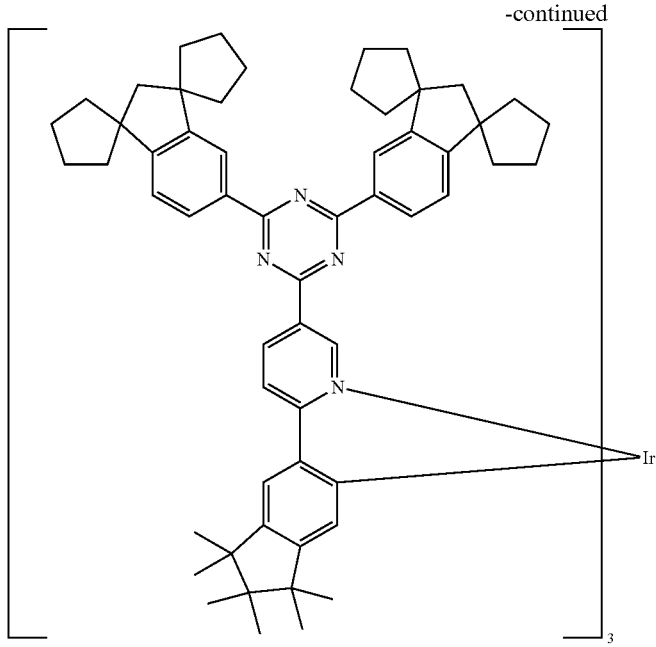
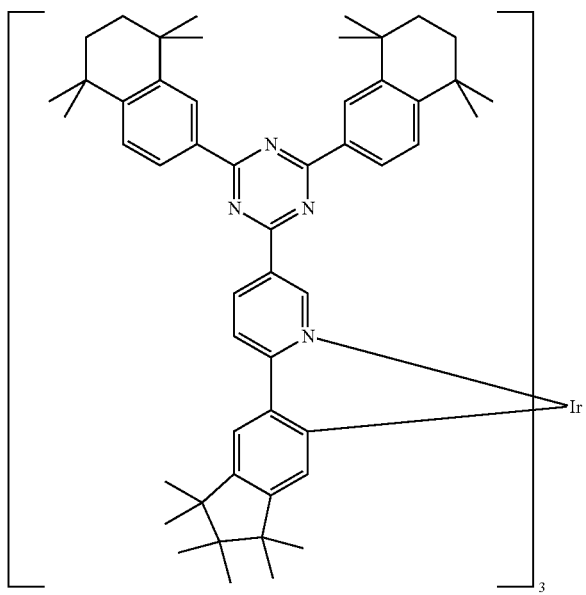

-continued
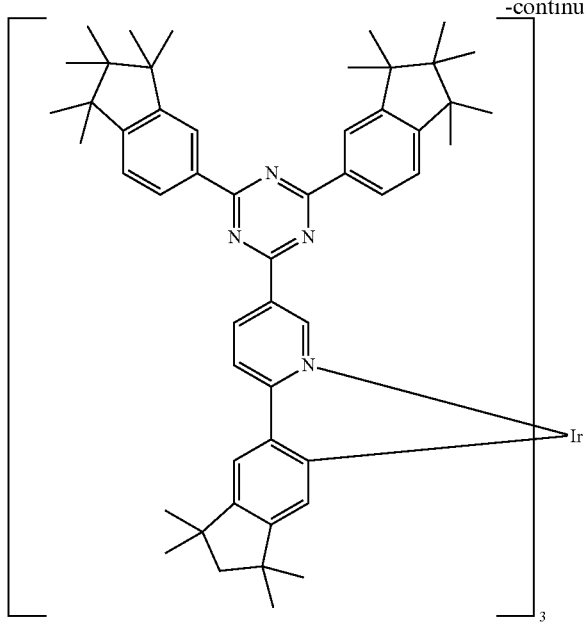
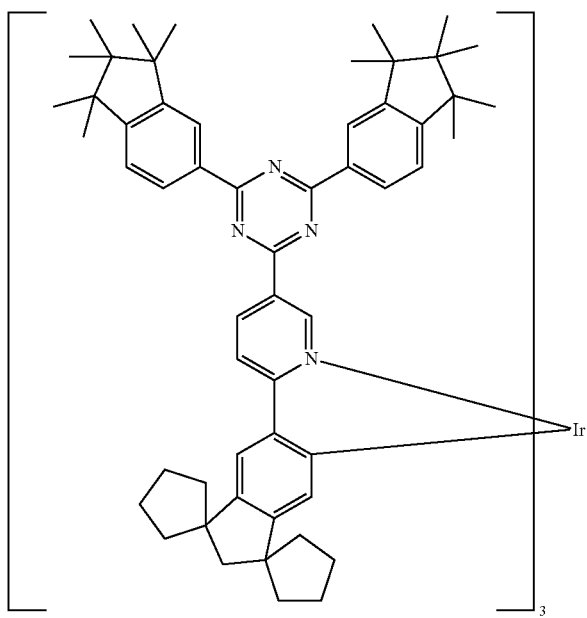

-continued
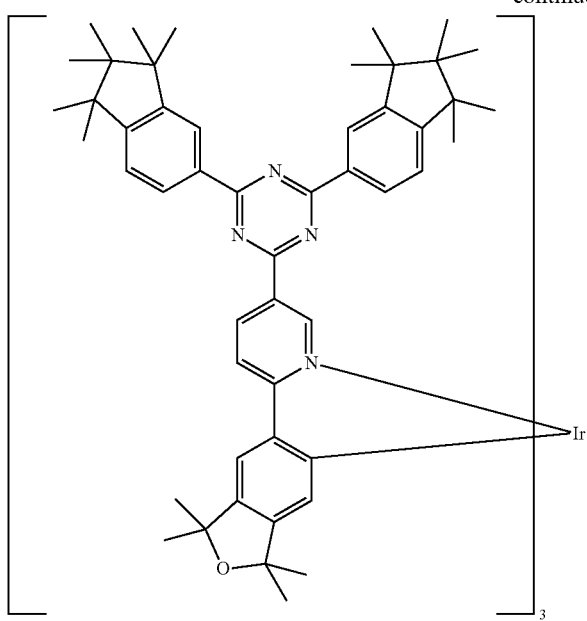
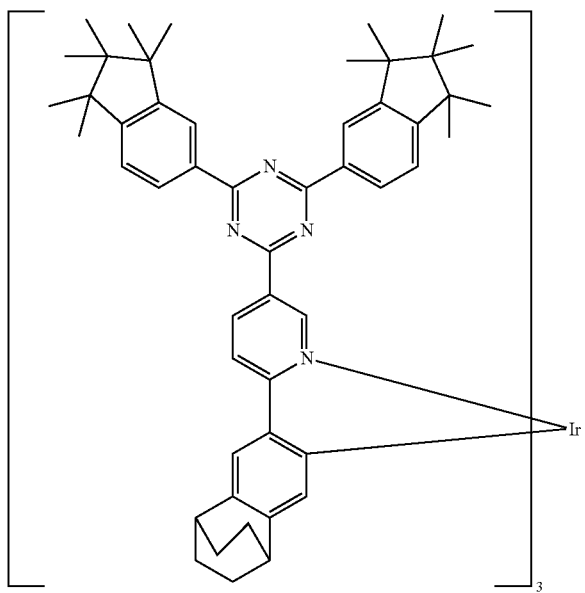

-continued
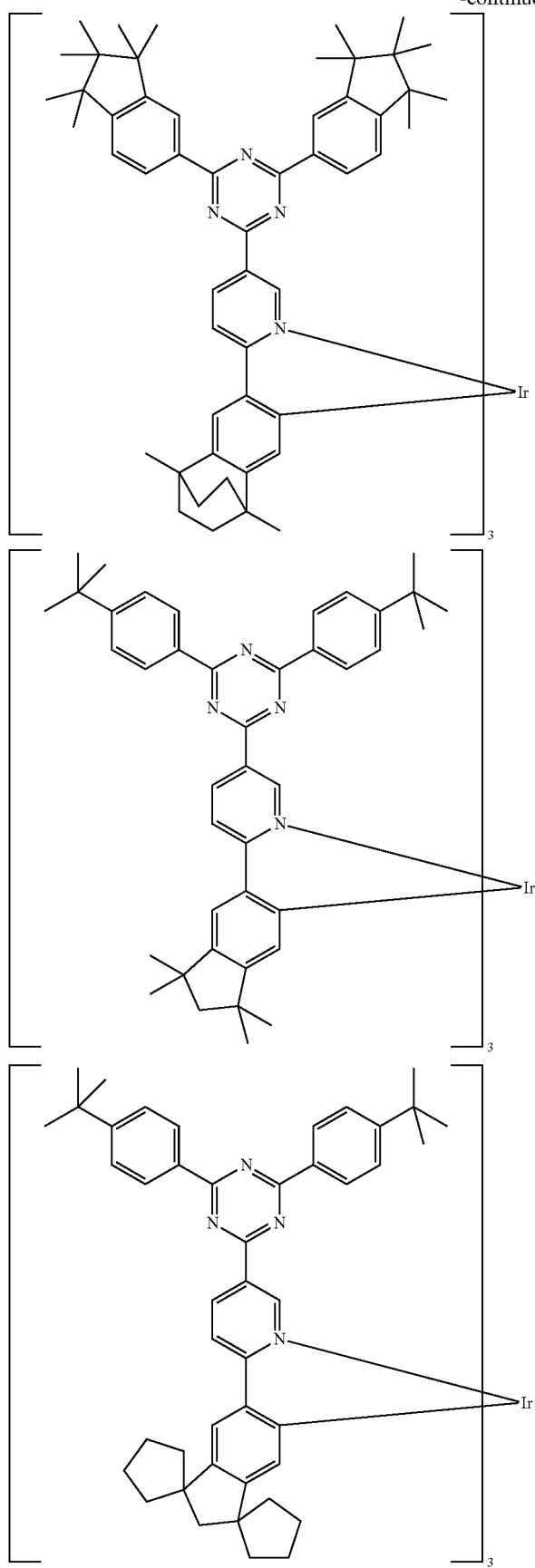

-continued
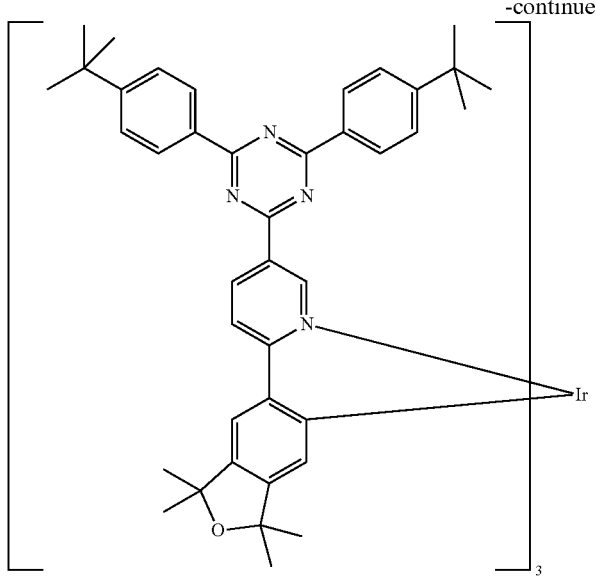
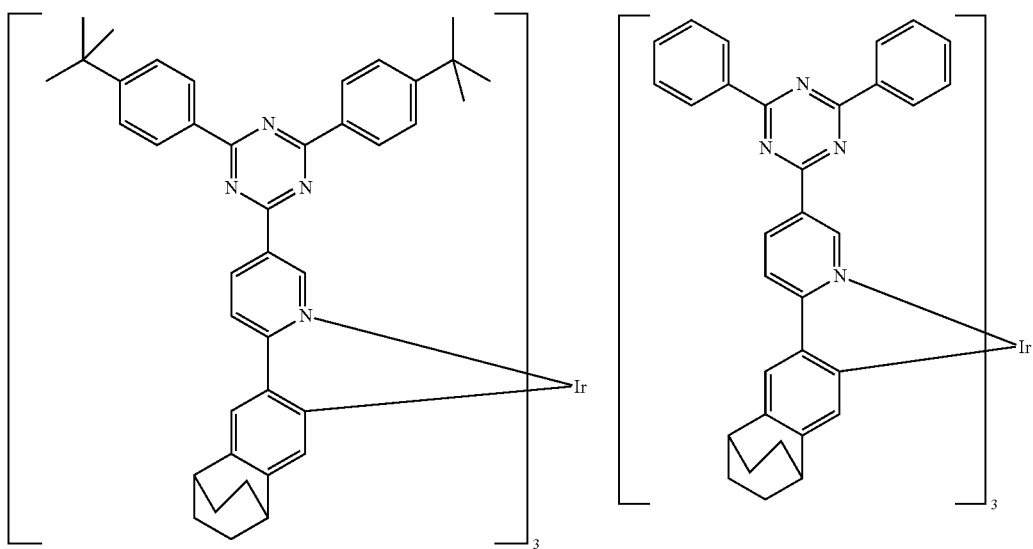
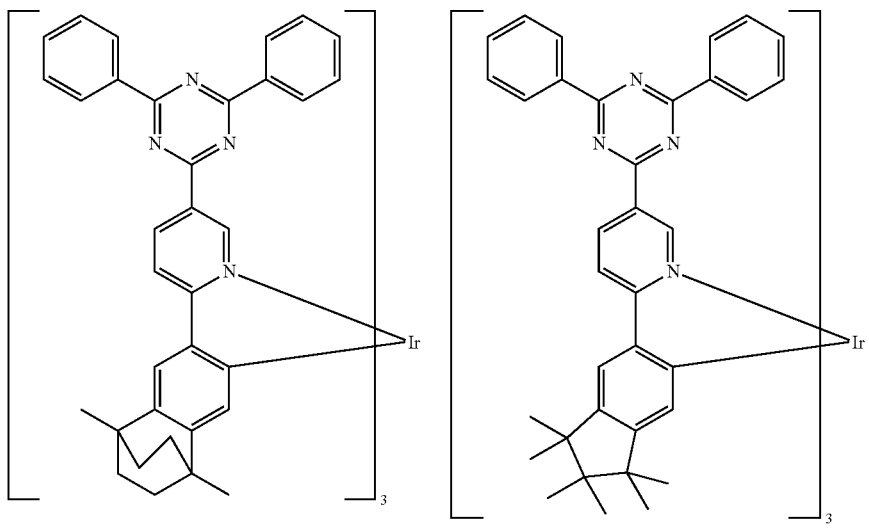

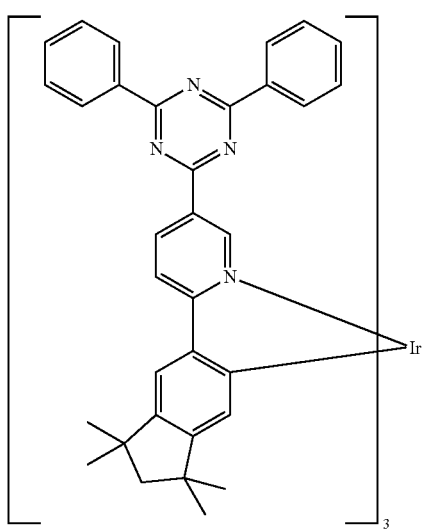
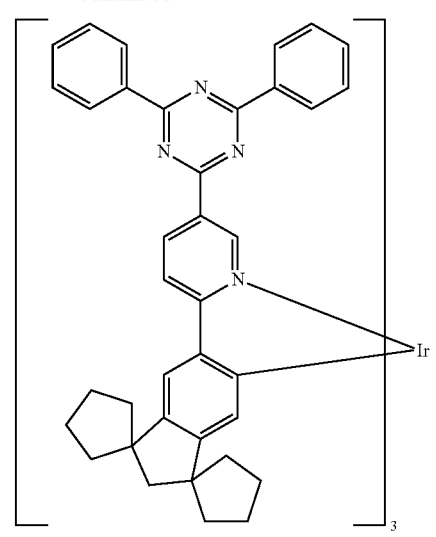
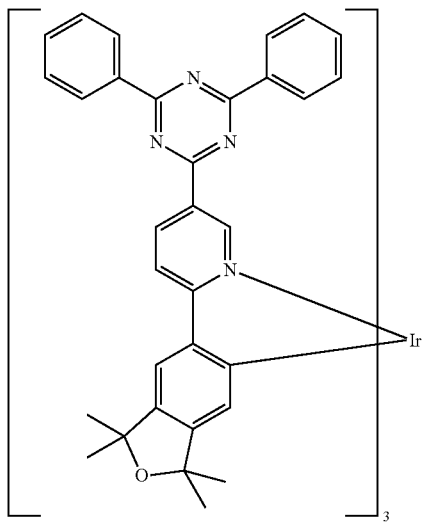
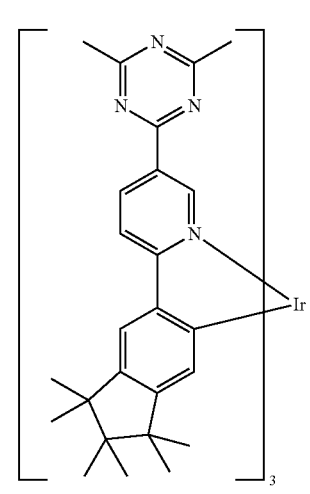
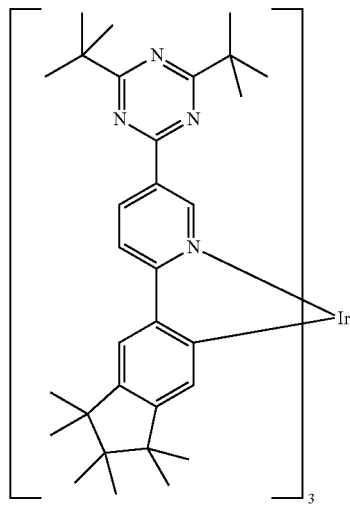
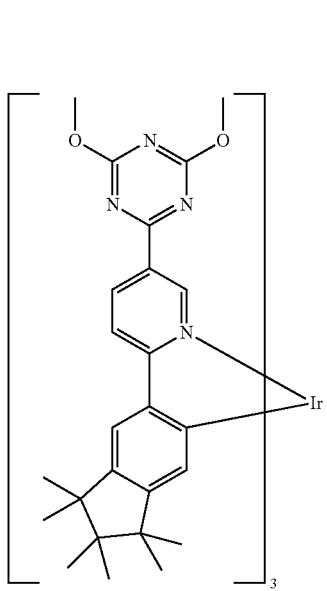
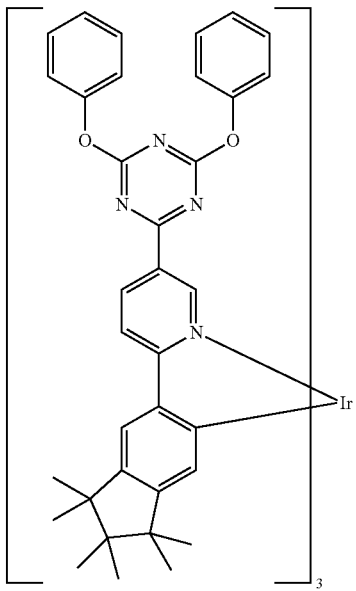

-continued
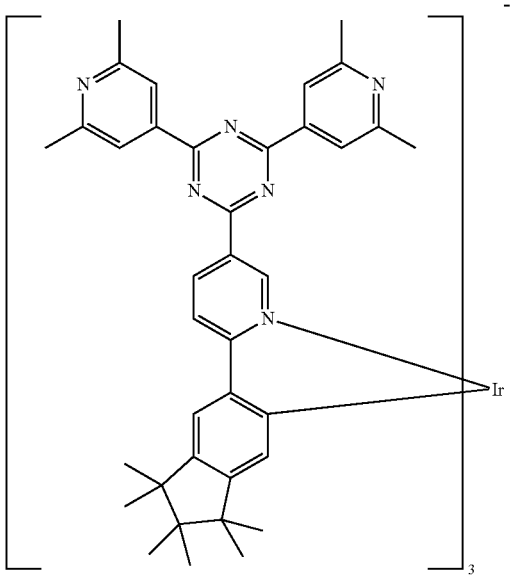
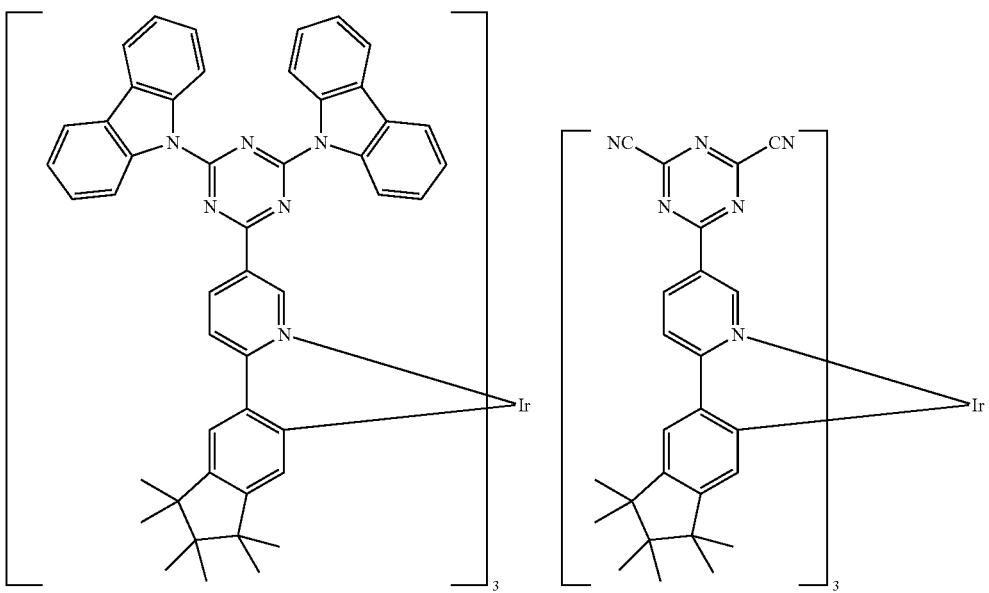
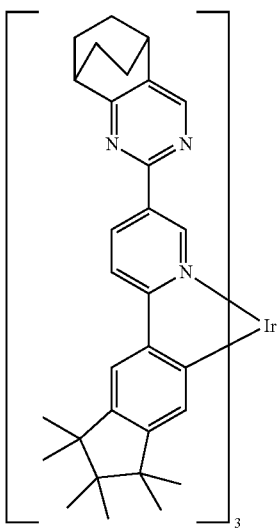 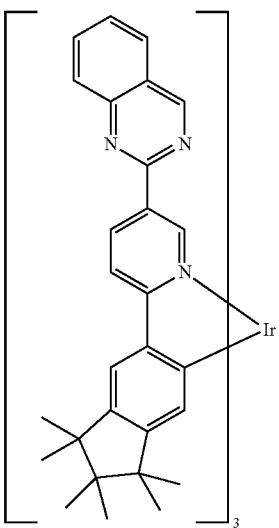 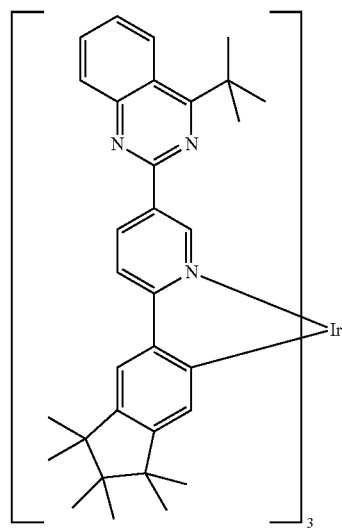

-continued
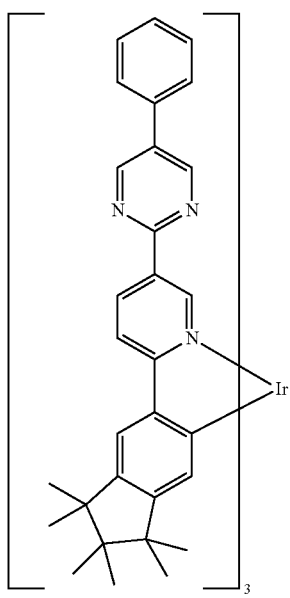 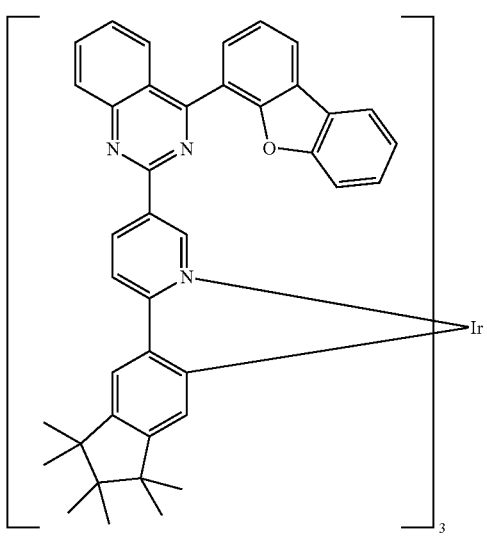
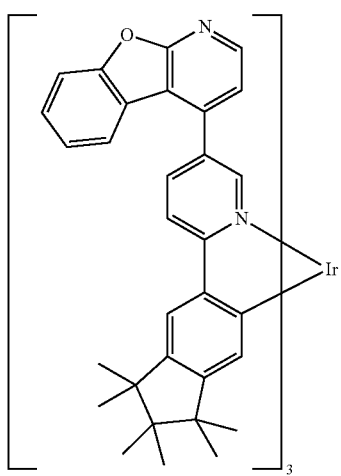 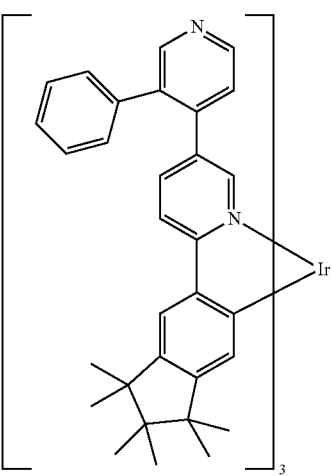

-continued
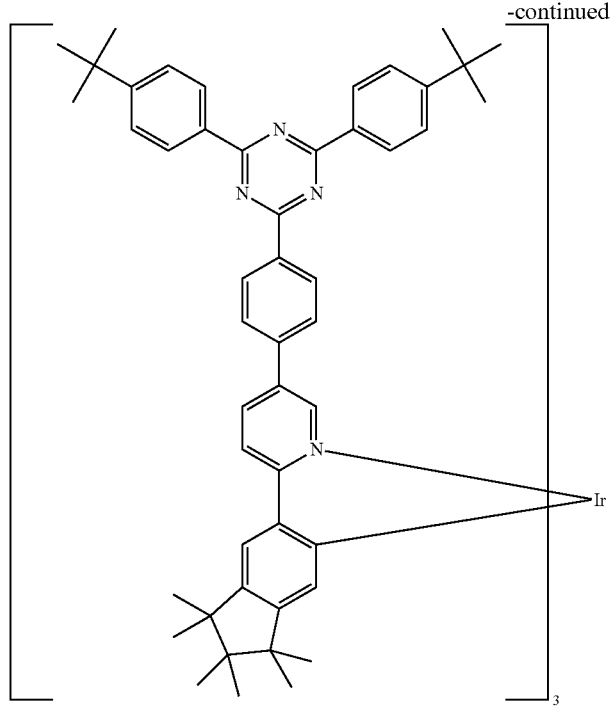
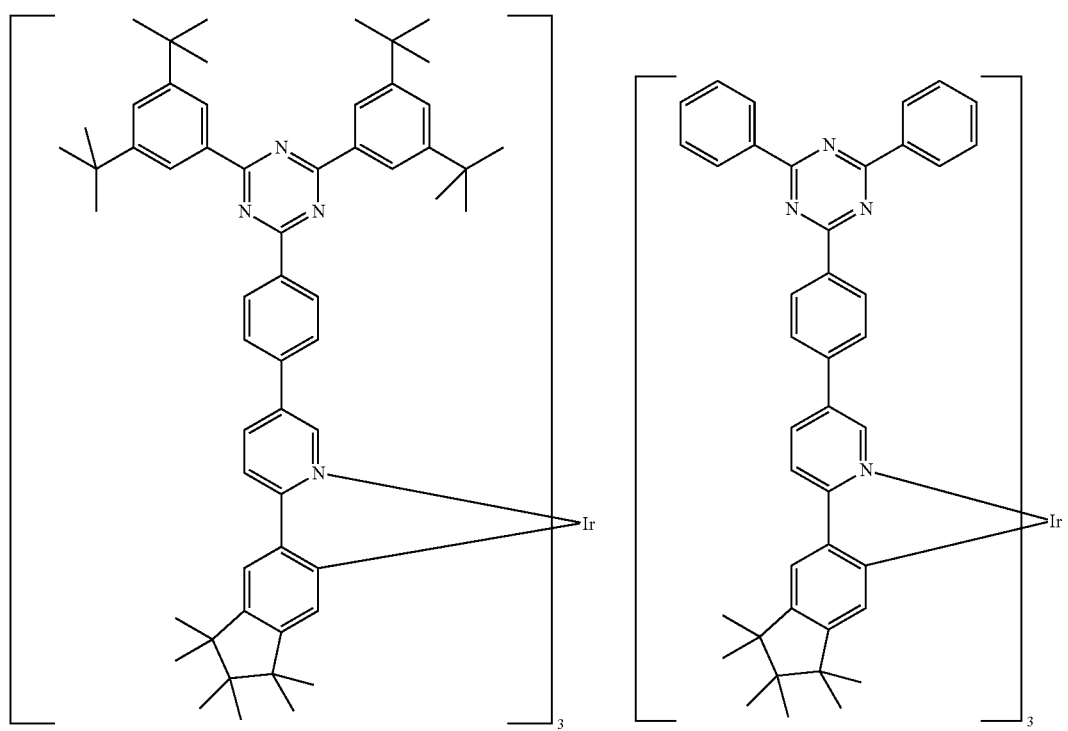

-continued
| 71 | 72 |
|---|---|
| 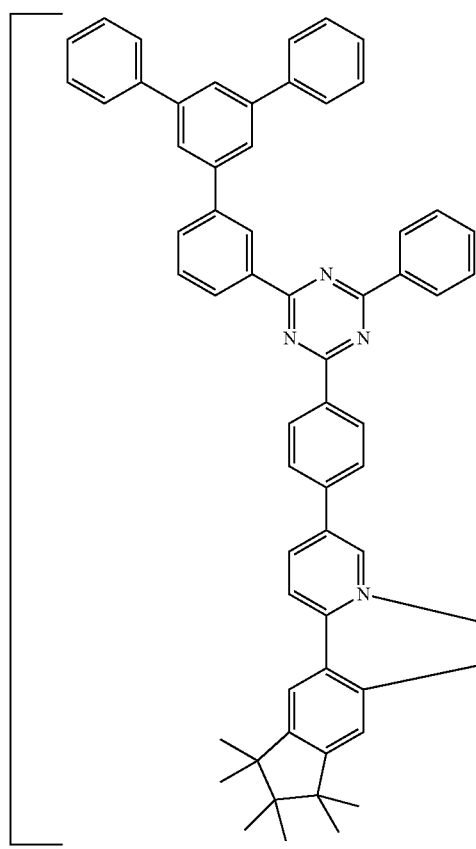 | 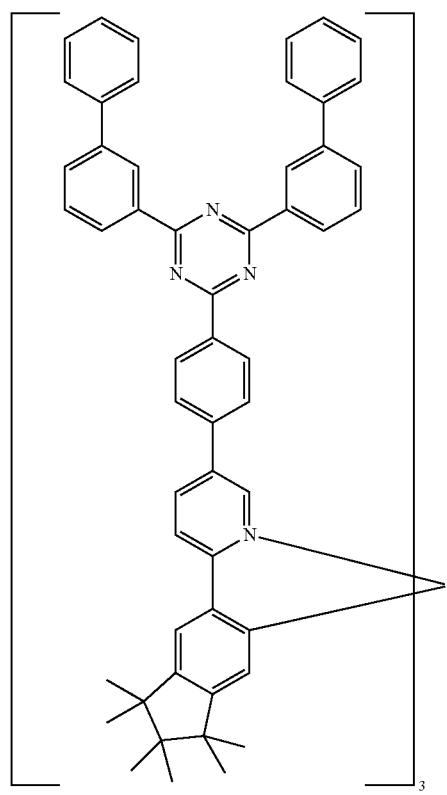 |
| 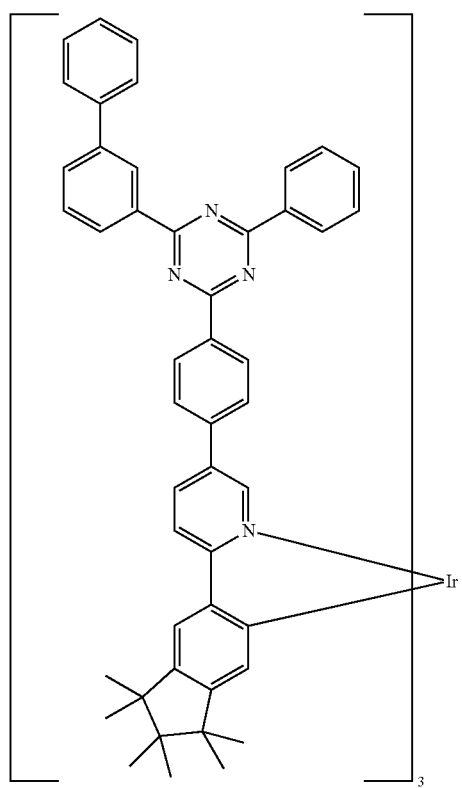 | 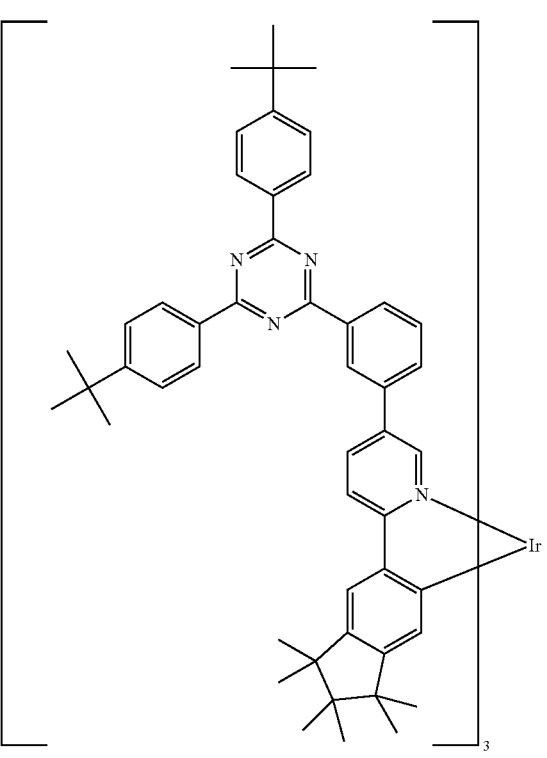 |

73 74
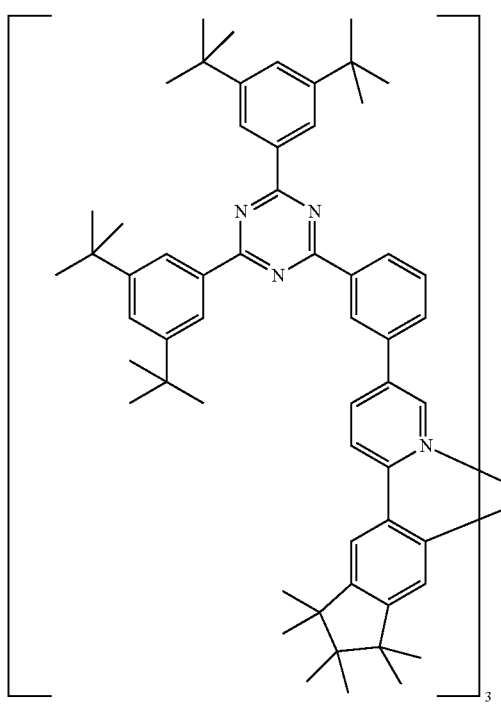
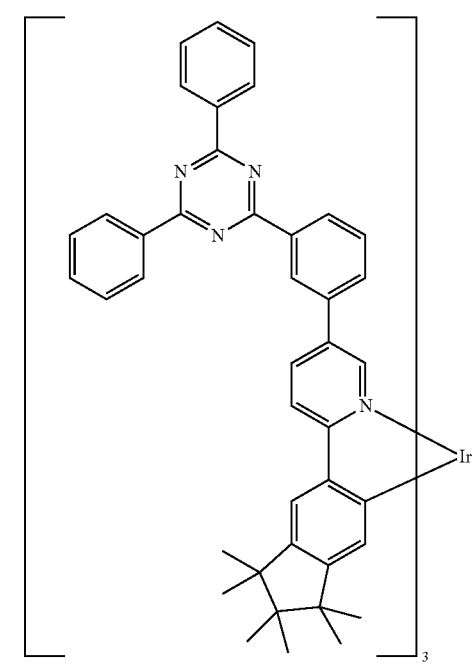
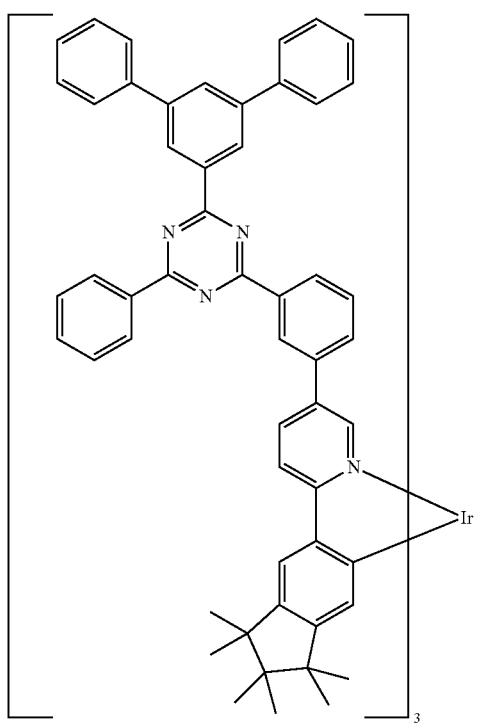
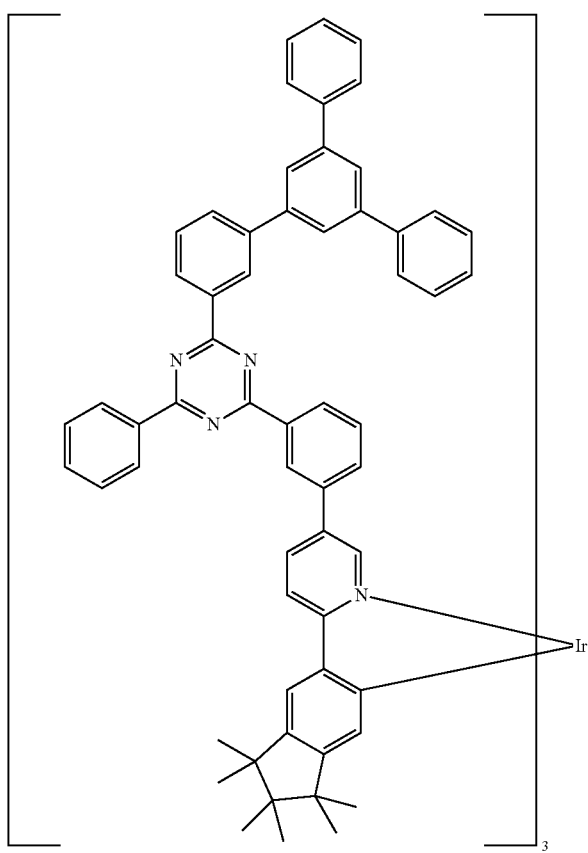

75
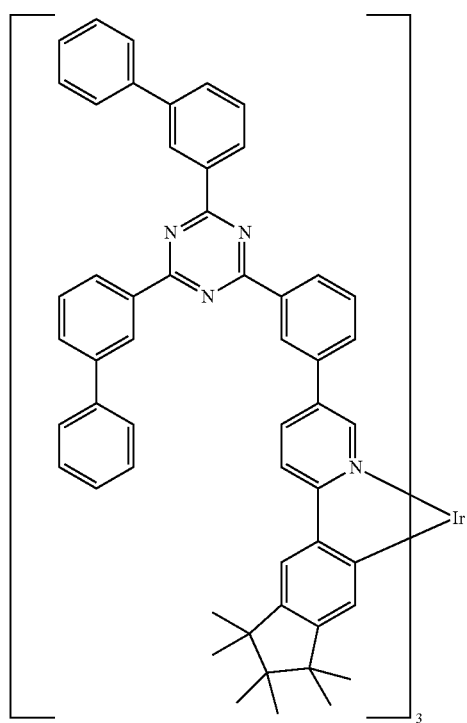 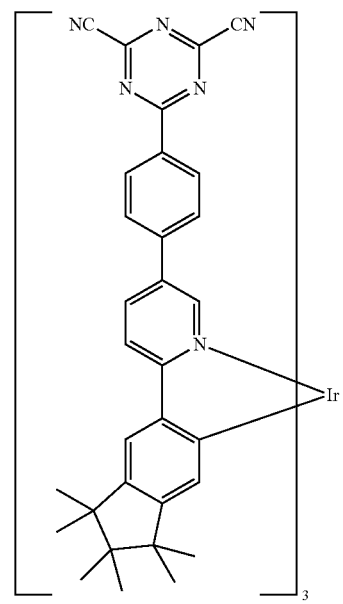 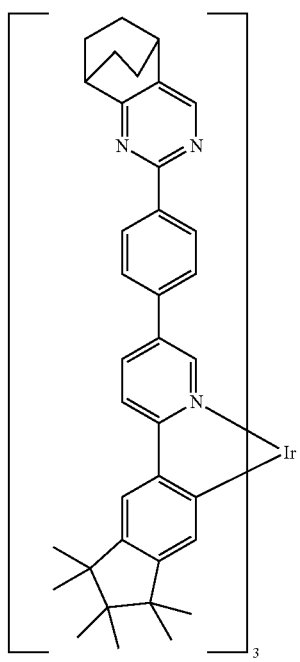
-continued
76
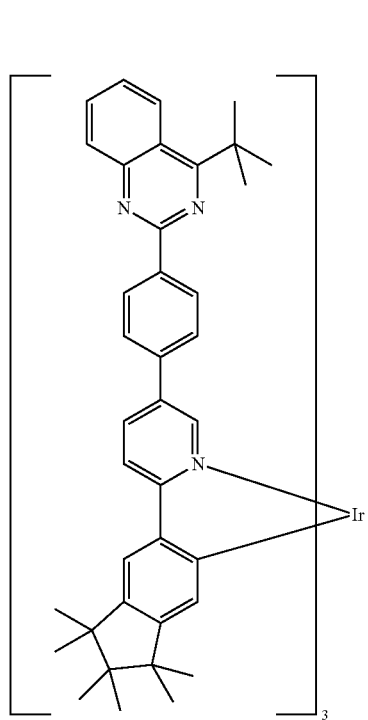 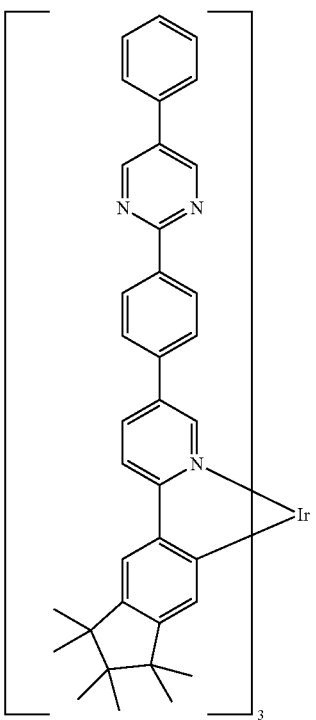 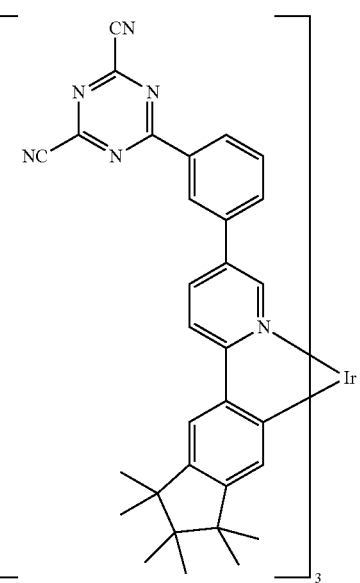

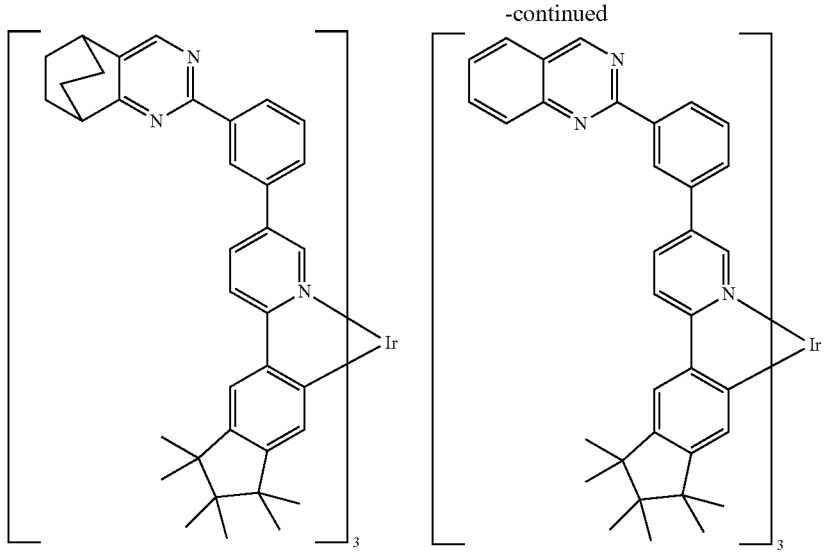
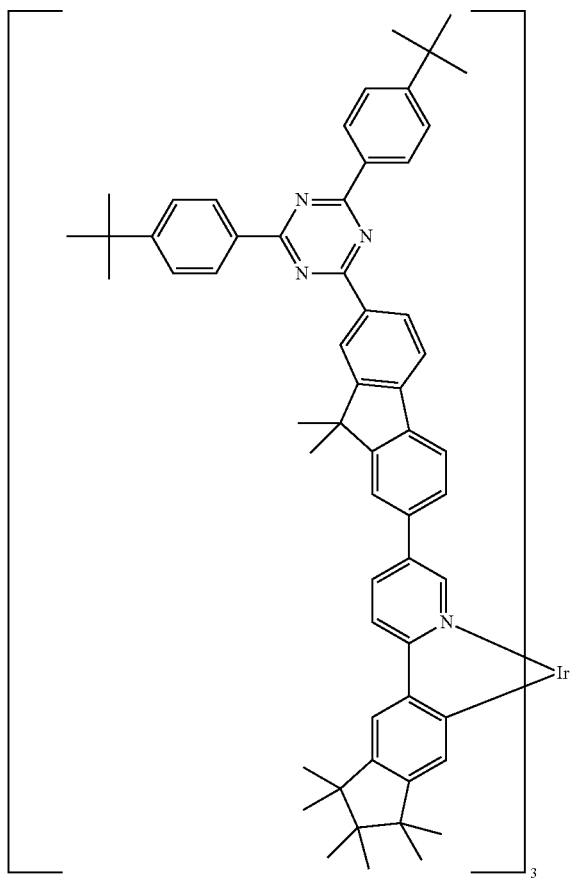

-continued
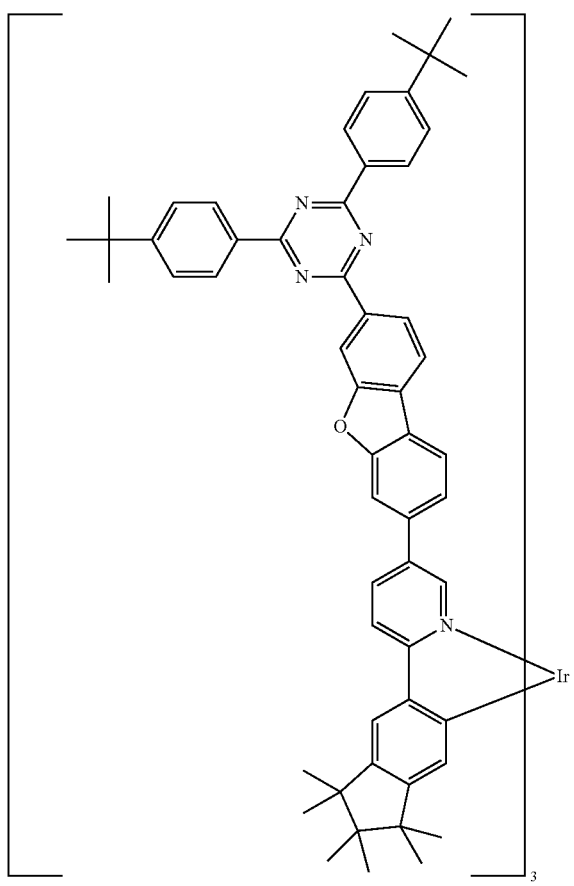
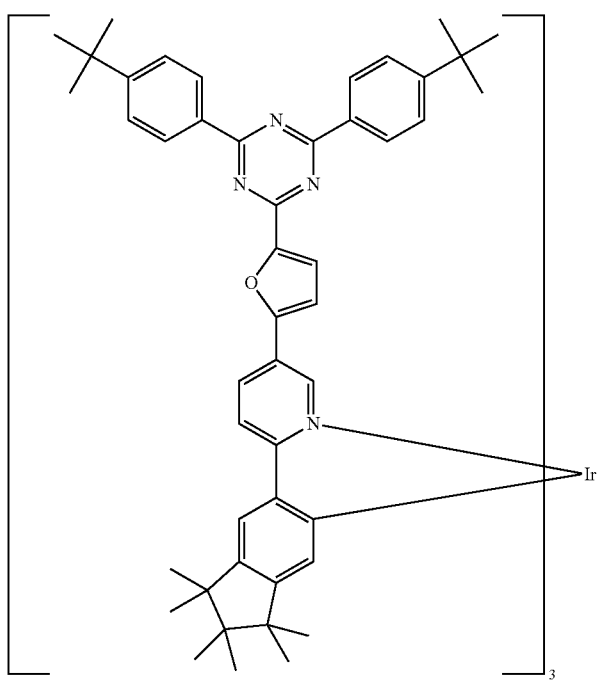

-continued
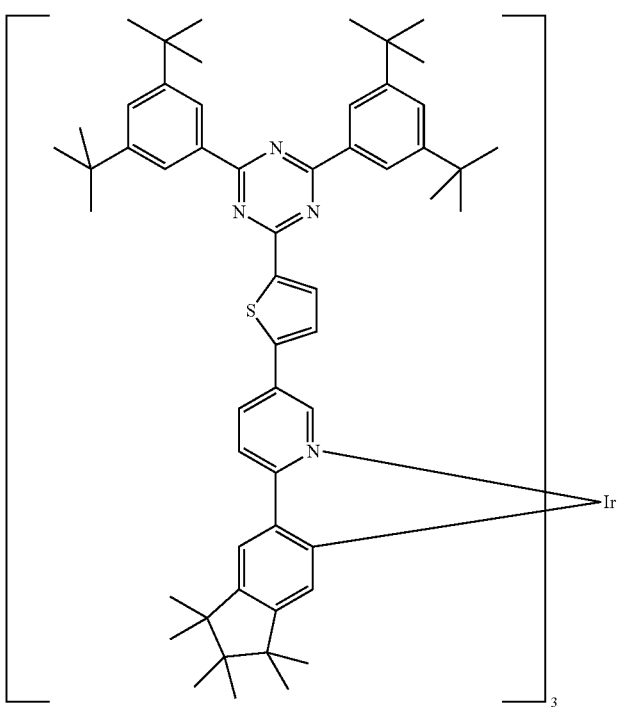
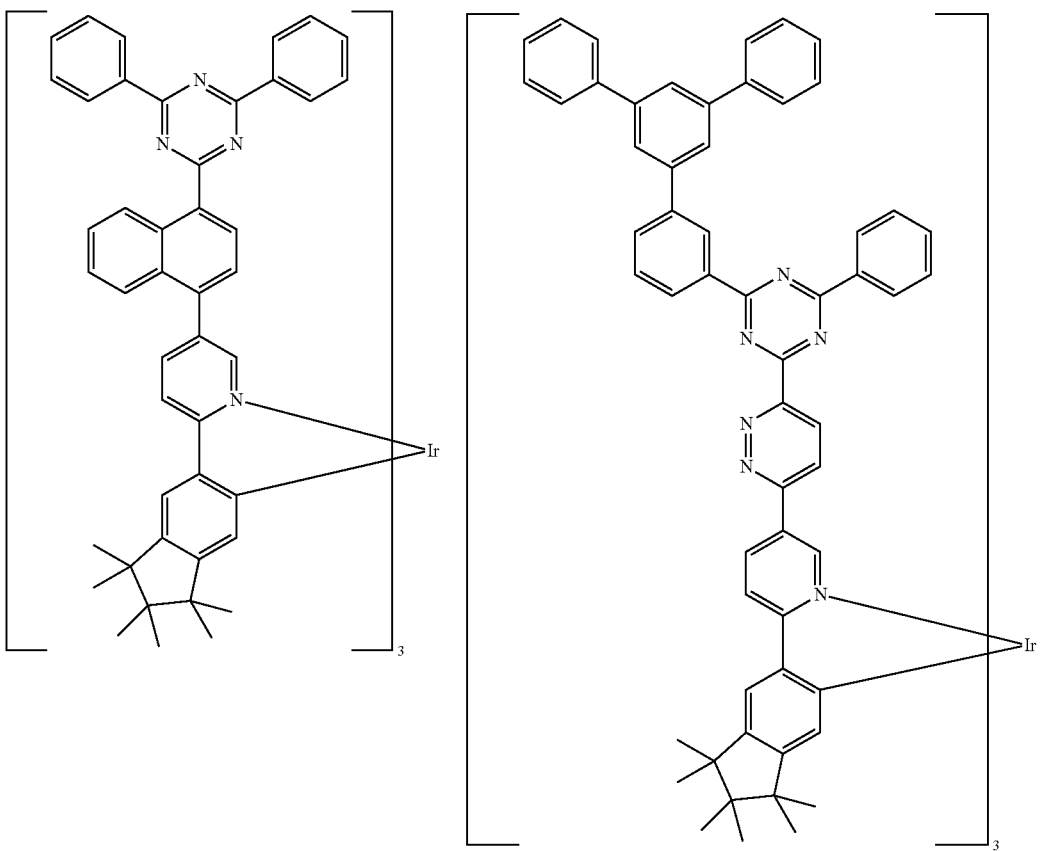

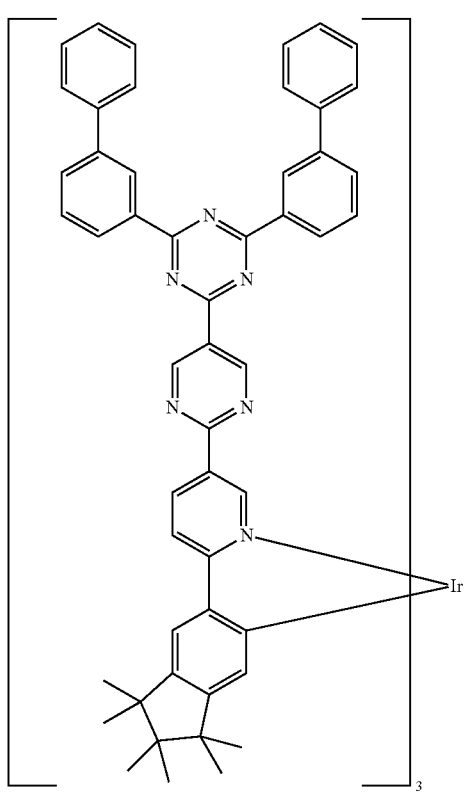
83
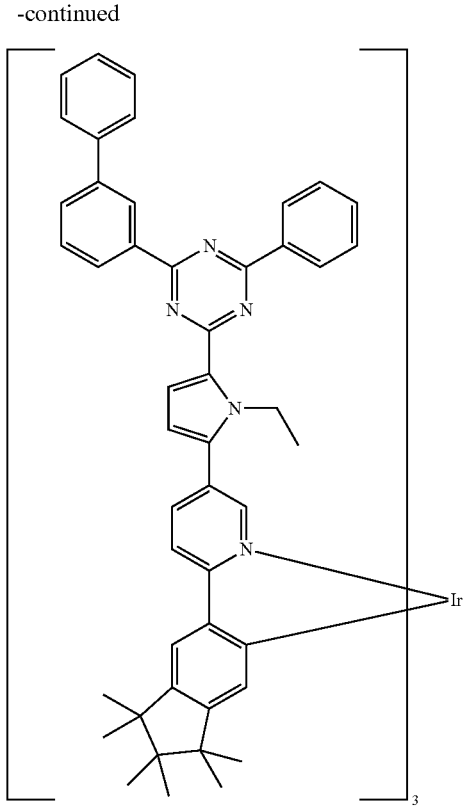
84
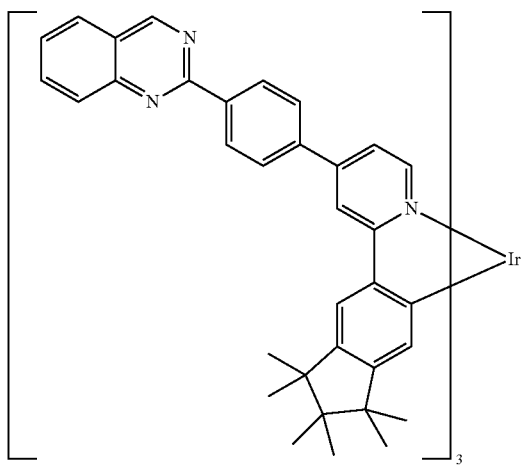

-continued
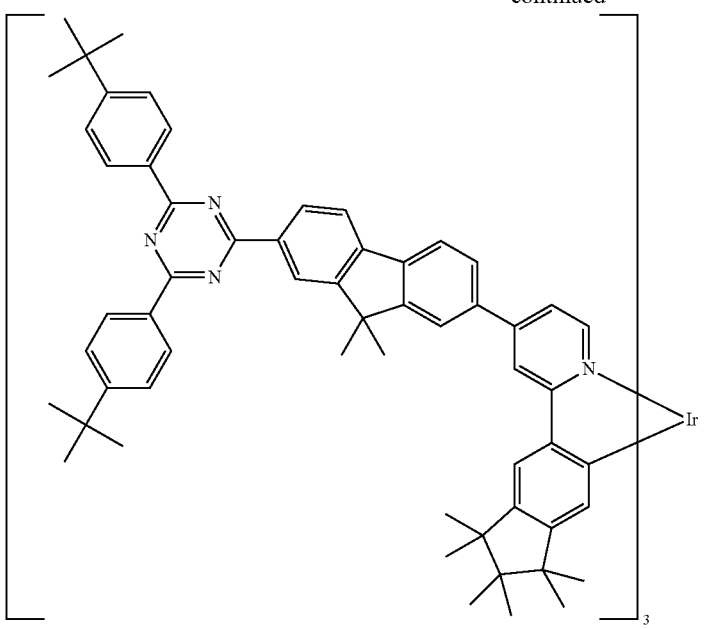
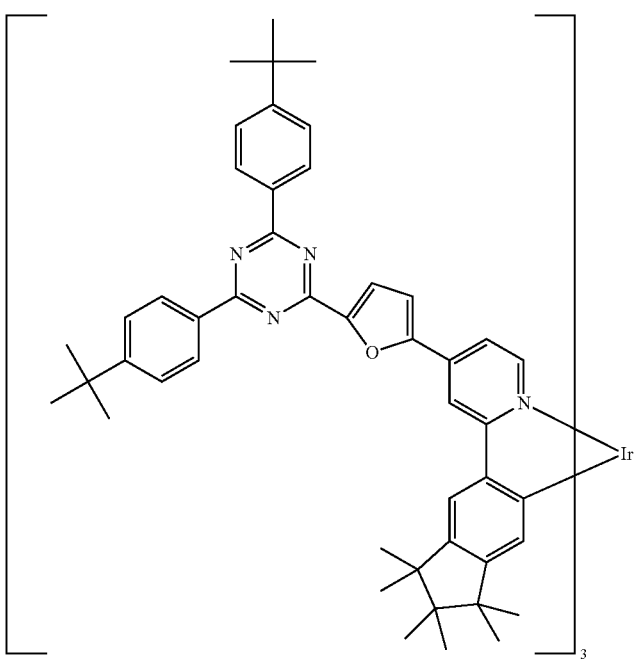

-continued
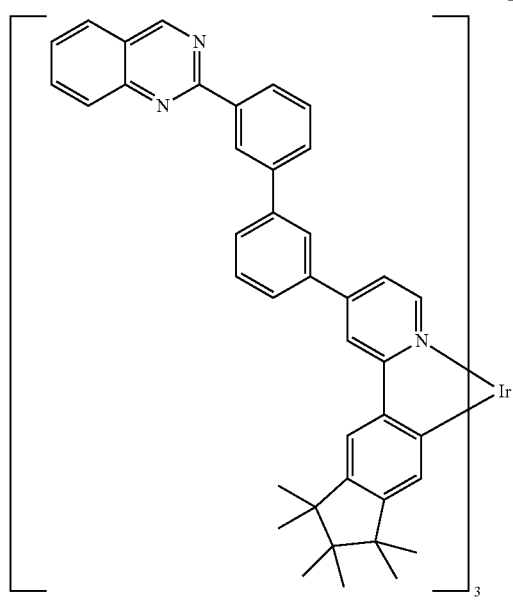
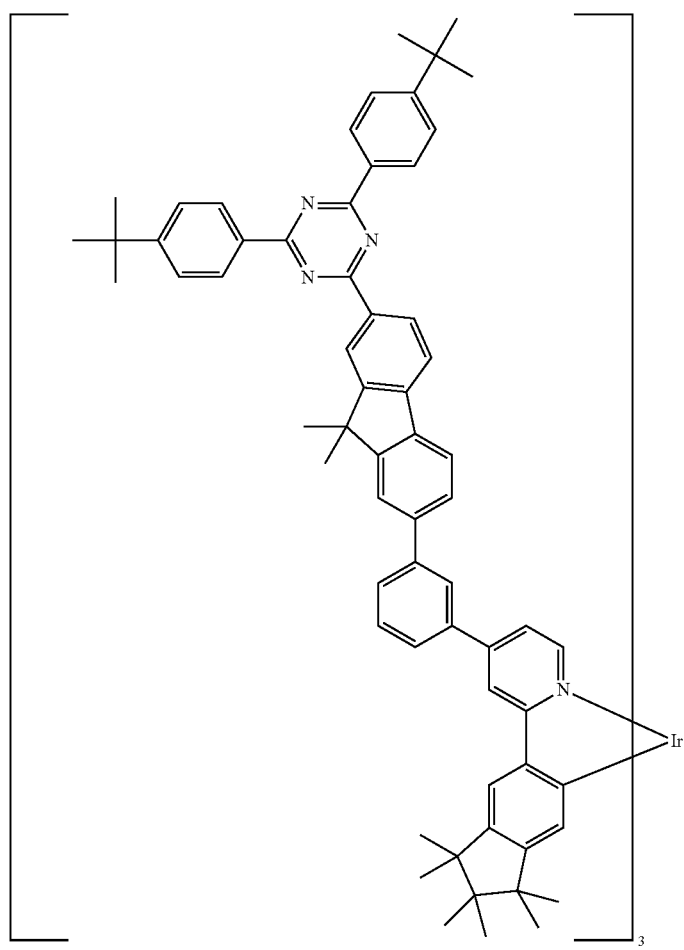

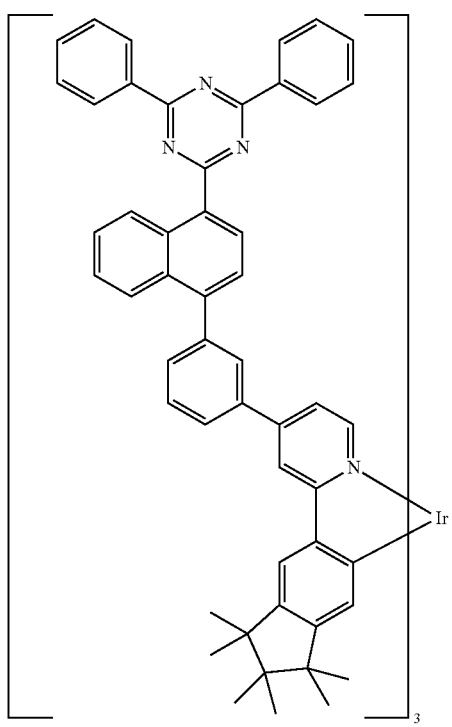
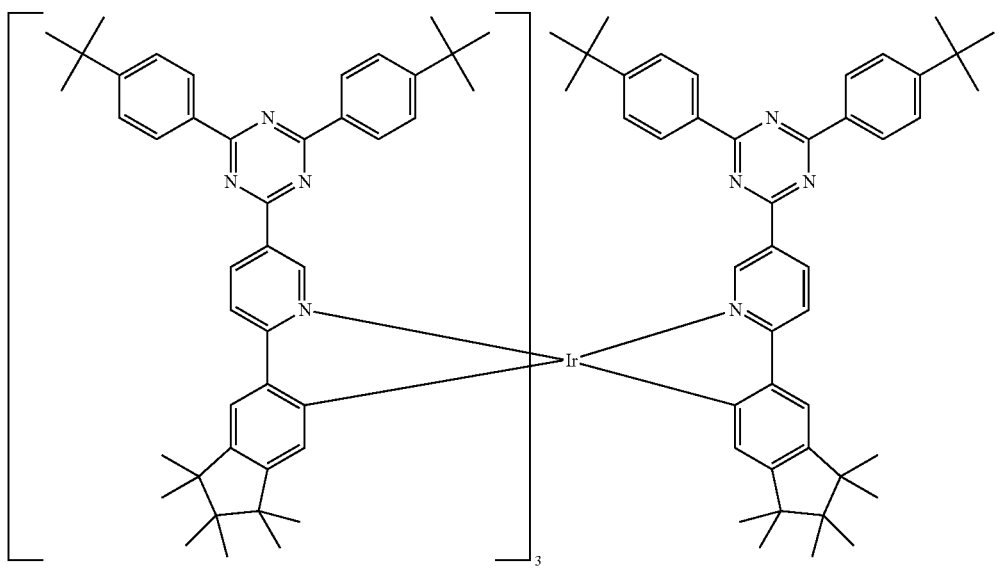

-continued
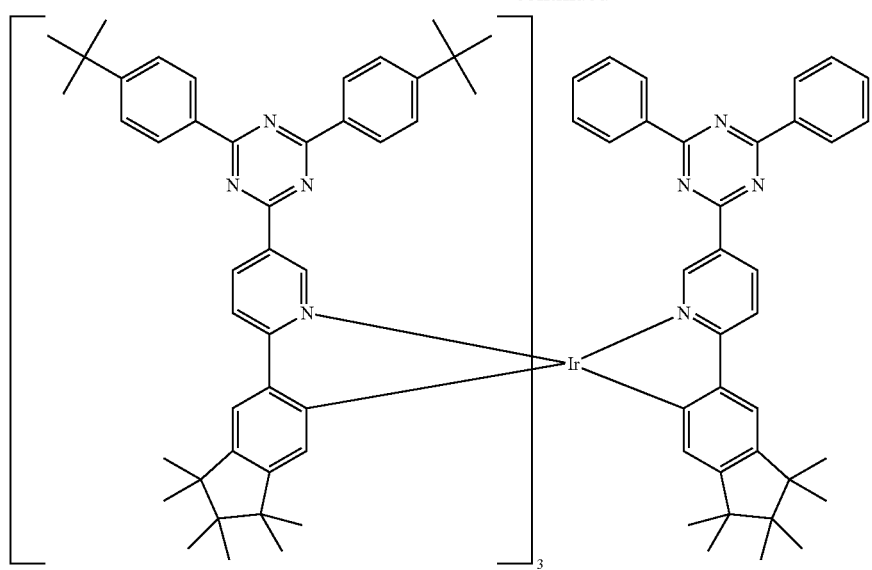
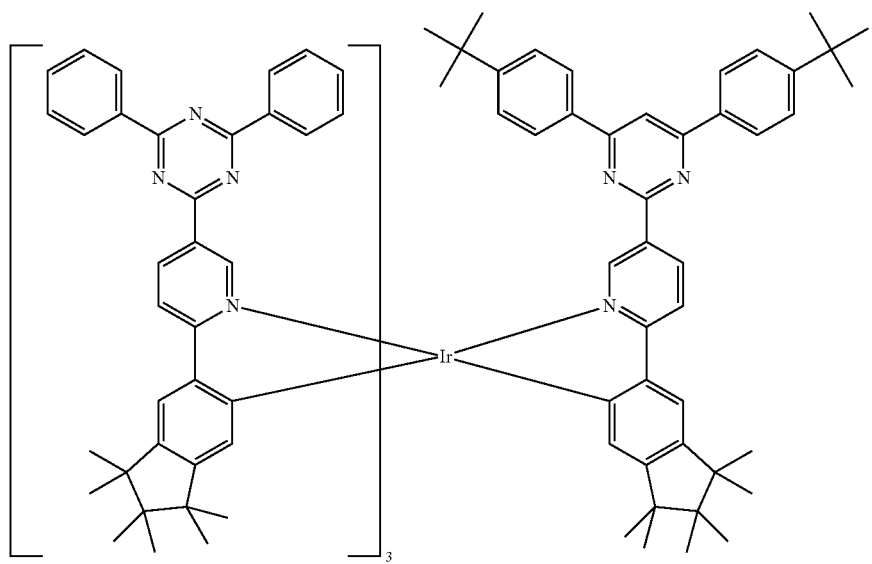

-continued
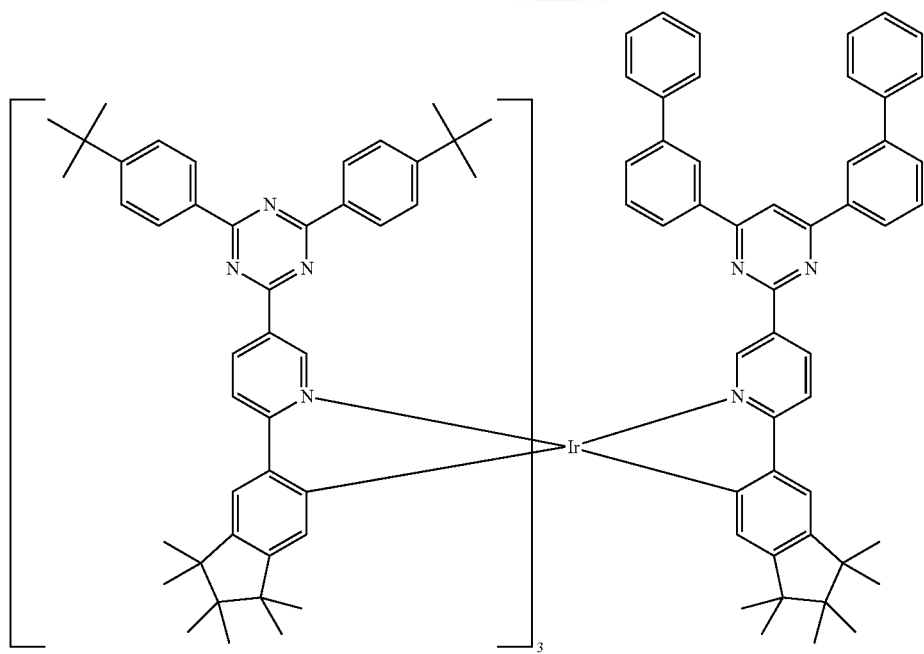
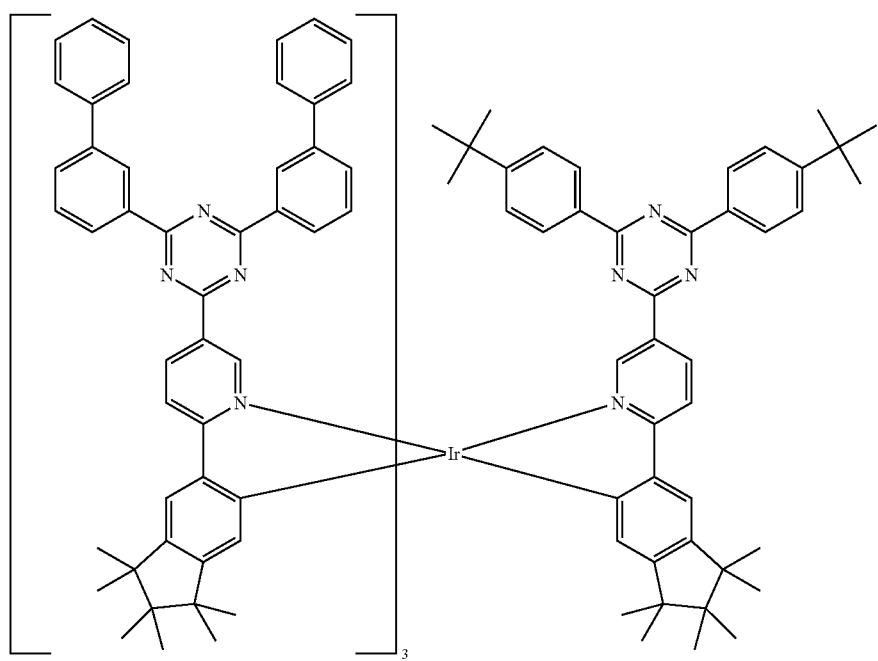

95
96
-continued
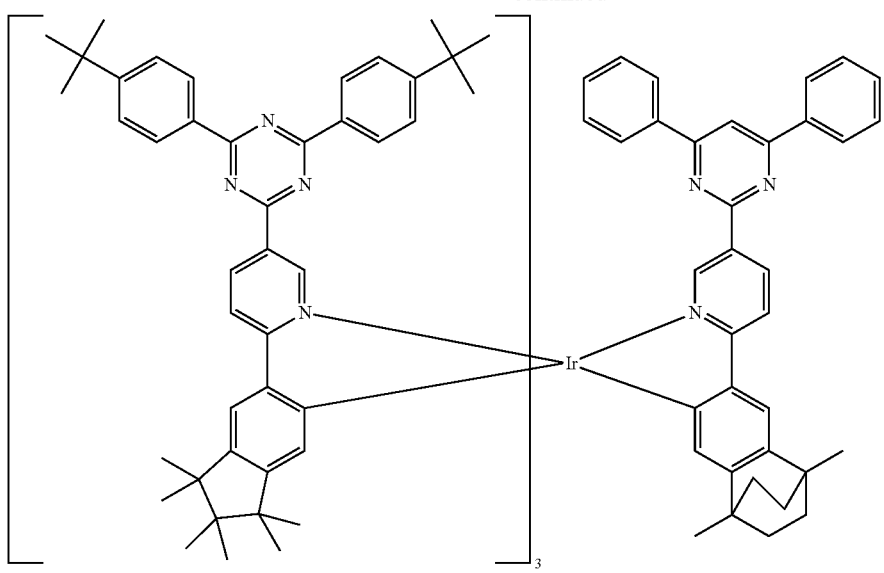
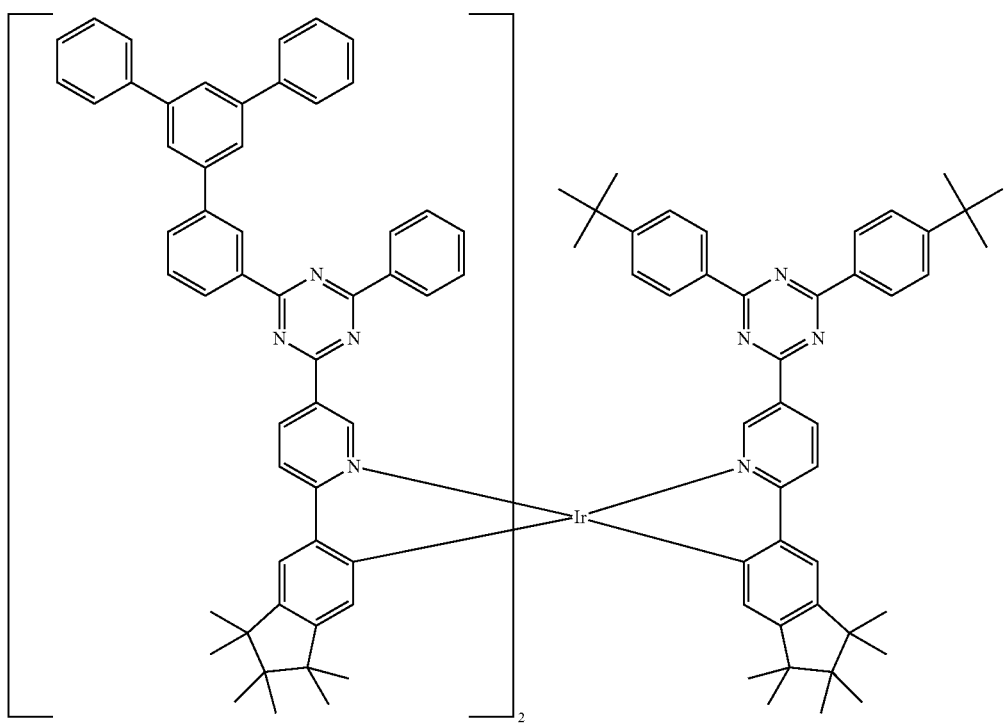

-continued
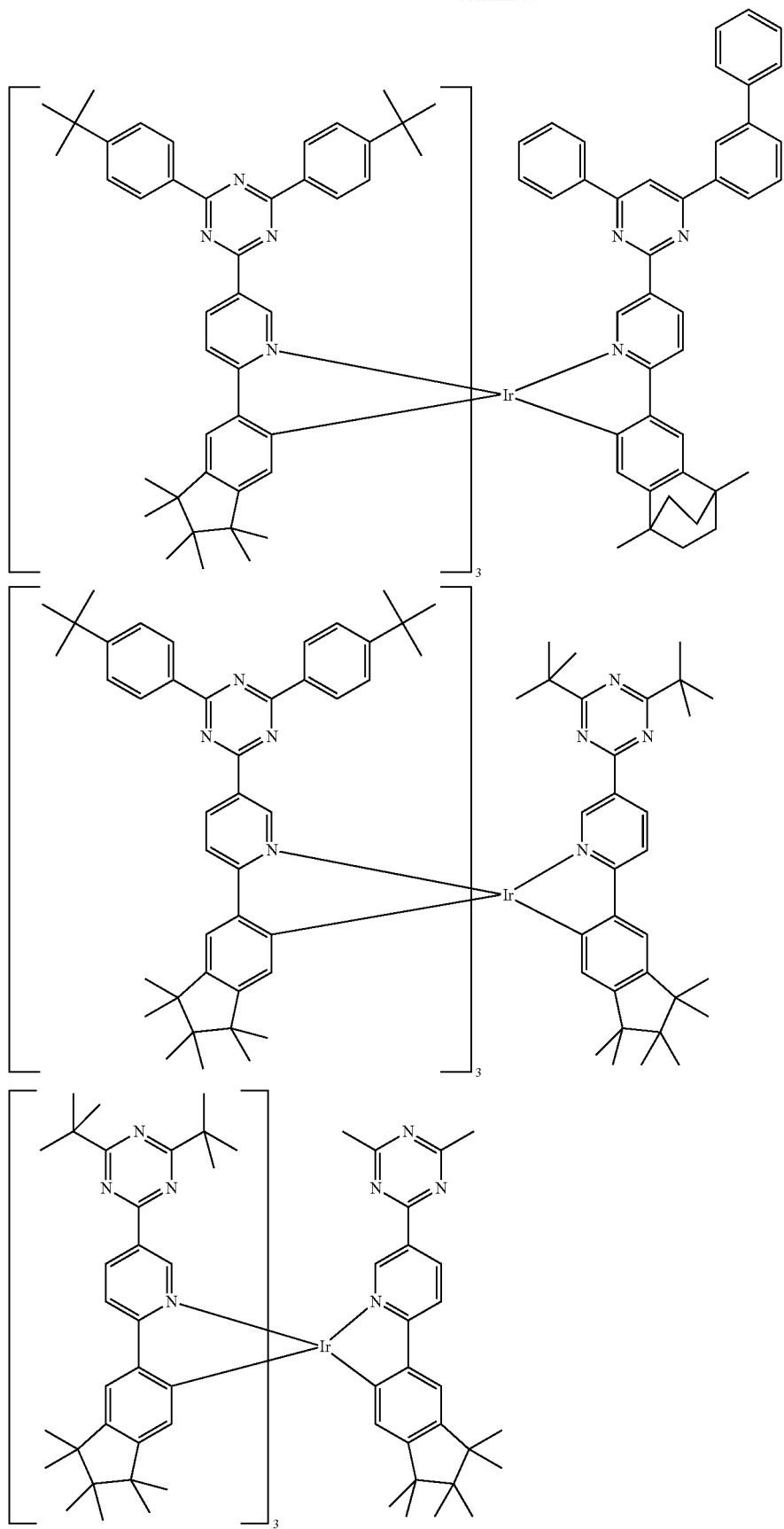

-continued
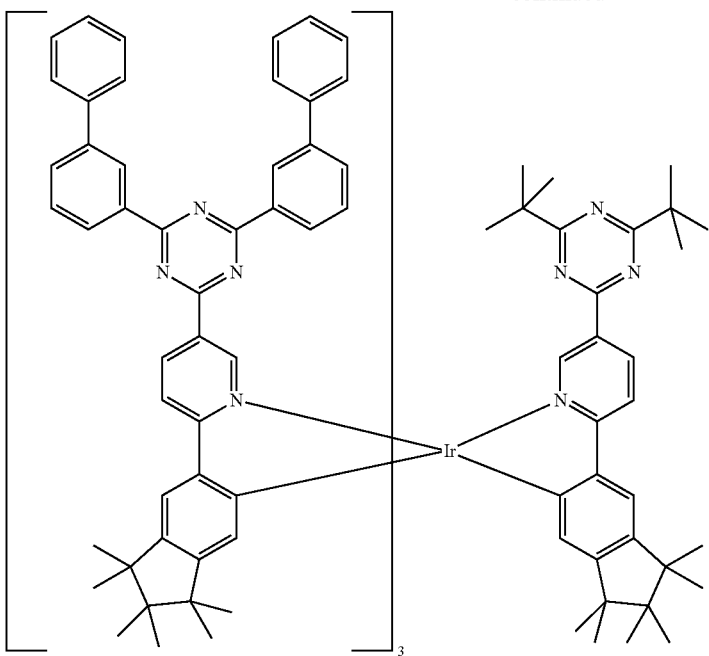
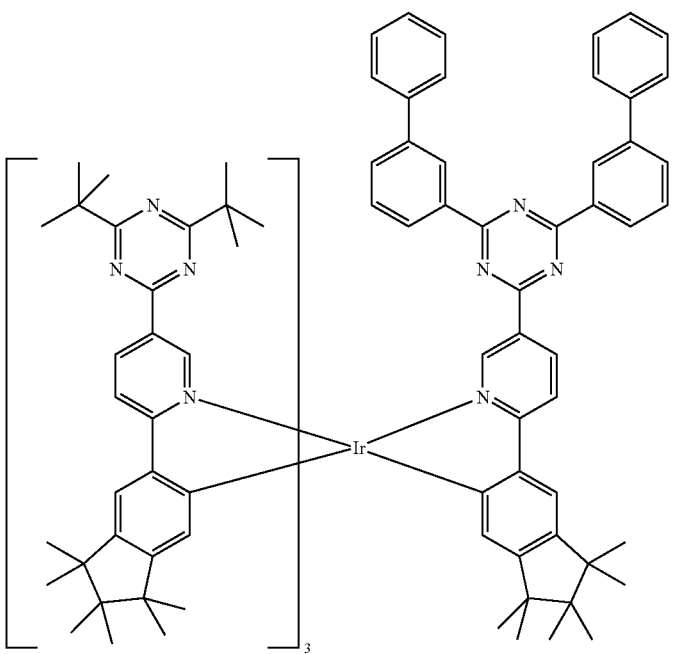

-continued
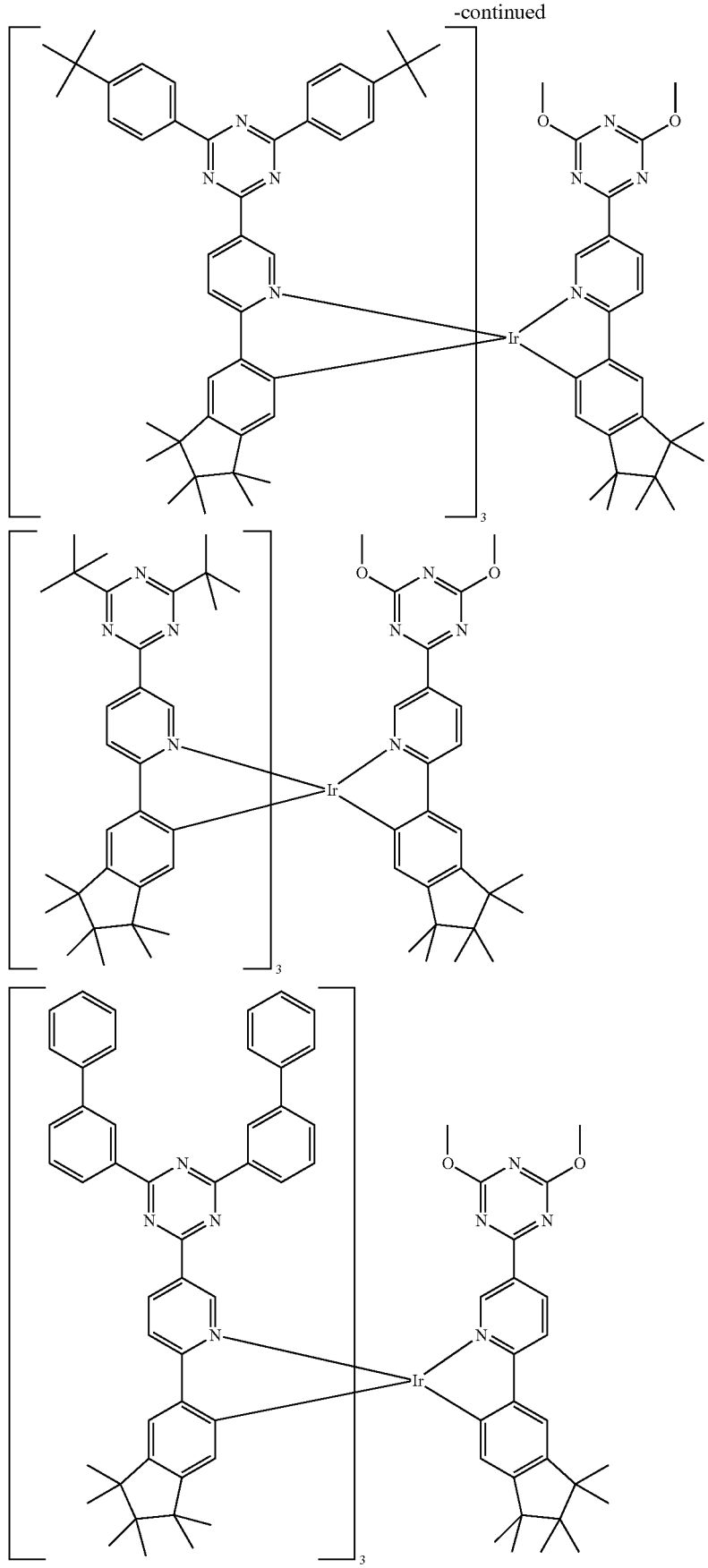

-continued
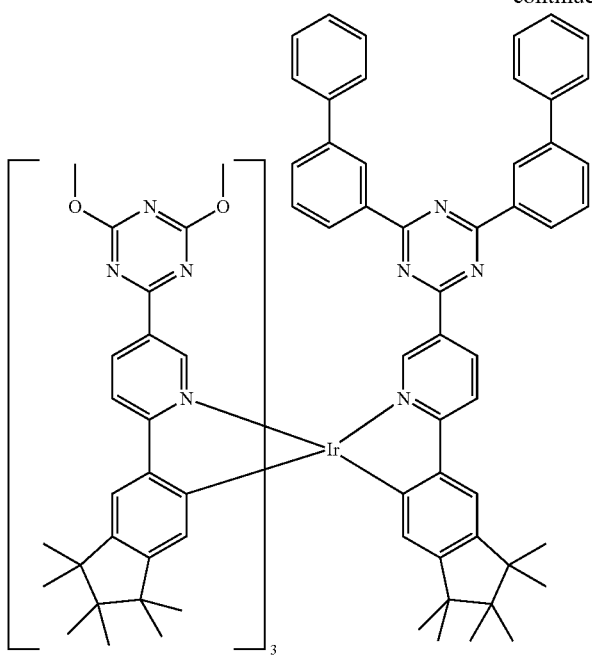
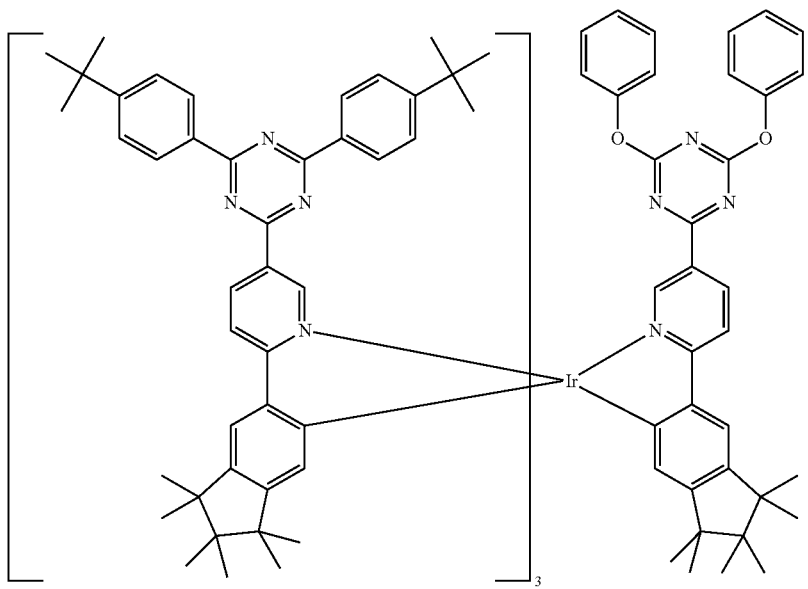

-continued
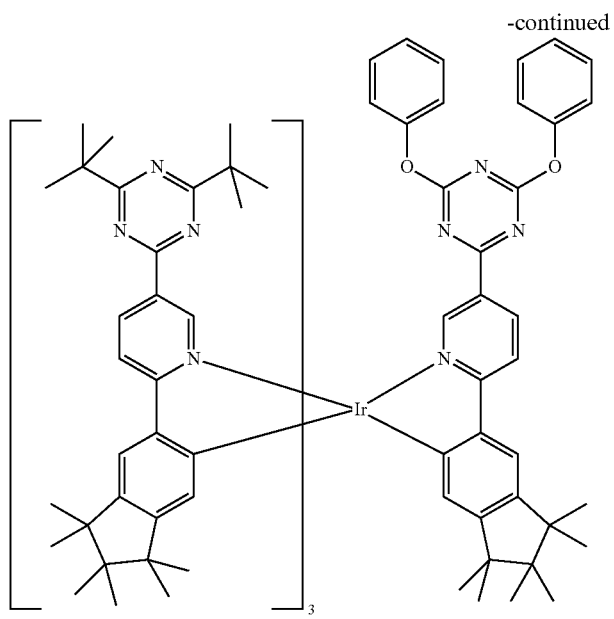
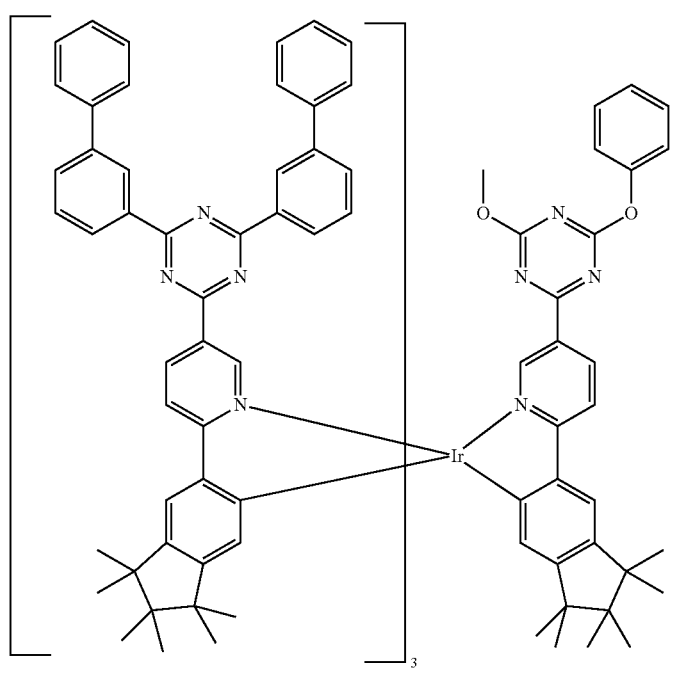

-continued
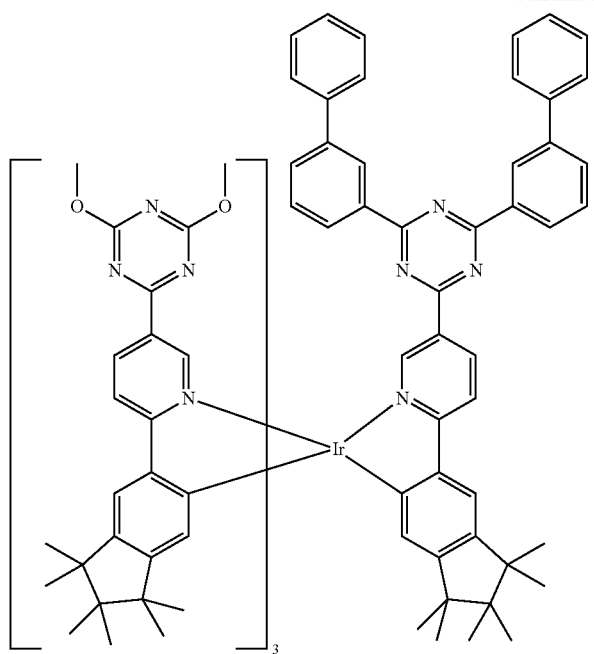
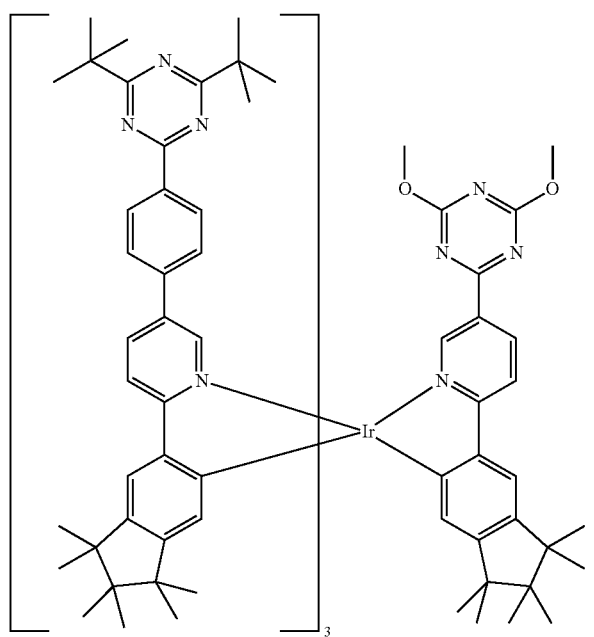

109
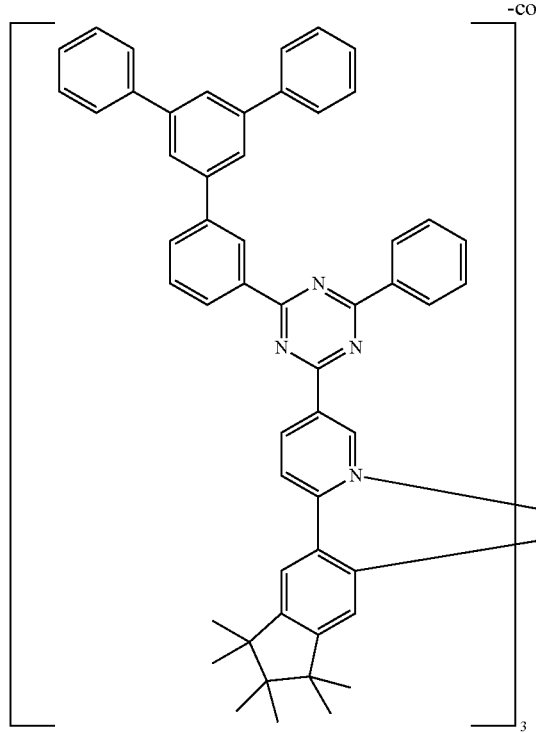
110
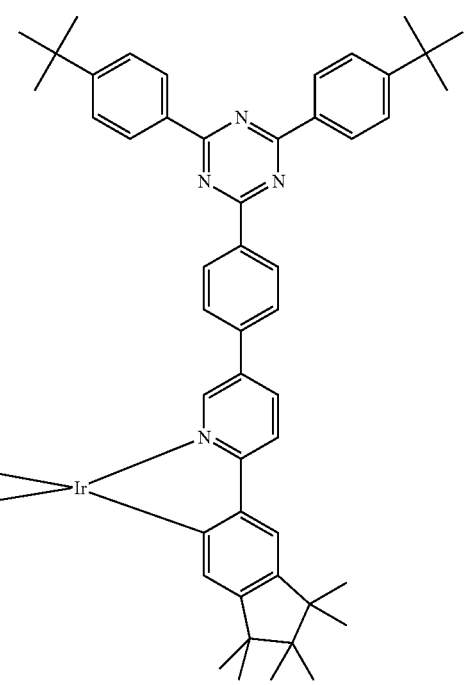
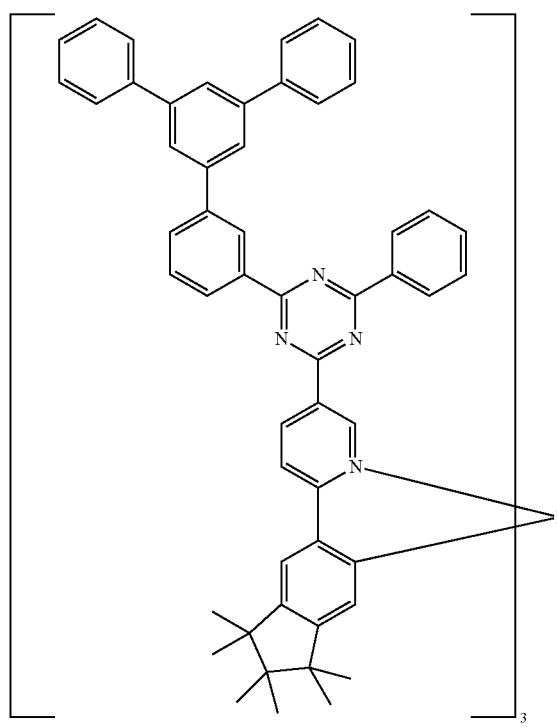

111 112
-continued
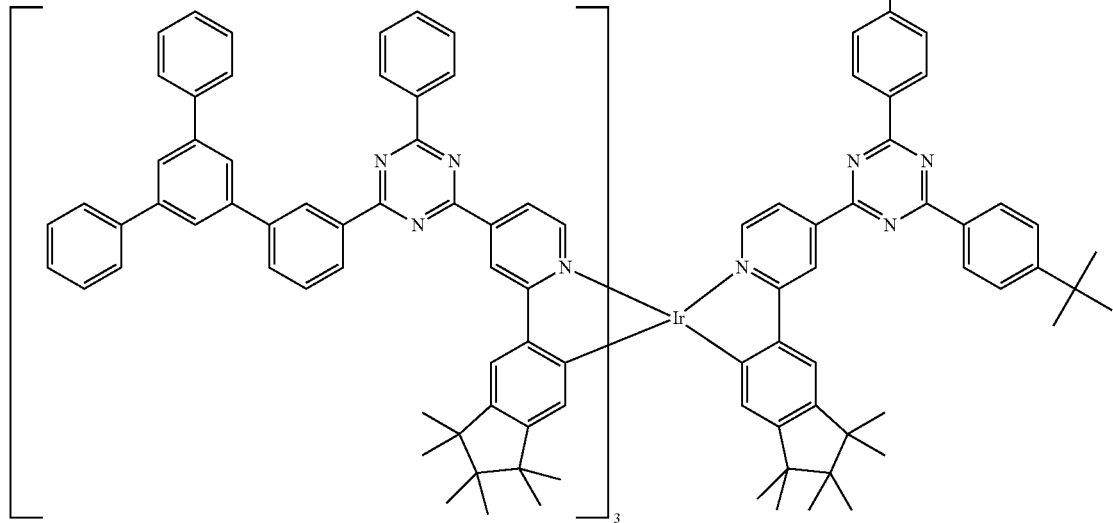
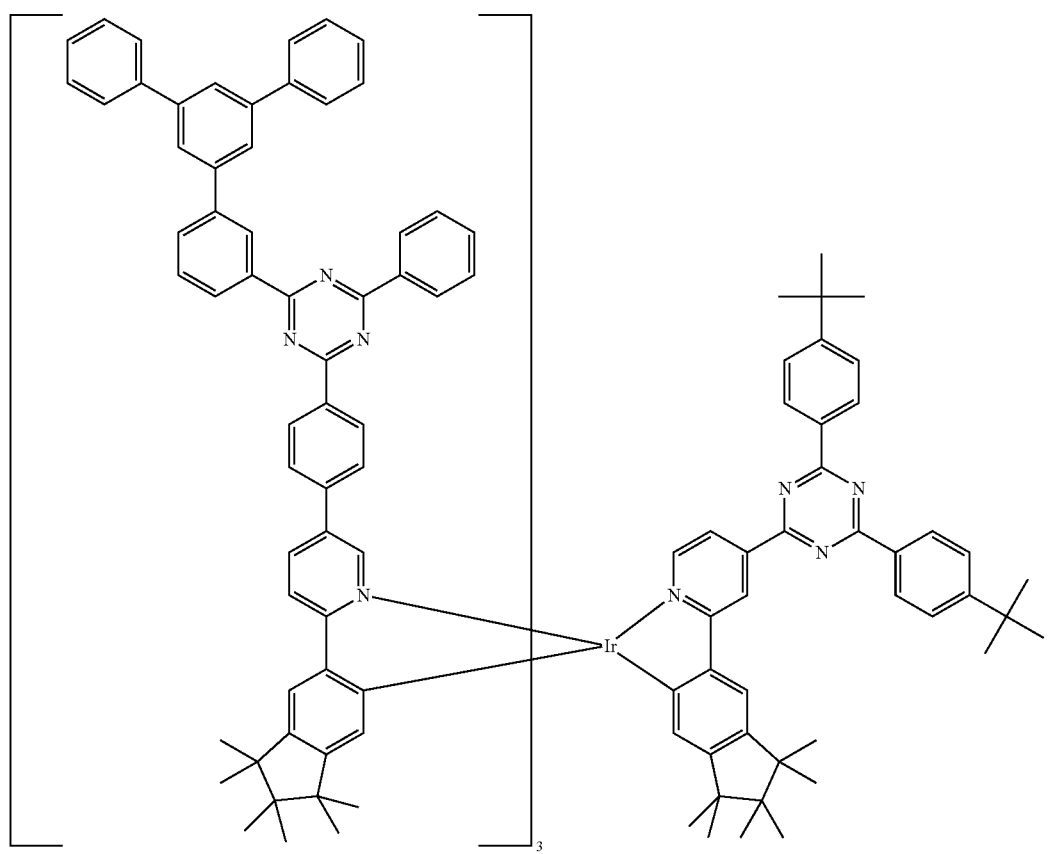

113 114
-continued
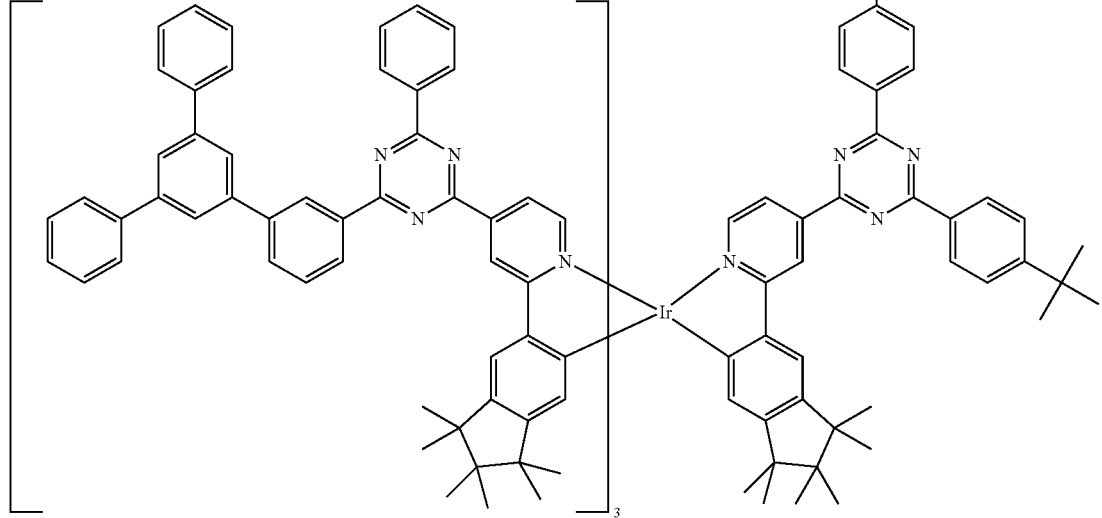
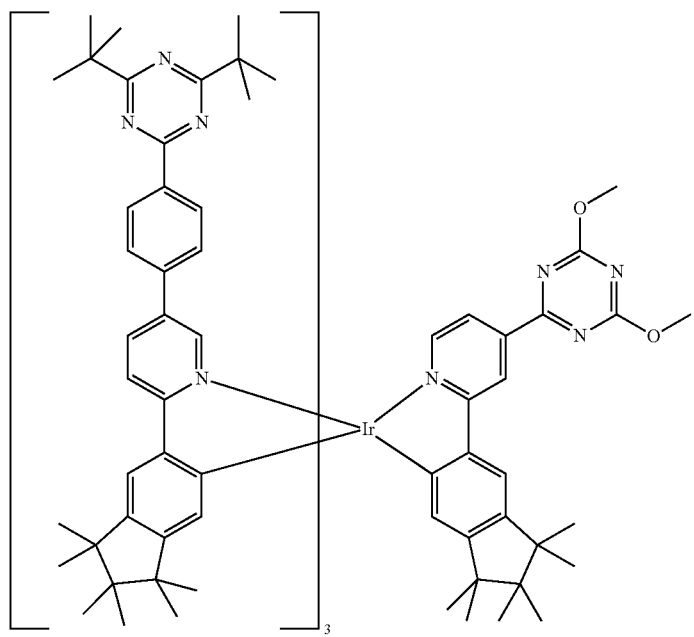

115 116
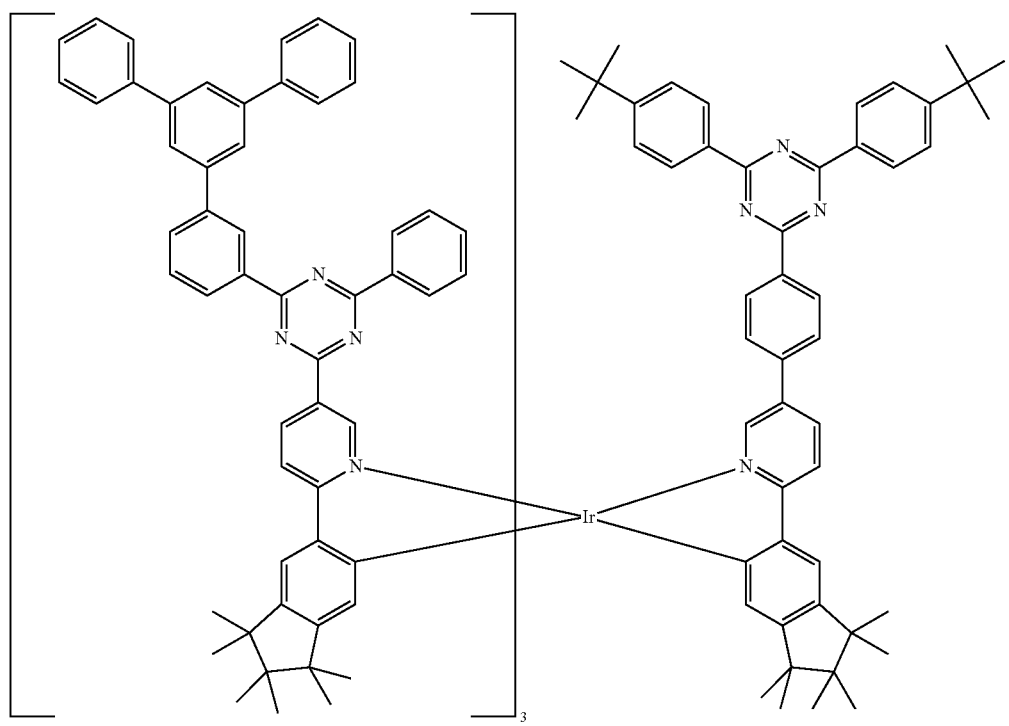
-continued
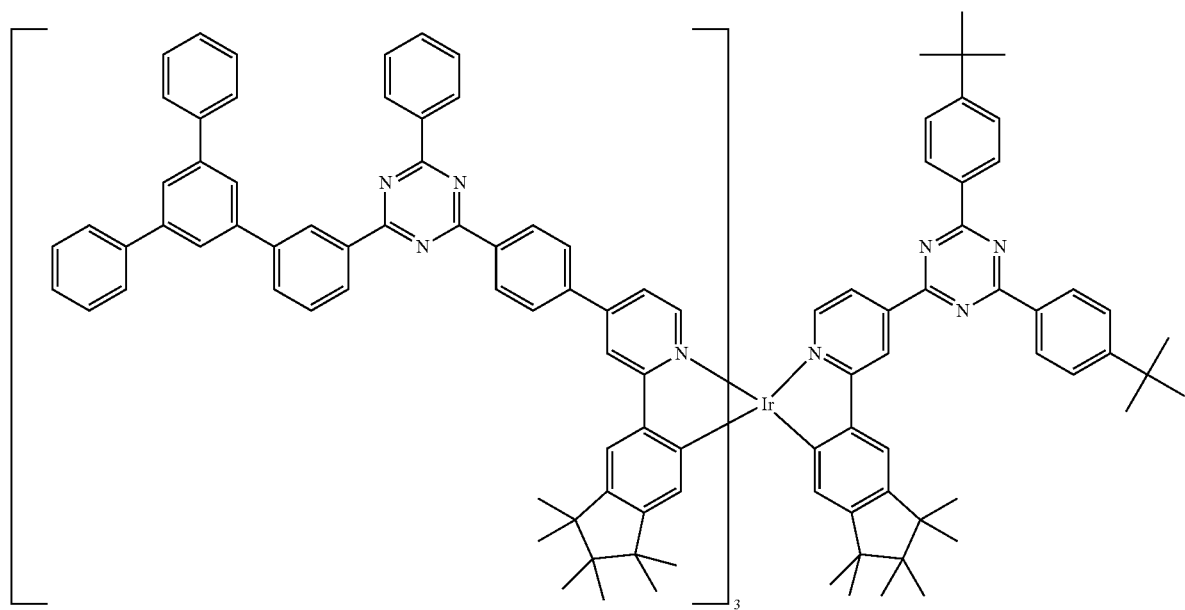

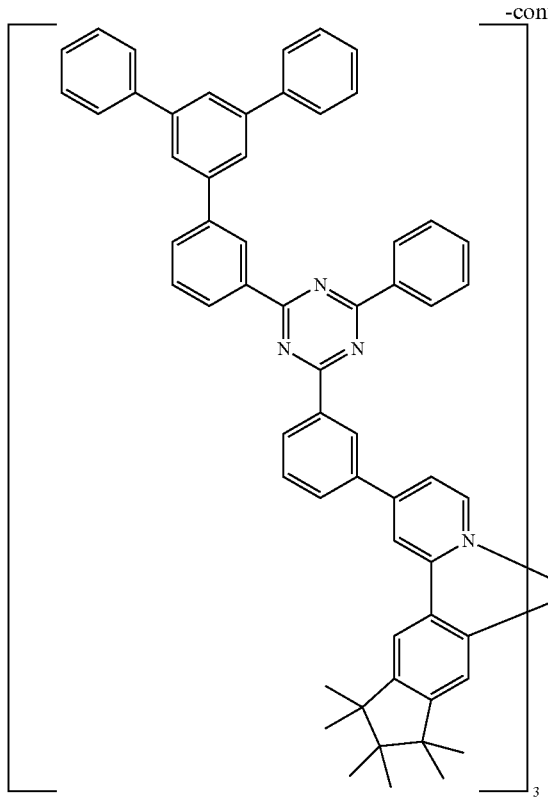
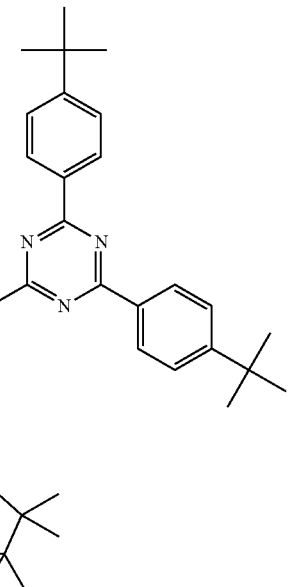

The metal complexes according to the invention can in principle be prepared by various processes. However, the processes described below have proven particularly suitable.

The present invention therefore furthermore relates to a process for the preparation of the compounds of the formula (1) according to the invention by reaction of the corresponding free ligands with iridium alkoxides of the formula (39), with iridium ketoketonates of the formula (40), with iridium halides of the formula (41) or with dimeric iridium complexes of the formula (42) or (43), $Ir(OR^1)_n$             formula (39)

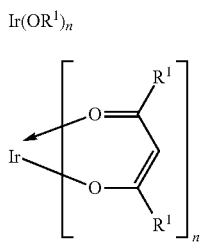

formula (40)

$IrHal_n$             formula (41)

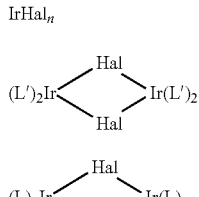

formula (42)

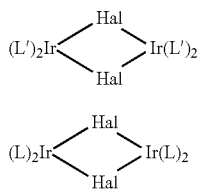

formula (43)

where the symbols and indices L', m, n and $R^1$ have the meanings indicated above, and Hal=F, Cl, Br or I.

It is likewise possible to use iridium compounds which carry both alkoxide and/or halide and/or hydroxyl and also ketoketonate radicals. These compounds may also be charged. Corresponding iridium compounds which are particularly suitable as starting materials are disclosed in WO 2004/085449. $[IrCl_2(acac)_2]^-$, for example $Na[IrCl_2(acac)_2]$, is particularly suitable. Further particularly suitable iridium starting materials are iridium(III) tris(acetylacetonate) and iridium(III) tris(2,2,6,6-tetramethyl-3,5-heptane-dionate).

The synthesis can also be carried out by reaction of the ligands L with iridium complexes of the formula $[Ir(L')_2(HOMe)_2]A$ or $[Ir(L')_2(NCMe)_2]A$ or by reaction of the ligands L' with iridium complexes of the formula $[Ir(L)_2(HOMe)_2]A$ or $[Ir(L)_2(NCMe)_2]A$, where A in each case represents a non-coordinating anion, such as, for example, triflate, tetrafluoroborate, hexafluorophosphate, etc., in dipolar protic solvents, such as, for example, ethanol, isopropanol, ethylene glycol, propylene glycol, glycerol, diethylene glycol, triethylene glycol, etc.

The synthesis of the complexes is preferably carried out as described in WO 2002/060910 and in WO 2004/085449. Heteroleptic complexes can also be synthesised, for example, in accordance with WO 05/042548. The synthesis here can also be activated, for example, thermally, photochemically and/or by microwave radiation. Furthermore, the synthesis can also be carried out in an autoclave at elevated pressure and/or elevated temperature.

The reactions can be carried out without addition of solvents or melting aids in a melt of the corresponding ligands to be o-metallated. Solvents or melting aids can be added if necessary. Suitable solvents are protic or aprotic solvents, such as aliphatic and/or aromatic alcohols (methanol, ethanol, isopropanol, t-butanol, etc.), oligo- and poly-alcohols (ethylene glycol, 1,2-propanediol, glycerol, etc.), alcohol ethers (ethoxyethanol, diethylene glycol, triethylene glycol, polyethylene glycol, etc.), ethers (di- and triethylene glycol dimethyl ether, diphenyl ether, etc.), aromatic, heteroaromatic and/or aliphatic hydrocarbons (toluene, xylene, mesitylene, chlorobenzene, pyridine, lutidine, quinoline, isoquinoline, tridecane, hexadecane, etc.), amides (DMF, DMAC, etc.), lactams (NMP), sulfoxides (DMSO) or sulfones (dimethyl sulfone, sulfolane, etc.). Suitable melting aids are compounds which are in solid form at room temperature, but melt on warming of the reaction mixture and dissolve the reactants, so that a homogeneous melt forms. Biphenyl, m-terphenyl, triphenylene, 1,2-, 1,3-, 1,4-bisphenoxybenzene, triphenylphosphine oxide, 18-crown-6, phenol, 1-naphthol, hydroquinone, etc., are particularly suitable.

Still a further suitable synthetic route to the compounds according to the invention starts from an iridium complex which, instead of the group —(Ar)$_p$-HetAr, carries a reactive leaving group, in particular chlorine, bromine or iodine, on the phenylpyridine ligand. This can be coupled to a boronic acid or boronic acid derivative, in particular a boronic acid ester of the group —(Ar)$_p$-HetAr to give the compound according to the invention. Alternatively, the reactive leaving group can be converted into a boronic acid or boronic acid derivative and then coupled to the group —(Ar)$_p$-HetAr, which still carries a reactive leaving group, in particular chlorine, bromine or iodine.

The invention furthermore relates to the corresponding free ligands of the compounds of the following formula (44), which are valuable intermediates for the synthesis of the compounds of the formula (1):

formula (44)

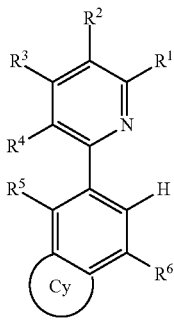

where the symbols used have the meanings given above. The preferences for the symbols used given above for the Iridium complex equally also apply to the compound of the formula (44).

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore furthermore relates to a formulation comprising a compound according to the invention and at least one further compound. The further compound may be, for example, a solvent, in particular one of the above-mentioned solvents or a mixture of these solvents. However, the further compound may also be a further organic or Inorganic compound which is likewise employed in the electronic device, for example a matrix material. This further compound may also be polymeric.

The complexes of the formula (1) described above or the preferred embodiments indicated above and also the compounds of the formula (44) can be used as active component in an electronic device. The present invention therefore furthermore relates to the use of a compound of the formula (1) or formula (44) or according to one of the preferred embodiments in an electronic device. The compounds according to the invention can furthermore be employed for the generation of singlet oxygen, in photocatalysis or in oxygen sensors.

The present invention still furthermore relates to an electronic device comprising at least one compound of the formula (1) or formula (44) or according to one of the preferred embodiments.

An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) or formula (44) given above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising at least one compound of the formula (1) given above in at least one layer. Particular preference is given to organic electroluminescent devices. Active components are generally the organic or inorganic materials which have been introduced between the anode and cathode, for example charge-Injection, charge-transport or charge-blocking materials, but in particular emission materials and matrix materials. The compounds according to the invention exhibit particularly good properties as emission material in organic electroluminescent devices. A preferred embodiment of the invention is therefore organic electroluminescent devices.

The organic electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or Inorganic p/n junctions. Interlayers, which have, for example, an exciton-blocking function and/or control the charge balance in the electroluminescent device, may likewise be introduced between two emitting layers. However, it should be pointed out that each of these layers does not necessarily have to be present.

The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. A preferred embodiment is three-layer systems, where the three layers exhibit blue, green and orange or red emission (see, for example, WO 2005/011013), or systems which have more than three emitting layers. A further preferred embodiment is two-layer systems, where the two layers exhibit either blue and yellow or cyan and orange emission. Two-layer systems are of particular interest for lighting applications. Embodiments of this type with the compounds according to the invention are particularly suitable, since they frequently exhibit yellow or orange emission. The white-emitting electroluminescent devices can be employed for lighting applications or as backlight for displays or with colour filters as displays.

In a preferred embodiment of the invention, the organic electroluminescent device comprises the compound of the formula (1) or the preferred embodiments indicated above as emitting compound in one or more emitting layers.

In a further preferred embodiment of the invention, the organic electroluminescent device comprises the compound of the formula (44) or the preferred embodiments as matrix material, in particular for phosphorescent emitters, in one or more emitting layers or as hole-blocking material in a hole-blocking layer or as electron-transport material in an electron-transport layer.

If the compound of the formula (1) is employed as emitting compound in an emitting layer, it is preferably employed in combination with one or more matrix materials. The mixture comprising the compound of the formula (1) and the matrix material comprises between 1 and 99% by vol., preferably between 2 and 90% by vol., particularly preferably between 3 and 40% by vol., especially between 5 and 15% by vol., of the compound of the formula (1), based on the entire mixture comprising emitter and matrix material. Correspondingly, the mixture comprises between 99.9 and 1% by vol., preferably between 98 and 10% by vol., particularly preferably between 97 and 60% by vol., in particular between 95 and 85% by vol., of the matrix material or matrix materials, based on the entire mixture comprising emitter and matrix material.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diaza-silole derivatives, for example in accordance with WO 2010/054729, diaza-phosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, beryllium complexes, dibenzofuran derivatives, for example in accordance with WO 2009/148015, or bridged carbazole derivatives, for example in accordance with US 2009/0136779, WO 2010/050778, WO 2011/042107 or WO 2011/088877. Further suitable matrix materials are the compounds of the formula (44) given above.

It may also be preferred to employ a plurality of different matrix materials as a mixture. Suitable for this purpose are, in particular, mixtures of at least one electron-transporting matrix material and at least one hole-transporting matrix material or mixtures of at least two electron-transporting matrix materials or mixtures of at least one hole- or electron-transporting matrix material and at least one further material having a large band gap, which is thus substantially electrically inert and does not participate or does not participate to a significant extent in charge transport, as described, for example, in WO 2010/108579. A preferred combination is, for example, the use of an aromatic ketone or a triazine derivative with a triarylamine derivative or a carbazole derivative as mixed matrix for the metal complex according to the invention.

It is furthermore preferred to employ a mixture of two or more triplet emitters together with a matrix. The triplet emitter having the shorter-wave emission spectrum serves as co-matrix for the triplet-emitter having the longer-wave emission spectrum. Thus, for example, blue- or green-emitting triplet emitters can be employed as co-matrix for the complexes of the formula (1) according to the invention.

The compounds according to the invention are also, in particular, suitable as phosphorescent emitters in organic electroluminescent devices, as described, for example, in WO 98/24271, US 2011/0248247 and US 2012/0223633. In these multicoloured display components, an additional blue emission layer is applied by vapour deposition over the entire area to all pixels, including those having a colour other than blue. It has been found here that the compounds according to the invention, if employed as emitters for the red pixel, result in very good emission together with the vapour-deposited blue emission layer.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, Li$_2$O, BaF$_3$, MgO, NaF, CsF, Cs$_2$CO$_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent or partially transparent in order either to facilitate irradiation of the organic material (O-SCs) or the coupling-out of light (OLEDs/PLEDs, O-LASERs). A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

All materials as are used in accordance with the prior art for the layers can generally be used in the further layers, and the person skilled in the art will be able to combine each of these materials with the materials according to the Invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are coated by means of a sublimation process, in which the materials are vapour-deposited in vacuum sublimation units at an initial pressure of usually less than 10$^{-5}$ mbar, preferably less than 10$^{-6}$ mbar. It is also possible for the initial pressure to be even lower, for example less than 10$^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between 10$^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

The electronic devices according to the invention, in particular organic electroluminescent devices, are distinguished by the following surprising advantages over the prior art 1. The compounds according to the invention have a very narrow emission spectrum and thus a very low full width at half maximum of the emission. This results in greater colour purity of the red emission of the compounds, meaning that they are more suitable for use in red pixels in displays than corresponding compounds which, although containing a group HetAr, do not contain a group of one of the formulae (4) to (10).
2. Organic electroluminescent devices comprising compounds of the formula (1) as emitting materials have very good efficiency. In particular, they have better efficiency than electroluminescent devices which comprise analogous compounds which do not contain a condensed-on aliphatic five-membered ring of one of the formulae (4) to (10).
3. The compounds according to the invention have very high solubility and can therefore be processed extremely well from solution.
4. Organic electroluminescent devices comprising compounds of the formula (1) as emitting materials have a very good lifetime. In particular, they have a better lifetime than electroluminescent devices which comprise analogous compounds which do not contain a condensed-on aliphatic five-membered ring of one of the formulae (4) to (10).
5. The compounds according to the invention have a very low aggregation tendency, which results in very low triplet-triplet annihilation.

These advantages mentioned above are not accompanied by an impairment of the other electronic properties.

The invention is explained in greater detail by the following examples, without wishing to restrict it thereby. The person skilled in the art will be able to use the descriptions to synthesise further compounds according to the invention without inventive step and use them in electronic devices and will thus be able to carry out the invention throughout the range disclosed.

EXAMPLES

The following syntheses are carried out, unless indicated otherwise, in dried solvents under a protective-gas atmosphere. The metal complexes are additionally handled with exclusion of light or under yellow light. The solvents and reagents can be purchased, for example, from VWR, Sigma-ALDRICH or ABCR. The respective numbers in square brackets or the numbers indicated for individual compounds relate to the CAS numbers of the compounds known from the literature.

A: Synthesis of the Synthones

Example S1: 5-Bromo-2-(1,1,2,2,3,3-hexamethylindan-5-yl)pyridine

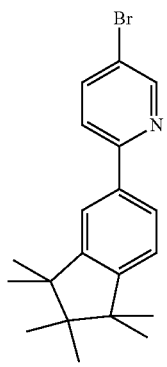 [SMILES: CC1(C)c2ccc(-c3ccc(Br)cn3)cc2C(C)(C)C1(C)C]

92.5 g of 2-(1,1,2,2,3,3-hexamethylindan-5-yl)-4,4,5,5-tetramethyl-1,3,2-dioxaborolane (282 mmol, [1562418-16-9]), 80.0 g of 5-bromo-2-iodopyridine (282 mmol, [223463-13-6]) and 275 g of caesium carbonate (844 mmol) are weighed out into a 4 l four-necked flask with reflux condenser, argon connection, precision glass stirrer and internal thermometer, the flask is blanketed with argon, and 1400 ml of deionised water, 1100 ml of 1,4-dioxane and 550 ml of absolute ethanol are added. The suspension is homogenised for 5 minutes, and 4.7 g of 1,1'-bis(diphenylphosphino)ferrocene (DPPF, 8.5 mmol) and 1.9 g of palladium acetate (8.5 mmol) are then added. The reaction mixture is warmed at 80° C. overnight. After cooling, 750 ml of ethyl acetate are added, and the phases are separated. The aqueous phase is re-extracted with ethyl acetate. The organic phases are combined, washed with water and saturated NaCl solution and dried over sodium sulfate. The mixture is filtered through a 5 cm layer of Celite with ethyl acetate as eluent, and the solvent is subsequently removed in vacuo. The product is distilled in a high vacuum ($4\times10^{-5}$ mbar, 185° C.) and purified by column chromatography on silica gel with toluene as eluent, giving 75.1 g (75%) of a colourless crystalline solid.

The brominated synthones can be prepared by the general procedure:

| Ex. | Starting material 1 | Starting material 2 | Product | Yield |
|---|---|---|---|---|
| S2 | 1312464-73-5 | 223463-13-6 | | 72% |
| S3 | 1562418-19-2 | 223463-13-6 | | 61% |

-continued

| Ex. | Starting material 1 | Starting material 2 | Product | Yield |
|---|---|---|---|---|
| S4 | 1562418-17-0 | 223463-13-6 | | 77% |
| S5 | 1562418-21-6 | 223463-13-6 | | 71% |
| S6 | 1562418-23-8 | 223463-13-6 | | 55% |
| S7 | 1562418-25-0 | 223463-13-6 | | 61% |

| Ex. | Starting material 1 | Starting material 2 | Product | Yield |
|---|---|---|---|---|
| S8 | 1562418-27-2 | 223463-13-6 | | 73% |
| S9 | 1562418-29-4 | 223463-13-6 | | 57% |
| S10 | 1562418-31-8 | 223463-13-6 | | 69% |
| S11 | 1562418-33-0 | 223463-13-6 | | 62% |

-continued
| Ex. | Starting material 1 | Starting material 2 | Product | Yield |
|---|---|---|---|---|
| S12 | 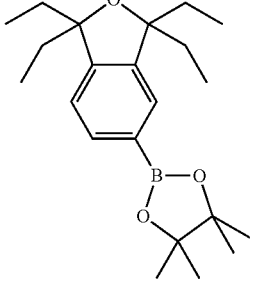<br>1562418-35-2 | 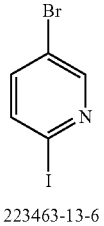<br>223463-13-6 | 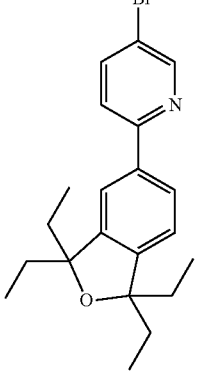 | 56% |
| S13 | 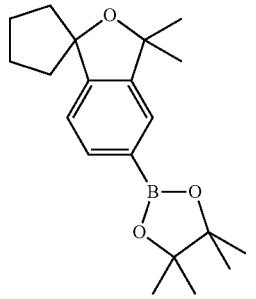<br>1562418-37-4 | 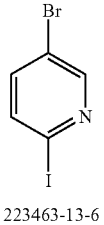<br>223463-13-6 | 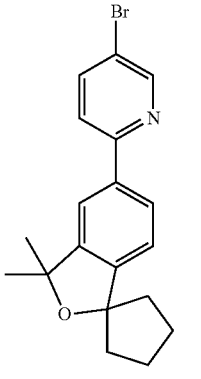 [SMILES: CC1(C)OC2(CCCC2)c2ccc(-c3ccc(Br)cn3)cc21] | 65% |
| S14 | 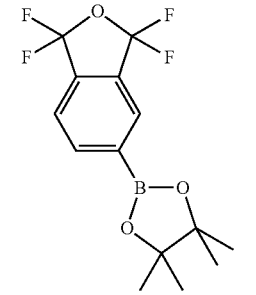<br>1562418-39-6 | 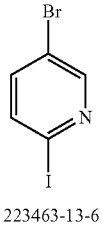<br>223463-13-6 | 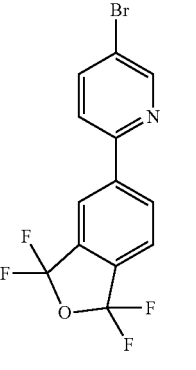 [SMILES: FC1(F)OC(F)(F)c2cc(-c3ccc(Br)cn3)ccc21] | 48% |
| S15 | 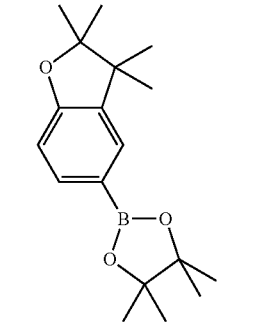<br>1562418-41-0 | 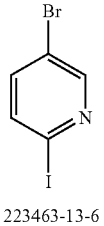<br>223463-13-6 | 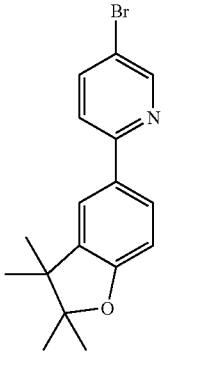 [SMILES: CC1(C)Oc2ccc(-c3ccc(Br)cn3)cc2C1(C)C] | 61% |

-continued
| Ex. | Starting material 1 | Starting material 2 | Product | Yield |
|---|---|---|---|---|
| S16 | 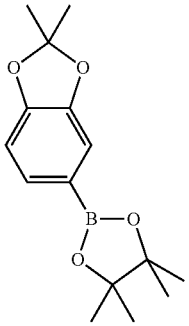<br>1562418-43-2 | 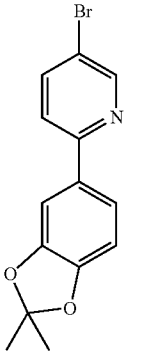 [SMILES: CC1(C)Oc2ccc(-c3ccc(Br)cn3)cc2O1]<br>223463-13-6 | 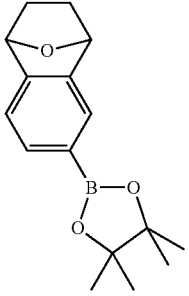 | 59% |
| S17 | 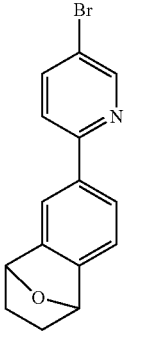<br>1562418-44-3 | 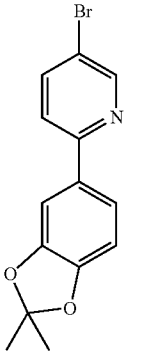 [SMILES: CC1(C)Oc2ccc(-c3ccc(Br)cn3)cc2O1]<br>223463-13-6 | 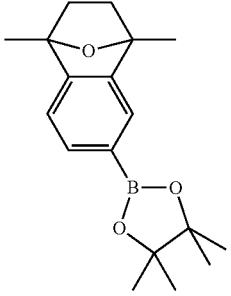 | 71% |
| S18 | 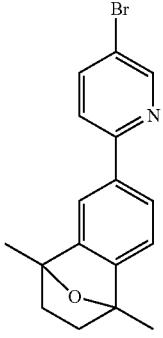<br>1562418-47-6 | 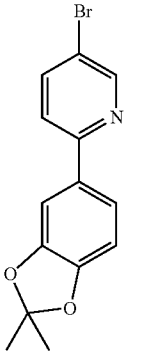 [SMILES: CC1(C)Oc2ccc(-c3ccc(Br)cn3)cc2O1]<br>223463-13-6 | 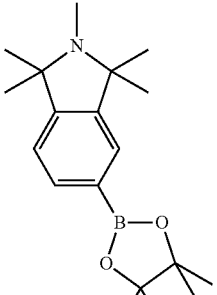 | 68% |
| S19 | 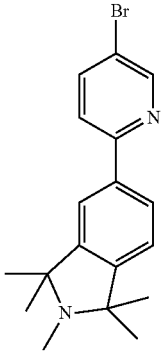 [SMILES: CN1C(C)(C)c2ccc(-c3ccc(Br)cn3)cc2C1(C)C]<br>1562418-49-8 | 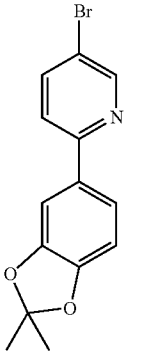 [SMILES: CC1(C)Oc2ccc(-c3ccc(Br)cn3)cc2O1]<br>223463-13-6 |  | 80% |

-continued

| Ex. | Starting material 1 | Starting material 2 | Product | Yield |
|---|---|---|---|---|
| S20 | 1562418-51-2 | 223463-13-6 | | 51% |
| S21 | 1562418-16-9 | 941294-57-1 | | 80% |
| S22 | 1312464-73-5 | 941294-57-1 | | 82% |
| S23 | 1562418-27-2 | 941294-57-1 | | 78% |

-continued
| Ex. | Starting material 1 | Starting material 2 | Product | Yield |
|---|---|---|---|---|
| S24 | 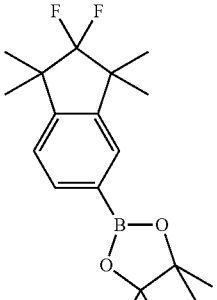 1562418-25-0 | 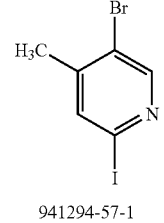 941294-57-1 | 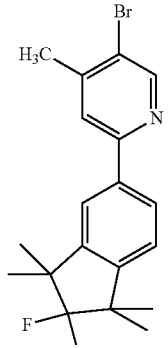 | 74% |
| S25 | 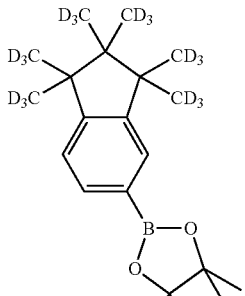 1562418-17-0 | 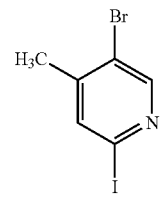 941294-57-1 | 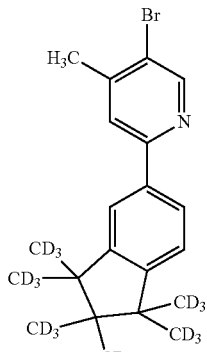 | 84% |
| S26 | 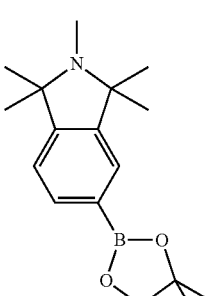 1562418-49-8 | 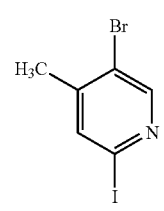 941294-57-1 | 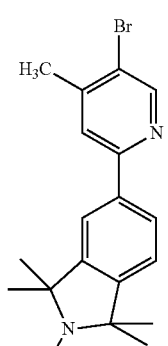 [SMILES: Cc1cc(-c2ccc3c(c2)C(C)(C)CC3(C)C)ncc1Br] | 77% |
| S27 | 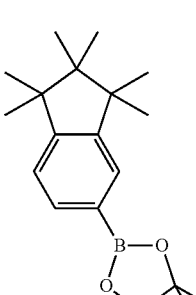 1562418-16-9 | 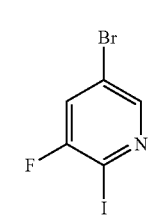 1260665-95-9 | 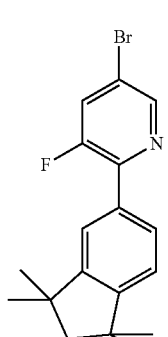 | 62% |

-continued
| Ex. | Starting material 1 | Starting material 2 | Product | Yield |
|---|---|---|---|---|
| S28 | 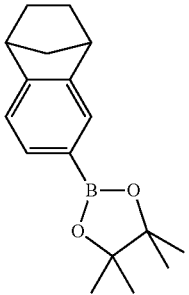<br>1562418-27-2 | 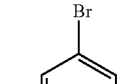<br>1260665-95-9 | 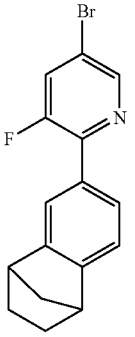 | 67% |
| S29 | 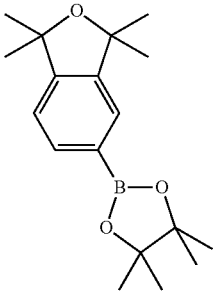<br>1562418-33-0 | 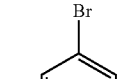<br>1260665-95-9 | 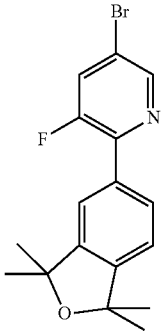 [SMILES: CC1(C)OC(C)(C)c2cc(-c3ncc(Br)cc3F)ccc21] | 59% |
| S30 | 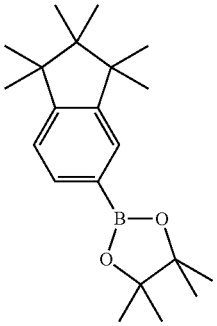<br>1562418-16-9 | 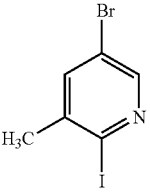<br>376587-52-9 | 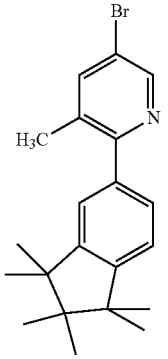 [SMILES: Cc1cc(Br)cnc1-c1ccc2c(c1)C(C)(C)C(C)(C)C2(C)C] | 51% |
| S31 | 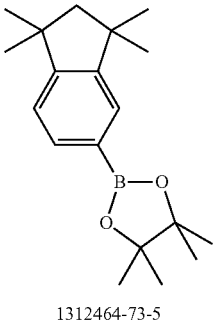<br>1312464-73-5 | 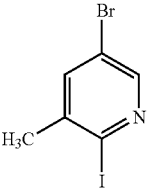<br>376587-52-9 | 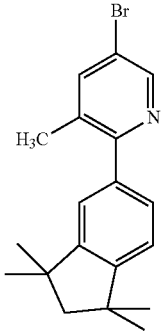 [SMILES: Cc1cc(Br)cnc1-c1ccc2c(c1)C(C)(C)CC2(C)C] | 52% |

-continued

| Ex. | Starting material 1 | Starting material 2 | Product | Yield |
|---|---|---|---|---|
| S32 | 1562418-27-2 | 376587-52-9 | | 49% |
| S33 | 1562418-16-9 | 1260669-95-1 | | 49% |
| S34 | 1312464-73-5 | 1260669-95-1 | | 52% |
| S35 | 1562418-27-2 | 1260669-95-1 | | 46% |

-continued

| Ex. | Starting material 1 | Starting material 2 | Product | Yield |
|---|---|---|---|---|
| S36 | 1562418-16-9 | 927800-97-3 | | 80% |
| S37 | 1562418-27-2 | 927800-97-3 | | 82% |
| S38 | 1562418-25-0 | 927800-97-3 | | 75% |
| S39 | 1562418-16-9 | 1346540-97-3 | | 55% |

-continued
| Ex. | Starting material 1 | Starting material 2 | Product | Yield |
|---|---|---|---|---|
| S40 | 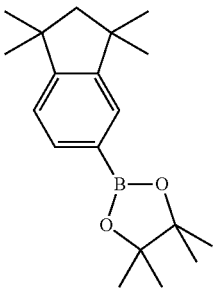<br>1312464-73-5 | 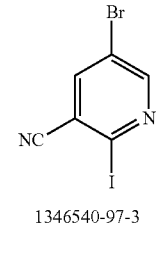<br>1346540-97-3 | 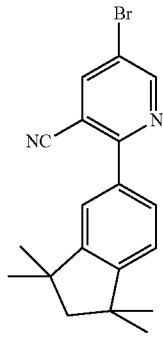 [SMILES: CC1(C)CC(C)(C)c2cc(-c3ncc(Br)cc3C#N)ccc21] | 55% |
| S41 | 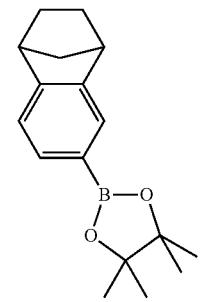<br>1562418-27-2 | 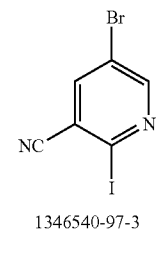<br>1346540-97-3 | 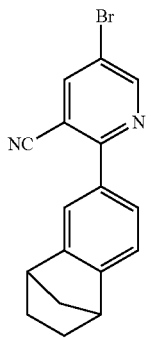 [SMILES: N#Cc1cc(Br)cnc1-c1ccc2c(c1)C1CCC2C1] | 51% |
| S42 | 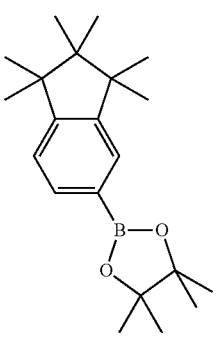<br>1562418-16-9 | 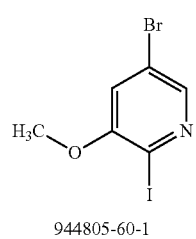<br>944805-60-1 | 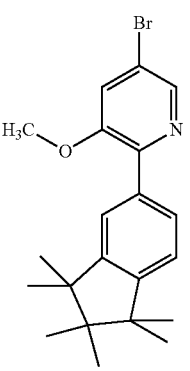 [SMILES: COc1cc(Br)cnc1-c1ccc2c(c1)C(C)(C)C(C)(C)C2(C)C] | 50% |
| S43 | 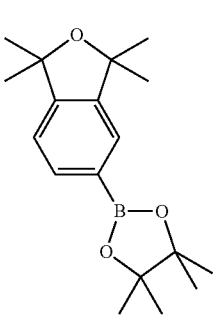<br>1562418-33-0 | 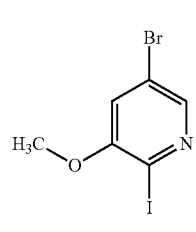<br>944805-60-1 | 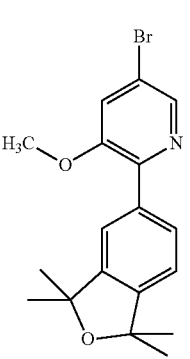 [SMILES: COc1cc(Br)cnc1-c1ccc2c(c1)C(C)(C)OC2(C)C] | 47% |

-continued
| Ex. | Starting material 1 | Starting material 2 | Product | Yield |
|---|---|---|---|---|
| S44 | 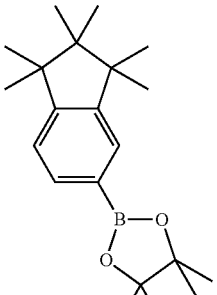<br>1562418-16-9 | 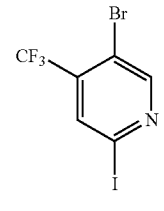<br>1443792-54-8 | 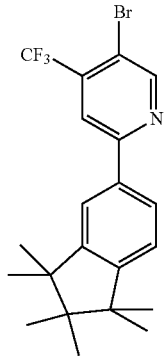 [SMILES: CC1(C)c2ccc(-c3cc(C(F)(F)F)c(Br)cn3)cc2C(C)(C)C1(C)C] | 49% |
| S45 | 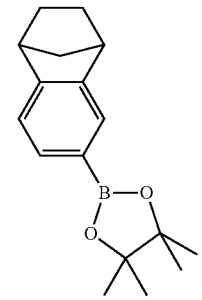<br>1562418-27-2 | 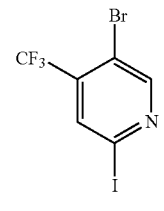<br>1443792-54-8 | 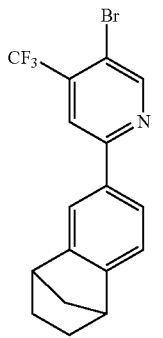 [SMILES: FC(F)(F)c1cc(-c2ccc3c(c2)C2CCC3C2)ncc1Br] | 51% |
| S46 | 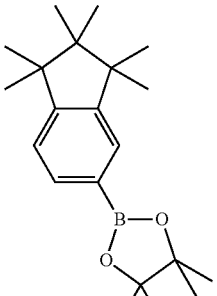<br>1562418-16-9 | 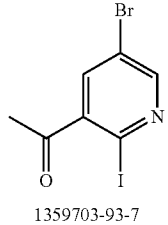<br>1359703-93-7 | 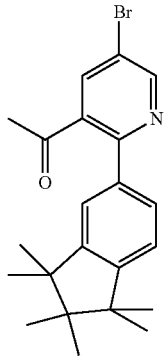 [SMILES: CC(=O)c1cc(Br)cnc1-c1ccc2c(c1)C(C)(C)C(C)(C)C2(C)C] | 41% |
| S47 | 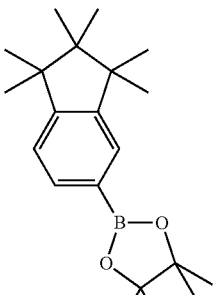<br>1562418-16-9 | 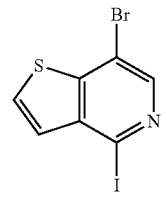<br>1203579-77-4 | 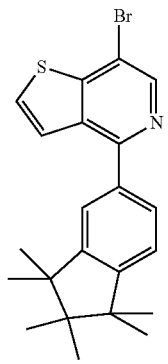 [SMILES: CC1(C)c2ccc(-c3ncc(Br)c4sccc34)cc2C(C)(C)C1(C)C] | 85% |

| Ex. | Starting material 1 | Starting material 2 | Product | Yield |
|---|---|---|---|---|
| S48 | 1562418-47-6 | 1203579-77-4 | | 78% |
| S49 | 1562418-16-9 | 1236062-30-8 | | 65% |
| S50 | 1562418-16-9 | 890302-29-1 | | 58% |
| S51 | 1312464-73-5 | 890302-29-1 | | 52% |

-continued
| Ex. | Starting material 1 | Starting material 2 | Product | Yield |
|---|---|---|---|---|
| S52 | 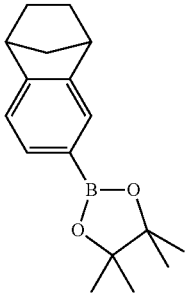  1562418-27-2 | 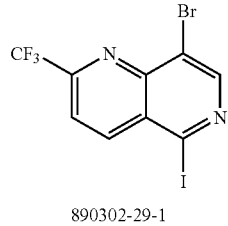 [SMILES: FC(F)(F)c1ccc2c(I)ncc(Br)c2n1]  890302-29-1 | 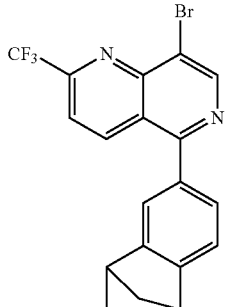 | 52% |
| S53 | 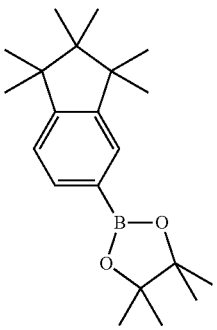  1562418-16-9 | 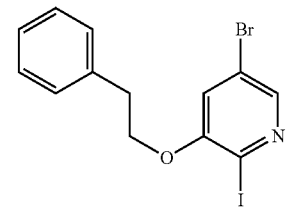  1342906-74-4 | 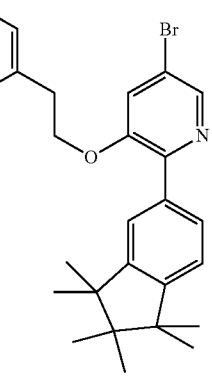 | 67% |
| S54 | 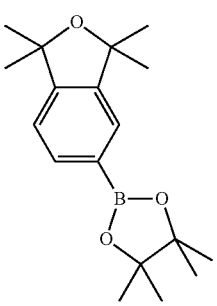  1562418-33-0 | 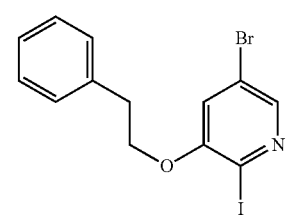  1342906-74-4 | 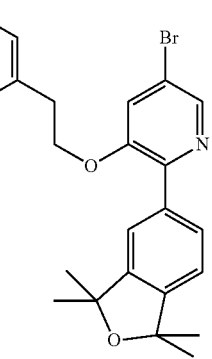 | 64% |
| S55 | 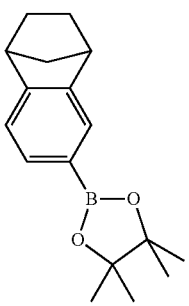  1562418-27-2 | 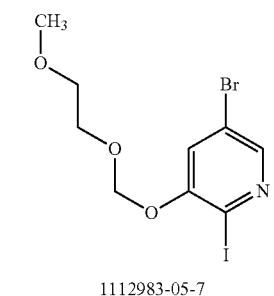  1112983-05-7 | 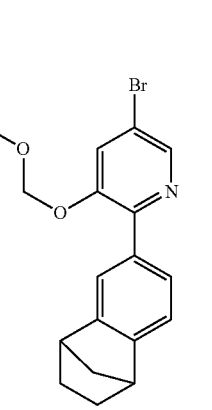 | 59% |

Example S147: Borylation of the Brominated Synthones for the Example of 2-(1,1,2,2,3,3-hexamethylindan-5-yl)-5-(4,4,5,5-tetramethyl-1,3,2-dioxaborolan-2-yl)pyridine

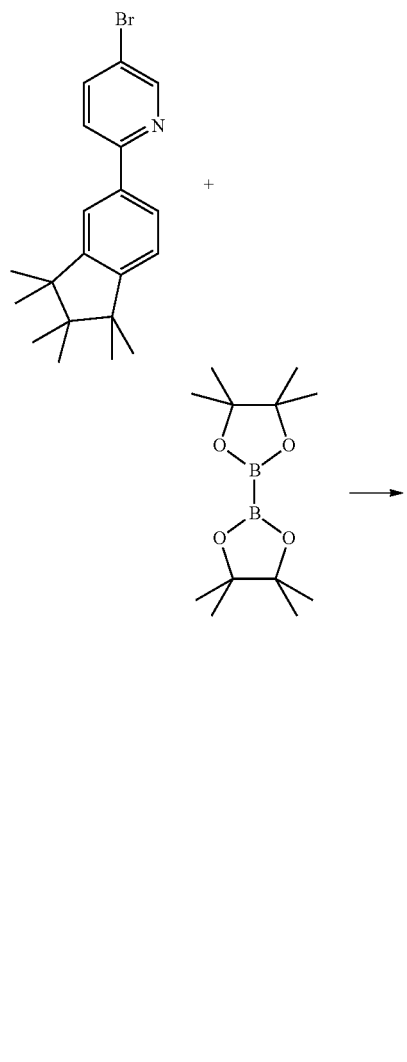

30 g (83.7 mmol) of S1, 22 g (86.6 mmol) of bis(pinacolato)diborane [73183-34-3], 50 g (510 mm) of potassium acetate 127-08-2 and 3 g (4.1 mmol) of 1,1-bis(diphenylphosphino)ferrocenepalladium(II) dichloride [95464-05-4] are weighed out into a 2 l four-necked flask with reflux condenser, precision glass stirrer, heating bath and argon connection, and 700 ml of 1,4-dioxane and 700 ml of toluene are added. The reaction mixture is blanketed with argon and stirred under reflux for 24 h. After cooling, the reaction solution is filtered through Celite, and the phases are separated. The aqueous phase is extracted twice with 50 ml of toluene, and the organic phases are combined, dried over sodium sulfate and freed from solvent in vacuo, giving a dark solid, which is employed further without further purification.

The following borylated synthones can be prepared by the general procedure:

| Ex. | Starting material 1 | Product | Yield |
|---|---|---|---|
| S100 | S1 | (structure) | 95% |
| S101 | S2 | (structure) | 92% |
| S102 | S3 | (structure) | 92% |

| Ex. | Starting material 1 | Product | Yield |
|---|---|---|---|
| S103 | 34 | 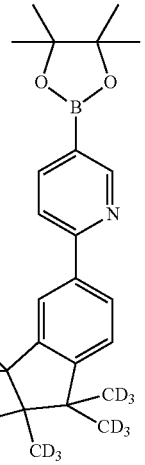 | 94% |
| S104 | S5 | 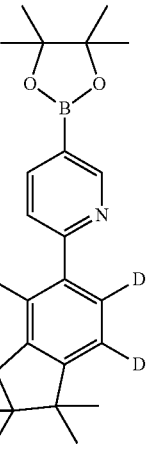 | 95% |
| S105 | S6 | 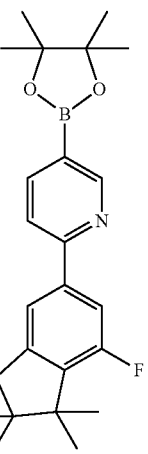 | 92% |
| Ex. | Starting material 1 | Product | Yield |
|---|---|---|---|
| S106 | S7 | 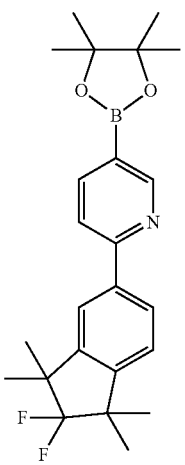 | 90% |
| S107 | S8 | 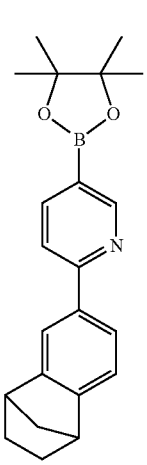 [SMILES: CC1(C)OB(c2ccc(-c3ccc4c(c3)C3CCC4C3)nc2)OC1(C)C] | 96% |
| S108 | S9 | 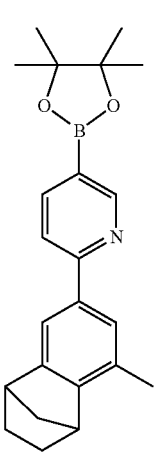 [SMILES: Cc1cc(-c2ccc(B3OC(C)(C)C(C)(C)O3)cn2)cc2c1C1CCC2C1] | 94% |

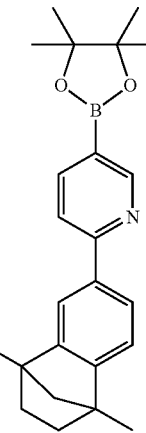
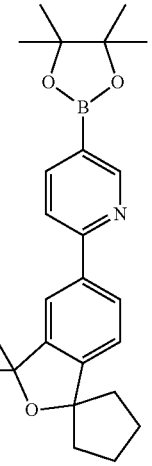
| Ex. | Starting material 1 | Product | Yield |
|---|---|---|---|
| S109 | S10 | 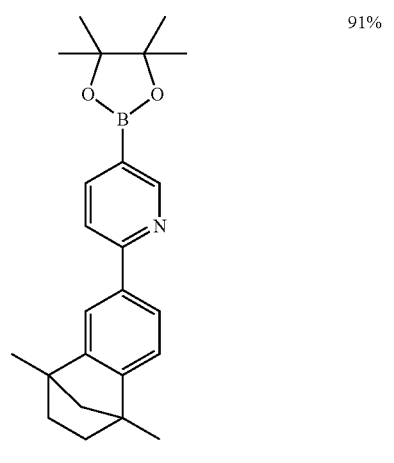 | 91% |
| S110 | S11 | 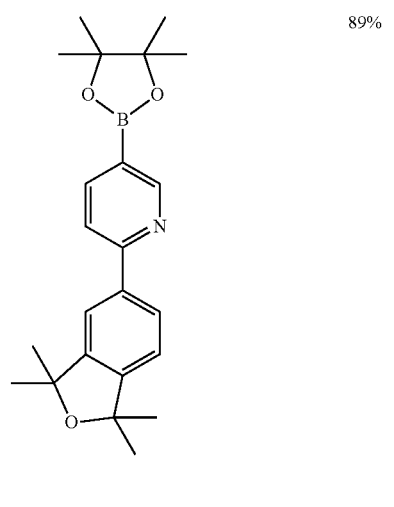 | 89% |
| S111 | S12 | 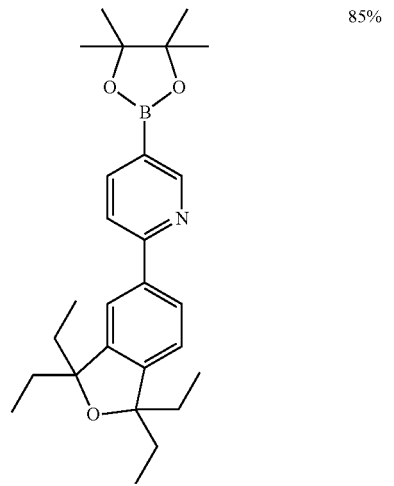 | 85% |
| Ex. | Starting material 1 | Product | Yield |
|---|---|---|---|
| S112 | S13 | | 88% |
| S113 | S14 | 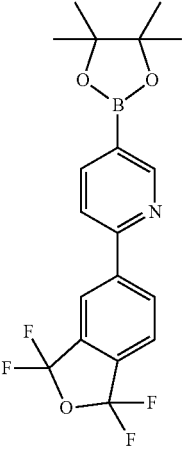 [SMILES: CC1(C)OB(c2ccc(-c3ccc4c(c3)C(F)(F)OC4(F)F)nc2)OC1(C)C] | 81% |
| S114 | S15 | 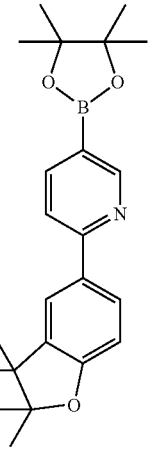 | 90% |

159
-continued
| Ex. | Starting material 1 | Product | Yield |
|---|---|---|---|
| S115 | S16 | 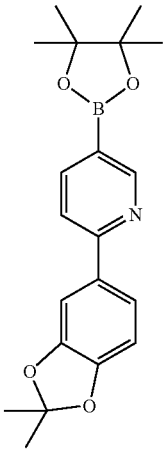 | 83% |
| S116 | S17 | 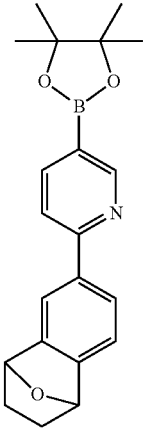 [SMILES: CC1(C)OB(c2ccc(-c3ccc4c(c3)C3CCC4O3)nc2)OC1(C)C] | 92% |
| S117 | S18 | 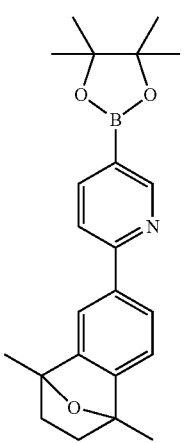 | 90% |
160
-continued
| Ex. | Starting material 1 | Product | Yield |
|---|---|---|---|
| S118 | S19 | 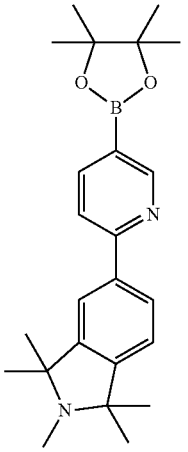 | 95% |
| S119 | S20 | 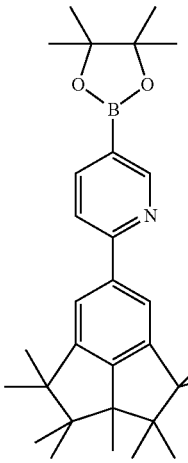 | 87% |
| S120 | S21 | 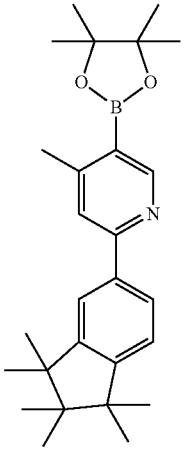 | 75% |

-continued
| Ex. | Starting material 1 | Product | Yield |
|---|---|---|---|
| S121 | S22 | 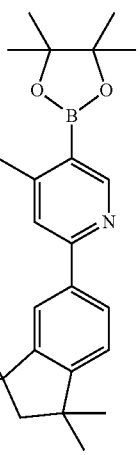 | 72% |
| S122 | S23 | 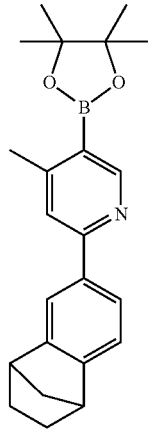 [SMILES: Cc1cc(-c2ccc3c(c2)C2CCC3C2)ncc1B1OC(C)(C)C(C)(C)O1] | 76% |
| S123 | S24 | 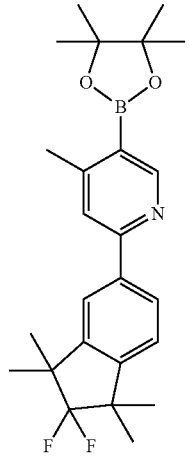 | 70% |
-continued
| Ex. | Starting material 1 | Product | Yield |
|---|---|---|---|
| S124 | S25 | 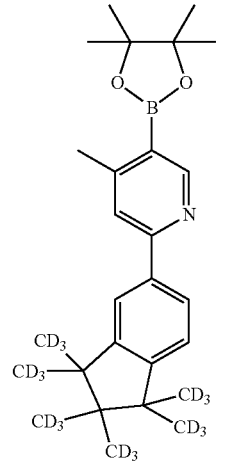 [SMILES: [2H]C([2H])([2H])C1(C([2H])([2H])[2H])c2ccc(-c3cc(C)c(B4OC(C)(C)C(C)(C)O4)cn3)cc2C(C([2H])([2H])[2H])(C([2H])([2H])[2H])C1(C([2H])([2H])[2H])C([2H])([2H])[2H]] | 75% |
| S125 | S26 | 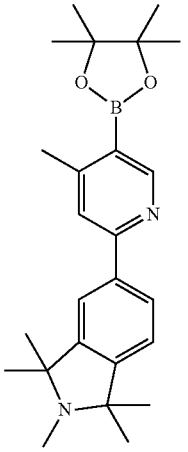 | 73% |
| S126 | S27 | 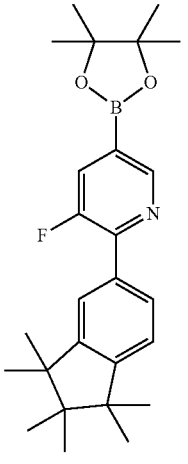 | 93% |

| Ex. | Starting material 1 | Product | Yield |
|---|---|---|---|
| S127 | S28 | 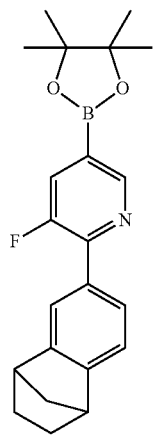 | 91% |
| S128 | S29 | 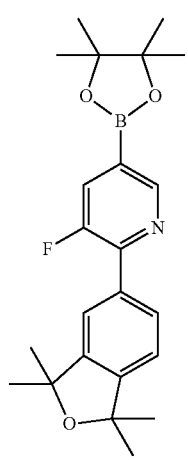 | 94% |
| S129 | S30 | 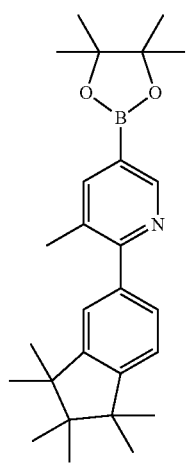 | 94% |
| Ex. | Starting material 1 | Product | Yield |
|---|---|---|---|
| S130 | S31 | 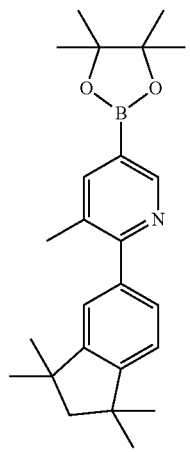 | 95% |
| S131 | S32 | 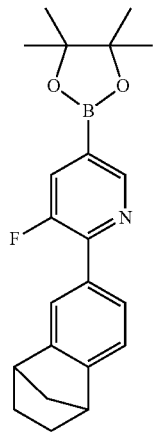 | 90% |
| S132 | S33 | 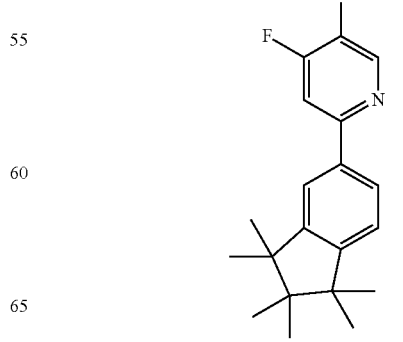 | 92% |

-continued
| Ex. | Starting material 1 | Product | Yield |
|---|---|---|---|
| S133 | S34 | | 89% |
| S134 | S35 | | 90% |
| S135 | S36 | | 94% |
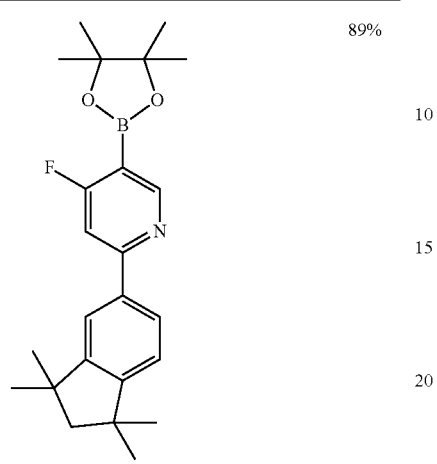
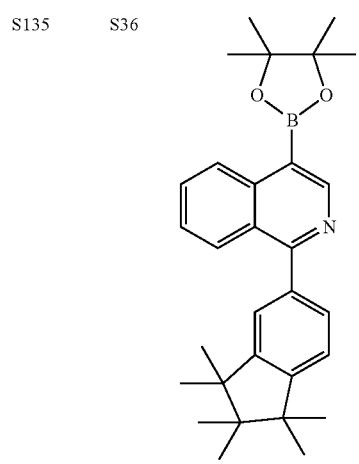
-continued
| Ex. | Starting material 1 | Product | Yield |
|---|---|---|---|
| S136 | S37 | | 91% |
| S137 | S38 | | 94% |
| S138 | S39 | | 95% |
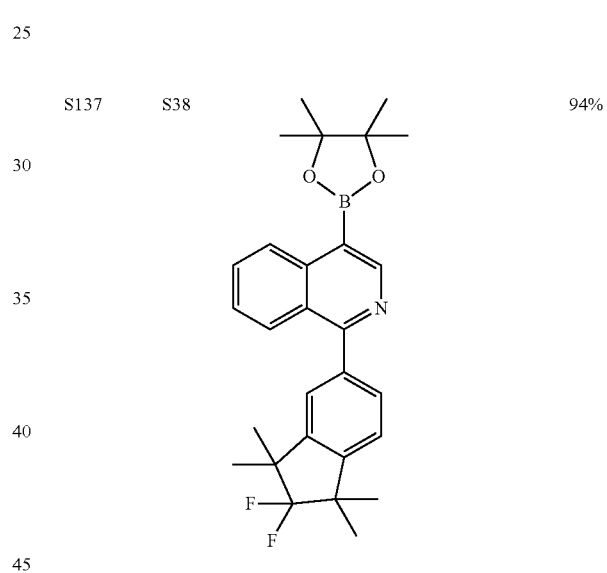
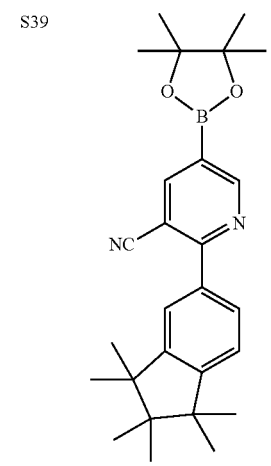

| Ex. | Starting material 1 | Product | Yield |
|---|---|---|---|
| S139 | S40 | 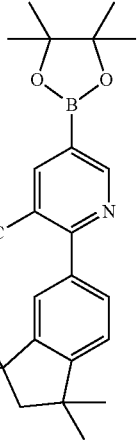 | 91% |
| S140 | S41 | 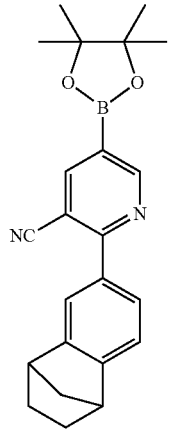 [SMILES: CC1(C)OB(c2cnc(-c3ccc4c(c3)C3CCC4C3)c(C#N)c2)OC1(C)C] | 93% |
| S141 | S42 | 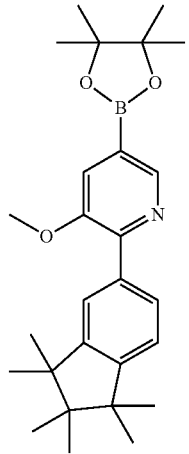 | 95% |
| Ex. | Starting material 1 | Product | Yield |
|---|---|---|---|
| S142 | S43 | 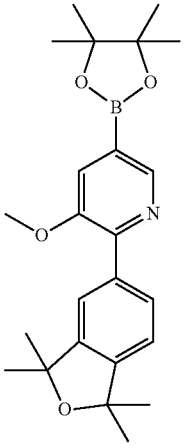 | 89% |
| S143 | S44 | 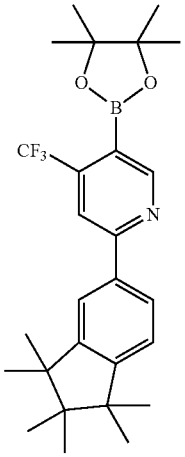 | 83% |
| S144 | S45 | 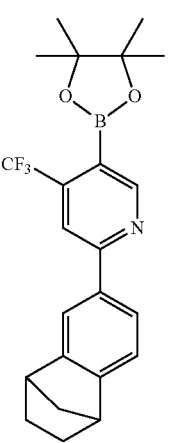 [SMILES: CC1(C)OB(c2cnc(-c3ccc4c(c3)C3CCC4C3)cc2C(F)(F)F)OC1(C)C] | 79% |

| Ex. | Starting material 1 | Product | Yield |
|---|---|---|---|
| S145 | S46 | 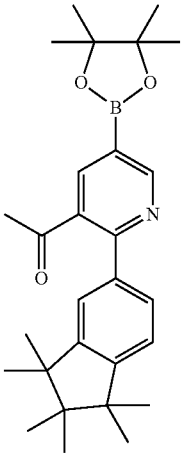 | 88% |
| S146 | S47 | 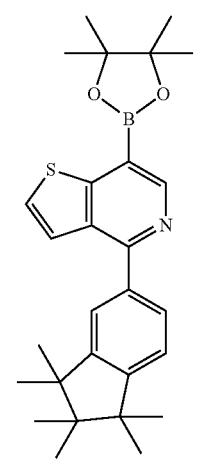 | 92% |
| S147 | S48 | 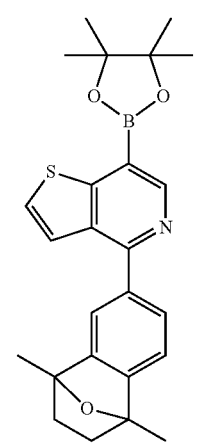 | 90% |
| Ex. | Starting material 1 | Product | Yield |
|---|---|---|---|
| S148 | S49 | 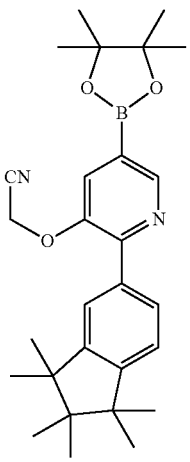 | 95% |
| S149 | S50 | 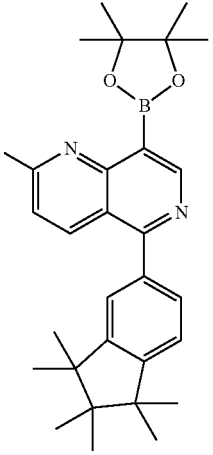 | 81% |
| S150 | S51 | 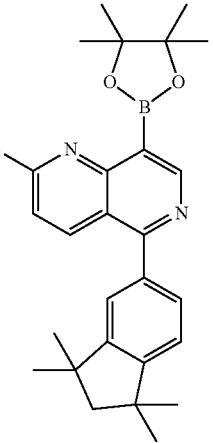 | 83% |

-continued

| Ex. | Starting material 1 | Product | Yield |
|---|---|---|---|
| S151 | S52 | 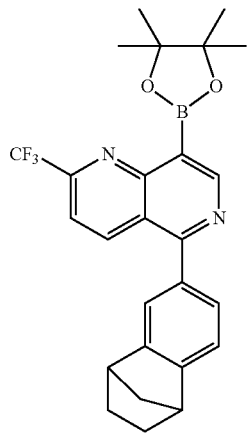 [SMILES: CC1(C)OB(c2cnc(-c3ccc4c(c3)C3CCC4C3)c3ccc(C(F)(F)F)nc23)OC1(C)C] | 79% |
| S152 | S53 | 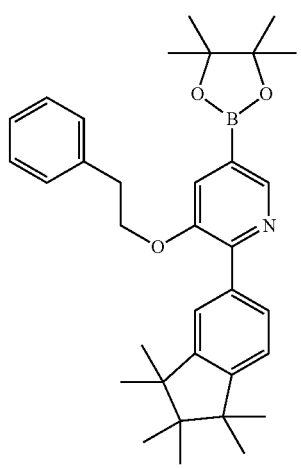 [SMILES: CC1(C)OB(c2cnc(-c3ccc4c(c3)C(C)(C)C(C)(C)C4(C)C)c(OCCc3ccccc3)c2)OC1(C)C] | 92% |
| S153 | S54 | 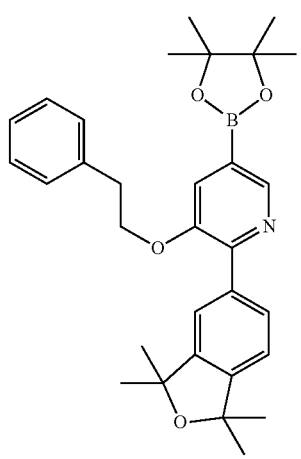 [SMILES: CC1(C)OC(C)(C)c2cc(-c3ncc(B4OC(C)(C)C(C)(C)O4)cc3OCCc3ccccc3)ccc21] | 88% |

-continued

| Ex. | Starting material 1 | Product | Yield |
|---|---|---|---|
| S154 | S55 | 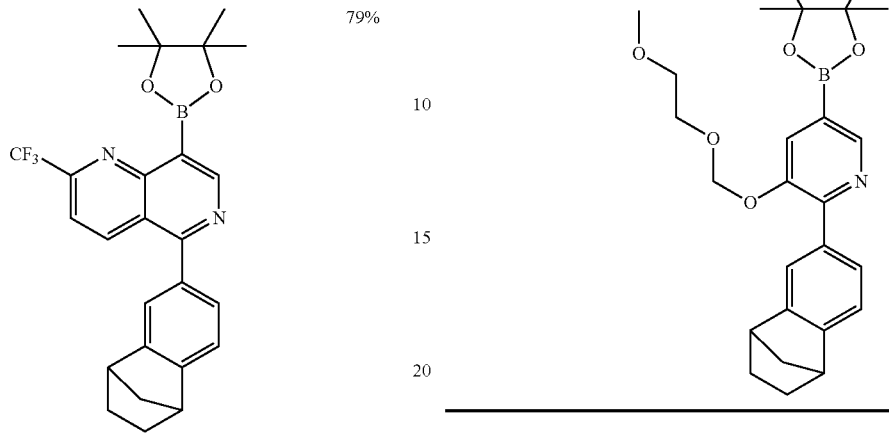 | 90% |

Synthesis of the Triazine Building Blocks

Illustrative Synthesis of 2-chloro-4,6-bis(3,5-di-tert-butylphenyl)-1,3,5-triazine (S1000)

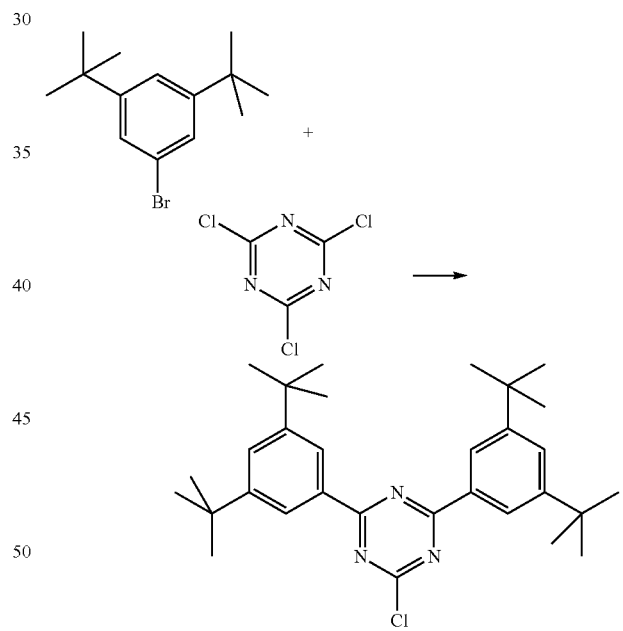

5.8 g (238.6 mmol) of magnesium turnings are initially introduced into a flask which has been dried by heating, and a solution of 73 g (271.1 mmol) of bromo-3,5-d-tert-butylbenzene in 400 ml of dry THF is slowly added dropwise so that the reaction solution constantly boils under reflux. When the addition is complete, the solution is heated under reflux for a further 2 h and then allowed to cool. 20 g (108.5 mmol) of cyanogen chloride in 400 ml of dry THF are initially introduced in a further flask and cooled to 0° C. The Grignard reagent is added dropwise at such a rate that an internal temperature of 20° C. is not exceeded. When the addition is complete, the reaction mixture is warmed at room temperature overnight. The reaction is stopped by addition of 500 ml of 1 N HCl solution with ice-cooling. The phases are separated, and the aqueous phase is rinsed a number of times with ethyl acetate. The organic phases are combined and dried using saturated NaCl solution, and the solvent is then removed in vacuo. Methanol is added to the pale-brown oil, and the mixture is heated under reflux. After cooling, the solid is filtered off with suction, washed with heptane and dried in vacuo, giving 23.6 g (48.0 mmol, 44% yield) of a colourless solid.

The following building blocks which are known from the literature can be employed analogously:

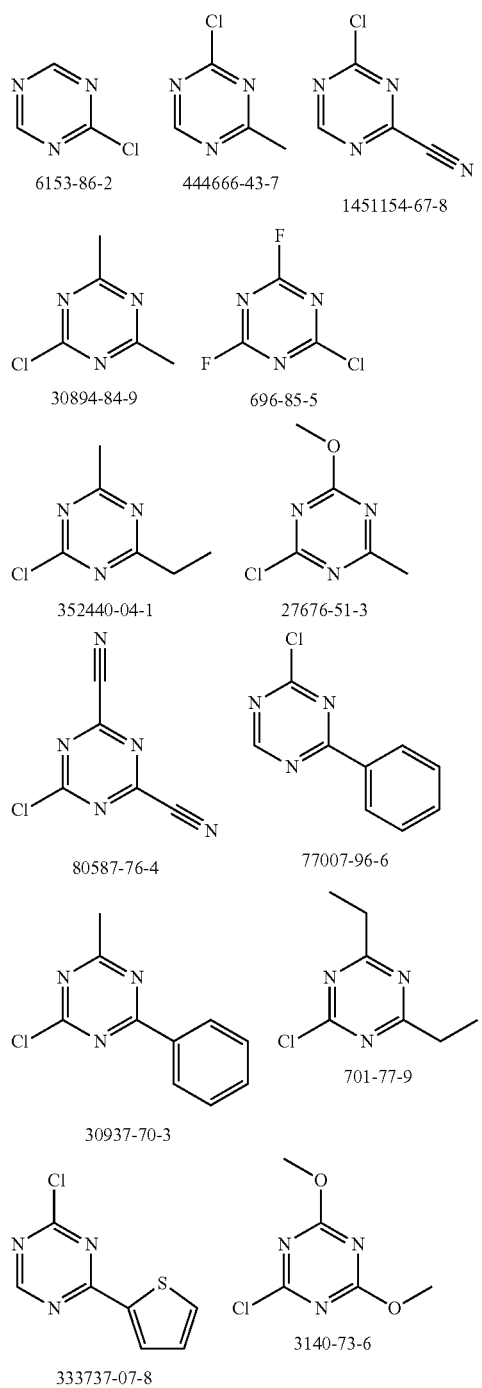

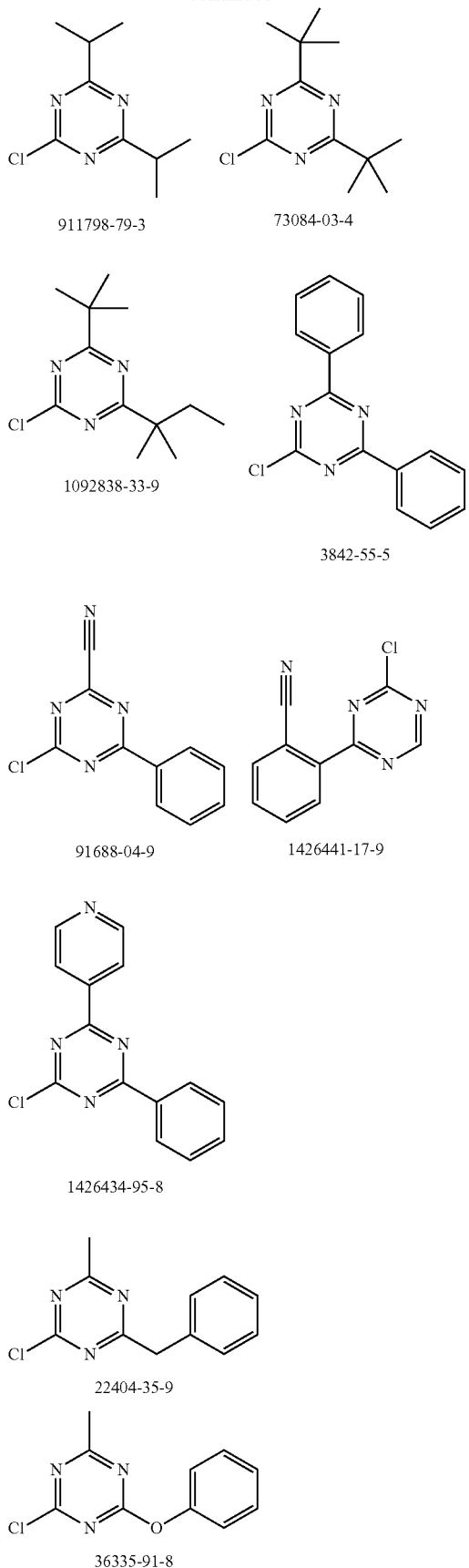

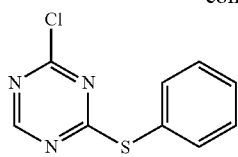
61810-06-8
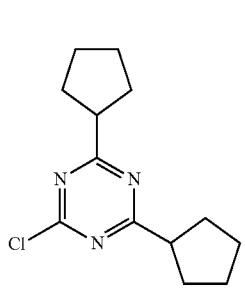
78941-28-3
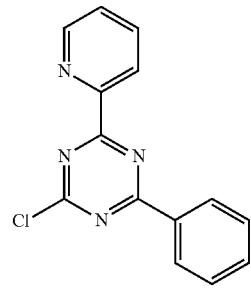
1477759-31-1
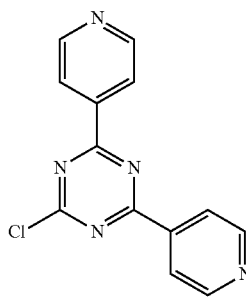
1253971-29-7
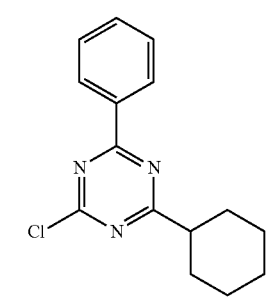
1426435-09-7
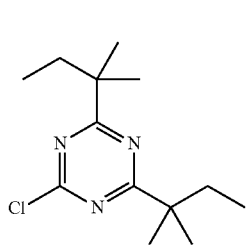
1092838-05-5
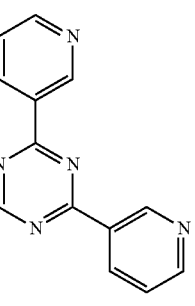
1418124-08-9
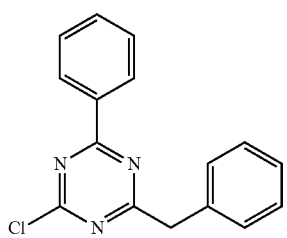
80984-77-6
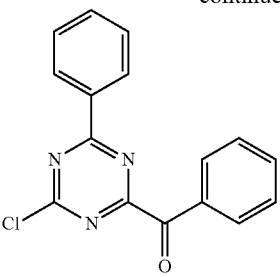
1345834-25-4
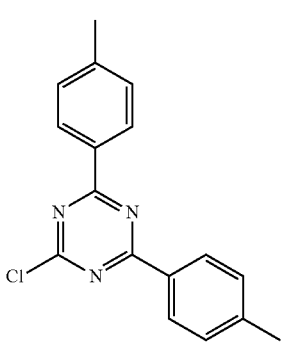
21902-34-1
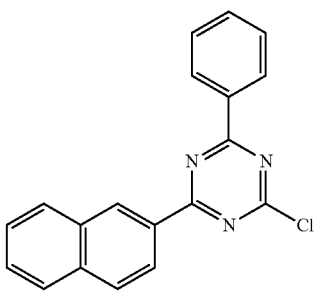
1342819-12-8
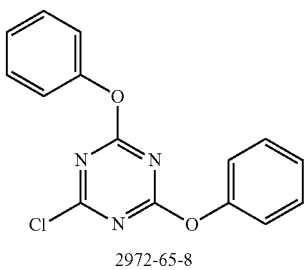
2972-65-8
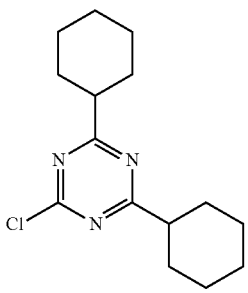
78941-35-2

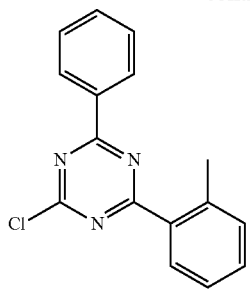
80984-76-5
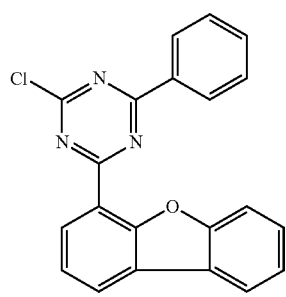
1472729-25-1
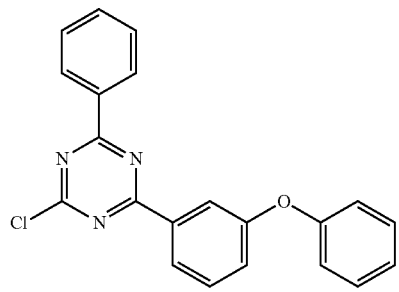
1426437-66-2
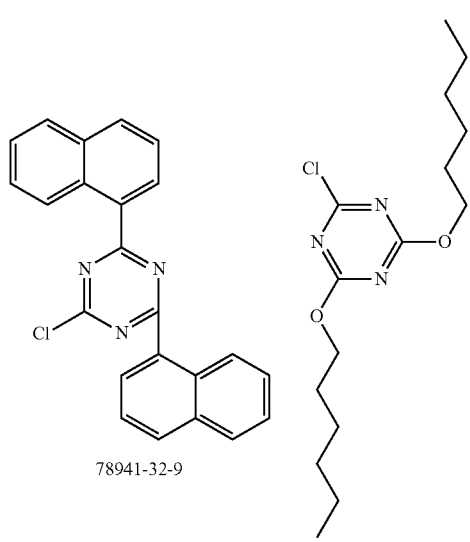
78941-32-9
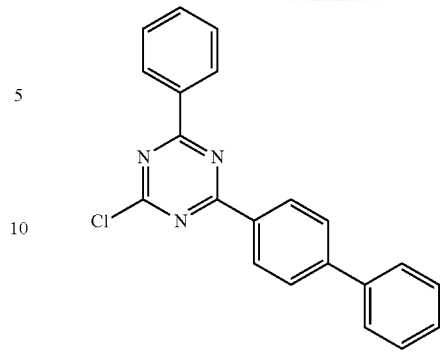
1472062-94-4
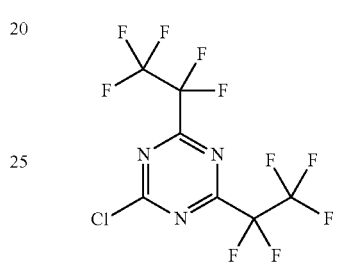
736-68-5
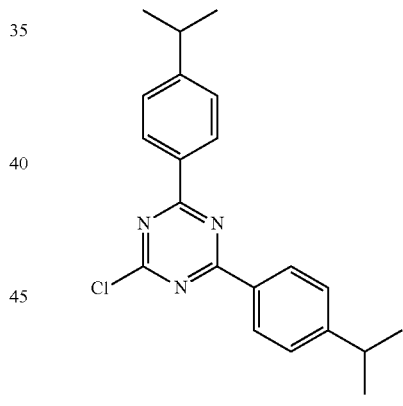
1383780-97-9
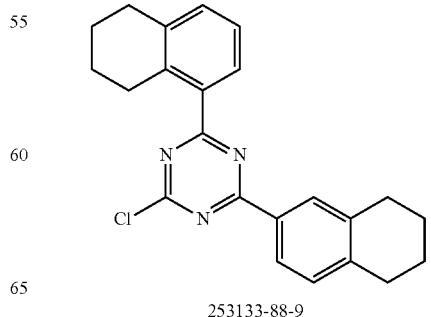
253133-88-9
38164-03-3

-continued
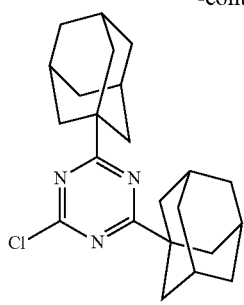
1092838-15-7
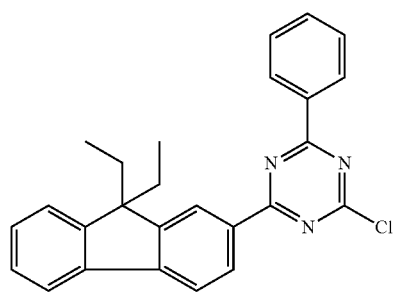
1015814-06-8
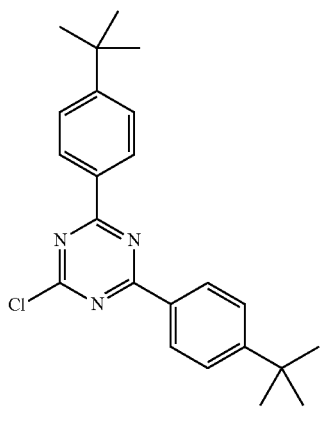
253158-13-3
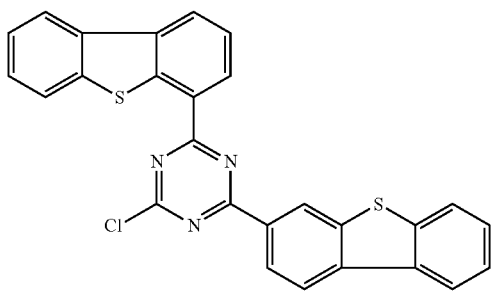
1387596-01-1
-continued
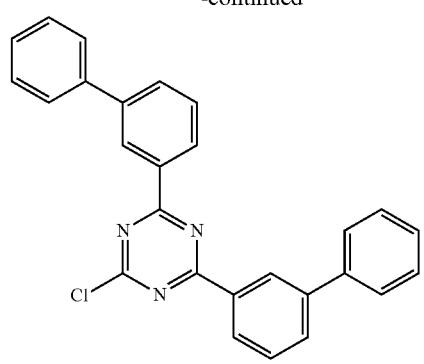
1205748-61-3
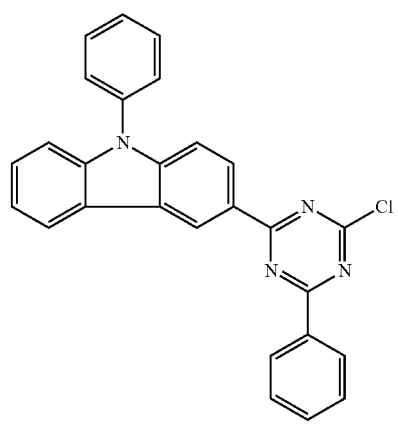
14756785-42-8
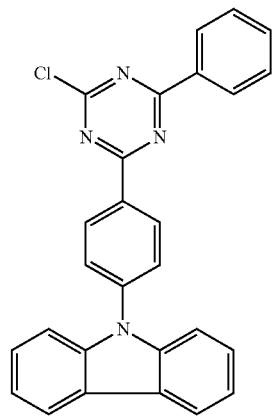
1477759-28-6
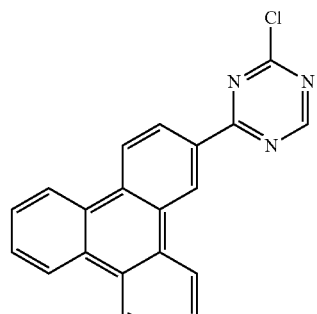
1404058-67-8

181
-continued
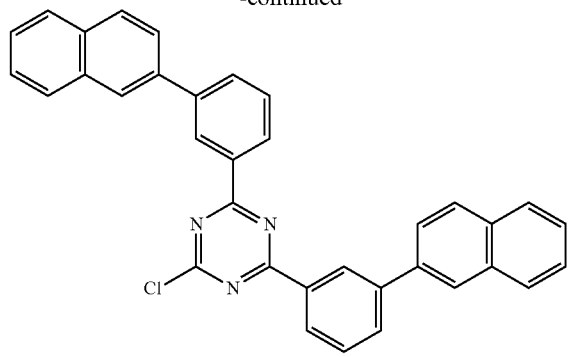
1253971-19-5
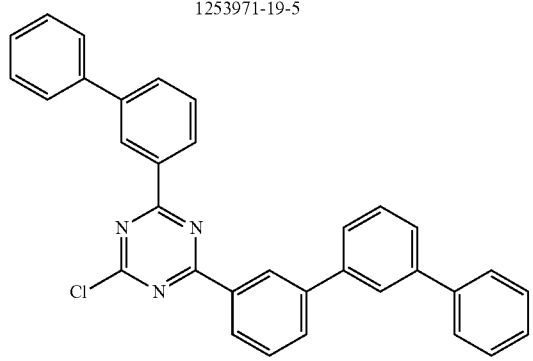
1402225-90-4
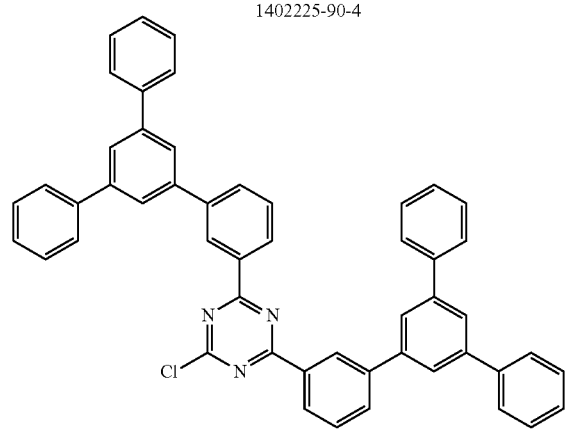
1233200-61-7
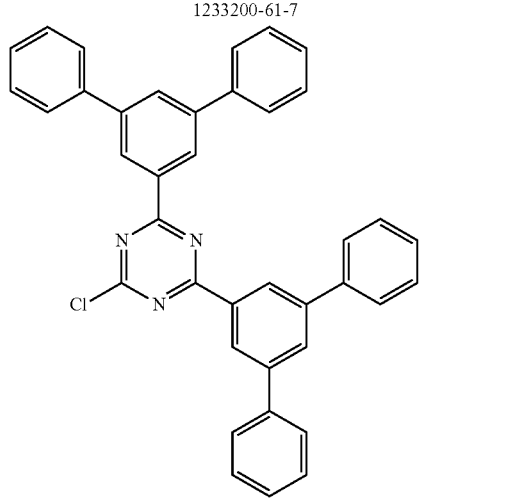
1205748-51-1
182
-continued
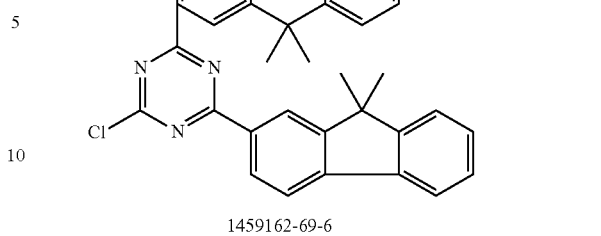
1459162-69-6
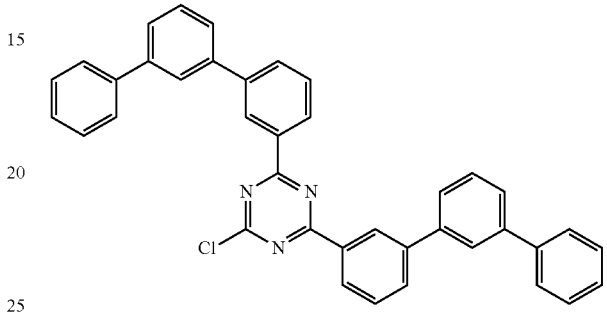
1205748-49-7
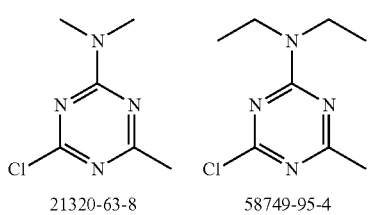
21320-63-8        58749-95-4
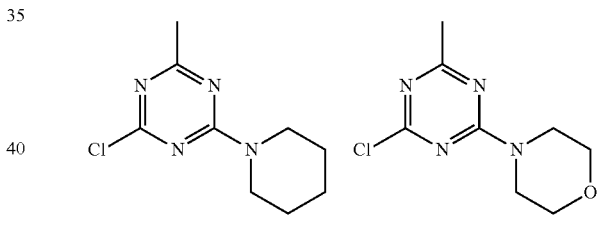
1071621-58-3        57639-20-0
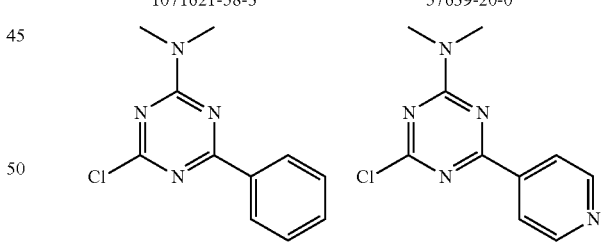
36323-70-3        36818-25-4
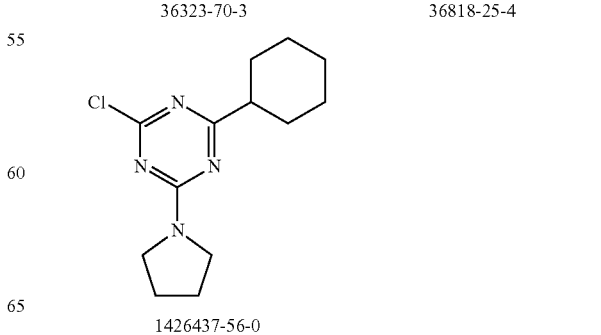
1426437-56-0

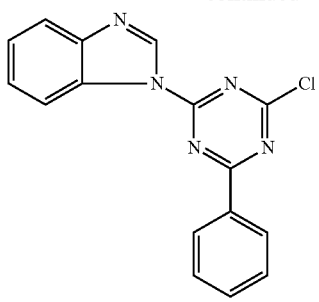
1454596-47-4
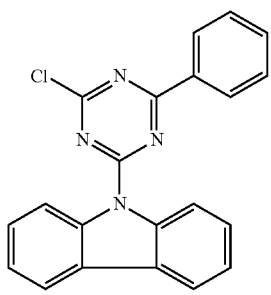
1268244-56-9
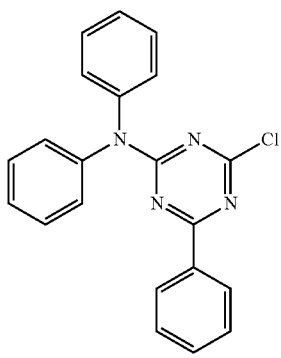
1260032-07-2
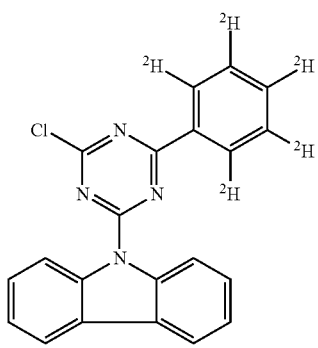
1480589-64-7
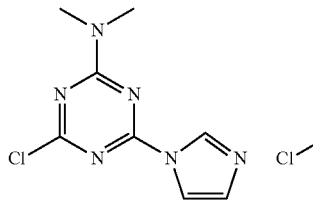
153430-09-2
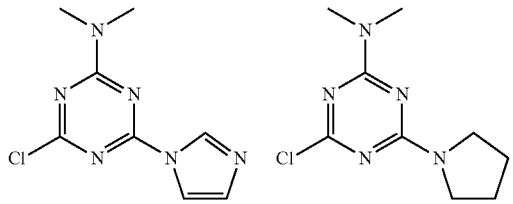
189078-42-0
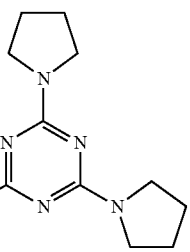
111669-20-6
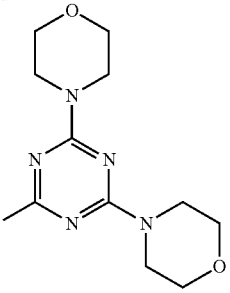
7597-22-0
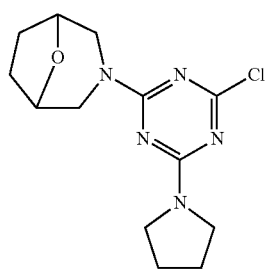
1197160-83-0
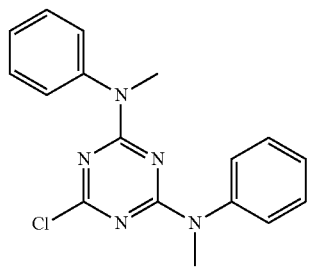
3995-43-5
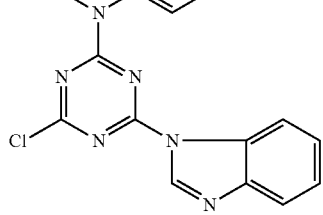
1398814-60-2
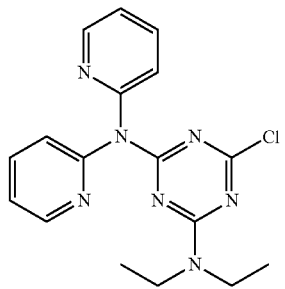
1492967-74-4

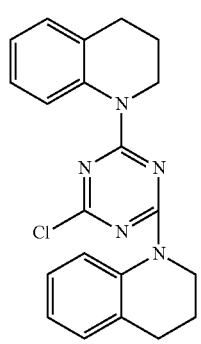
489422-72-2
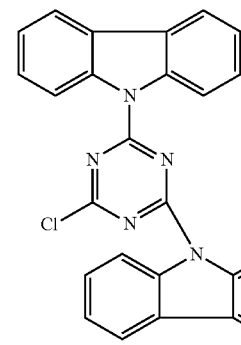
877615-05-9
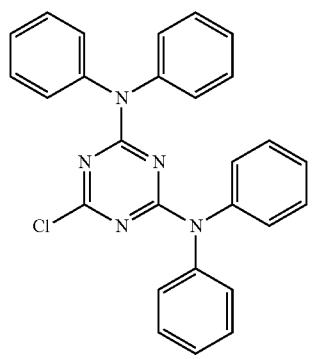
83820-01-3
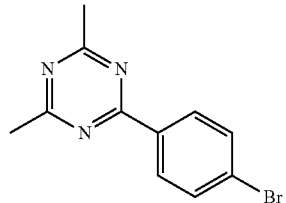
83253-21-8
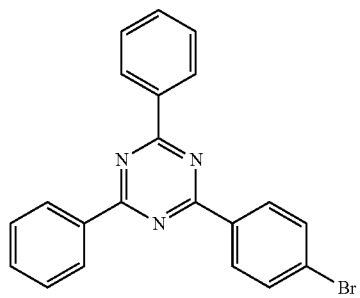
23449-08-3
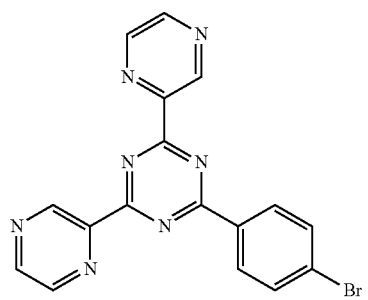
1016896-86-8
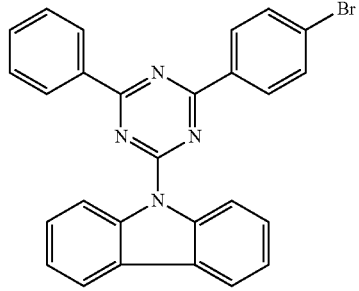
1616413-67-2
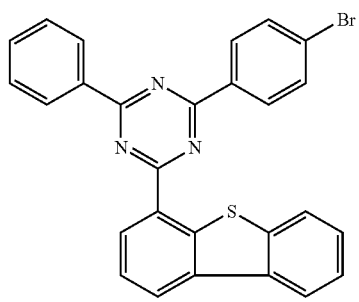
1476799-07-1
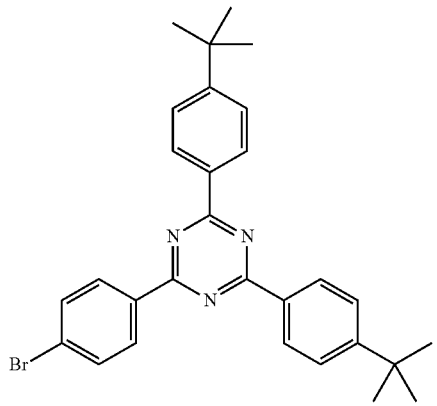
927898-18-8
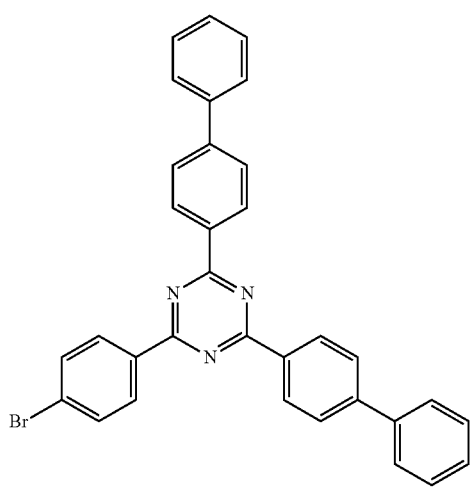
877456-11-6

-continued

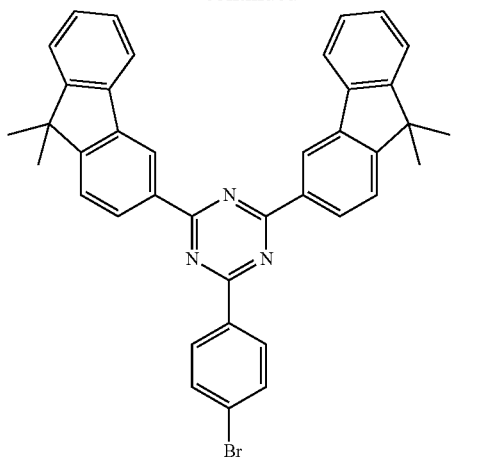
1646531-99-8

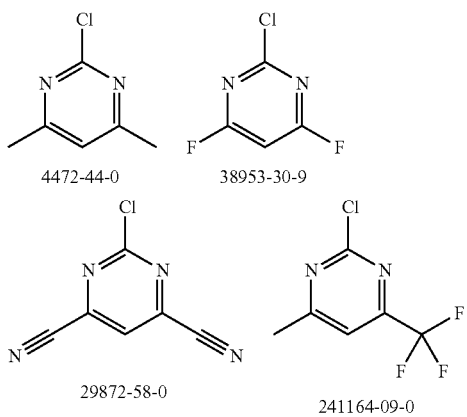
4472-44-0    38953-30-9
29872-58-0    241164-09-0
32785-40-3    701162-19-1

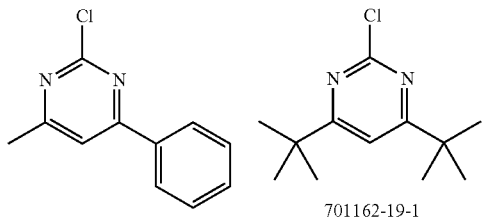
2915-16-4

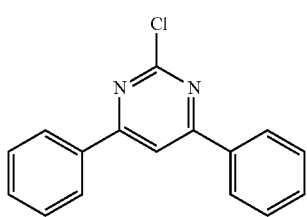
1035556-77-4

B: Synthesis of the Ligands

Example L47: 5-Bromo-2-(1,1,2,2,3,3-hexamethyl-indan-5-yl)pyridine

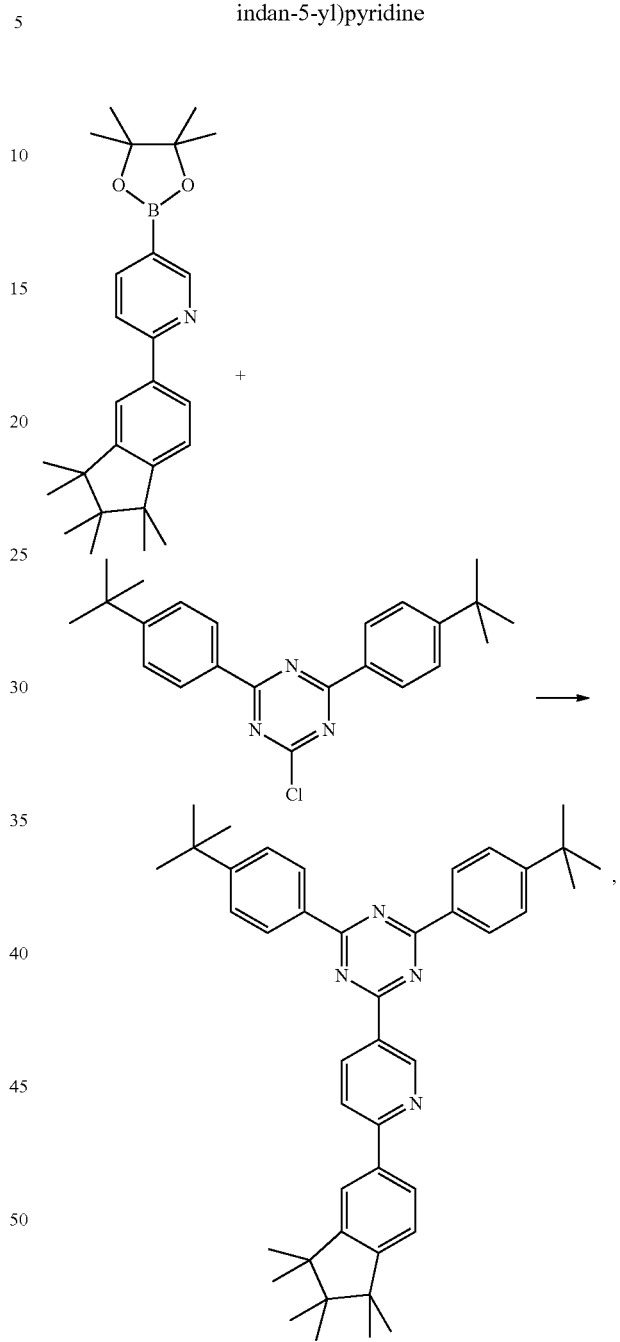

33 g (86.9 mmol) of 2,4-bis(4-tert-butylphenyl)-6-chloro-1,3,5-triazine S4, 1 g (4.5 mmol) of palladium(II) acetate, 2.7 g (8.9 mmol) of tri-o-tolylphosphine [6163-58-2], 55 g (259.4 mmol) of anhydrous potassium phosphate are weighed out for 35 g (86.3 mmol) of S2, the mixture is rendered inert, and 1 l of toluene, 500 ml of water and 500 ml of 1,4-dioxane are added. The reaction mixture s stirred under reflux for 24 h. After cooling, the reaction mixture is evaporated to dryness in a rotary evaporator, and the residue is purified by column chromatography on silica gel with toluene/heptane (1:1) as eluent. The oily residue is washed by boiling with methanol, filtered off and dried, giving 37.6 g (60.4 mmol, 70%) of a colourless solid L47.
The following ligands can furthermore be prepared analogously to the procedure:
| Synthone | S1<br>6153-86-2 | S1<br>444666-43-7 |
|---|---|---|
| Yield | 31% | 45% |
| Ligand | 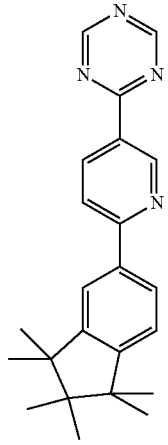<br>L1 | 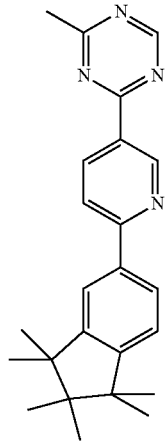<br>L2 |
| Synthone | S1<br>696-85-5 | S1<br>352440-04-1 |
|---|---|---|
| Yield | 38% | 47% |
| Ligand | 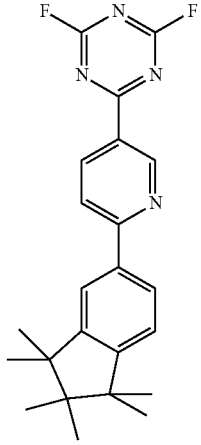<br>L5 | 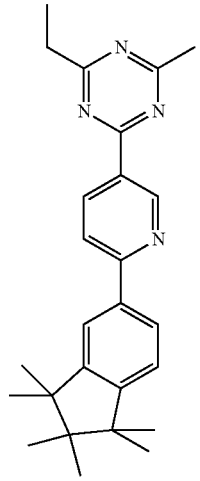<br>L6 |

|  |  |  |
|---|---|---|
| Synthone | S1<br>77007-96-6 | S1<br>0937-70-3 |
| Yield | 47% | 53% |
| Ligand | 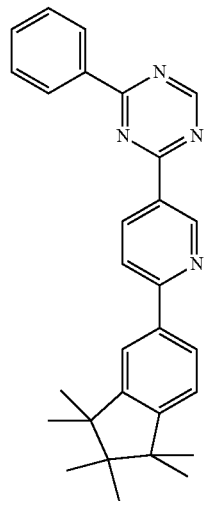<br>L9 | 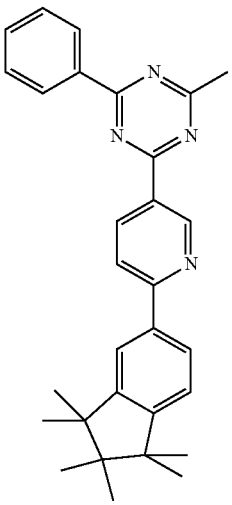<br>L10 |
|  |  |  |
|---|---|---|
| Synthone | S1<br>3140-73-6 | S1<br>911798-79-3 |
| Yield | 46% | 64% |
| Ligand | 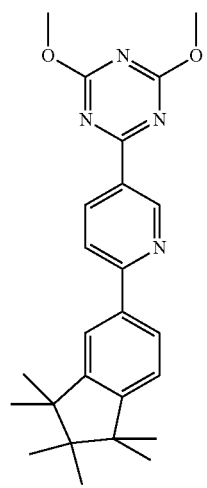<br>L13 | 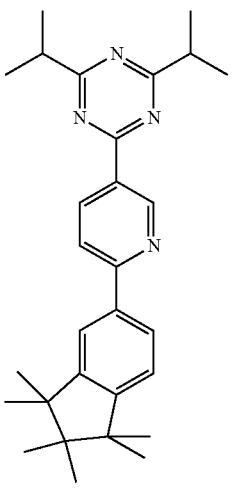<br>L14 |

| Synthone | S1<br>3842-55-5 | S1<br>91688-04-9 |
|---|---|---|
| Yield | 71% | 62% |
| Ligand | 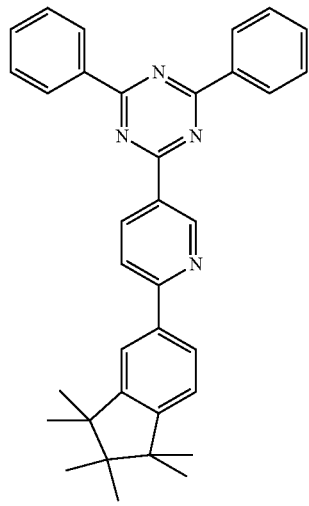<br>L17 | 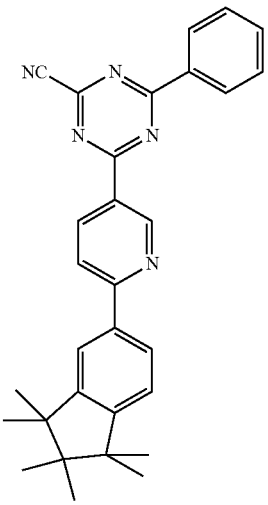<br>L18 |
| Synthone | S1<br>22404-35-9 | S1<br>36335-91-8 |
| Yield | 67% | 65% |
| Ligand | 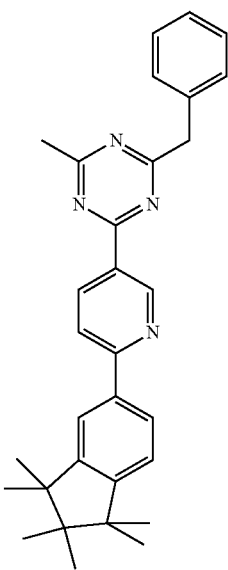<br>L21 | 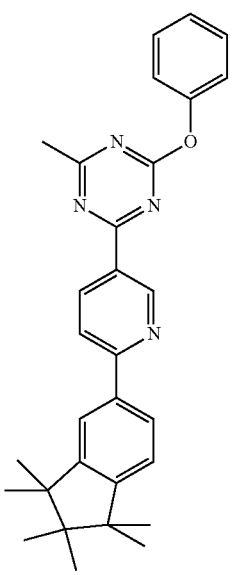<br>L22 |

| Synthone | S1 1477759-31-1 | S1 1253971-29-7 |
|---|---|---|
| Yield | 71% | 73% |
| Ligand |  L25 |  L26 |
| Synthone | S1 1418124-08-9 | S1 80984-77-6 |
|---|---|---|
| Yield | 65% | 70% |
| Ligand |  L29 | 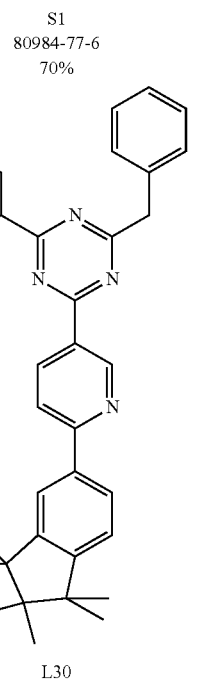 L30 |

| Synthone | S1<br>1342819-12-8 | S1<br>2972-65-8 |
|---|---|---|
| Yield | 70% | 67% |
| Ligand | 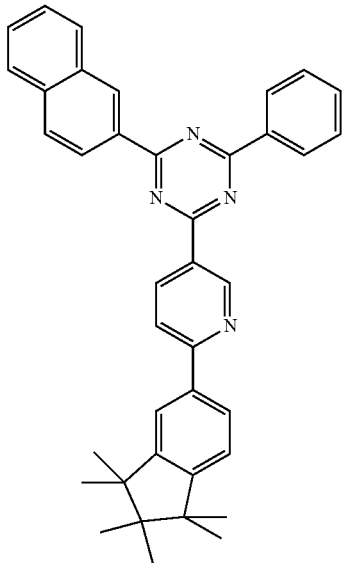<br>L33 | 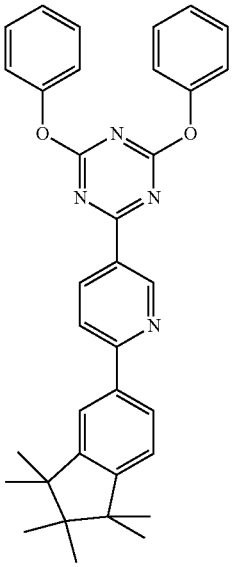<br>L34 |
| Synthone | S1<br>1472729-25-1 | S1<br>1426437-66-2 |
|---|---|---|
| Yield | 72% | 67% |
| Ligand | 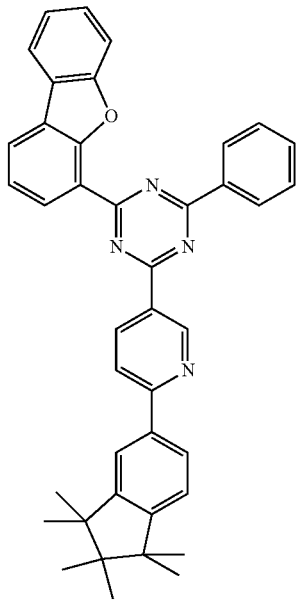<br>L37 | 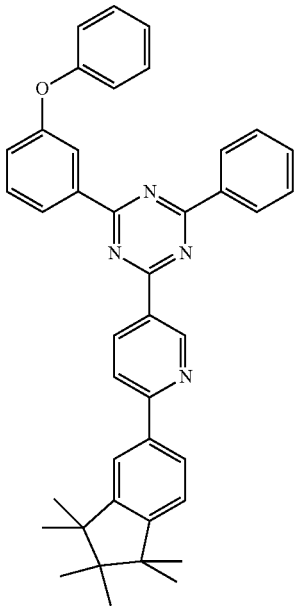<br>L38 |

| Synthone | S1 | S1 |
|---|---|---|
| | 1472062-94-4 | 736-68-5 |
| Yield | 70% | 76% |
| Ligand | 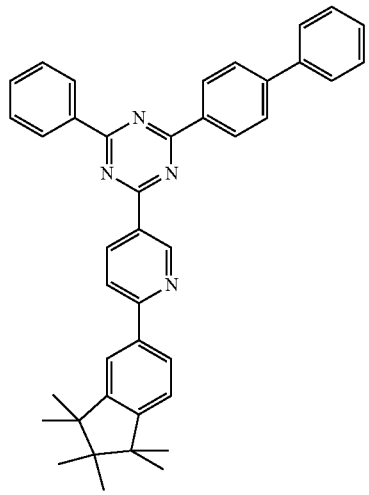 L41 | 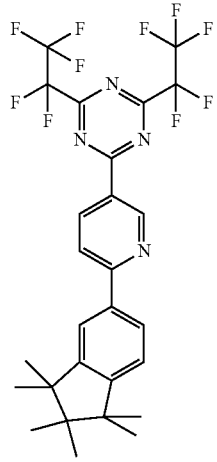 L42 |
| Synthone | S1 | S1 |
|---|---|---|
| | 1092838-15-7 | 1015814-06-8 |
| Yield | 70% | 55% |
| Ligand | 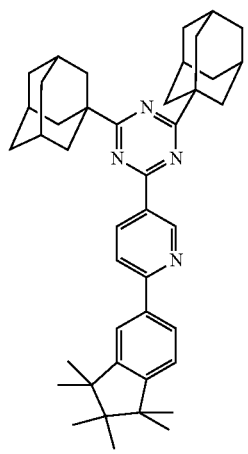 L45 | 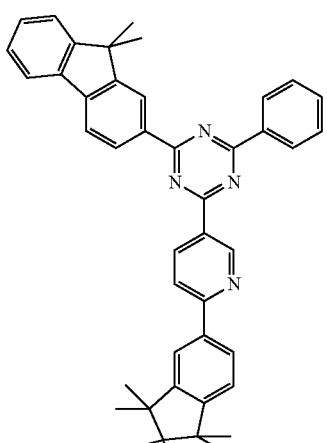 L46 |

| Synthone | S1 | S1 |
|---|---|---|
| | 1205748-61-3 | 1476785-42-8 |
| Yield | 51% | 70% |
| Ligand | 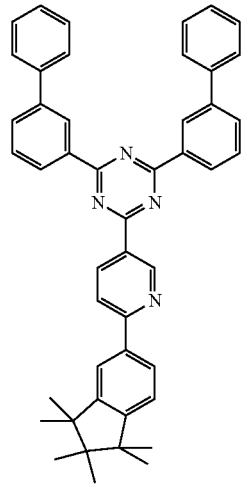 L49 | 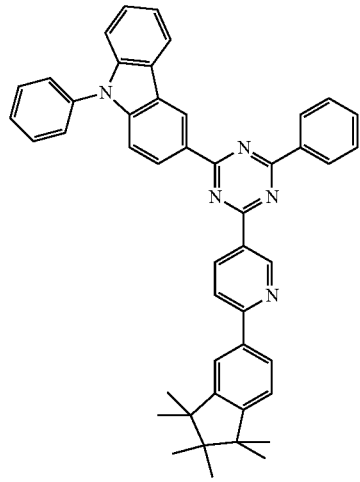 L50 |
| Synthone | S1 | S1 |
|---|---|---|
| | 1253971-19-5 | 1402225-90-4 |
| Yield | 67% | 76% |
| Ligand | 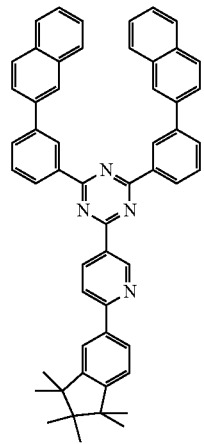 L53 | 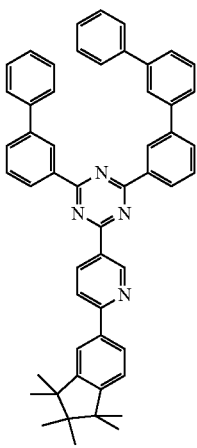 L54 |

-continued
| Synthone | S1 | S1 |
|---|---|---|
|  | 1459162-69-6 | 1205748-49-7 |
| Yield | 76% | 71% |
| Ligand | 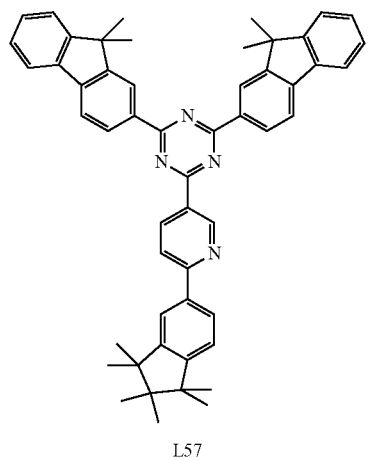 L57 | 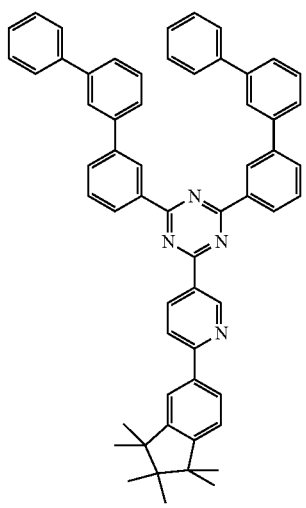 L58 |
| Synthone | S1 | S1 |
|---|---|---|
|  | 1071621-58-3 | 57639-20-0 |
| Yield | 58% | 55% |
| Ligand | 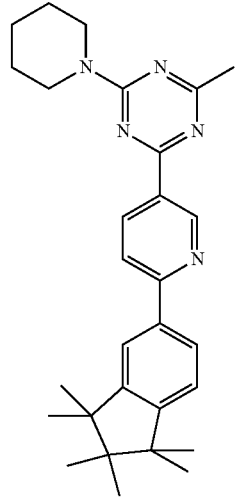 L61 | 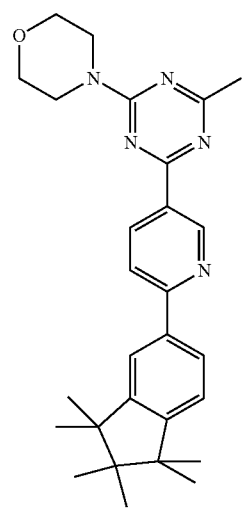 L62 |

| Synthone | S1 1426437-56-0 | S1 1454596-47-4 |
|---|---|---|
| Yield | 61% | 52% |
| Ligand | 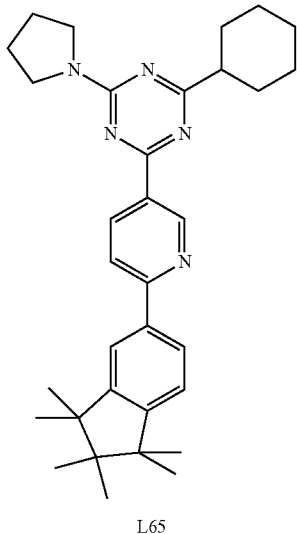 [SMILES: CC1(C)c2ccc(-c3ccc(-c4nc(C5CCCCC5)nc(N5CCCC5)n4)cn3)cc2C(C)(C)C1(C)C] L65 | 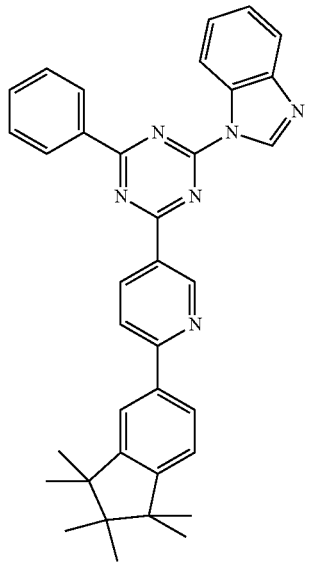 L66 |
| Synthone | S1 1480589-64-7 | S1 153430-09-2 |
| Yield | 72% | 44% |
| Ligand | 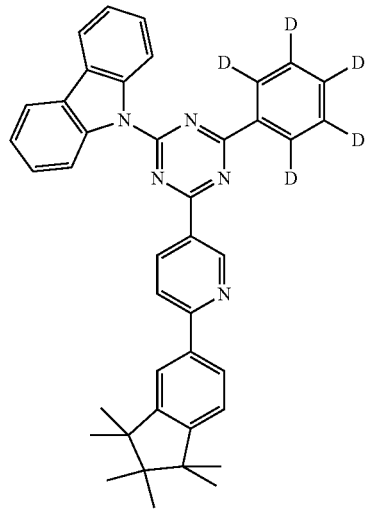 L69 | 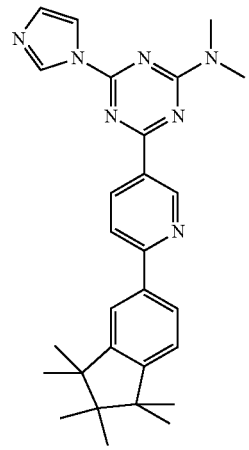 L70 |

| Synthone | S1 7597-22-0 | S1 1197160-83-0 |
|---|---|---|
| Yield | 55% | 59% |
| Ligand | | |
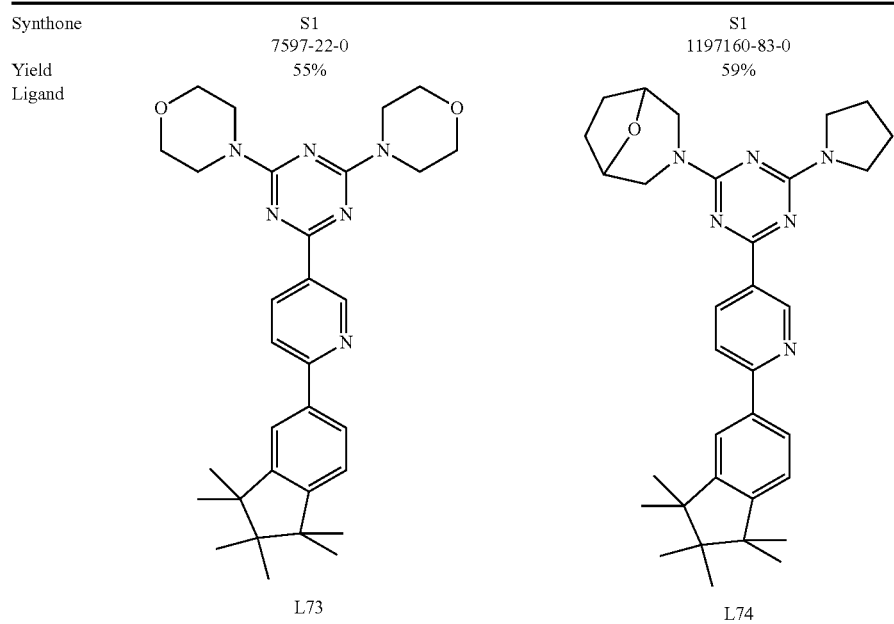
| | L73 | L74 |
|---|---|---|
| Synthone | S1 1492967-74-4 | S1 489422-72-2 |
|---|---|---|
| Yield | 61% | 59% |
| Ligand | | |
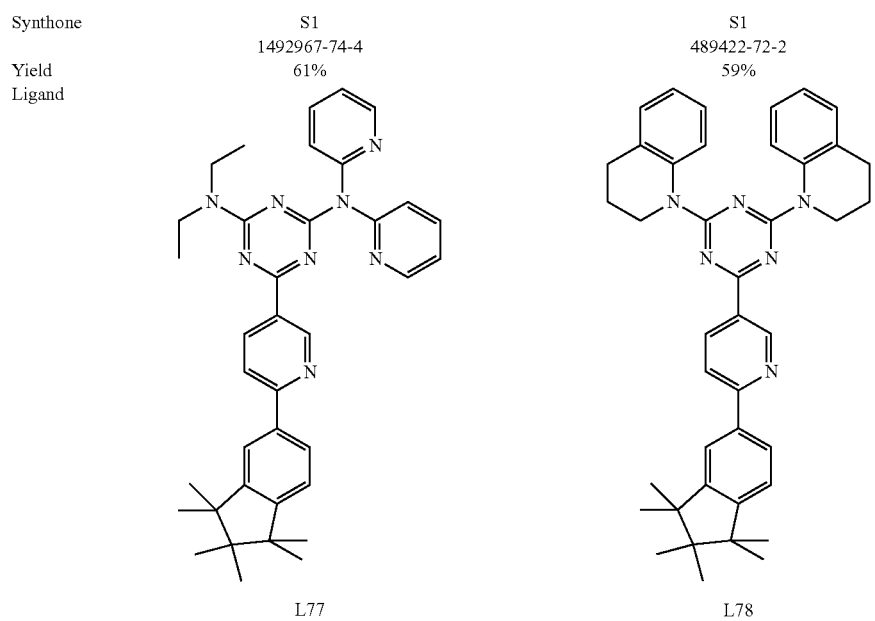
| | L77 | L78 |
|---|---|---|

| Synthone | S1 83253-21-8 | S1 23449-08-3 |
|---|---|---|
| Yield | 81% | 84% |
| Ligand | 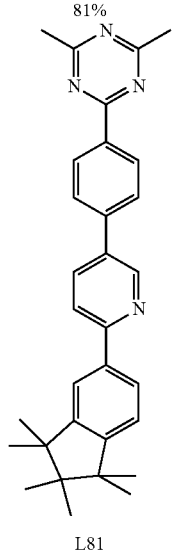 L81 | 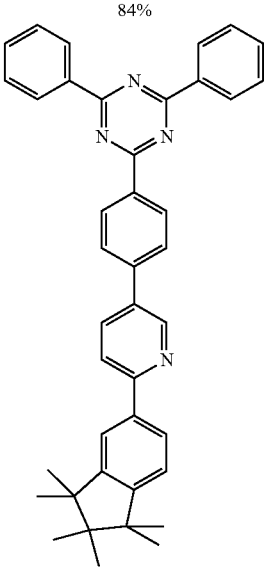 L82 |
| Synthone | S1 1476799-07-1 | S1 927898-18-8 |
|---|---|---|
| Yield | 85% | 77% |
| Ligand | 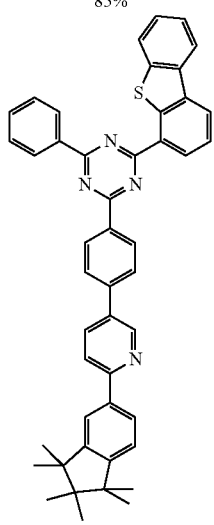 L85 | 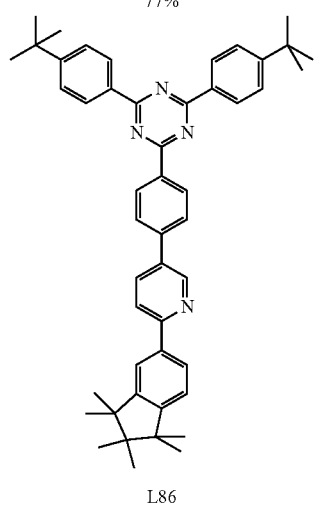 L86 |

| | | |
|---|---|---|
| Synthone | S1<br>4472-44-0 | S1<br>38953-30-9 |
| Yield | 66% | 52% |
| Ligand | 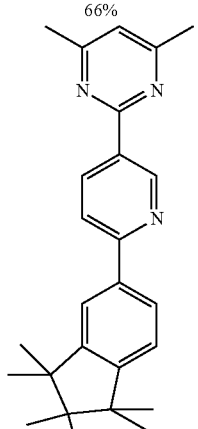<br>L89 | 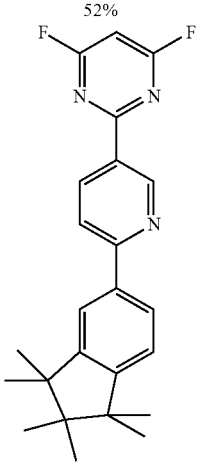<br>L90 |
| Synthone | S1<br>71162-19-1 | S1<br>3278540-3 |
| Yield | 66% | 69% |
| Ligand | 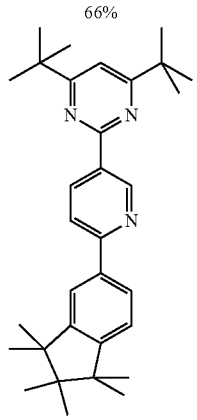<br>L93 | 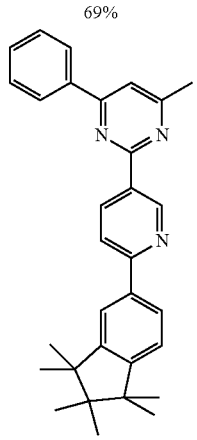<br>L94 |
| Synthone | S2<br>30894-84-9 | S2<br>696-85-5 |
| Yield | 58% | 51% |
| Ligand | 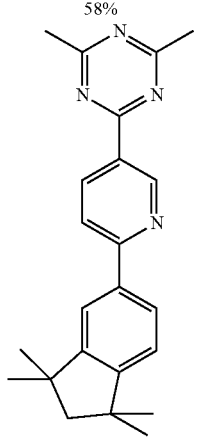<br>L97 | 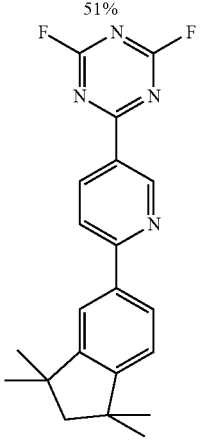<br>L98 |

| Synthone | S2 | S2 |
|---|---|---|
| | 3842-55-5 | 78941-35-2 |
| Yield | 74% | 71% |
| Ligand | 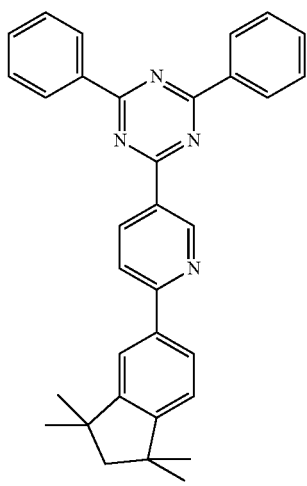 | 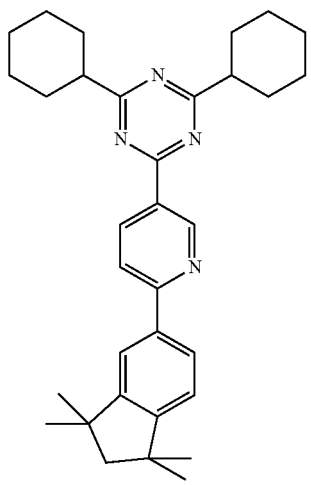 |
| | L101 | L102 |
| Synthone | S2 | S2 |
|---|---|---|
| | 253158-13-3 | 1476785-42-8 |
| Yield | 74% | 71% |
| Ligand | 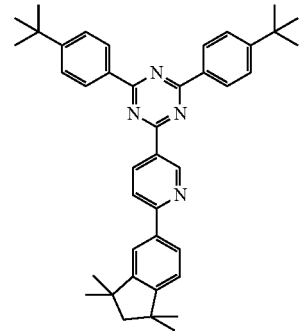 | 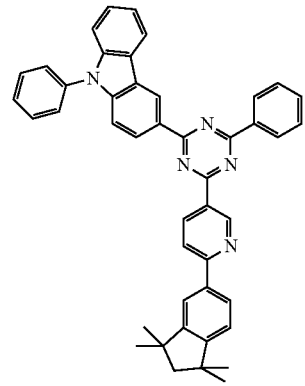 |
| | L105 | L106 |

| Synthone | S2<br>1205748-49-7 | S2<br>36323-70-3 |
|---|---|---|
| Yield | 70% | 66% |
| Ligand | 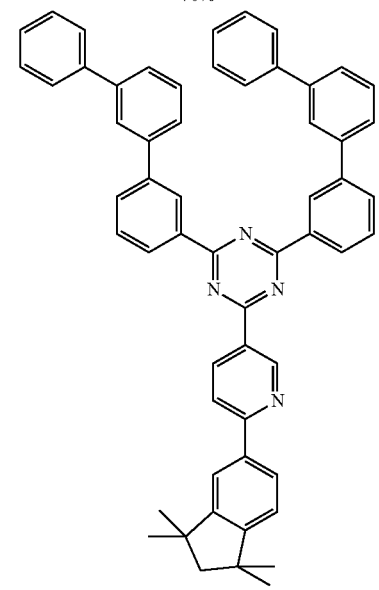<br>L109 | 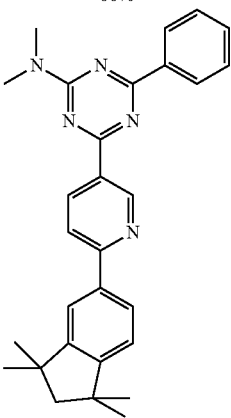<br>L110 |
| Synthone | S2<br>1260032-07-2 | S2<br>927898-18-8 |
|---|---|---|
| Yield | 74% | 78% |
| Ligand | 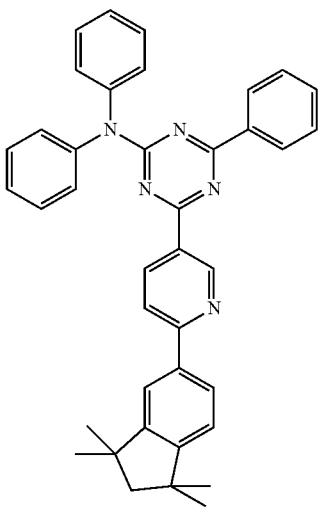<br>L113 | 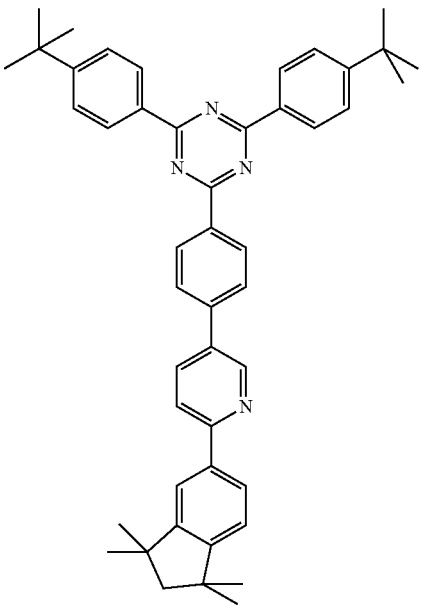<br>L114 |

-continued
| Synthone | S3 | S3 |
| --- | --- | --- |
|  | 253158-13-3 | 73084-03-4 |
| Yield | 75% | 73% |
| Ligand | | |
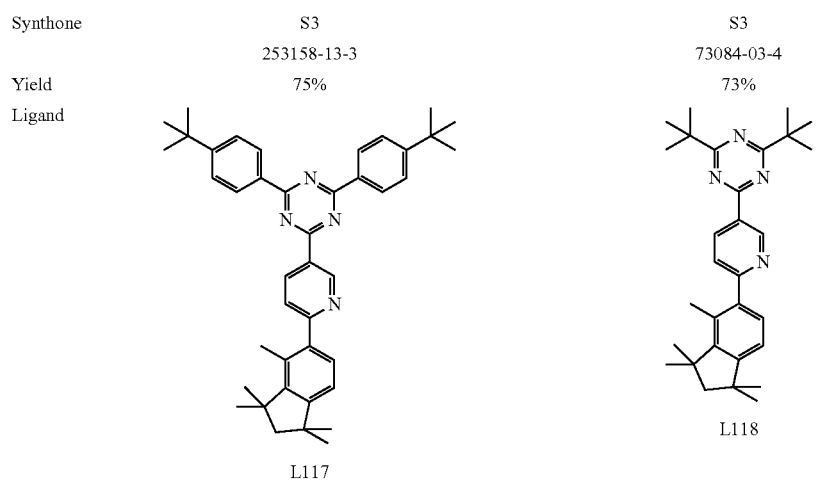
L117    L118
| Synthone | S5 | S |
| --- | --- | --- |
|  | 253158-13-3 | 73084-03-4 |
| Yield | 77% | 82% |
| Ligand | | |
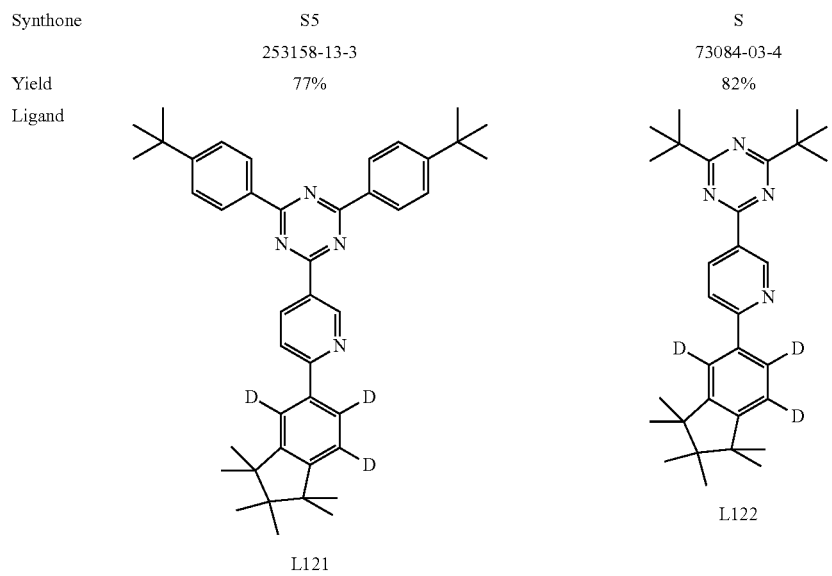
L121    L122

| Synthone | S7 1205748-49-7 | S7 0937-70-3 |
|---|---|---|
| Yield | 73% | 66% |
| Ligand | 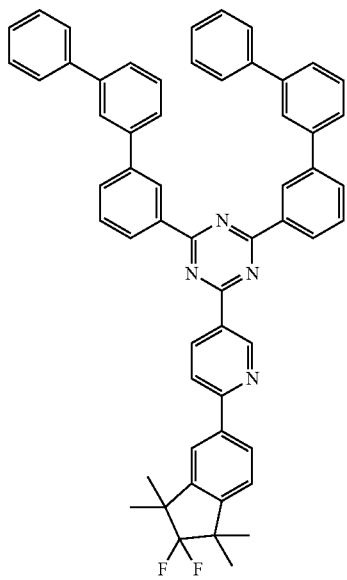 L125 | 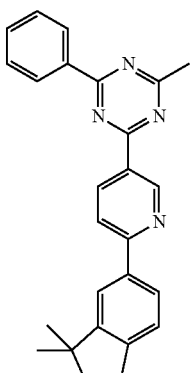 L126 |
| Synthone | S9 1260032-07-2 | S9 71162-19-1 |
|---|---|---|
| Yield | 71% | 69% |
| Ligand | 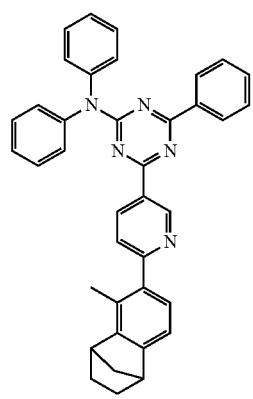 L129 | 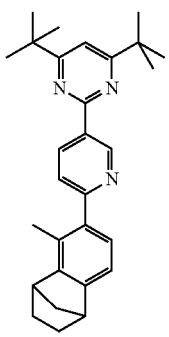 L130 |

-continued
| | | |
|---|---|---|
| Synthone | S11<br>3842-55-5 | S11<br>78941-35-2 |
| Yield | 66% | 73% |
| Ligand | 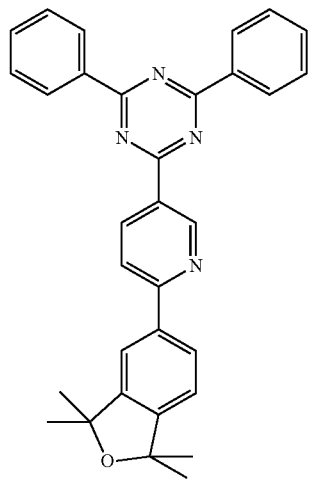<br>L133 | 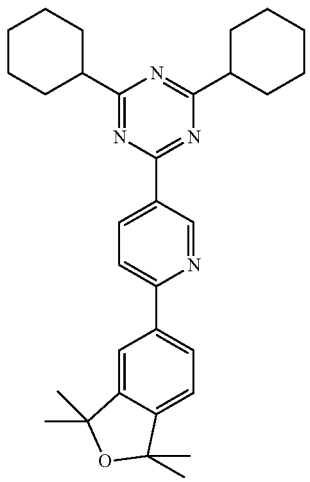<br>L134 |
| Synthone | S13<br>472729-25-1 | S13<br>1205748-49-7 |
| Yield | 70% | 68% |
| Ligand | 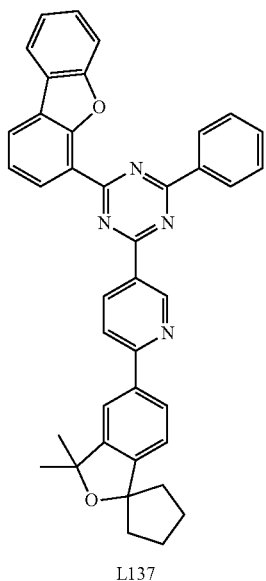<br>L137 | 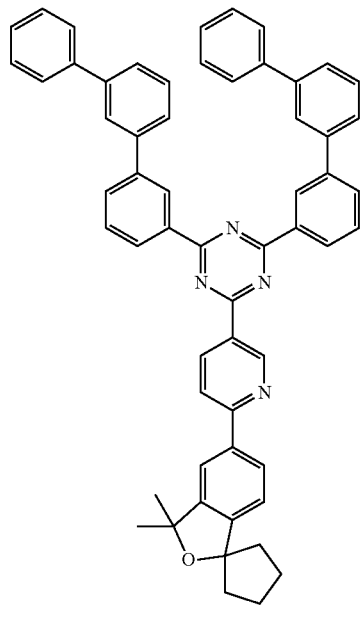 [SMILES: CC1(C)CC(C)(C)c2cc(-c3ccc(-c4nc(-c5cccc(-c6cccc(-c7ccccc7)c6)c5)nc(-c5cccc(-c6cccc(-c7ccccc7)c6)c5)n4)cn3)ccc21]<br>L138 |

-continued
| Synthone | S15 | S15 |
|---|---|---|
|  | 1260032-07-2 | 927898-18-8 |
| Yield | 73% | 83% |
| Ligand | 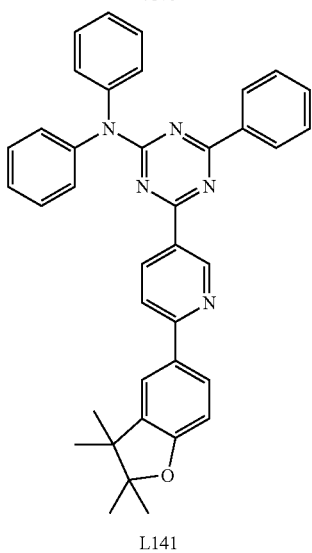 L141 | 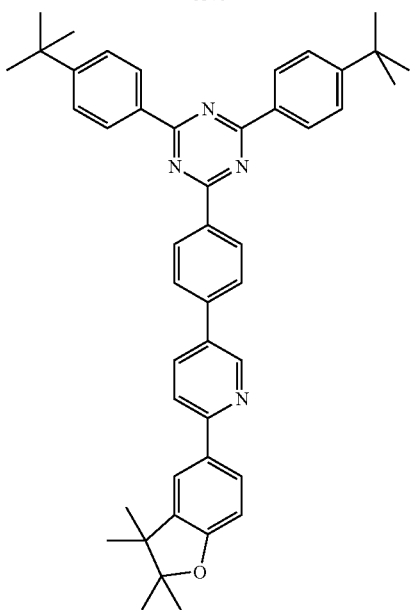 L142 |
| Synthone | S17 | S17 |
|---|---|---|
|  | 73084-03-4 | 253158-13-3 |
| Yield | 72% | 75% |
| Ligand | 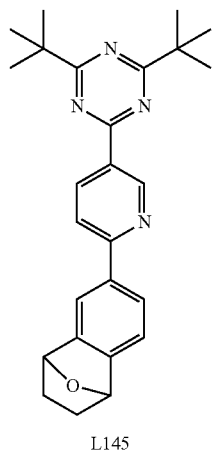 L145 | 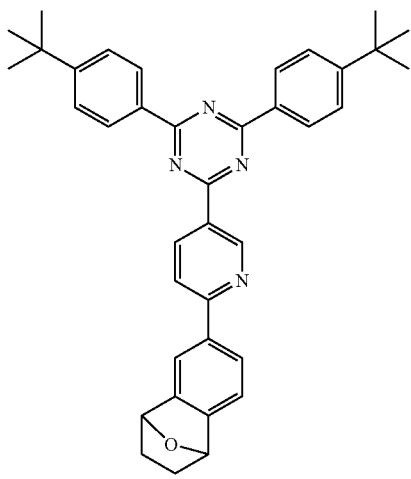 L146 |

-continued
| Synthone | S19<br>696-85-5 | S19<br>1383780-97-9 |
|---|---|---|
| Yield | 57% | 79% |
| Ligand | 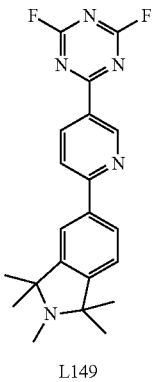 [SMILES: CN1C(C)(C)c2ccc(-c3ccc(-c4nc(F)nc(F)n4)cn3)cc2C1(C)C]<br>L149 | 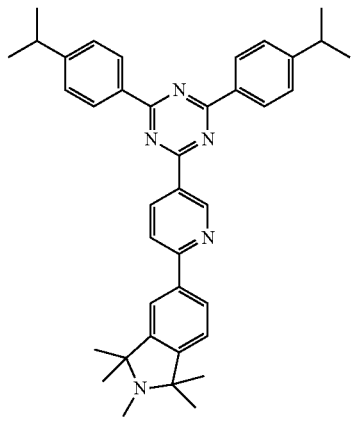<br>L150 |
| Synthone | S21<br>73084-03-4 | S21<br>253158-13-3 |
| Yield | 65% | 61% |
| Ligand | 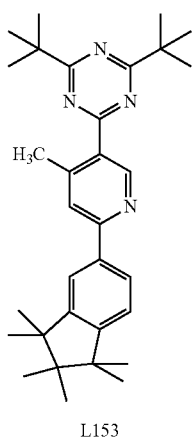 [SMILES: Cc1cc(-c2ccc3c(c2)C(C)(C)C(C)(C)C3(C)C)ncc1-c1nc(C(C)(C)C)nc(C(C)(C)C)n1]<br>L153 | 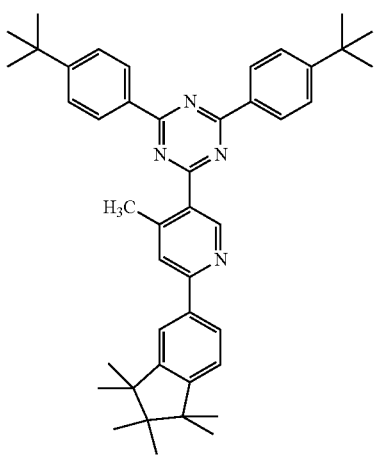<br>L154 |
| Synthone | S23<br>253158-13-3 | S23<br>32785-40-3 |
| Yield | 61% | 57% |
| Ligand | 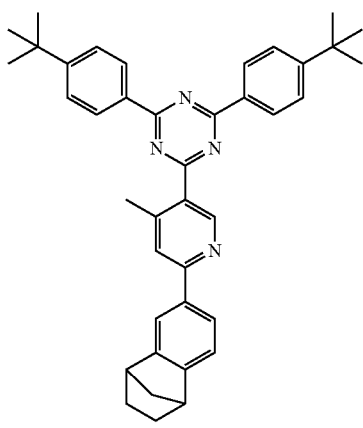<br>L157 | 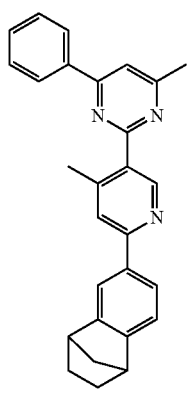<br>L158 |

| Synthone | S25 | S25 |
|---|---|---|
| | 1472729-25-1 | 1233200-61-7 |
| Yield | 59% | 55% |
| Ligand | 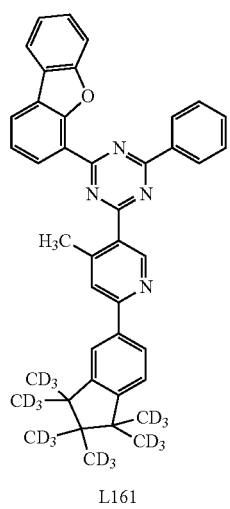 L161 | 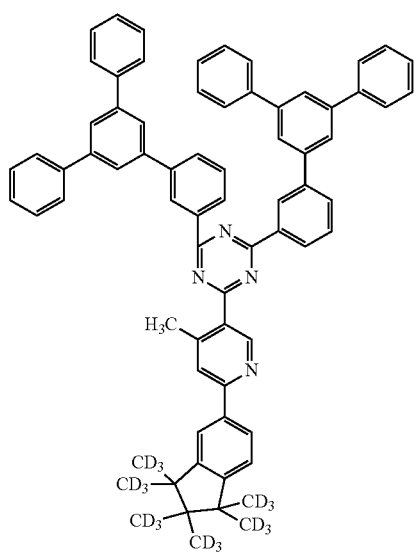 L162 |
| Synthone | S27 | S27 |
|---|---|---|
| | 1398814-60-2 | 253158-13-3 |
| Yield | 45% | 56% |
| Ligand | 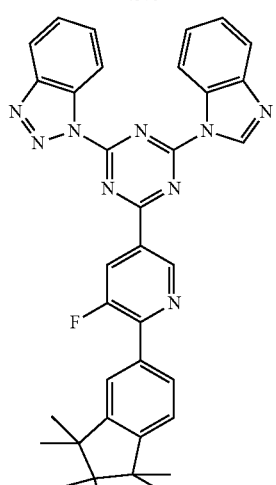 L165 | 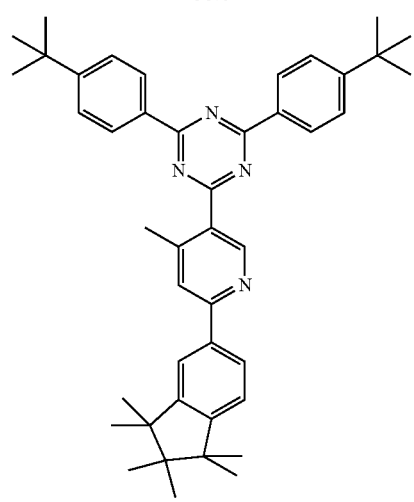 L166 |

-continued
| Synthone | S29 | S29 |
|---|---|---|
| | 3842-55-5 | 71162-19-1 |
| Yield | 63% | 67% |
| Ligand | 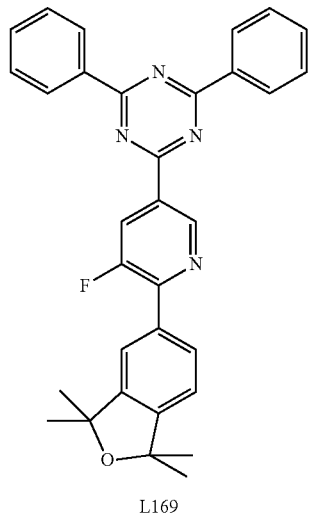 | 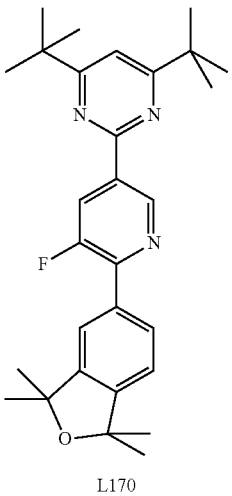 |
| | L169 | L170 |
| Synthone | S31 | S31 |
| | 696-85-5 | 36323-70-3 |
| Yield | 49% | 55% |
| Ligand | 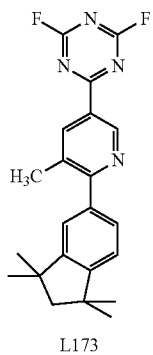 | 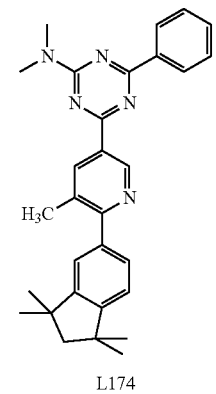 |
| | L173 | L174 |
| Synthone | S33 | S33 |
| | 399543-5 | 489422-72-2 |
| Yield | 62% | 71% |
| Ligand | 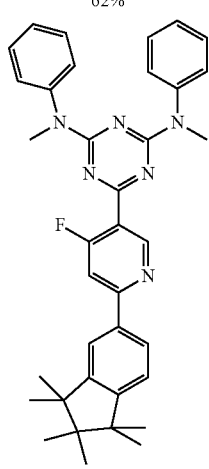 | 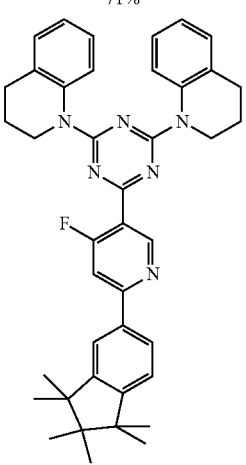 |
| | L177 | L178 |

| Synthone | S35 | S35 |
|---|---|---|
|  | 73084-03-4 | 1233200-61-7 |
| Yield | 55% | 61% |
| Ligand | 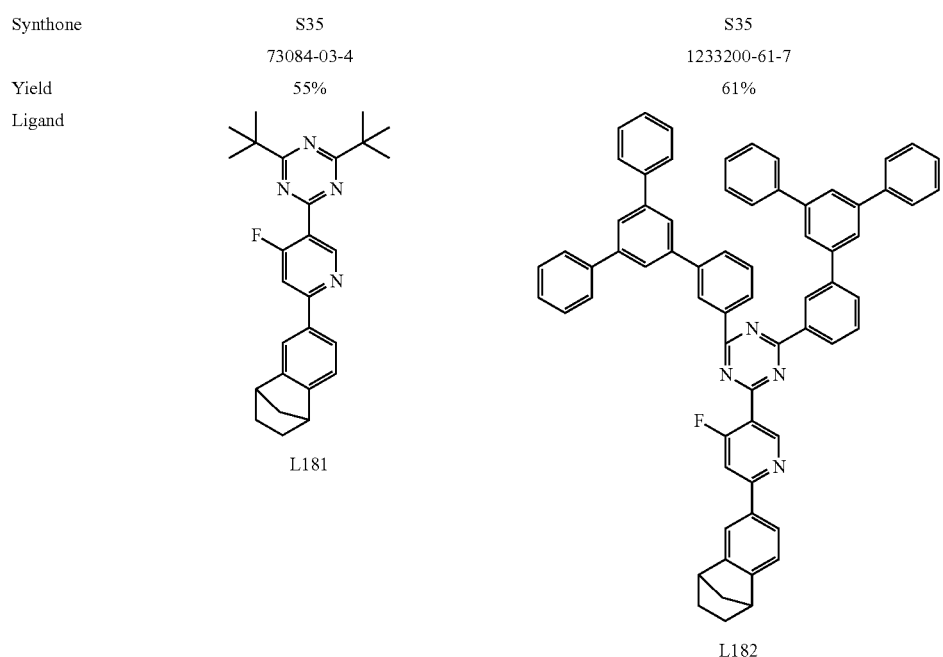 | |
L181
L182
| Synthone | S37 | S37 |
|---|---|---|
|  | 1260032-07-2 | 1477759-28-6 |
| Yield | 57% | 52% |
| Ligand | 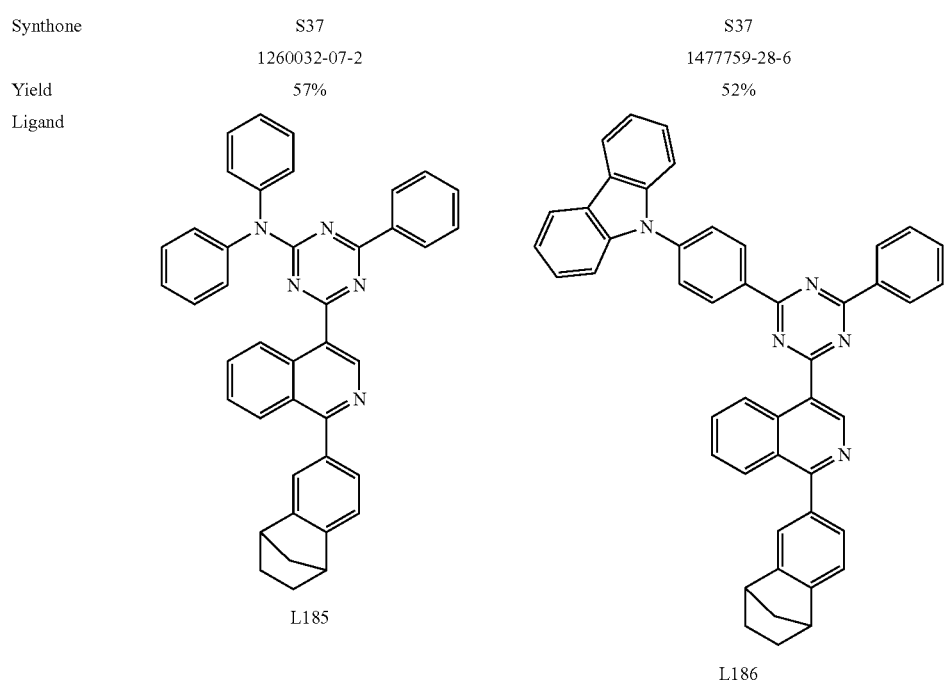 | |
L185
L186

| Synthone | S39 | S39 |
|---|---|---|
| | 1646531-99-8 | 29872-58-0 |
| Yield | 81% | 47% |
| Ligand | 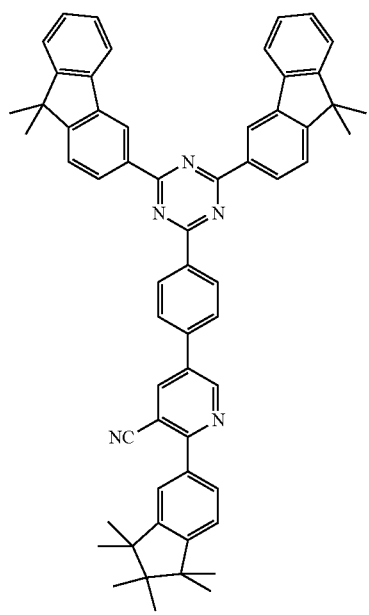 L189 | 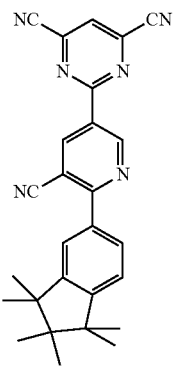 L190 |
| Synthone | S41 | S41 |
|---|---|---|
| | 1383780-97-9 | 1477759-28-6 |
| Yield | 67% | 63% |
| Ligand | 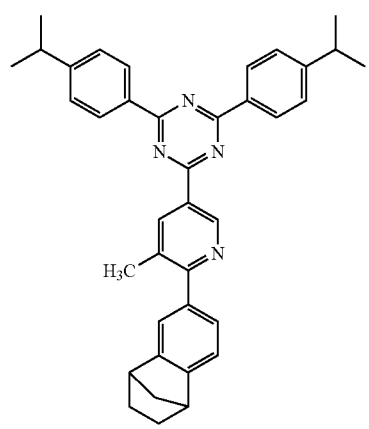 L193 | 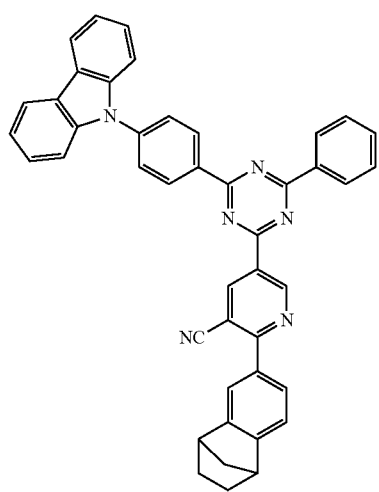 L194 |

-continued
| Synthone | S43 | S43 |
|---|---|---|
|  | 489422-72-2 | 71162-19-1 |
| Yield | 67% | 68% |
| Ligand | 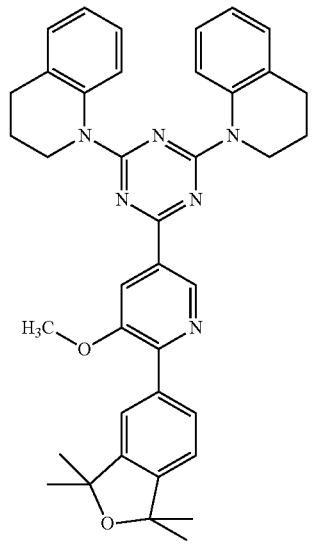 L197 | 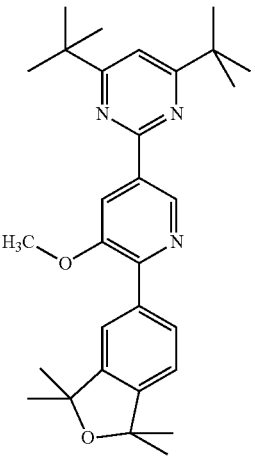 L198 |
| Synthone | S45 | S45 |
|---|---|---|
|  | 83253-21-8 | 253158-13-3 |
| Yield | 55% | 47% |
| Ligand | 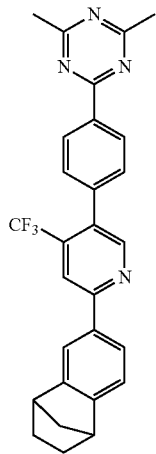 L201 | 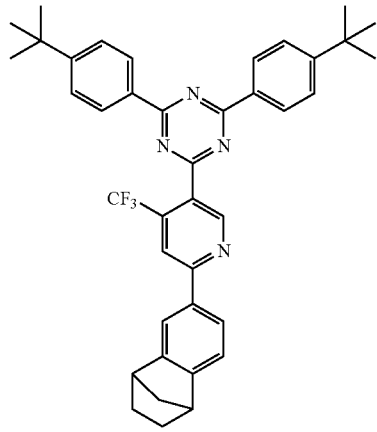 L202 |

-continued
| Synthone | S47 | S47 |
|---|---|---|
| | 1454596-47-4 | 1454596-47-4 |
| Yield | 64% | 64% |
| Ligand | 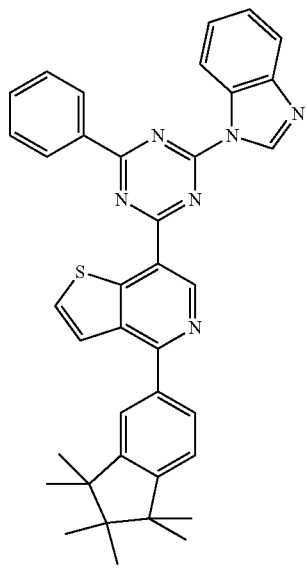 L205 | 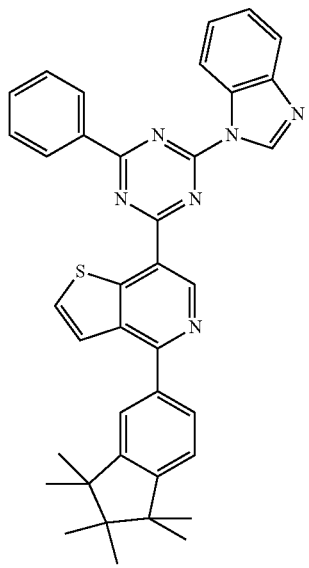 L206 |
| Synthone | S49 | S49 |
|---|---|---|
| | 1459162-69-6 | 36818-25-4 |
| Yield | 56% | 62% |
| Ligand | 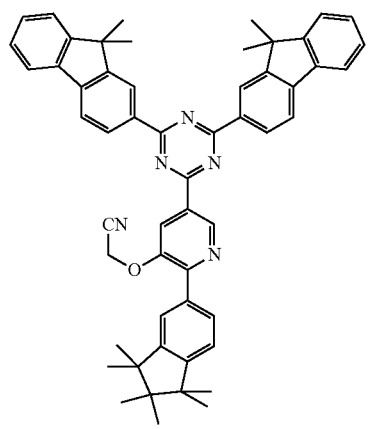 L209 | 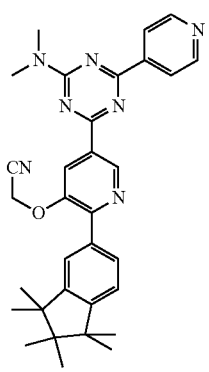 L210 |

| Synthone | S51 | S51 |
|---|---|---|
| | 3842-55-5 | 78941-35-2 |
| Yield | 39% | 40% |
| Ligand | | |
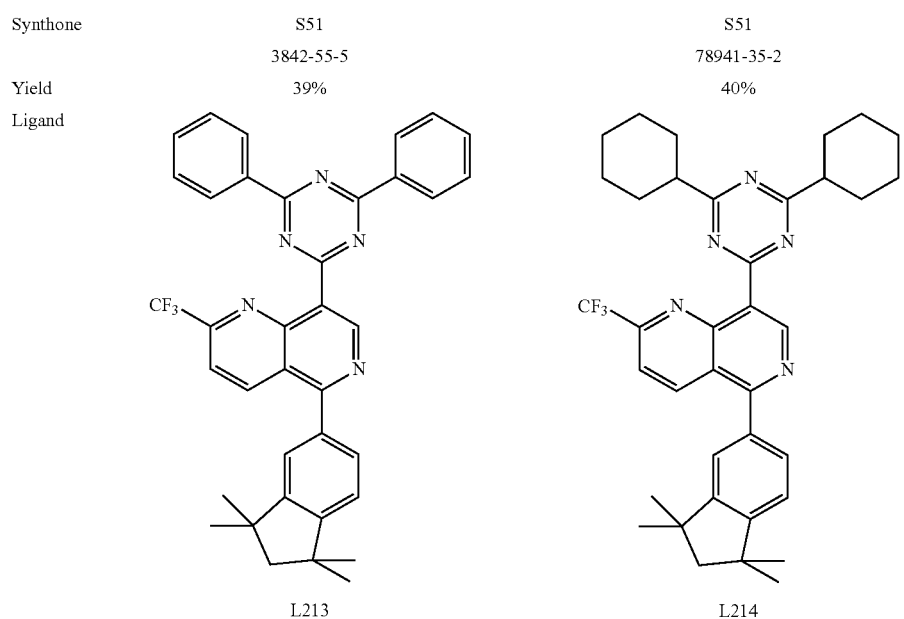
L213        L214
| Synthone | S53 | S53 |
|---|---|---|
| | 71162-19-1 | 83253-21-8 |
| Yield | 59% | 68% |
| Ligand | | |
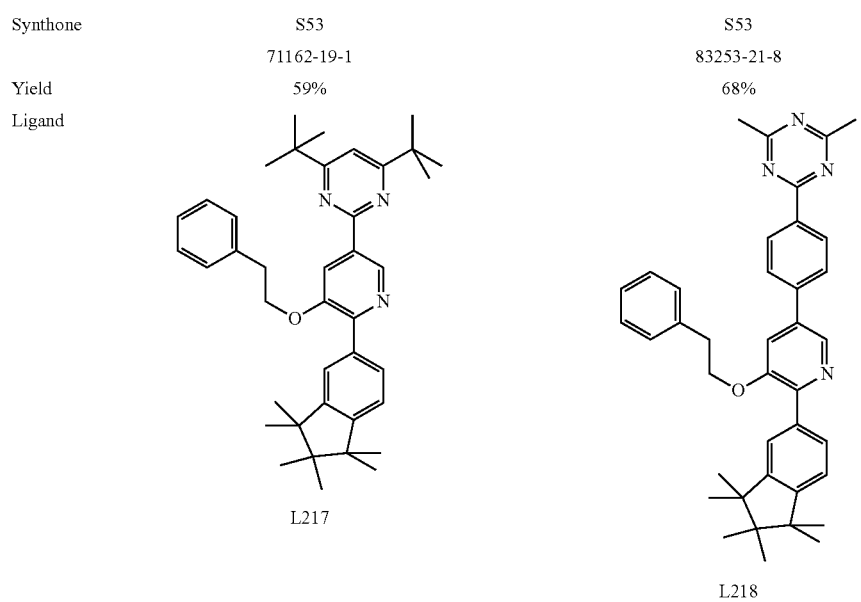
L217        L218

| Synthone | S55 | S55 |
|---|---|---|
| | 1383780-97-9 | 489422-72-2 |
| Yield | 63% | 65% |
| Ligand | 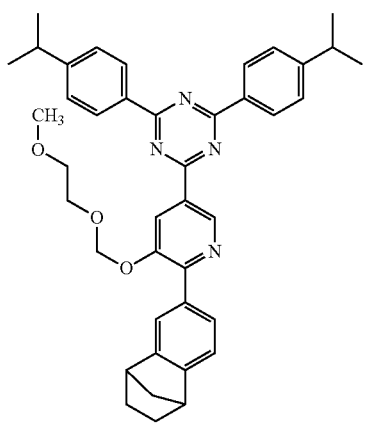<br>L221 | 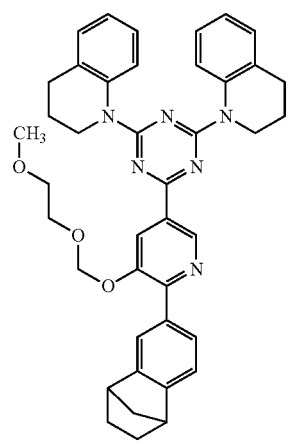<br>L222 |
| Synthone | S1 | S1 |
|---|---|---|
| | 1451154-67-8 | 30894-84-9 |
| Yield | 35% | 45% |
| Ligand | 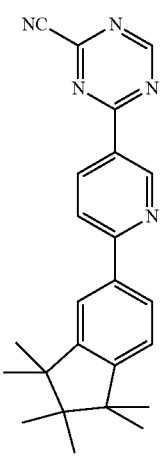<br>L3 | 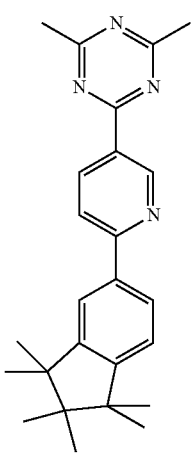<br>L4 |

| | | |
|---|---|---|
| Synthone | S1<br>27676-51-3 | S1<br>80587-76-4 |
| Yield | 41% | 31% |
| Ligand | 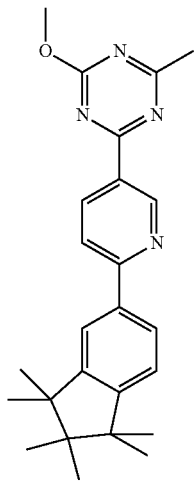<br>L7 | 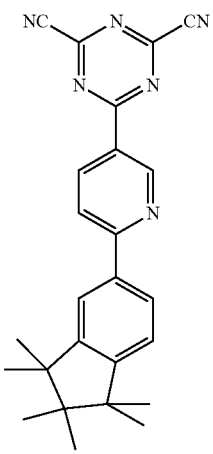<br>L8 |
| Synthone | S1<br>701-77-9 | S1<br>333737-07-8 |
| Yield | 49% | 39% |
| Ligand | 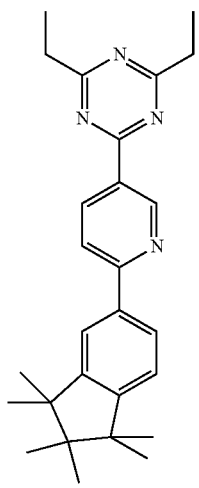<br>L11 | 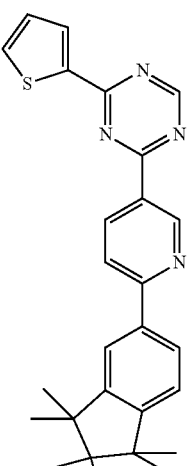<br>L12 |

| Synthone | S1 | S1 |
|---|---|---|
| | 73084-03-4 | 1092838-33-9 |
| Yield | 62% | 65% |
| Ligand | 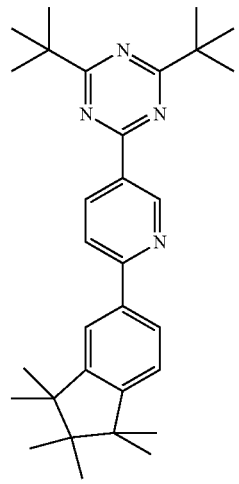 L15 | 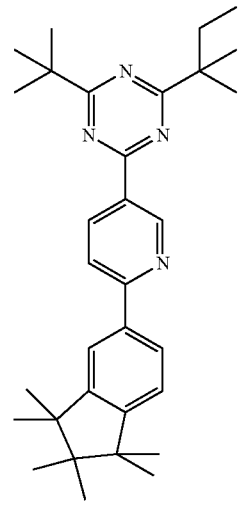 L16 |
| Synthone | S1 | S1 |
|---|---|---|
| | 1426441-17-9 | 1426434-95-8 |
| Yield | 45% | 69% |
| Ligand | 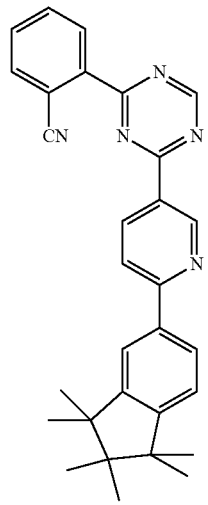 L19 | 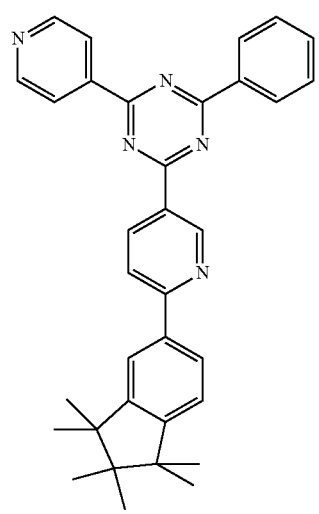 L20 |

| Synthone | S1 61810-06-8 | S1 78941-28-3 |
|---|---|---|
| Yield | 61% | 74% |
| Ligand | 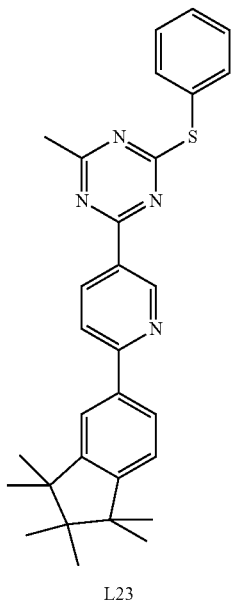 [SMILES: Cc1nc(Sc2ccccc2)nc(-c2ccc(-c3ccc4c(c3)C(C)(C)C(C)(C)C4(C)C)nc2)n1]<br>L23 | 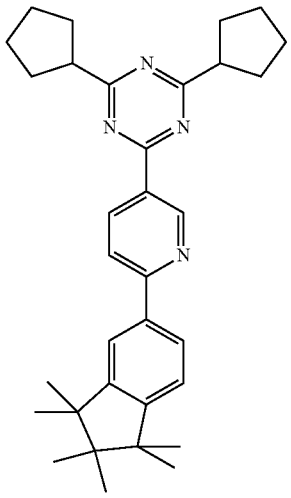<br>L24 |
| Synthone | S1 1426435-09-7 | S1 1092838-05-5 |
| Yield | 67% | 68% |
| Ligand | 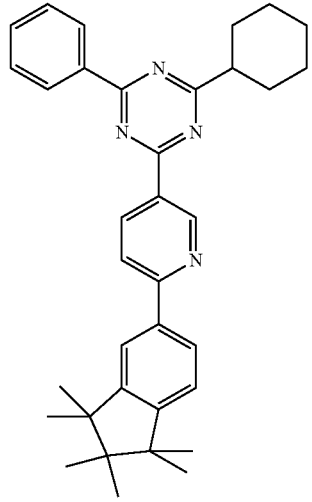<br>L27 | 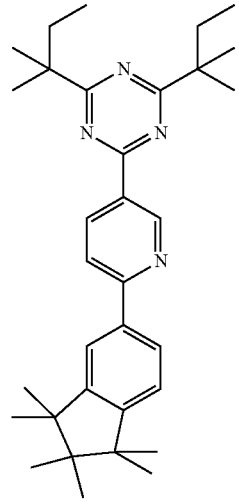<br>L28 |

| Synthone | S1 1345834-25-4 | S1 21902-34-1 |
|---|---|---|
| Yield | 55% | 75% |
| Ligand | 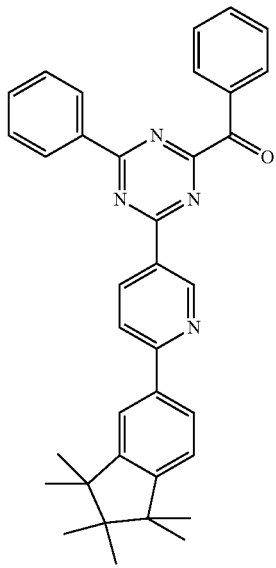 L31 | 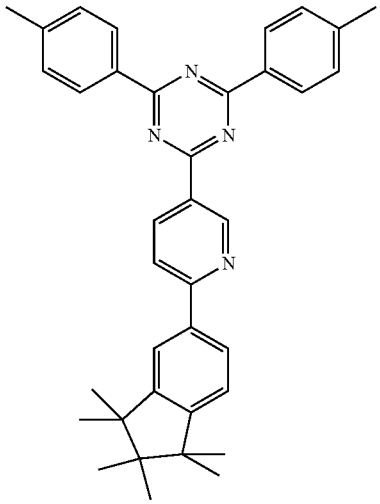 L32 |
| Synthone | S1 78941-35-2 | S1 80984-76-5 |
|---|---|---|
| Yield | 74% | 77% |
| Ligand | 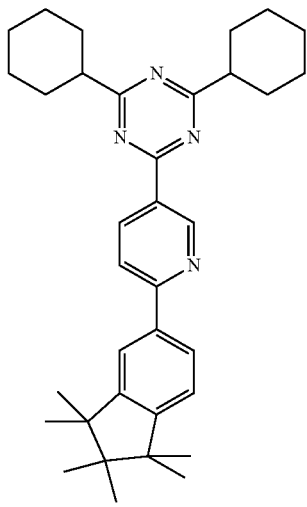 L35 | 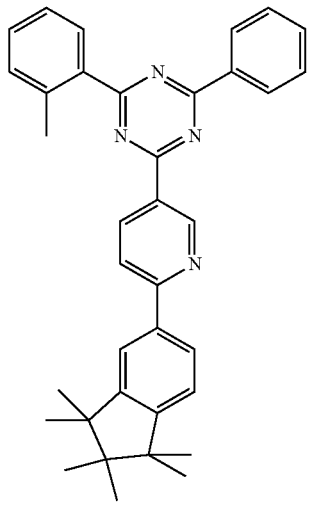 L36 |

| Synthone | S1 | S1 |
|---|---|---|
| | 78941-32-9 | 38164-03-3 |
| Yield | 65% | 73% |
| Ligand | 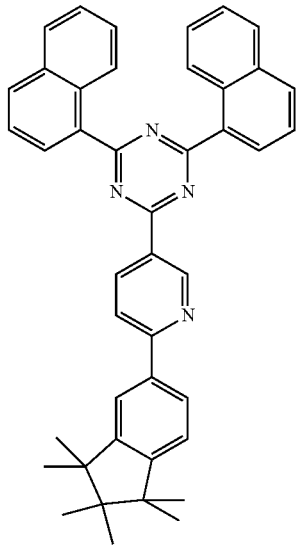 L39 | 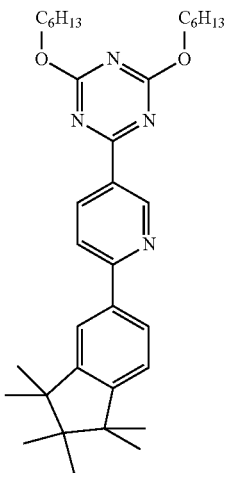 L40 |
| Synthone | S1 | S1 |
|---|---|---|
| | 1383780-97-9 | 253133-88-9 |
| Yield | 72% | 75% |
| Ligand | 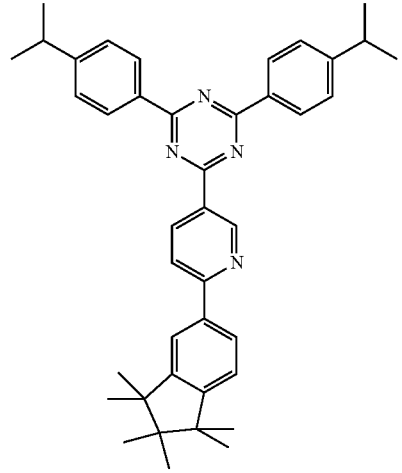 L43 | 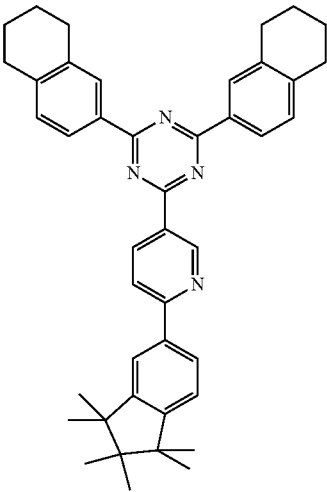 L44 |

| | | |
|---|---|---|
| Synthone | S1<br>253158-13-3 | S1<br>1387596-01-1 |
| Yield | 70% | 78% |
| Ligand | 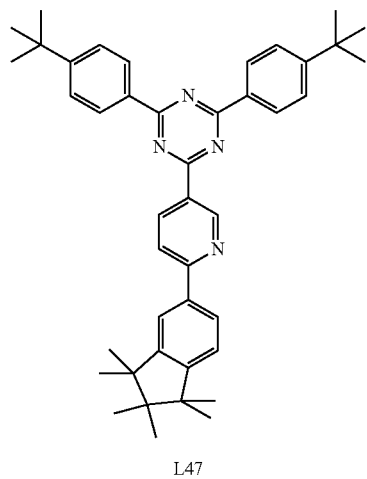<br>L47 | 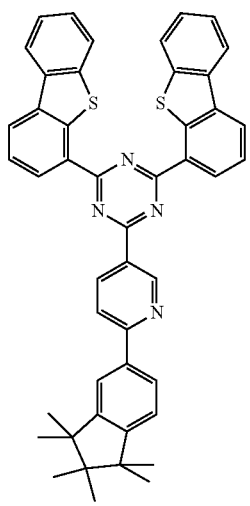<br>L48 |
| Synthone | S1<br>1477759-28-6 | S1<br>1404058-67-8 |
| Yield | 70% | 58% |
| Ligand | 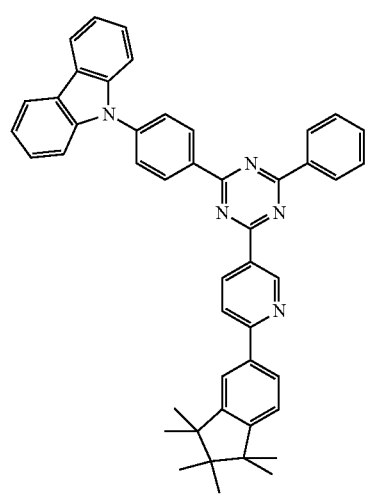<br>L51 | 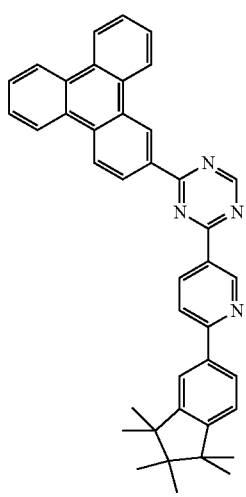<br>L52 |

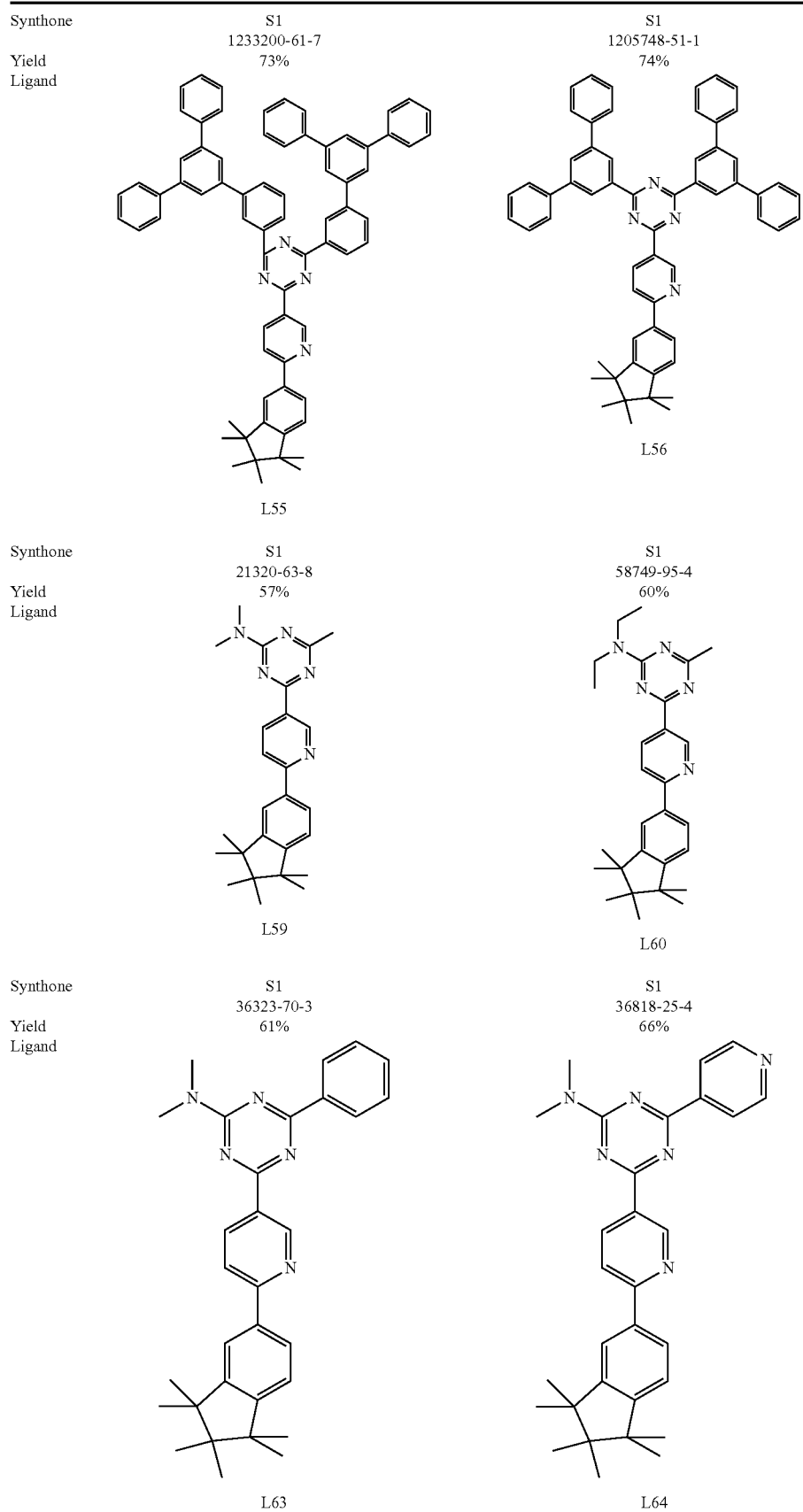

| Synthone | S1 | S1 |
|---|---|---|
| | 1268244-56-9 | 1260032-07-2 |
| Yield | 77% | 72% |
| Ligand | L67 | L68 |

| Synthone | S1 | S1 |
|---|---|---|
| | 189078-42-0 | 111669-20-6 |
| Yield | 56% | 57% |
| Ligand | L71 | L72 |

| Synthone | S1 3995-43-5 | S1 1398814-60-2 |
|---|---|---|
| Yield | 69% | 56% |
| Ligand | 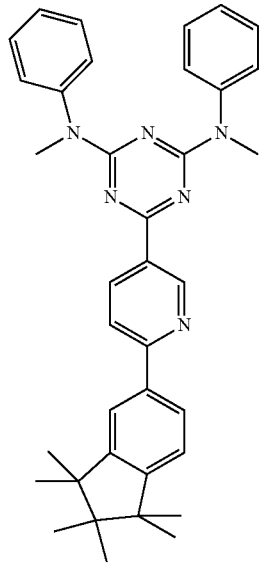 L75 | 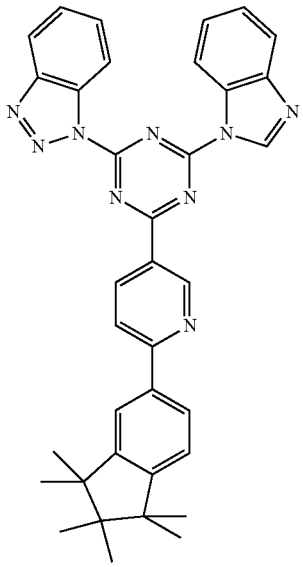 L76 |
| Synthone | S1 877615-05-9 | S1 83820-01-3 |
| Yield | 78% | 74% |
| Ligand | 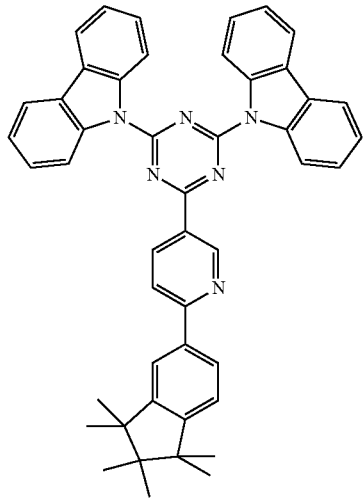 L79 | 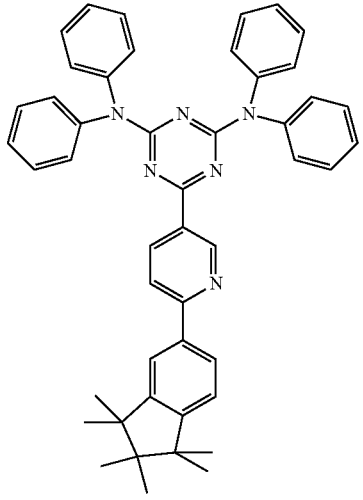 L80 |

| Synthone | S1 1016896-86-8 | S1 1616413-67-2 |
|---|---|---|
| Yield | 79% | 83% |
| Ligand | 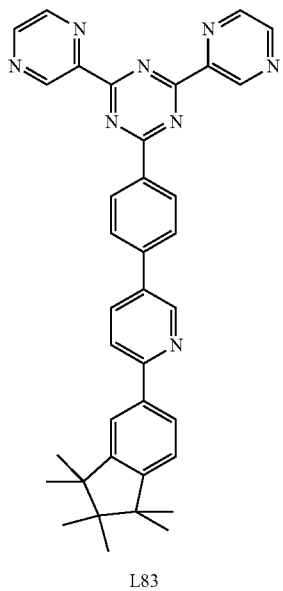 [SMILES: CC1(C)c2ccc(-c3ccc(-c4ccc(-c5nc(-c6cnccn6)nc(-c6cnccn6)n5)cc4)cn3)cc2C(C)(C)C1(C)C] L83 | 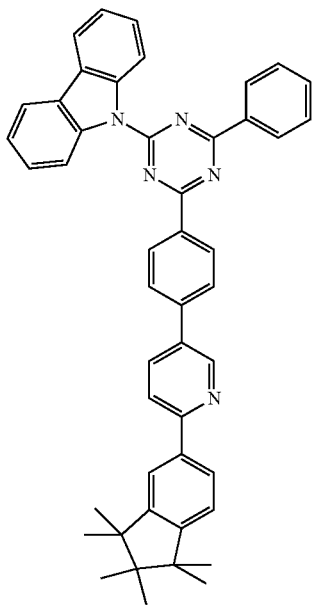 L84 |
| Synthone | S1 877456-11-6 | S1 1646531-99-8 |
|---|---|---|
| Yield | 81% | 77% |
| Ligand | 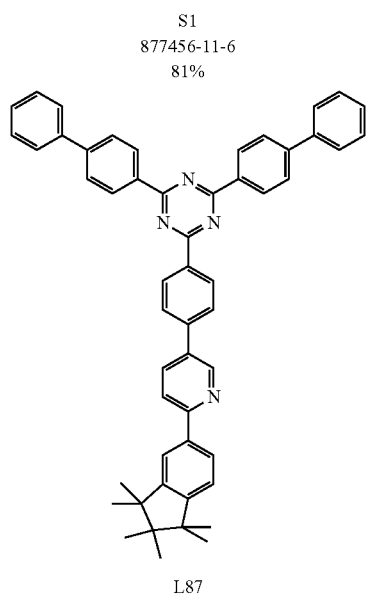 L87 | 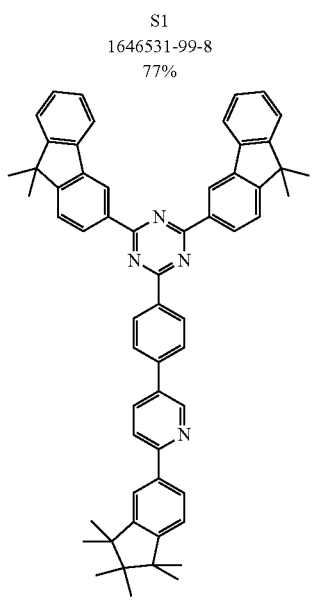 L88 |

-continued
| Synthone | S1 | S1 |
|---|---|---|
|  | 29872-58-0 | 241164-09-0 |
| Yield | 44% | 57% |
| Ligand | L91 | L92 |
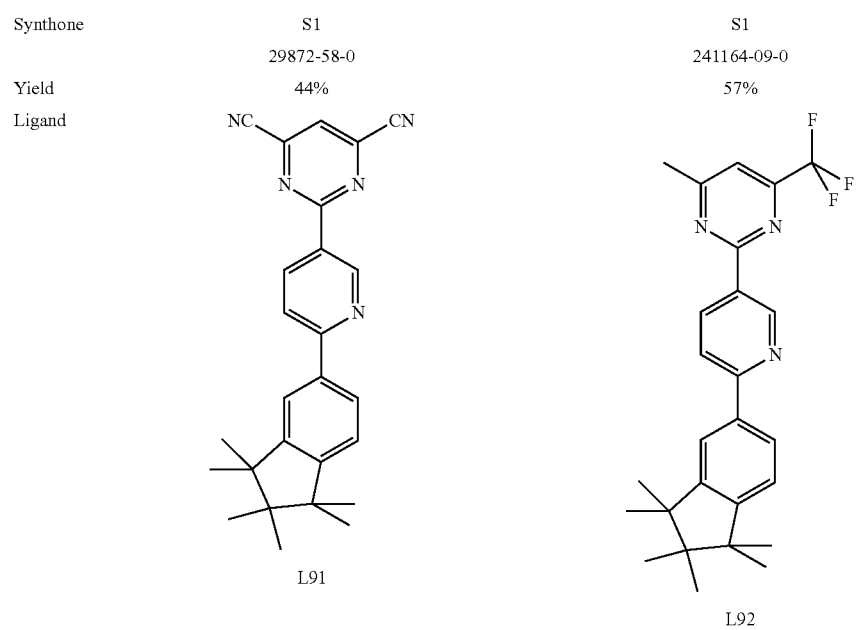
| Synthone | S1 | S1 |
|---|---|---|
|  | 2915-16-4 | 1035556-77-4 |
| Yield | 72% | 69% |
| Ligand | L95 | L96 |
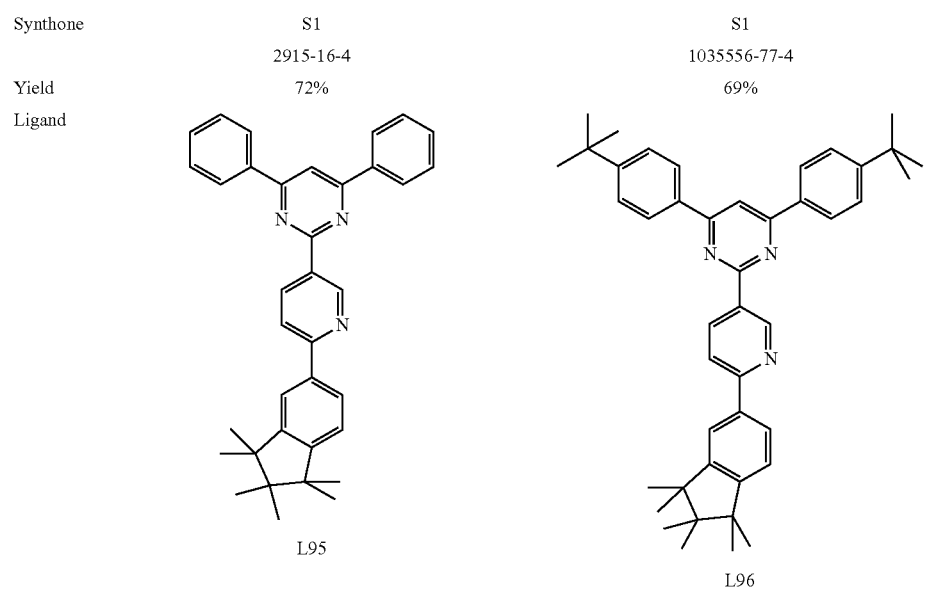

| | | |
|---|---|---|
| Synthone | S2 0937-70-3 | S2 73084-03-4 |
| Yield | 63% | 74% |
| Ligand | 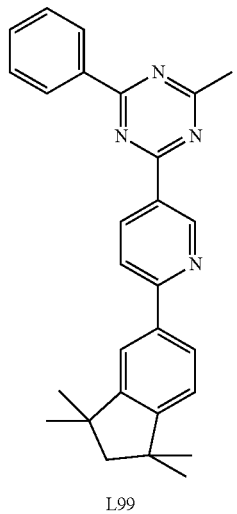 L99 | 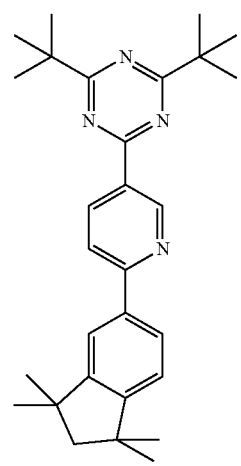 L100 |
| Synthone | S2 1472729-25-1 | S2 78941-32-9 |
| Yield | 77% | 65% |
| Ligand | 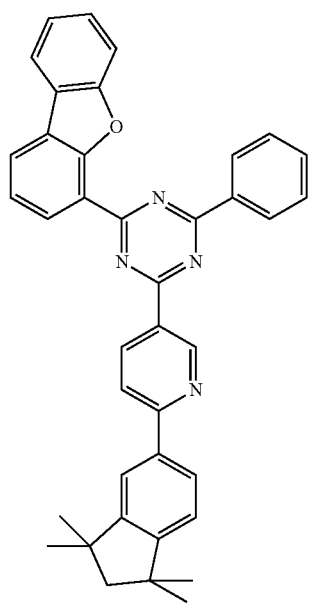 L103 | 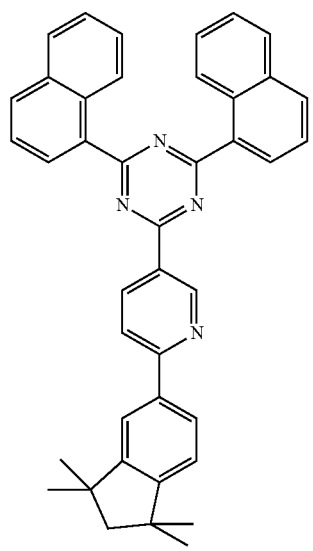 L104 |

| Synthone | S2 | S2 |
|---|---|---|
| | 1233200-61-7 | 1459162-69-6 |
| Yield | 75% | 72% |
| Ligand | 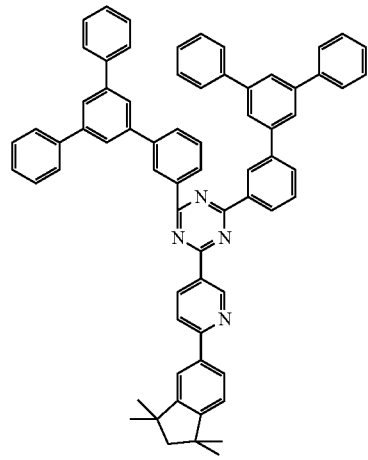 L107 | 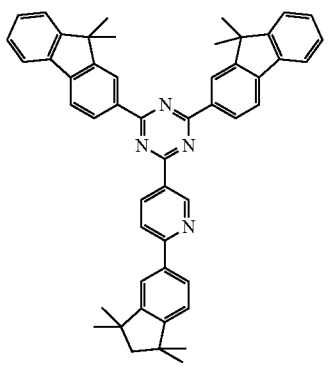 L108 |
| Synthone | S2 | S2 |
|---|---|---|
| | 3995-43-5 | 1268244-56-9 |
| Yield | 68% | 73% |
| Ligand | 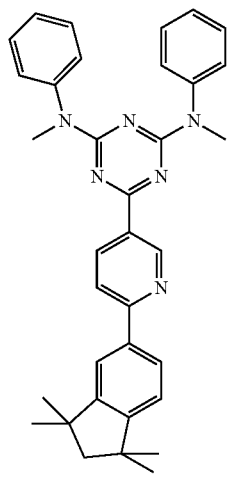 L111 | 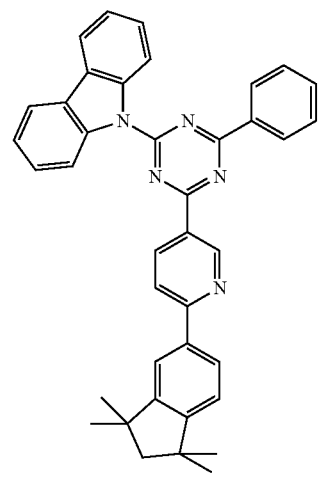 L112 |

| Synthone | S2 | S2 |
|---|---|---|
|  | 71162-19-1 | 2915-16-4 |
| Yield | 72% | 71% |
| Ligand | 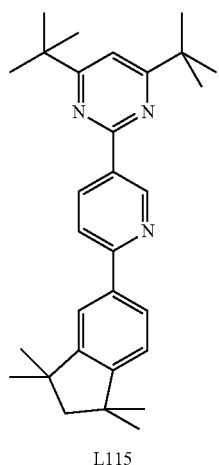 L115 | 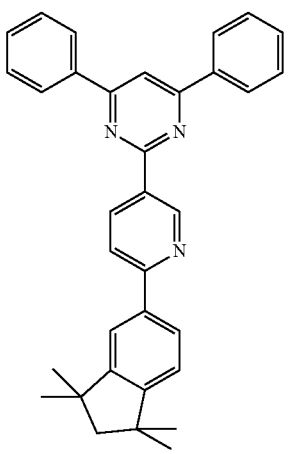 L116 |
| Synthone | S4 | S4 |
|---|---|---|
|  | 253158-13-3 | 1233200-61-7 |
| Yield | 77% | 79% |
| Ligand | 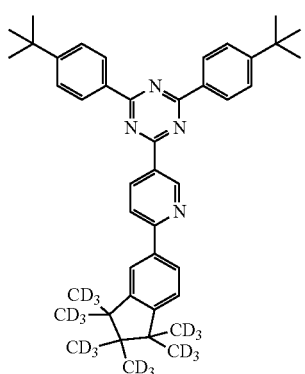 L119 | 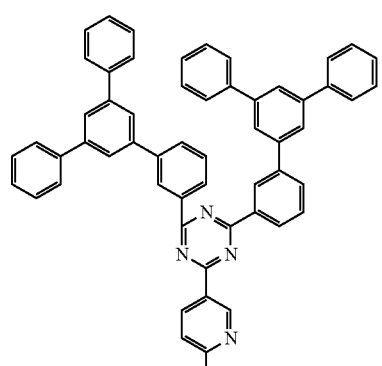 L120 |

-continued
| Synthone | S6 | S6 |
| --- | --- | --- |
| | 253158-13-3 | 73084-03-4 |
| Yield | 76% | 71% |
| Ligand | L123 | L124 |
| Synthone | S8 | S8 |
| | 3842-55-5 | 253158-13-3 |
| Yield | 73% | 77% |
| Ligand | L127 | L128 |
| Synthone | S10 | S10 |
| | 1459162-69-6 | 83253-21-8 |
| Yield | 75% | 82% |
| Ligand | L131 | L132 |
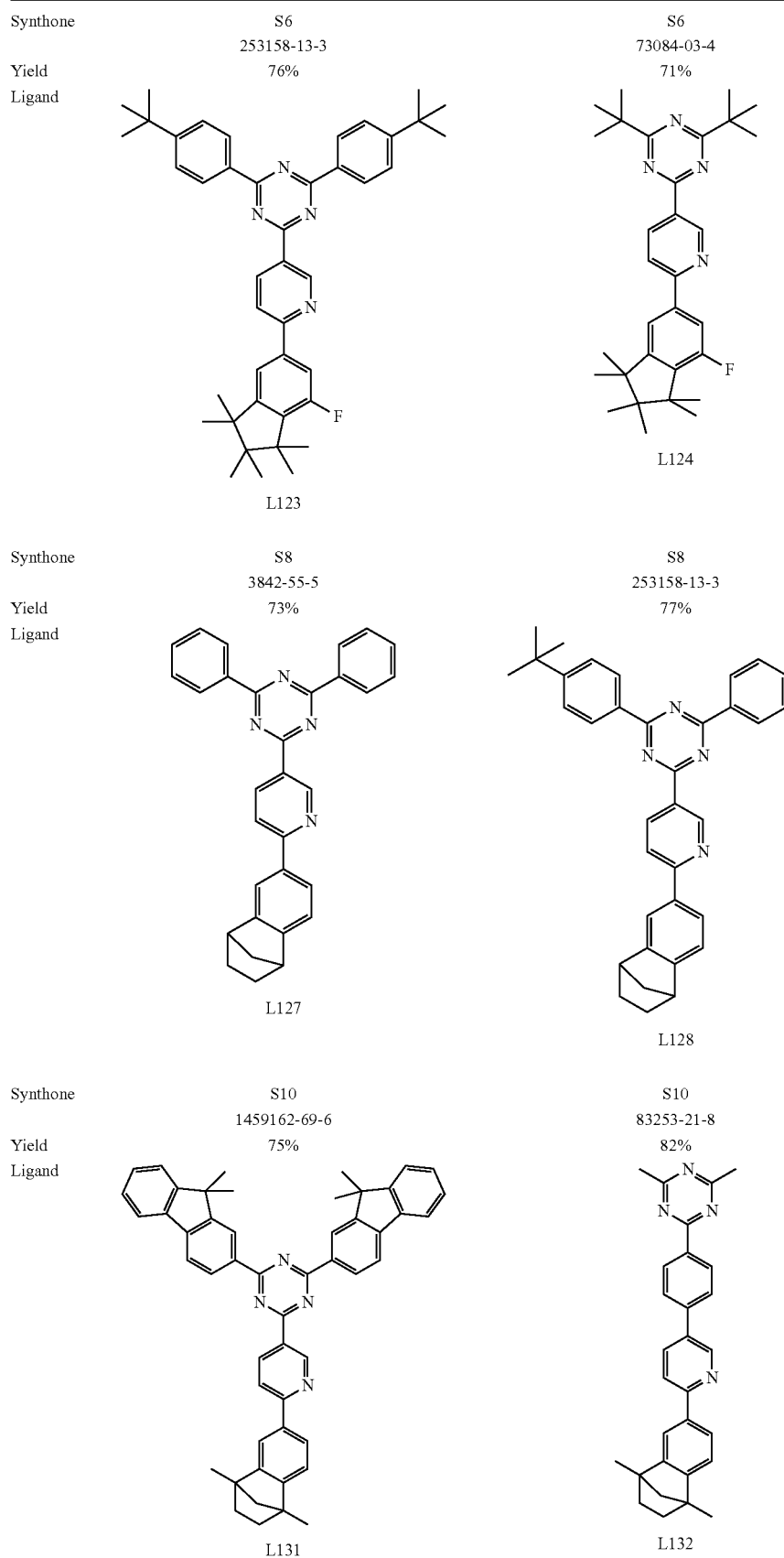

| Synthone | S12 32785-40-3 | S12 1260032-07-2 |
|---|---|---|
| Yield | 68% | 64% |
| Ligand | 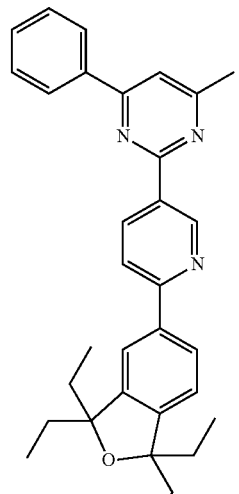 L135 | 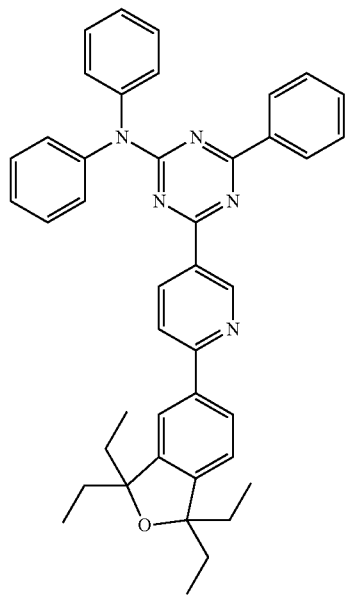 L136 |
| Synthone | S14 253158-13-3 | S14 73084-03-4 |
|---|---|---|
| Yield | 59% | 63% |
| Ligand | 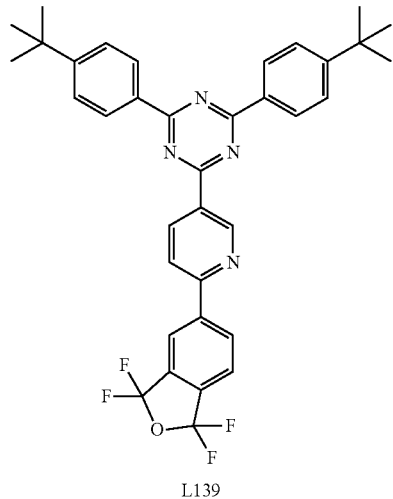 [SMILES: CC(C)(C)c1ccc(-c2nc(-c3ccc(C(C)(C)C)cc3)nc(-c3ccc(-c4ccc5c(c4)C(F)(F)OC5(F)F)nc3)n2)cc1] L139 | 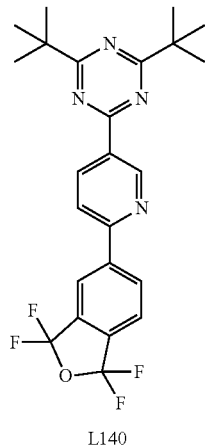 [SMILES: CC(C)(C)c1nc(-c2ccc(-c3ccc4c(c3)C(F)(F)OC4(F)F)nc2)nc(C(C)(C)C)n1] L140 |

| | |
|---|---|
| Synthone | S16 |
| | 36323-70-3 |
| Yield | 64% |
| Ligand | 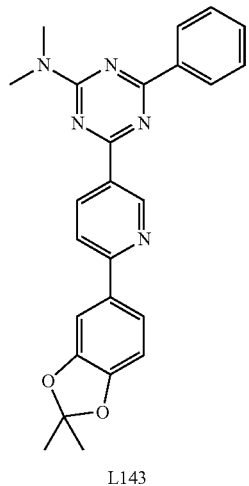<br>L143 |
| | |
|---|---|
| Synthone | S16 |
| | 3995-43-5 |
| Yield | 59% |
| Ligand | 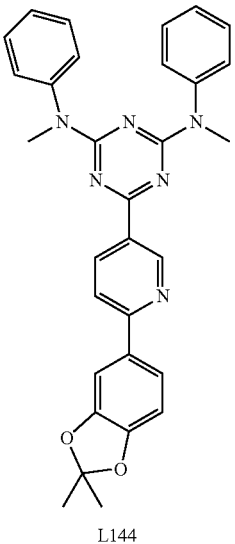<br>L144 |
| | |
|---|---|
| Synthone | S18 |
| | 32785-40-3 |
| Yield | 66% |
| Ligand | 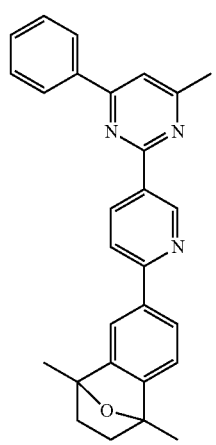<br>L147 |
| | |
|---|---|
| Synthone | S18 |
| | 2915-16-4 |
| Yield | 72% |
| Ligand | 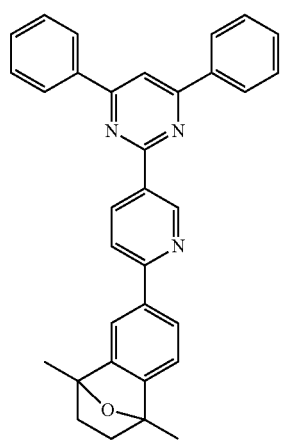<br>L148 |

-continued
| | | |
|---|---|---|
| Synthone | S20 | S20 |
| | 1477759-28-6 | 1476785-42-8 |
| Yield | 72% | 72% |
| Ligand | 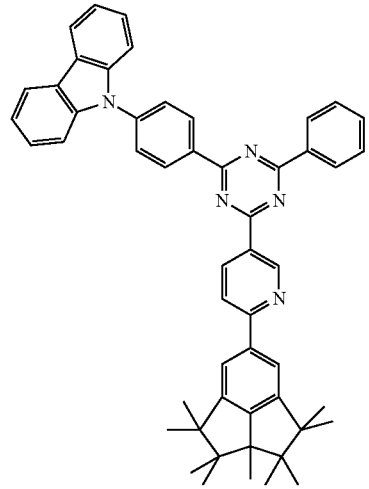<br>L151 | 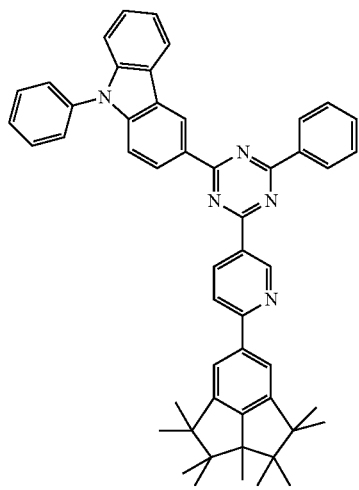<br>L152 |
| Synthone | S22 | S22 |
| | 73084-03-4 | 253158-13-3 |
| Yield | 59% | 61% |
| Ligand | 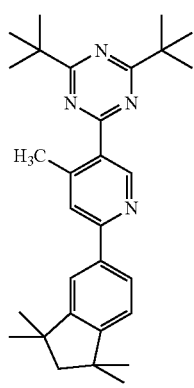<br>L155 | 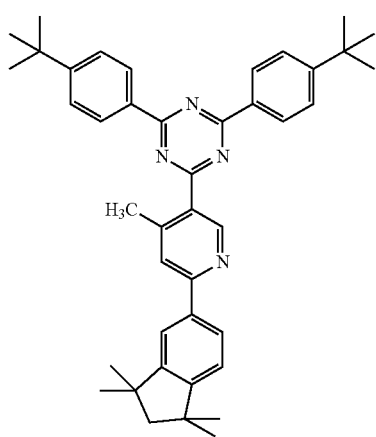<br>L156 |

| Synthone | S24 | S24 |
|---|---|---|
| | 927898-18-8 | 36323-70-3 |
| Yield | 59% | 63% |
| Ligand | 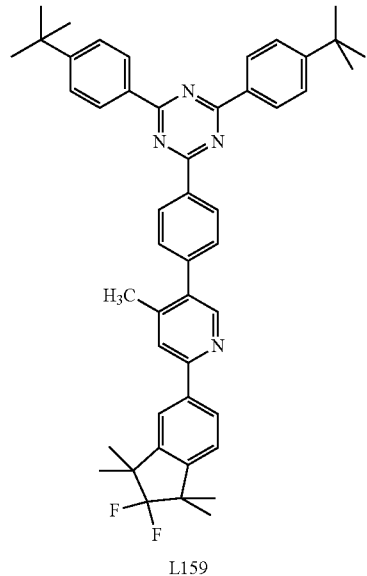 L159 | 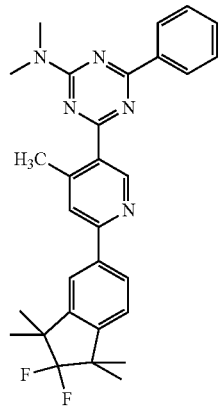 L160 |
| Synthone | S26 | S26 |
|---|---|---|
| | 111669-20-6 | 1205748-49-7 |
| Yield | 58% | 47% |
| Ligand | 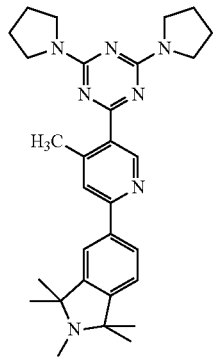 L163 | 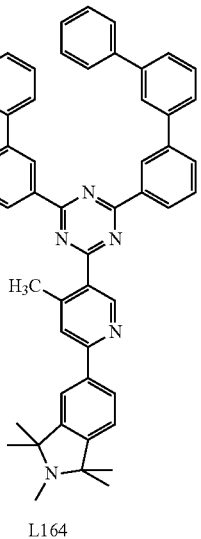 L164 |

| Synthone | S28 | S28 |
|---|---|---|
|  | 1260032-07-2 | 1205748-49-7 |
| Yield | 65% | 63% |
| Ligand | 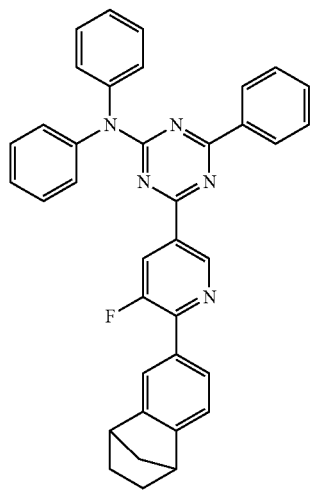 L167 | 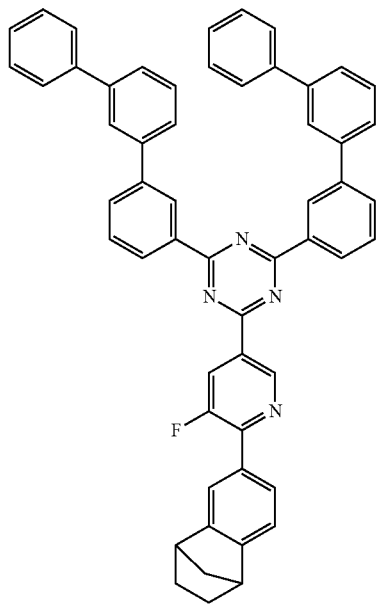 L168 |
| Synthone | S30 | S30 |
|---|---|---|
|  | 83253-21-8 | 1454596-47-4 |
| Yield | 69% | 55% |
| Ligand | 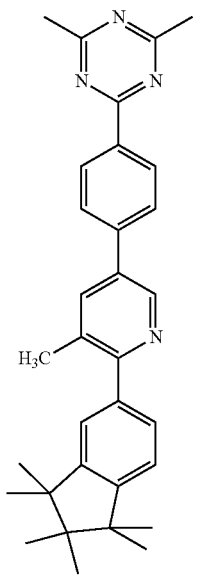 L171 | 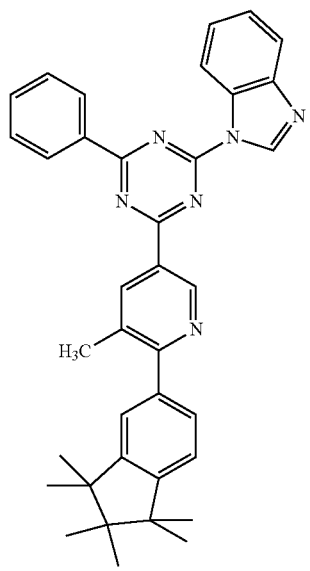 L172 |

| Synthone | S32 | S32 |
|---|---|---|
|  | 1205748-49-7 | 1459162-69-6 |
| Yield | 62% | 67% |
| Ligand | 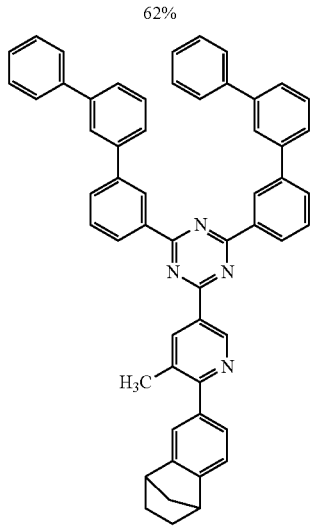 L175 | 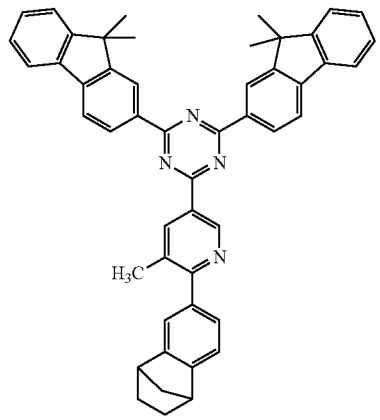 L176 |
| Synthone | S34 | S34 |
|---|---|---|
|  | 253158-13-3 | 1477759-28-6 |
| Yield | 66% | 62% |
| Ligand | 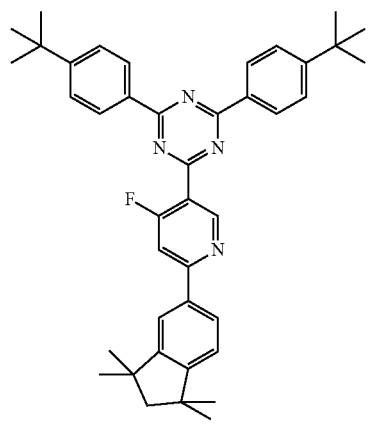 L179 | 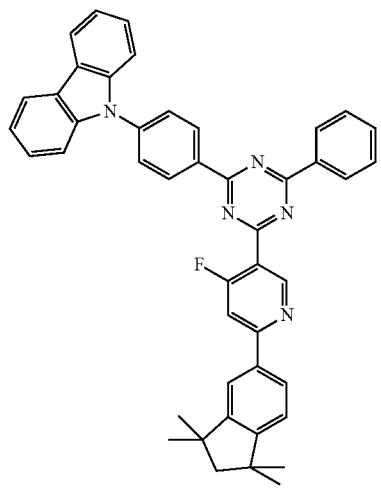 L180 |

| Synthone | S36 253158-13-3 | S36 73084-03-4 |
|---|---|---|
| Yield | 58% | 53% |
| Ligand | 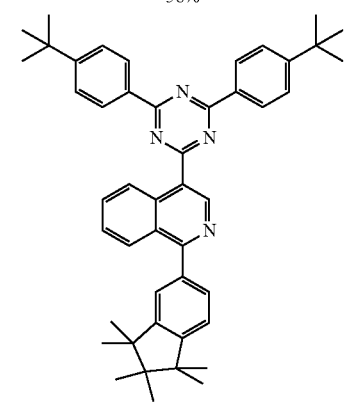 L183 | 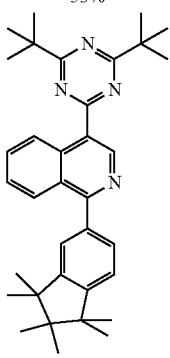 L184 |
| Synthone | S38 927898-18-8 | S38 1268244-56-9 |
|---|---|---|
| Yield | 42% | 50% |
| Ligand | 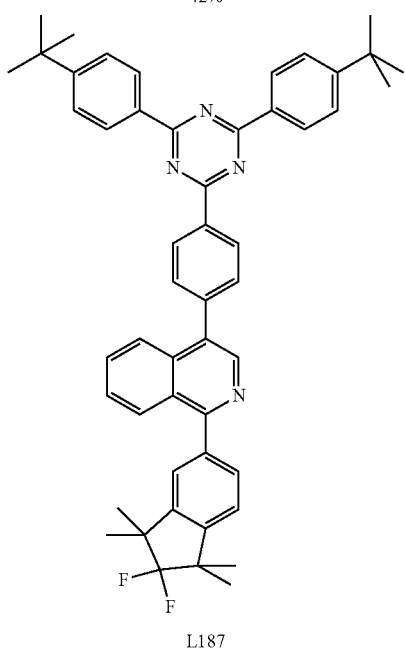 L187 | 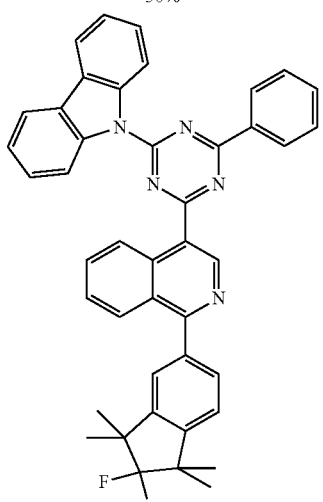 L188 |

| | | |
|---|---|---|
| Synthone | S40<br>1402225-90-4 | S40<br>1268244-56-9 |
| Yield | 67% | 53% |
| Ligand | 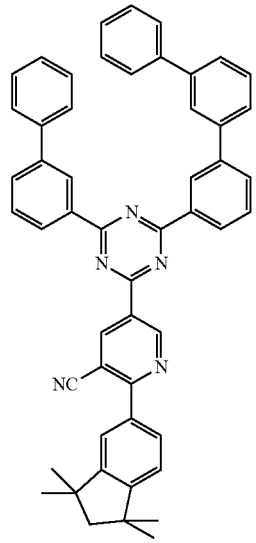<br>L191 | 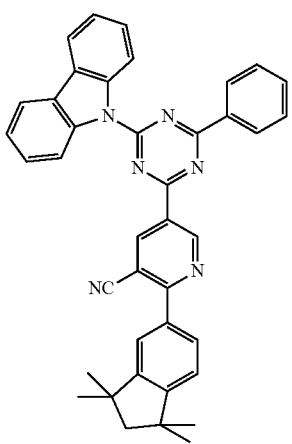<br>L192 |
| | | |
|---|---|---|
| Synthone | S42<br>0937-70-3 | S42<br>3842-55-5 |
| Yield | 69% | 73% |
| Ligand | 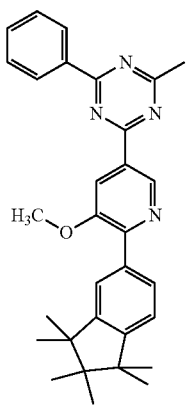<br>L195 | 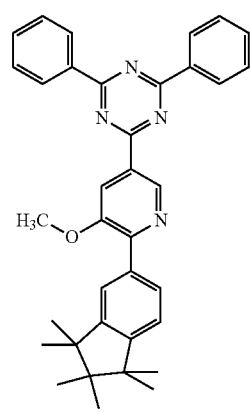<br>L196 |

-continued
| | | | |
|---|---|---|---|
| Synthone | S44<br>36323-70-3 | | S44<br>29872-58-0 |
| Yield | 62% | | 59% |
| Ligand | 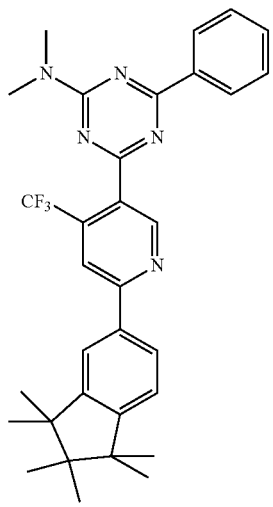<br>L199 | | 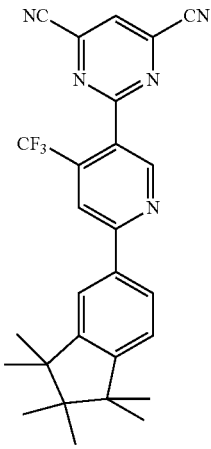<br>L200 |
| | | | |
|---|---|---|---|
| Synthone | S46<br>1260032-07-2 | | S46<br>927898-18-8 |
| Yield | 47% | | 40% |
| Ligand | 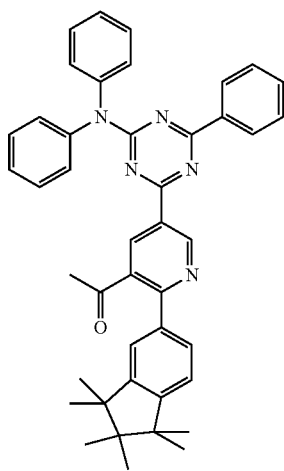<br>L203 | | 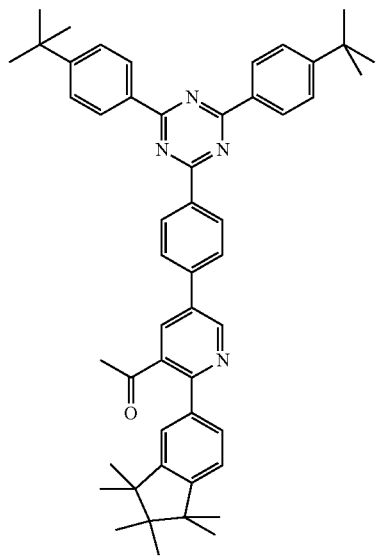<br>L204 |

| | | |
|---|---|---|
| Synthone | S48 | S48 |
| | 153430-09-2 | 57639-20-0 |
| Yield | 69% | 65% |
| Ligand | L207 | L208 |
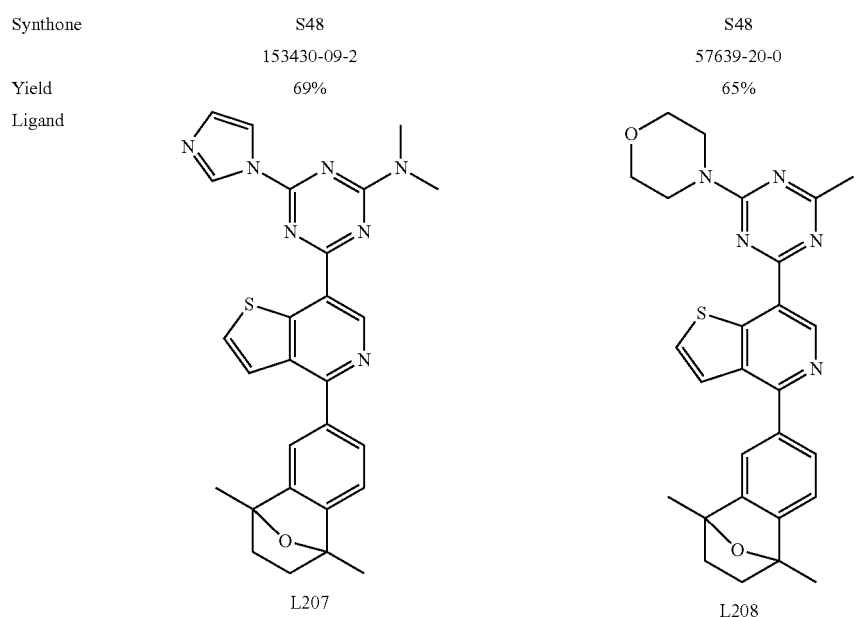
| | | |
|---|---|---|
| Synthone | S50 | S50 |
| | 78941-35-2 | 1472729-25-1 |
| Yield | 43% | 38% |
| Ligand | L211 | L212 |
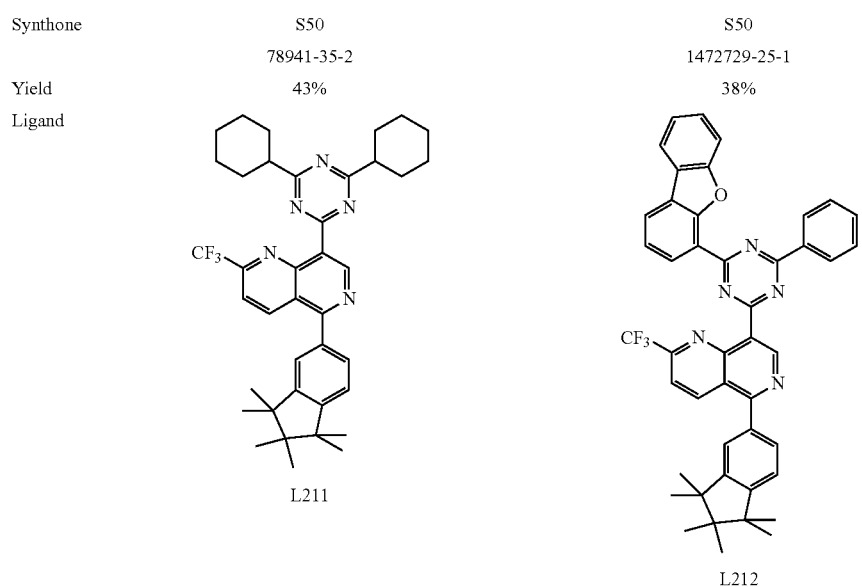

| Synthone | S52 | S52 |
|---|---|---|
| | 1472729-25-1 | 78941-32-9 |
| Yield | 42% | 35% |
| Ligand | | |
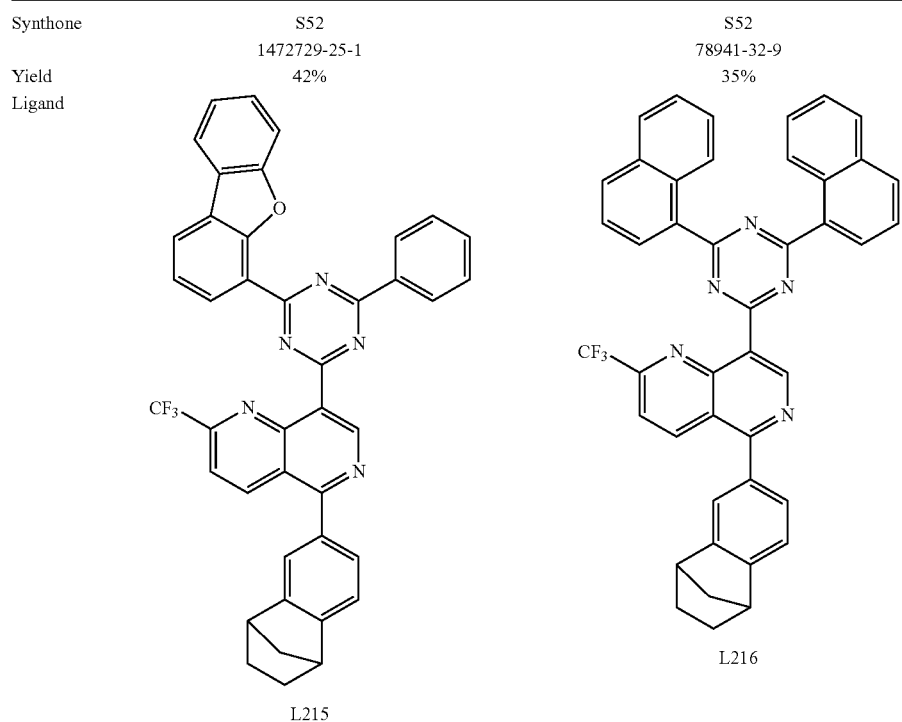
L215      L216
| Synthone | S54 | S54 |
|---|---|---|
| | 1383780-97-9 | 1477759-28-6 |
| Yield | 63% | 58% |
| Ligand | | |
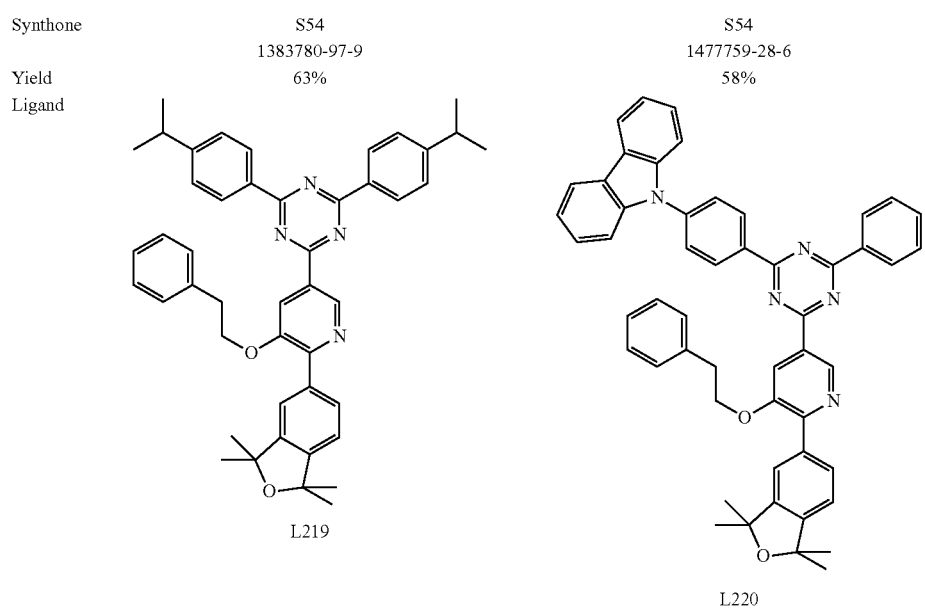
L219      L220

| Synthone | S1 |
|---|---|
| | S1000 |
| Yield | 58% |
| Ligand | 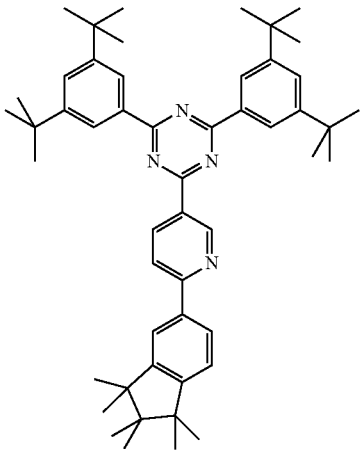 |
| | L223 |

Synthesis of the Metal Complexes

1) Homoleptic Tris-Facial Iridium Complexes of the Phenylpyridine, Phenylimidazole or Phenylbenzimidazole Type Variant A: Trisacetylacetonatoiridium(III) as Iridium Stating Material A mixture of 10 mmol of trisacetylacetonatoiridium(III) [15635-87-7] and 40-60 mmol (preferably 40 mmol) of the ligand L, optionally 1-10 g—typically 3 g—of an inert high-baling additive as melting aid or solvent, for example hexadecane, m-terphenyl, triphenylene, bisphenyl ether, 3-phenoxytoluene, 1,2-, 1,3-, 1,4-bis-phenoxybenzene, triphenylphosphine oxide, sulfolane, 18-crown-6, triethylene glycol glycerol, polyethylene glycols, phenol, 1-naphthol, hydroquinone, etc., and a glass-clad magnetic stirrer bar are melted under vacuum ($10^{-5}$ mbar) into a thick-walled 50 ml glass ampoule. The ampoule is heated at the temperature indicated for the time indicated, with the molten mixture being stirred with the aid of a magnetic stirrer. In order to prevent sublimation of the ligands at relatively cold points of the ampoule, the entire ampoule must have the temperature indicated. Alternatively, the synthesis can be carried out in a stirred autoclave with glass insert. After cooling (NOTE: the ampoules are usually under pressure!), the ampoule is opened, the sinter cake is stirred for 3 h with 100 g of glass beads (diameter 3 mm) in 100 ml of a suspension medium (the suspension medium is selected so that the ligand is readily soluble therein, but the metal complex has low solubility therein; typical suspension media are methanol, ethanol, dichloromethane, acetone, THF, ethyl acetate, toluene, etc.) and mechanically digested at the same time. The fine suspension is decanted off from the glass beads, the solid is filtered off with suction, rinsed with 50 ml of the suspension medium and dried in vacuo. The dry solid is placed on an aluminium oxide bed (aluminium oxide, basic, activity grade 1) with a depth of 3-5 cm in a continuous hot extractor and then extracted with an extractant (initially introduced amount about 500 ml, the extractant is selected so that the complex is readily soluble therein at elevated temperature and has low solubility therein at low temperature; particularly suitable extractants are hydrocarbons, such as toluene, xylenes, mesitylene, naphthalene, o-dichlorobenzene; halogenated aliphatic hydrocarbons are generally unsuitable since they may halogenate or decompose the complexes). When the extraction is complete, the extractant is evaporated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, with the aluminium oxide bed being omitted from the 2nd extraction. When a purity of 99.5-99.9% has been achieved, the metal complex is heated or chromatographed. The heating is carried out in a high vacuum (p about $10^{-6}$ mbar) in the temperature range from about 200-300° C. Complexes which are readily soluble in organic solvents can alternatively also be chromatographed on silica gel.

If chiral ligands are employed, the derived fac-metal complexes are obtained as a diastereomer mixture. The enantiomers Λ,Δ of point group C3 generally have significantly lower solubility in the extractant than the enantiomers of point group C1, which consequently become enriched in the mother liquor. Separation of the C3 diastereomers from the C1 diastereomers in this way is frequently possible. In addition, the diastereomers can also be separated chromatographically. If ligands of point group C1 are employed in enantiomerically pure form, a diastereomer pair Λ,Δ of point group C3 is formed. The diastereomers can be separated by crystallisation or chromatography and thus obtained as enantiomerically pure compounds.

Variant B: Tris(2,2,6,6-tetramethyl-3,5-heptanedionato)iridium(III) as Iridium Starting Material Procedure analogous to variant A, using 10 mmol of tris(2,2,6,6-tetramethyl-3,5-heptanedionato)iridium [99581-86-9] instead of 10 mmol of trisacetylacetonatoiridium(III) [15635-87-7]. The use of this starting material is advantageous since the purity of the crude products obtained is frequently better than in the case of Variant A. In addition, the build-up of pressure in the ampoule is frequently not as pronounced.

Variant C: Sodium [cis,trans-dichlorobis(acetylacetonato)] iridate(III) as Iridium Starting Material A mixture of 10 mmol of sodium [cis,trans-dichlorobis(acetylacetonato)]-iridate(III) [876296-21-8] and 60 mmol of the ligand in 50 ml of ethylene glycol, propylene glycol or diethylene glycol is heated under gentle reflux under a gentle stream of argon for the time indicated. After cooling to 60° C., the mixture is diluted with a mixture of 50 ml of ethanol and 50 ml of 2 N hydrochloric acid with stirring, the mixture is stirred for a further 1 h, and the solid which has precipitated out is filtered off with suction, washed three times with 30 ml of ethanol each time and then dried in vacuo. Purification by hot extraction or chromatography and fractional sublimation, as described under A.

Variant D:

Step 1:

A mixture of 10 mmol of iridium chloride and 24 mmol of the ligand L and a glass-dad magnetic stirrer bar are melted under vacuum ($10^{-5}$ mbar) into a thick-walled 50 ml glass ampoule. The ampoule is heated at the temperature indicated for the time indicated, with the molten mixture being stirred with the aid of a magnetic stirrer. After cooling—NOTE: the ampoules are usually under pressure!—the ampoule is opened, the sinter cake is stirred for 3 h with 100 g of glass beads (diameter 3 mm) in 100 ml of the suspension medium indicated (the suspension medium is selected so that the ligand is ready soluble therein, but the chloro dimer of the formula $[Ir(L)_2Cl]_2$ has low solubility therein; typical suspension media are DCM, acetone, ethyl acetate, toluene, etc.) and mechanically digested at the same time. The fine suspension is decanted off from the glass beads, the solid ($[Ir(L)_2Cl]_2$, which also contains about 2 eq. of NaCl, called the crude chloro dimer below, is filtered off with suction and dried in vacuo.

Step 2:

The crude chloro dimer of the formula $[Ir(L)_2Cl]_2$ is suspended in 200 ml of THF, 20 mmol of the ligand L, 20 mmol of silver(I) trifluoroacetate and 30 mmol of potassium carbonate are added to the suspension, and the mixture is heated under reflux for 24 h. After cooling, the THF is removed in vacuo. The residue is taken up in 200 ml of a mixture of ethan and conc. ammonia solution (1:1, vv). The suspension is stirred at room temperature for 1 h, the solid is filtered off with suction, washed twice with 50 ml of a mixture of ethanol and conc. ammonia solution (1:1, vv) each time and twice with 50 ml of ethanol each time and then dried in vacuo. Hot extraction and sublimation as in variant A.

Examples according to Variants A to D:

| Ex. | $Ir(L1)_3$ | $Ir(L2)_3$ |
|---|---|---|
| Ligand L | L1 | L2 |
| Ir complex | 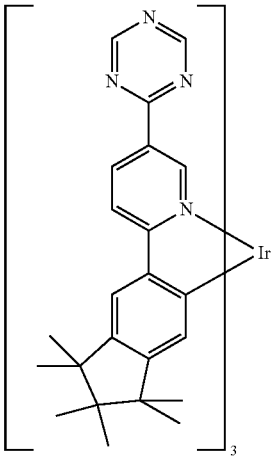 | 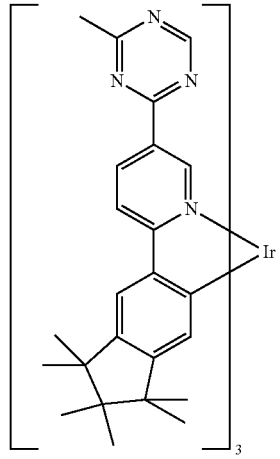 |
| Variant | D | D |
| Reaction medium | — | — |
| Melting aid | — | — |
| Reaction temp | 260° C. | 270° C. |
| Reaction time | 24 h | 24 h |
| Suspension medium | EtOH | EtOH |
| Extractant | m-Dichlorobenzene | Toluene |
| Yield | 12% | 16% |

-continued

| Ex. | Ir(L3)₃ | Ir(L4)₃ |
|---|---|---|
| Ligand L | L3 | L4 |
| Ir complex | [structure] | [structure] |
| Variant | D | A |
| Reaction medium | — | — |
| Melting aid | — | Hydroquinone |
| Reaction temp | 270° C. | 270° C. |
| Reaction time | 24 h | 24 h |
| Suspension medium | EtOH | EtOH |
| Extractant | p-Xylene | Toluene |
| Yield | 4% | 16% |

| Ex. | Ir(L5)₃ | Ir(L6)₃ |
|---|---|---|
| Ligand L | L5 | L6 |
| Ir complex | [structure] | [structure] |
| Variant | B | A |
| Reaction medium | — | — |
| Melting aid | Sulfolane | Hydroquinone |
| Reaction temp | 285° C. | 270° C. |
| Reaction time | 24 h | 24 h |
| Suspension medium | EtOH | EtOH |
| Extractant | p-Xylene | Ethyl acetate |
| Yield | 6% | 17% |

| Ex. | Ir(L7)₃ | Ir(L8)₃ |
|---|---|---|
| Ligand L | L7 | L8 |
| Ir complex | | |
| Variant | A | A |
| Reaction medium | — | — |
| Melting aid | Hydroquinone | Hydroquinone |
| Reaction temp | 260° C. | 260° C. |
| Reaction time | 48 h | 24 h |
| Suspension medium | EtOH | EtOH |
| Extractant | p-Xylene | m-Dichloro-benzene |
| Yield | 14% | 13% |

| Ex. | Ir(L9)₃ | Ir(L10)₃ |
|---|---|---|
| Ligand L | L9 | L10 |
| Ir complex | | |
| Variant | D | A |
| Reaction medium | — | — |
| Melting aid | — | Hydroquinone |
| Reaction temp. | 270° C. | 270° C. |
| Reaction time | 24 h | 24 h |
| Suspension medium | EtOH | EtOH |
| Extractant | Mesitol | p-Xylene |
| Yield | 7% | 11% |

-continued

| Ex. | Ir(L11)₃ | Ir(L12)₃ |
|---|---|---|
| Ligand L | L11 | L12 |
| Ir complex | | |
| Variant | A | A |
| Reaction medium | — | — |
| Melting aid | Hydroquinone | Hydroquinone |
| Reaction temp. | 275° C. | 260° C. |
| Reaction time | 24 h | 48 h |
| Suspension medium | EtOH | EtOH |
| Extractant | Ethyl acetate | p-Xylene |
| Yield | 17% | 6% |

| Ex. | Ir(L13)₃ | Ir(L14)₃ |
|---|---|---|
| Ligand L | L13 | L14 |
| Ir complex | | |
| Variant | A | A |
| Reaction medium | — | — |
| Melting aid | Hydroquinone | — |
| Reaction temp. | 260° C. | 280° C. |
| Reaction time | 36 h | 24 h |
| Suspension medium | EtOH | EtOH |
| Extractant | m-Xylene | Ethyl acetate |
| Yield | 12% | 13% |

| Ex. | Ir(L15)₃ | Ir(L16)₃ |
|---|---|---|
| Ligand L | L15 | L16 |
| Ir complex | | |
| Variant | A | A |
| Reaction medium | — | — |
| Melting aid | — | Hydroquinone |
| Reaction temp. | 280° C. | 270° C. |
| Reaction time | 24 h | 24 h |
| Suspension medium | EtOH | EtOH |
| Extractant | Ethyl acetate | Ethyl acetate |
| Yield | 10% | 11% |

| Ex. | Ir(L17)₃ | Ir(L18)₃ |
|---|---|---|
| Ligand L | L17 | L18 |
| Ir complex | | |
| Variant | A | A |
| Reaction medium | — | — |
| Melting aid | Hydroquinone | Hydroquinone |
| Reaction temp. | 275° C. | 275° C. |
| Reaction time | 24 h | 24 h |
| Suspension medium | EtOH | EtOH |
| Extractant | m-Xylene | Toluene |
| Yield | 7% | 11% |

| Ex. | Ir(L19)₃ | Ir(L20)₃ |
|---|---|---|
| Ligand L | L19 | L20 |
| Ir complex | 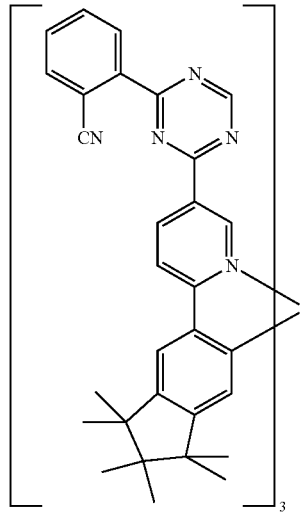 | 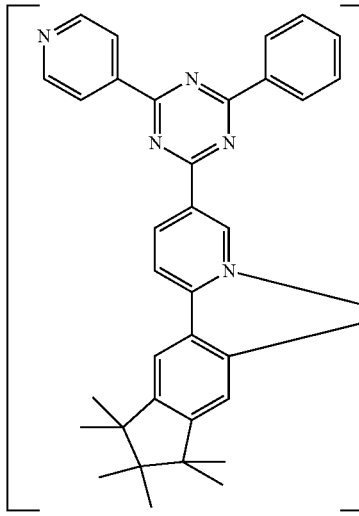 |
| Variant | A | A |
| Reaction medium | — | — |
| Melting aid | Hydroquinone | Hydroquinone |
| Reaction temp. | 265° C. | 270° C. |
| Reaction time | 36 h | 24 h |
| Suspension medium | EtOH | EtOH |
| Extractant | Toluene | Toluene |
| Yield | 9% | 13% |

| Ex. | Ir(L21)₃ | Ir(L22)₃ |
|---|---|---|
| Ligand L | L21 | L22 |
| Ir complex | 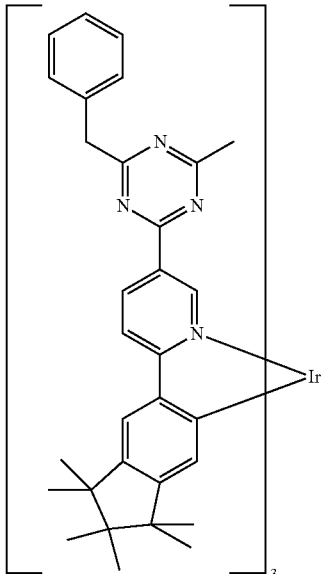 | 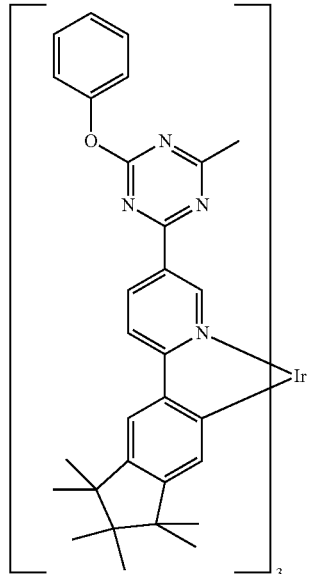 |
| Variant | A | A |
| Reaction medium | — | — |
| Melting aid | 1-Naphthol | 1-Naphthol |
| Reaction temp. | 260° C. | 265° C. |
| Reaction time | 36 h | 36 h |
| Suspension medium | EtOH | EtOH |
| Extractant | Toluene | Toluene |
| Yield | 5% | 13% |

| Ex. | Ir(L23)₃ | Ir(L24)₃ |
|---|---|---|
| Ligand L | L23 | L24 |
| Ir complex | 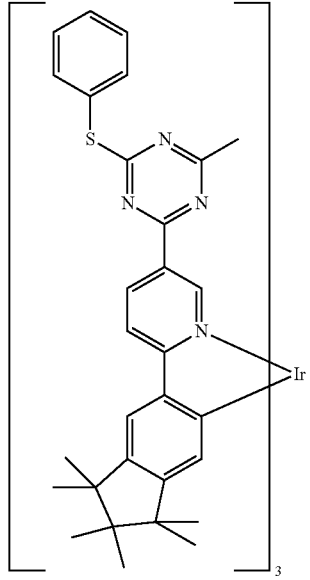 | 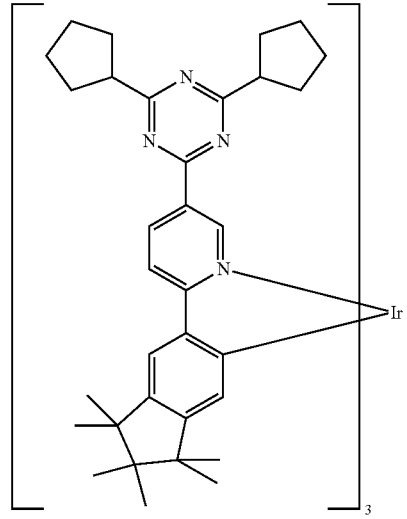 |
| Variant | A | A |
| Reaction medium | — | — |
| Melting aid | 1-Naphthol | Hydroquinone |
| Reaction temp. | 265° C. | 260° C. |
| Reaction time | 36 h | 24 h |
| Suspension medium | EtOH | EtOH |
| Extractant | Toluene | Ethyl acetate |
| Yield | 11% | 15% |
| Ex. | Ir(L25)₃ | Ir(L26)₃ |
| Ligand L | L25 | L26 |
| Ir complex | 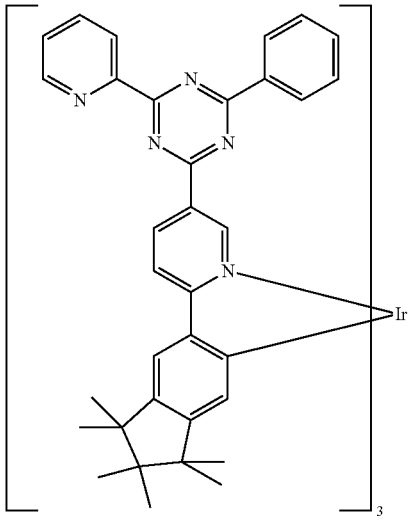 | 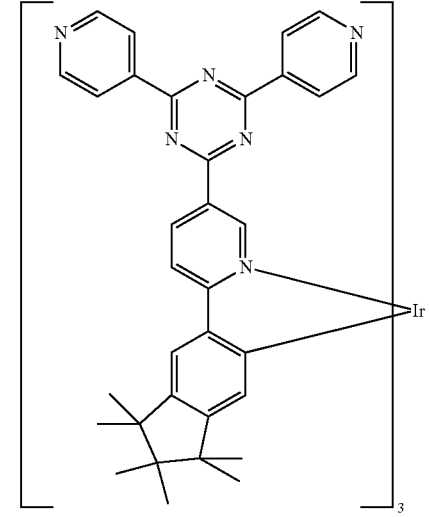 |
| Variant | A | A |
| Reaction medium | — | — |
| Melting aid | Hydroquinone | Hydroquinone |
| Reaction temp. | 275° C. | 275° C. |
| Reaction time | 24 h | 24 h |
| Suspension medium | EtOH | EtOH |
| Extractant | Toluene | Chlorobenzene |
| Yield | 9% | 7% |

-continued

| Ex. | Ir(L27)₃ | Ir(L28)₃ |
|---|---|---|
| Ligand L | L27 | L28 |
| Ir complex | 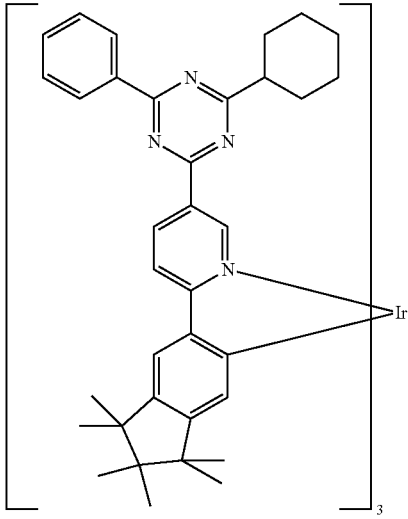 | 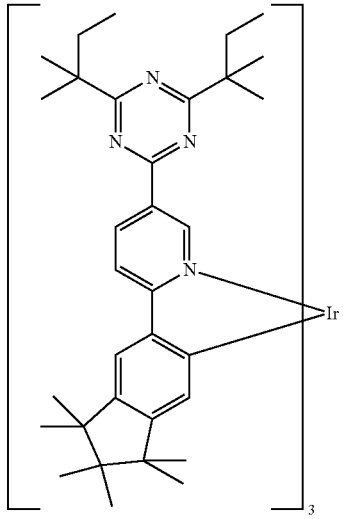 |
| Variant | A | A |
| Reaction medium | — | — |
| Melting aid | Hydroquinone | Hydroquinone |
| Reaction temp. | 275° C. | 265° C. |
| Reaction time | 24 h | 24 h |
| Suspension medium | EtOH | EtOH |
| Extractant | Ethyl acetate | Ethyl acetate |
| Yield | 13% | 16% |

| Ex. | Ir(L29)₃ | Ir(L30)₃ |
|---|---|---|
| Ligand L | L29 | L30 |
| Ir complex | 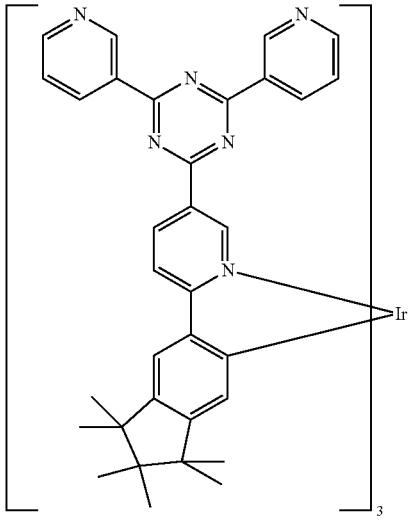 | 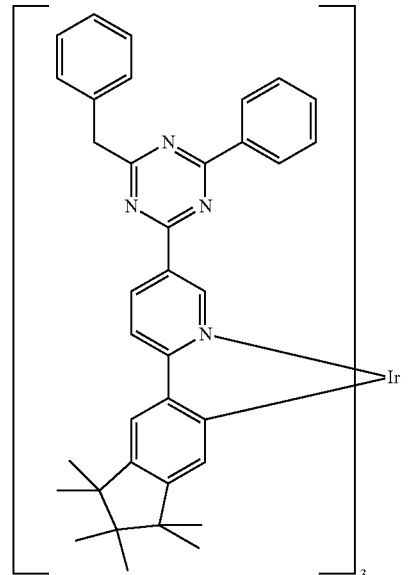 |
| Variant | A | A |
| Reaction medium | — | — |
| Melting aid | Hydroquinone | 1-Naphthol |
| Reaction temp. | 275° C. | 265° C. |
| Reaction time | 24 h | 24 h |
| Suspension medium | EtOH | EtOH |
| Extractant | Chlorobenzene | Toluene |
| Yield | 8% | 9% |

-continued

| Ex. | Ir(L31)₃ | Ir(L32)₃ |
|---|---|---|
| Ligand L Ir complex | L31 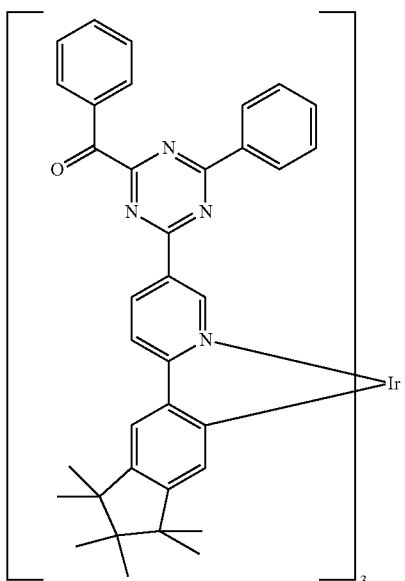 | L32 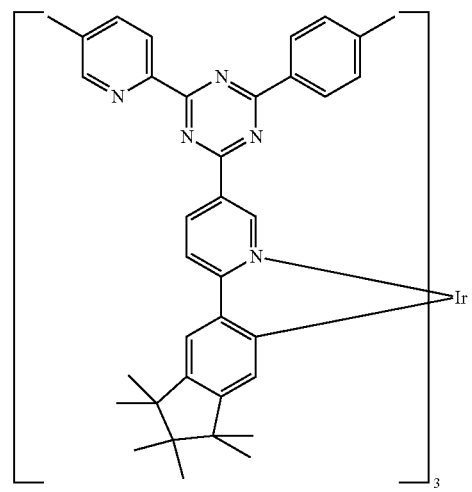 |
| Variant | A | A |
| Reaction medium | — | — |
| Melting aid | Hydroquinone | Hydroquinone |
| Reaction temp. | 260° C. | 275° C. |
| Reaction time | 24 h | 24 h |
| Suspension medium | EtOH | EtOH |
| Extractant | Toluene | Toluene |
| Yield | 6% | 12% |

| Ex. | Ir(L33)₃ | Ir(L34)₃ |
|---|---|---|
| Ligand L Ir complex | L33 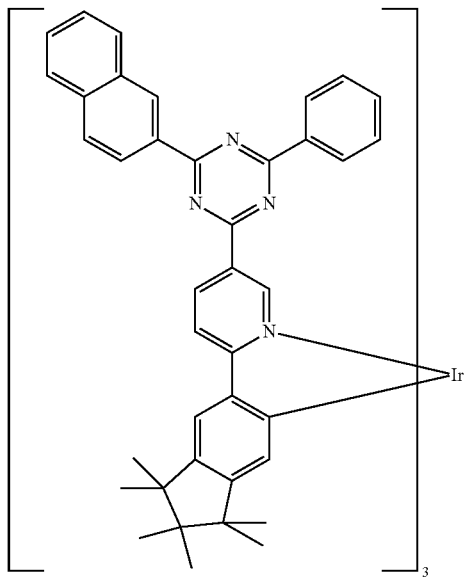 | L34 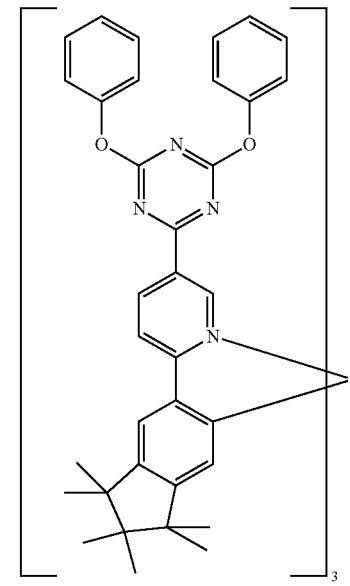 |
| Variant | A | A |
| Reaction medium | — | — |
| Melting aid | Hydroquinone | 1-Naphthol |
| Reaction temp. | 275° C. | 270° C. |
| Reaction time | 36 h | 24 h |
| Suspension medium | EtOH | EtOH |
| Extractant | Toluene | p-Xylene |
| Yield | 4% | 11% |

-continued
| Ex. | Ir(L35)₃ | Ir(L36)₃ |
|---|---|---|
| Ligand L | L35 | L36 |
| Ir complex | 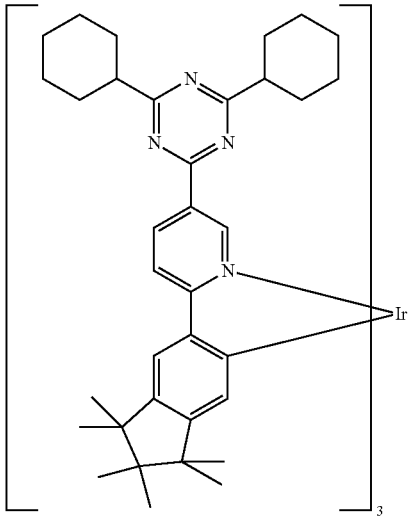 | 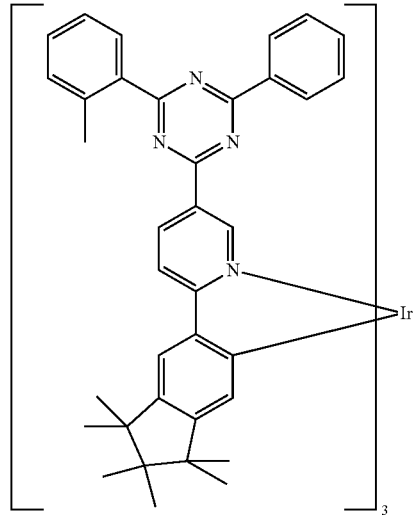 |
| Variant | A | A |
| Reaction medium | — | — |
| Melting aid | Hydroquinone | Hydroquinone |
| Reaction temp. | 260° C. | 275° C. |
| Reaction time | 24 h | 24 h |
| Suspension medium | EtOH | EtOH |
| Extractant | Ethyl acetate | Toluene |
| Yield | 17% | 11% |
| Ex. | Ir(L37)₃ | Ir(L38)₃ |
|---|---|---|
| Ligand L | L37 | L38 |
| Ir complex | 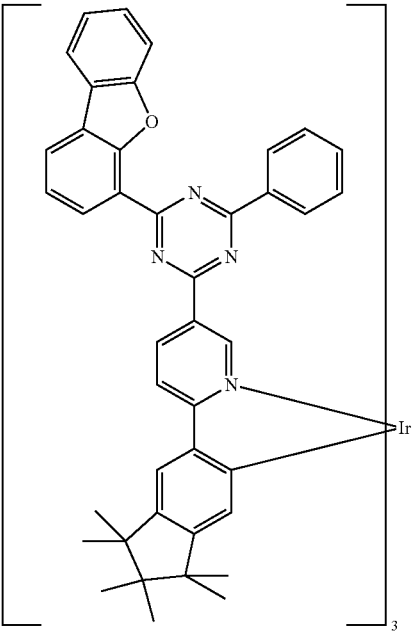 | 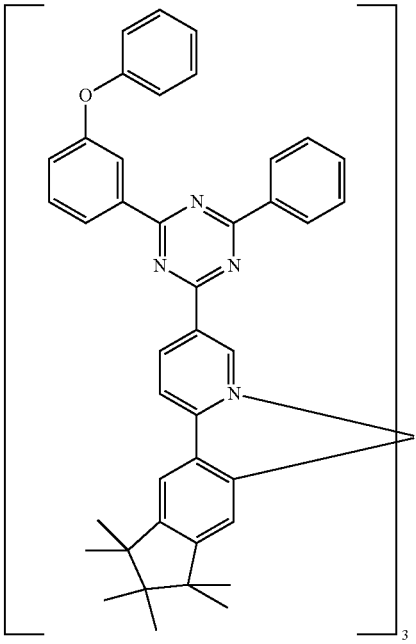 |

| | | |
|---|---|---|
| Variant | A | A |
| Reaction medium | — | — |
| Melting aid | Hydroquinone | 1-Naphthol |
| Reaction temp. | 275° C. | 265° C. |
| Reaction time | 24 h | 24 h |
| Suspension medium | EtOH | EtOH |
| Extractant | Chlorobenzene | Toluene |
| Yield | 13% | 8% |
| Ex. | Ir(L39)$_3$ | Ir(L40)$_3$ |
| Ligand L | L39 | L40 |
| Ir complex | 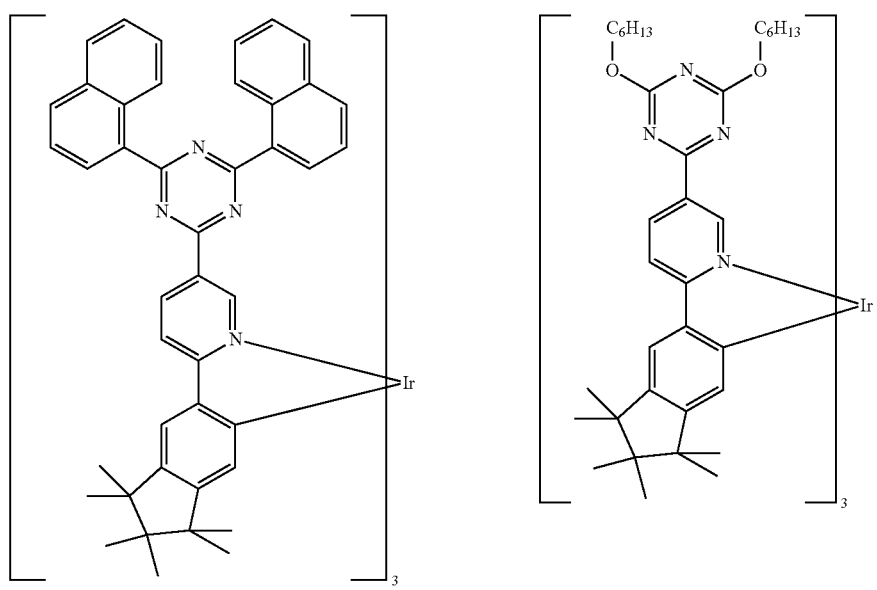 | |
| Variant | A | A |
| Reaction medium | — | — |
| Melting aid | Hydroquinone | 1-Naphthol |
| Reaction temp. | 275° C. | 270° C. |
| Reaction time | 36 h | 24 h |
| Suspension medium | EtOH | EtOH |
| Extractant | p-Dichlorobenzene | Butanol |
| Yield | 10% | 15% |

-continued

| Ex. | Ir(L41)₃ | Ir(L42)₃ |
| --- | --- | --- |
| Ligand L | L41 | L42 |
| Ir complex | | |
| Variant | A | A |
| Reaction medium | — | — |
| Melting aid | Hydroquinone | Hexadecane |
| Reaction temp. | 270° C. | 270° C. |
| Reaction time | 24 h | 24 h |
| Suspension medium | EtOH | EtOH |
| Extractant | Chlorobenzene | Chlorobenzene |
| Yield | 13% | 3% |

| Ex. | Ir(L43)₃ | Ir(L44)₃ |
| --- | --- | --- |
| Ligand L | L43 | L44 |
| Ir complex | | |
| Variant | A | A |
| Reaction medium | — | — |
| Melting aid | Hydroquinone | Hydroquinone |
| Reaction temp. | 260° C. | 260° C. |
| Reaction time | 24 h | 24 h |
| Suspension medium | EtOH | EtOH |
| Extractant | Toluene | Toluene |
| Yield | 9% | 12% |

-continued

| Ex. | Ir(L45)₃ | Ir(L46)₃ |
|---|---|---|
| Ligand L | L45 | L46 |
| Ir complex | | |
| Variant | A | A |
| Reaction medium | — | — |
| Melting aid | Hydroquinone | Hydroquinone |
| Reaction temp. | 275° C. | 270° C. |
| Reaction time | 24 h | 24 h |
| Suspension medium | EtOH | EtOH |
| Extractant | Toluene | Toluene |
| Yield | 6% | 11% |

| Ex. | Ir(L47)₃ | Ir(L48)₃ |
|---|---|---|
| Ligand L | L47 | L48 |
| Ir complex | | |

| | 323 | 324 |
|---|---|---|
| Variant | A | A |
| Reaction medium | — | — |
| Melting aid | Hydroquinone | Hydroquinone |
| Reaction temp. | 270° C. | 275° C. |
| Reaction time | 60 h | 36 h |
| Suspension medium | Methanol | EtOH |
| Extractant | Toluene | p-Dichloro-benzene |
| Yield | 12% | 12% |
| Ex. | Ir(L49)₃ | Ir(L50)₃ |
| Ligand L | L49 | L50 |
| Ir complex | | |

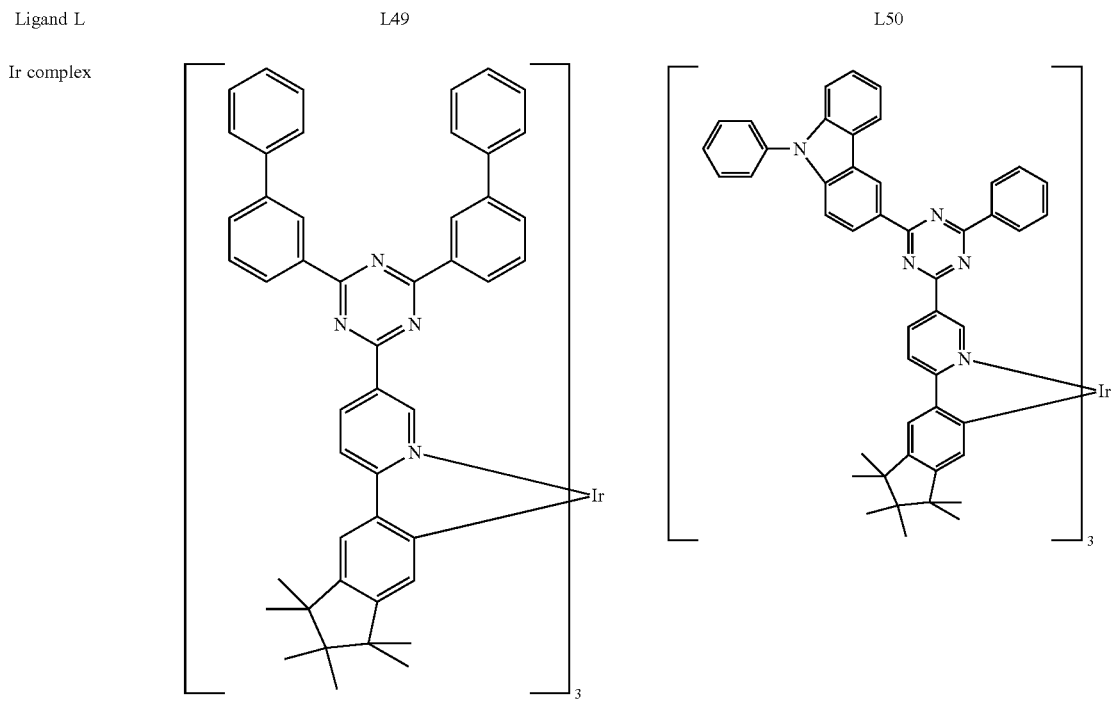

| | | |
|---|---|---|
| Variant | A | A |
| Reaction medium | — | — |
| Melting aid | Hydroquinone | Hydroquinone |
| Reaction temp. | 270° C. | 275° C. |
| Reaction time | 24 h | 24 h |
| Suspension medium | EtOH | EtOH |
| Extractant | Toluene | Ethyl acetate |
| Yield | 9% | 11% |

-continued

| Ex. | Ir(L51)₃ | Ir(L52)₃ |
|---|---|---|
| Ligand L | L51 | L52 |
| Ir complex | | |
| Variant | A | A |
| Reaction medium | — | — |
| Melting aid | Hydroquinone | Hydroquinone |
| Reaction temp. | 270° C. | 275° C. |
| Reaction time | 24 h | 36 h |
| Suspension medium | EtOH | EtOH |
| Extractant | Ethyl acetate | p-Dichlorobenzene |
| Yield | 10% | 5% |

| Ex. | Ir(L53)₃ | Ir(L54)₃ |
|---|---|---|
| Ligand L | L53 | L54 |
| Ir complex | 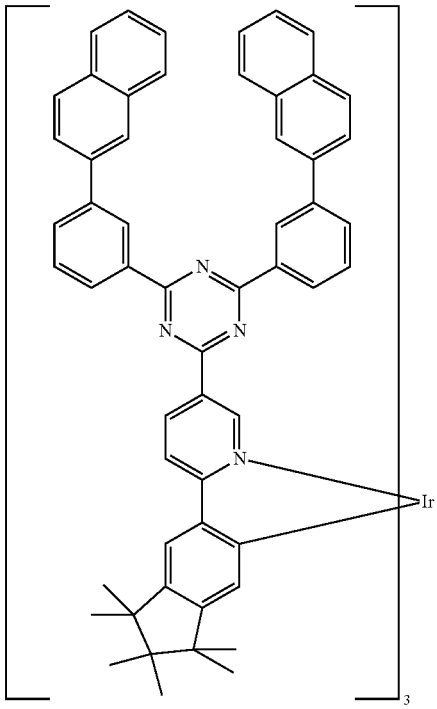 | 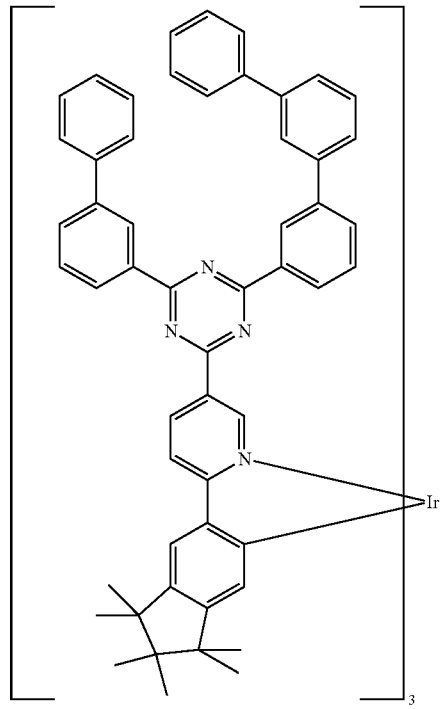 |
| Variant | A | A |
| Reaction medium | — | — |
| Melting aid | Hydroquinone | Hydroquinone |
| Reaction temp. | 270° C. | 275° C. |
| Reaction time | 24 h | 24 h |
| Suspension medium | EtOH | EtOH |
| Extractant | p-Xylene | Toluene |
| Yield | 6% | 12% |
| Ex. | Ir(L55)₃ | Ir(L56)₃ |
|---|---|---|
| Ligand L | L55 | L56 |
| Ir complex | 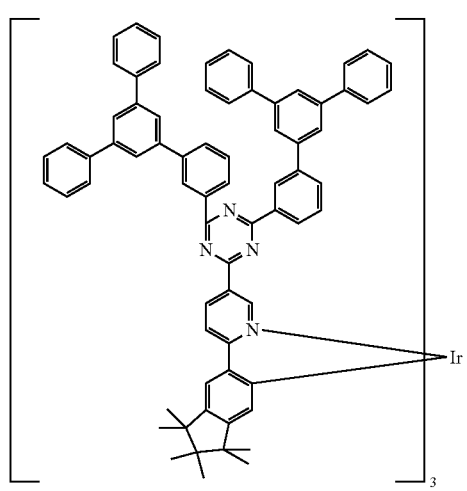 | 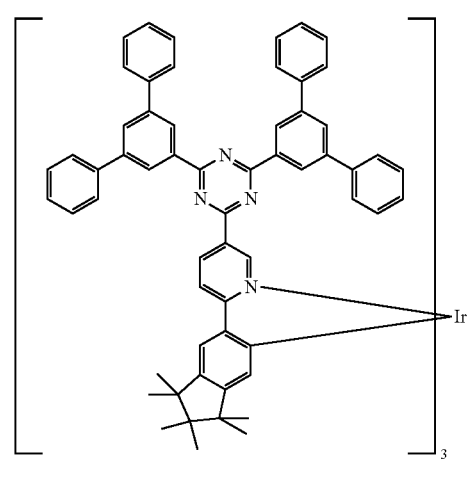 |
| Variant | A | A |
| Reaction medium | — | — |
| Melting aid | Hydroquinone | Hydroquinone |
| Reaction temp. | 275° C. | 275° C. |
| Reaction time | 24 h | 24 h |

-continued

| | | |
|---|---|---|
| Suspension medium | EtOH | EtOH |
| Extractant | Toluene | Toluene |
| Yield | 12% | 10% |
| Ex. | Ir(L57)₃ | Ir(L58)₃ |
| Ligand L | L57 | L58 |

Ir complex

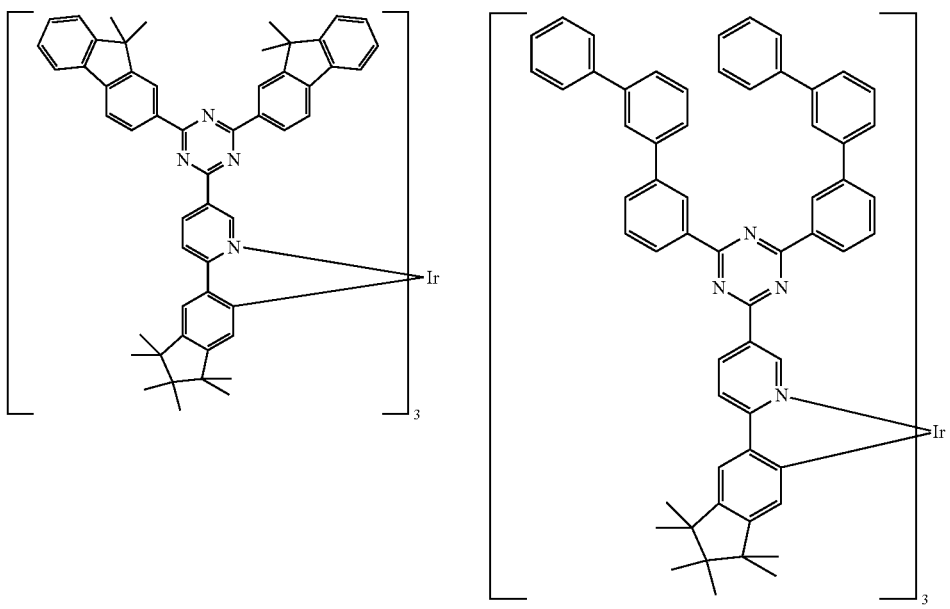

| | | |
|---|---|---|
| Variant | A | A |
| Reaction medium | — | — |
| Melting aid | Hydroquinone | Hydroquinone |
| Reaction temp. | 275° C. | 275° C. |
| Reaction time | 24 h | 24 h |
| Suspension medium | EtOH | EtOH |
| Extractant | Toluene | Toluene |
| Yield | 10% | 14% |
| Ex. | Ir(L59)₃ | Ir(L60)₃ |
| Ligand L | L59 | L60 |

Ir complex

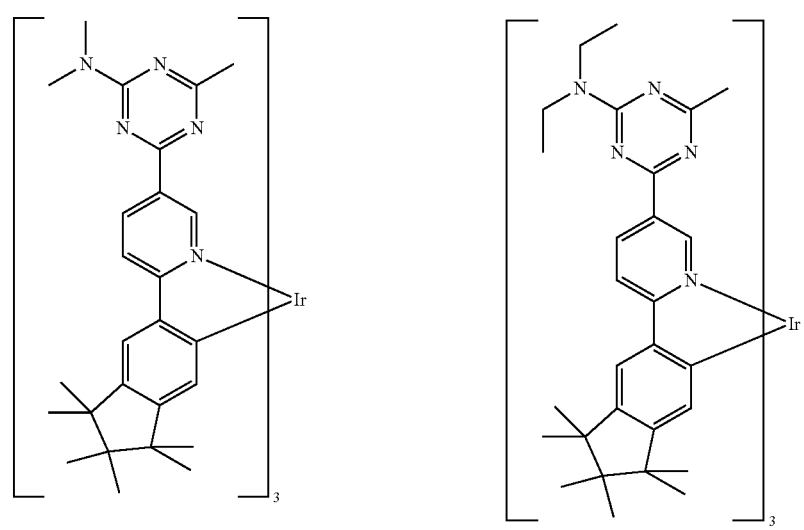

| | | |
|---|---|---|
| Variant | A | A |
| Reaction medium | — | — |
| Melting aid | Hydroquinone | Hydroquinone |
| Reaction temp. | 260° C. | 260° C. |

-continued

| | | |
|---|---|---|
| Reaction time | 48 h | 48 h |
| Suspension medium | EtOH | EtOH |
| Extractant | p-Xylene | Toluene |
| Yield | 7% | 4% |

| Ex. | Ir(L61)₃ | Ir(L62)₃ |
|---|---|---|
| Ligand L | L61 | L62 |
| Ir complex | 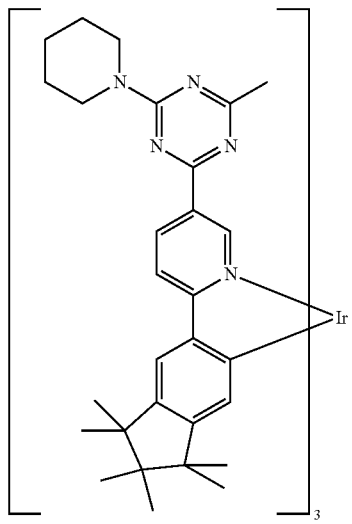 | 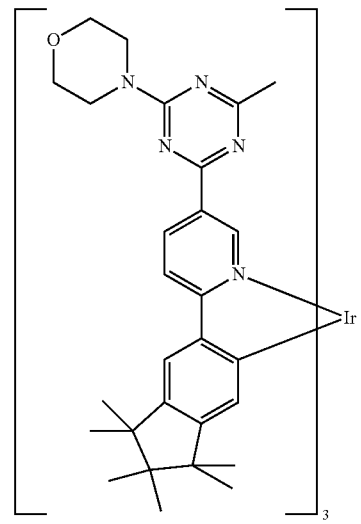 |
| Variant | A | A |
| Reaction medium | — | — |
| Melting aid | Hydroquinone | Hydroquinone |
| Reaction temp. | 260° C. | 250° C. |
| Reaction time | 24 h | 24 h |
| Suspension medium | EtOH | EtOH |
| Extractant | Ethyl acetate | Ethyl acetate |
| Yield | 8% | 3% |

| Ex. | Ir(L63)₃ | Ir(L64)₃ |
|---|---|---|
| Ligand L | L63 | L64 |
| Ir complex | 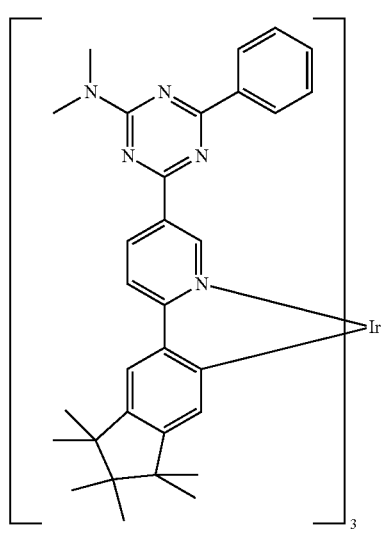 | 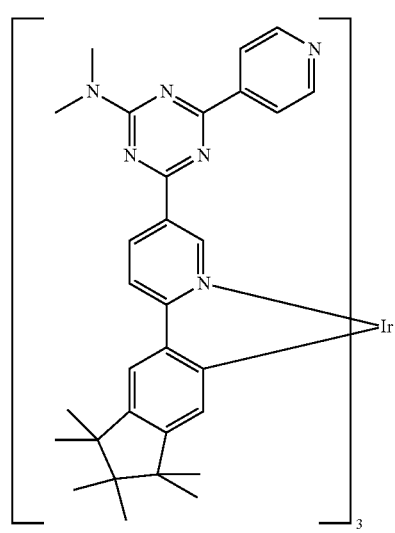 |
| Variant | A | A |
| Reaction medium | — | — |
| Melting aid | Hydroquinone | Hydroquinone |
| Reaction temp. | 270° C. | 260° C. |

| | | |
|---|---|---|
| Reaction time | 24 h | 48 h |
| Suspension medium | EtOH | EtOH |
| Extractant | Toluene | p-Xylene |
| Yield | 7% | 5% |

| Ex. | Ir(L65)₃ | Ir(L66)₃ |
|---|---|---|
| Ligand L | L65 | L66 |
| Ir complex | | |
| Variant | A | A |
| Reaction medium | — | — |
| Melting aid | Hydroquinone | Hydroquinone |
| Reaction temp. | 265° C. | 260° C. |
| Reaction time | 24 h | 48 h |
| Suspension medium | EtOH | EtOH |
| Extractant | Toluene | p-Dichloro-benzene |
| Yield | 11% | 8% |

| Ex. | Ir(L67)₃ | Ir(L68)₃ |
|---|---|---|
| Ligand L | L67 | L68 |
| Ir complex | | |

-continued

| Variant | A | A |
|---|---|---|
| Reaction medium | — | — |
| Melting aid | 1-Naphthol | 1-Naphthol |
| Reaction temp. | 275° C. | 265° C. |
| Reaction time | 24 h | 24 h |
| Suspension medium | EtOH | EtOH |
| Extractant | Chlorobenzene | Toluene |
| Yield | 4% | 7% |

| Ex. | Ir(L69)$_3$ | Ir(L70)$_3$ |
|---|---|---|
| Ligand L | L69 | L70 |
| Ir complex | | |

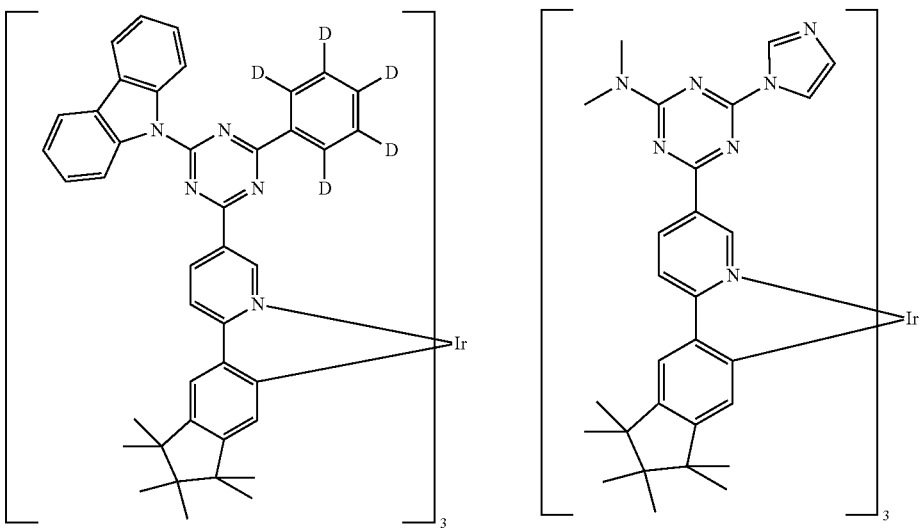

| Variant | A | A |
|---|---|---|
| Reaction medium | — | — |
| Melting aid | 1-Naphthol | Hydroquinone |
| Reaction temp. | 275° C. | 255° C. |
| Reaction time | 24 h | 48 h |
| Suspension medium | EtOH | EtOH |
| Extractant | Chlorobenzene | p-Dichlorobenzene |
| Yield | 3% | 4% |

| Ex. | Ir(L71)$_3$ | Ir(L72)$_3$ |
|---|---|---|
| Ligand L | L71 | L72 |
| Ir complex | | |

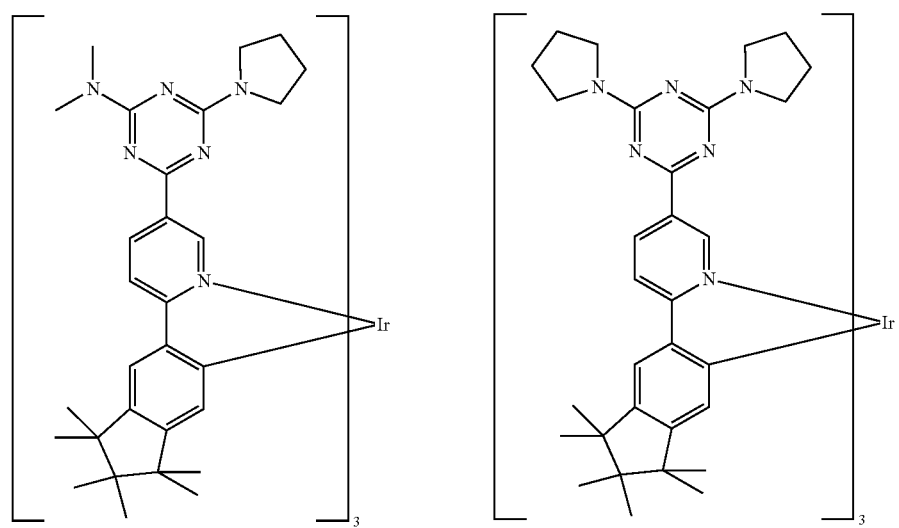

| Variant | A | A |
|---|---|---|
| Reaction medium | — | — |
| Melting aid | Hydroquinone | Hydroquinone |
| Reaction temp. | 260° C. | 255° C. |
| Reaction time | 48 h | 48 h |
| Suspension medium | EtOH | EtOH |
| Extractant | Toluene | Ethyl acetate |
| Yield | 4% | 8% |

| Ex. | Ir(L73)₃ | Ir(L74)₃ |
|---|---|---|
| Ligand L | L73 | L74 |
| Ir complex | | |

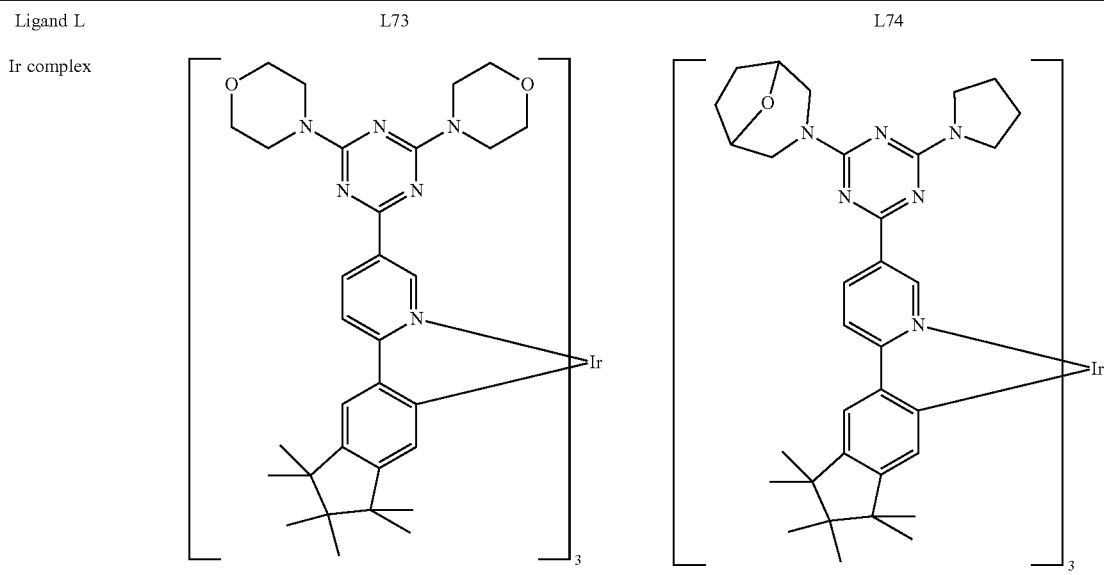

| Variant | A | A |
|---|---|---|
| Reaction medium | — | — |
| Melting aid | Hydroquinone | Hydroquinone |
| Reaction temp. | 250° C. | 265° C. |
| Reaction time | 24 h | 24 h |
| Suspension medium | EtOH | EtOH |
| Extractant | Ethyl acetate | Ethyl acetate |
| Yield | 6% | 3% |

| Ex. | Ir(L75)₃ | Ir(L76)₃ |
|---|---|---|
| Ligand L | L75 | L76 |
| Ir complex | | |

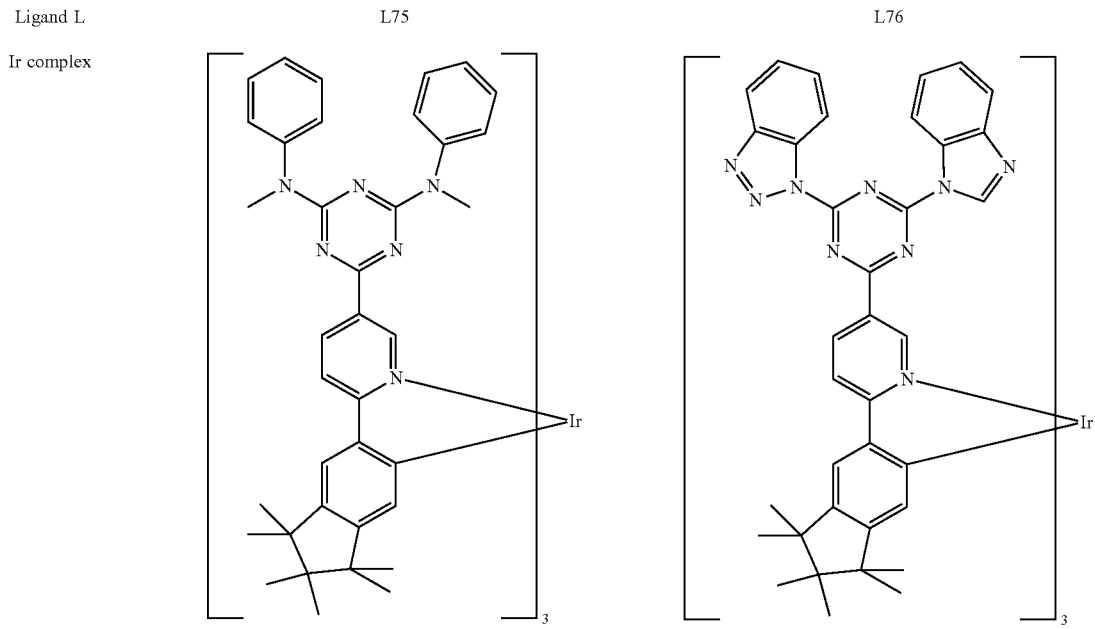

-continued

| | | |
|---|---|---|
| Variant | A | A |
| Reaction medium | — | — |
| Melting aid | Hydroquinone | Hydroquinone |
| Reaction temp. | 260° C. | 275° C. |
| Reaction time | 48 h | 24 h |
| Suspension medium | EtOH | EtOH |
| Extractant | Toluene | m-Dichloro-benzene |
| Yield | 7% | 5% |
| Ex. | Ir(L77)₃ | Ir(L78)₃ |
| Ligand L | L77 | L78 |
| Ir complex | | |

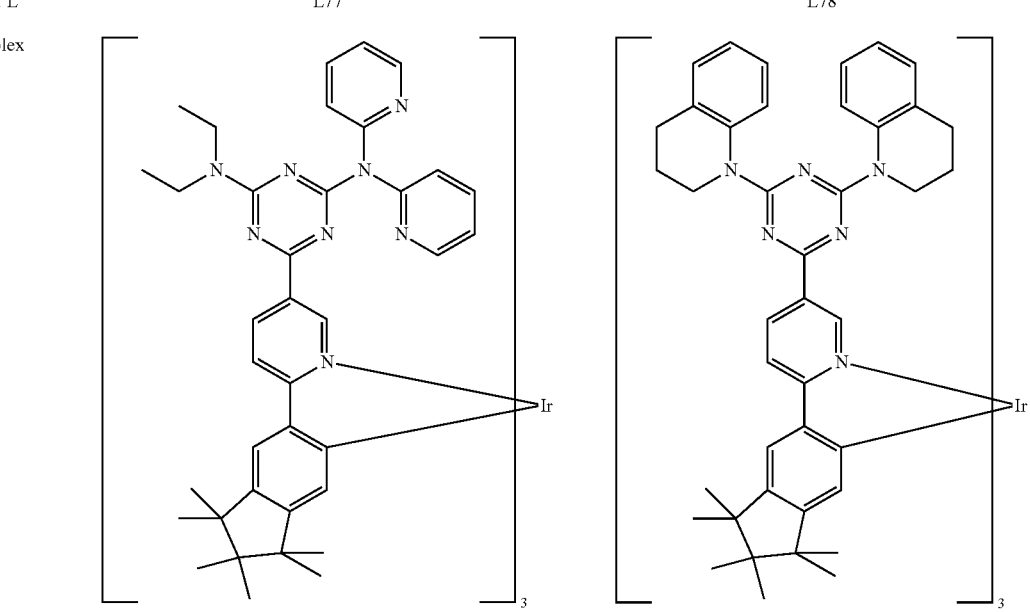

| | | |
|---|---|---|
| Variant | A | A |
| Reaction medium | — | — |
| Melting aid | 1-Naphthol | 1-Naphthol |
| Reaction temp. | 265° C. | 265° C. |
| Reaction time | 24 h | 24 h |
| Suspension medium | EtOH | EtOH |
| Extractant | Toluene | Toluene |
| Yield | 7% | 11% |
| Ex. | Ir(L79)₃ | Ir(L80)₃ |
| Ligand L | L79 | L80 |
| Ir complex | | |

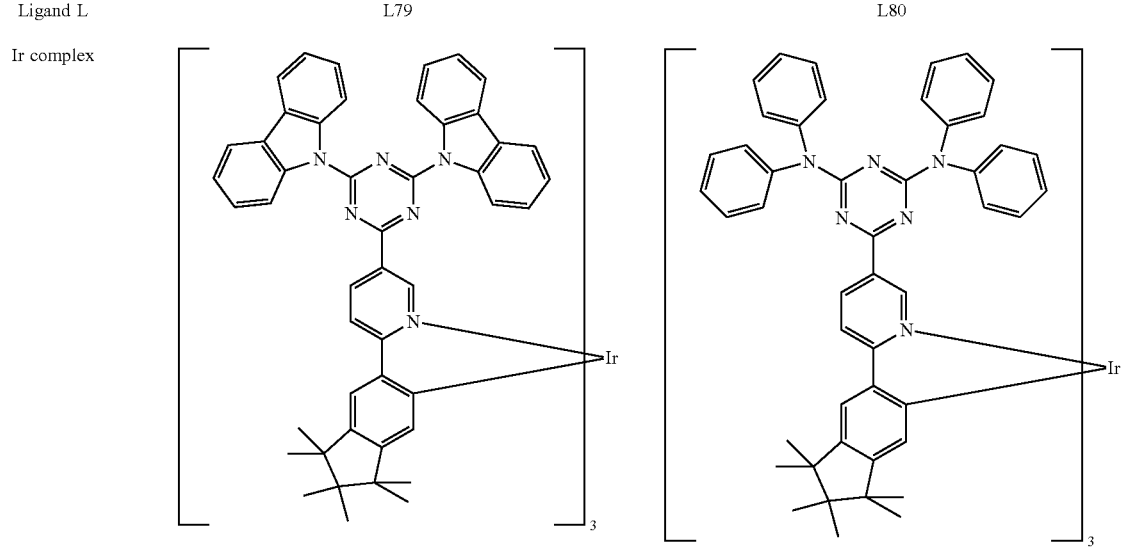

|  | 341 | 342 |
|---|---|---|
| Variant | A | A |
| Reaction medium | — | — |
| Melting aid | 1-Naphthol | 1-Naphthol |
| Reaction temp. | 275° C. | 265° C. |
| Reaction time | 36 h | 24 h |
| Suspension medium | EtOH | EtOH |
| Extractant | Chlorobenzene | Ethyl acetate |
| Yield | 13% | 12% |
| Ex. | Ir(L81)$_3$ | Ir(L82)$_3$ |
| Ligand L | L81 | L82 |
| Ir complex | 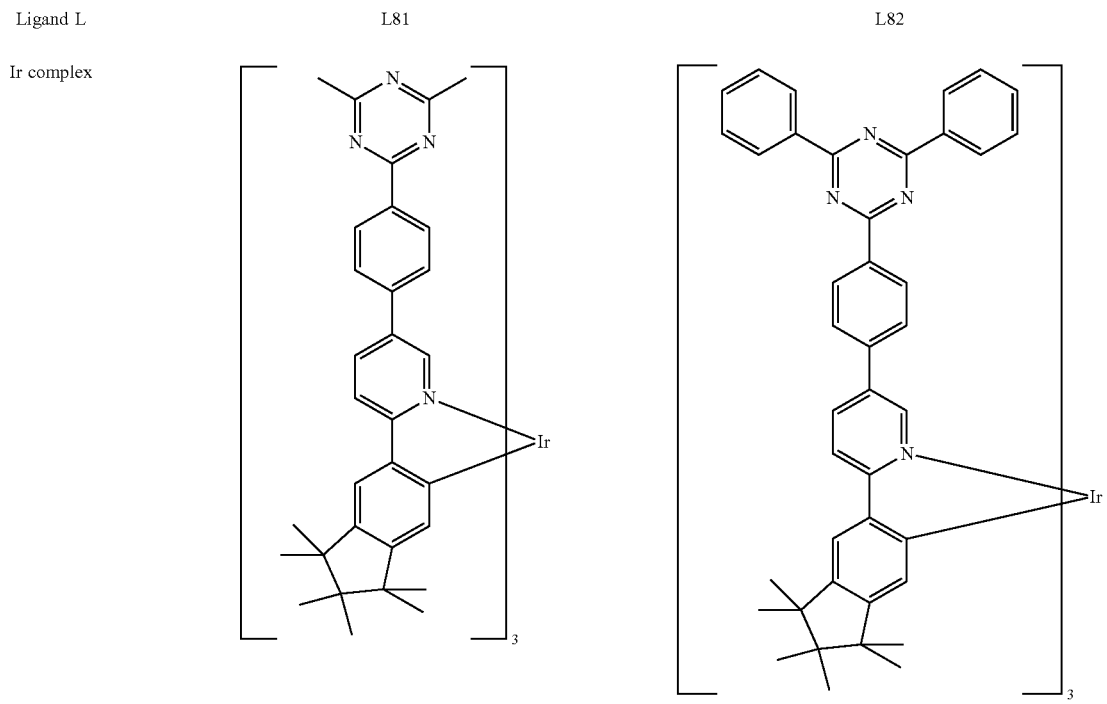 | |
| Variant | A | A |
| Reaction medium | — | — |
| Melting aid | Diphenyl ether | Diphenyl ether |
| Reaction temp. | 250° C. | 250° C. |
| Reaction time | 36 h | 48 h |
| Suspension medium | EtOH | EtOH |
| Extractant | Toluene | p-Xylene |
| Yield | 3% | 1% |

-continued

| Ex. | Ir(L83)₃ | Ir(L84)₃ |
|---|---|---|
| Ligand L | L83 | L84 |
| Ir complex | | |
| Variant | D | A |
| Reaction medium | — | — |
| Melting aid | — | Diphenyl ether |
| Reaction temp. | 250° C. | 250° C. |
| Reaction time | 48 h | 48 h |
| Suspension medium | EtOH | EtOH |
| Extractant | p-Xylene | Toluene |
| Yield | 3% | 2% |

| Ex. | Ir(L85)₃ | Ir(L86)₃ |
|---|---|---|
| Ligand L | L85 | L86 |
| Ir complex | 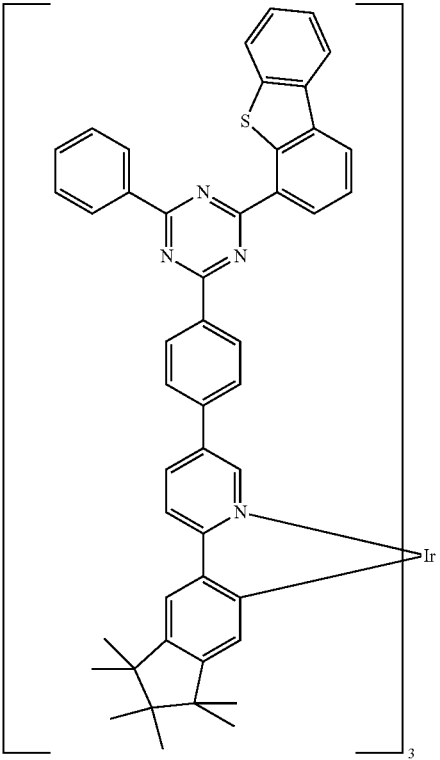 | 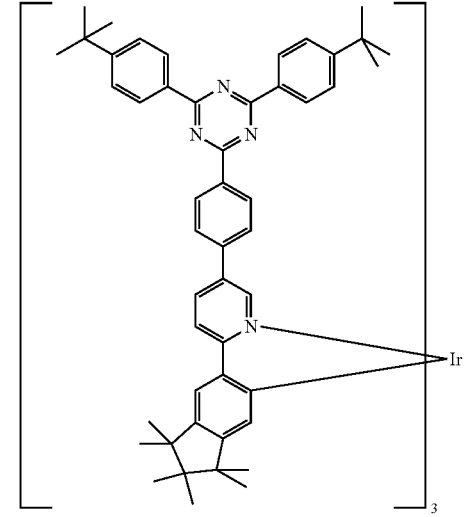 |
| Variant | A | A |
| Reaction medium | — | — |
| Melting aid | Diphenyl ether | Diphenyl ether |
| Reaction temp. | 250° C. | 250° C. |
| Reaction time | 48 h | 48 h |
| Suspension medium | EtOH | EtOH |
| Extractant | p-Xylene | Ethyl acetate |
| Yield | 3% | 3% |

-continued

| Ex. | Ir(L87)₃ | Ir(L88)₃ |
|---|---|---|
| Ligand L | L87 | L88 |
| Ir complex | | |
| Variant | A | A |
| Reaction medium | — | — |
| Melting aid | Diphenyl ether | Diphenyl ether |
| Reaction temp. | 250° C. | 250° C. |
| Reaction time | 48 h | 48 h |
| Suspension medium | EtOH | EtOH |
| Extractant | Toluene | Chlorobenzene |
| Yield | 2% | 4% |

| Ex. | Ir(L89)₃ | Ir(L90)₃ |
|---|---|---|
| Ligand L | L89 | L90 |
| Ir complex | | |
| Variant | A | A |
| Reaction medium | — | — |
| Melting aid | Hydroquinone | Hydroquinone |
| Reaction temp. | 270° C. | 275° C. |
| Reaction time | 24 h | 24 h |
| Suspension medium | EtOH | EtOH |
| Extractant | m-Dichlorobenzene | Chlorobenzene |
| Yield | 2% | 4% |

-continued

| Ex. | Ir(L91)₃ | Ir(L92)₃ |
|---|---|---|
| Ligand L | L91 | L92 |
| Ir complex | 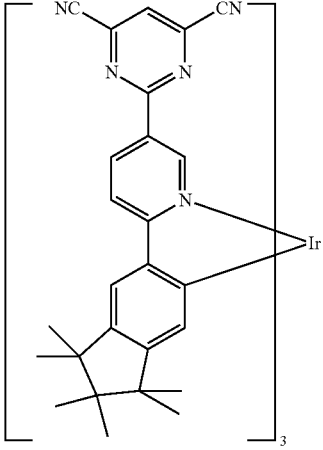 | 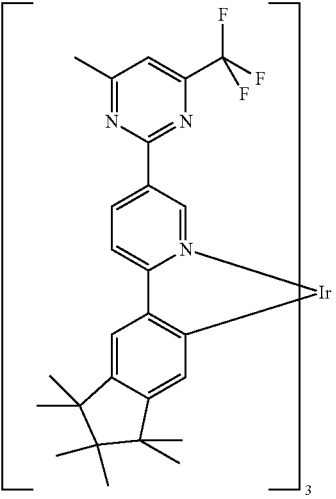 |
| Variant | D | A |
| Reaction medium | — | — |
| Melting aid | — | Hydroquinone |
| Reaction temp. | 270° C. | 270° C. |
| Reaction time | 24 h | 24 h |
| Suspension medium | EtOH | EtOH |
| Extractant | Chlorobenzene | Toluene |
| Yield | 6% | 3% |

| Ex. | Ir(L93)₃ | Ir(L94)₃ |
|---|---|---|
| Ligand L | L93 | L94 |
| Ir complex | 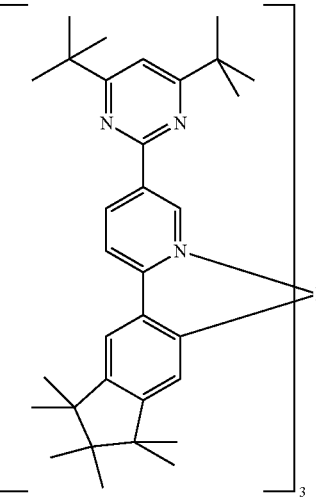 | 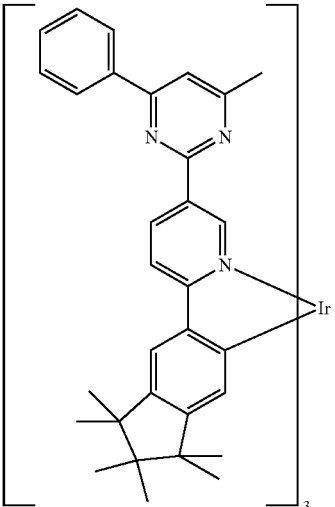 |
| Variant | A | A |
| Reaction medium | — | — |
| Melting aid | Hydroquinone | Hydroquinone |
| Reaction temp. | 265° C. | 265° C. |
| Reaction time | 24 h | 24 h |
| Suspension medium | EtOH | EtOH |
| Extractant | Ethyl acetate | Toluene |
| Yield | 6% | 3% |

| Ex. | Ir(L95)$_3$ | Ir(L96)$_3$ |
| --- | --- | --- |
| Ligand L | L95 | L96 |
| Ir complex | | |
| Variant | A | A |
| Reaction medium | — | — |
| Melting aid | Hydroquinone | Hydroquinone |
| Reaction temp. | 265° C. | 265° C. |
| Reaction time | 24 h | 24 h |
| Suspension medium | EtOH | EtOH |
| Extractant | Chlorobenzene | Ethyl acetate |
| Yield | 2% | 4% |

| Ex. | Ir(L97)$_3$ | Ir(L98)$_3$ |
| --- | --- | --- |
| Ligand L | L97 | L98 |
| Ir complex | | |
| Variant | A | A |
| Reaction medium | — | — |
| Melting aid | Hydroquinone | Hydroquinone |
| Reaction temp. | 275° C. | 265° C. |
| Reaction time | 24 h | 24 h |
| Suspension medium | EtOH | EtOH |
| Extractant | Chlorobenzene | Chlorobenzene |
| Yield | 10% | 8% |

| Ex. | Ir(L99)₃ | Ir(L100)₃ |
|---|---|---|
| Ligand L | L99 | L100 |
| Ir complex | | |
| Variant | A | A |
| Reaction medium | — | — |
| Melting aid | — | — |
| Reaction temp. | 270° C. | 280° C. |
| Reaction time | 24 h | 24 h |
| Suspension medium | EtOH | EtOH |
| Extractant | p-Xylene | Ethyl acetate |
| Yield | 9% | 7% |

| Ex. | Ir(L101)₃ | Ir(L102)₃ |
|---|---|---|
| Ligand L | L101 | L102 |
| Ir complex | | |
| Variant | A | A |
| Reaction medium | — | — |
| Melting aid | Hydroquinone | Hydroquinone |
| Reaction temp. | 275° C. | 270° C. |
| Reaction time | 24 h | 24 h |
| Suspension medium | EtOH | EtOH |
| Extractant | Toluene | Toluene |
| Yield | 11% | 14% |

| Ex. | Ir(L103)₃ | Ir(L104)₃ |
|---|---|---|
| Ligand L | L103 | L104 |
| Ir complex | 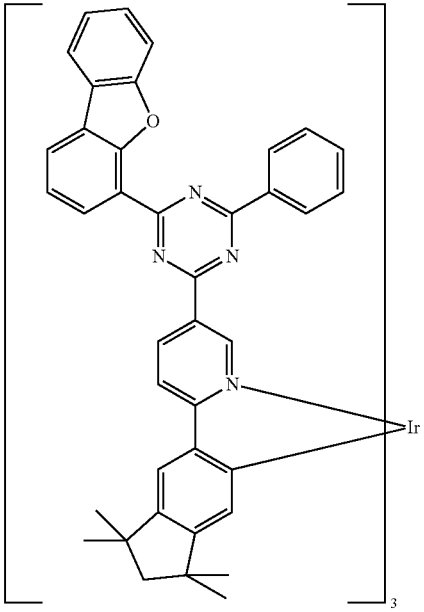 | 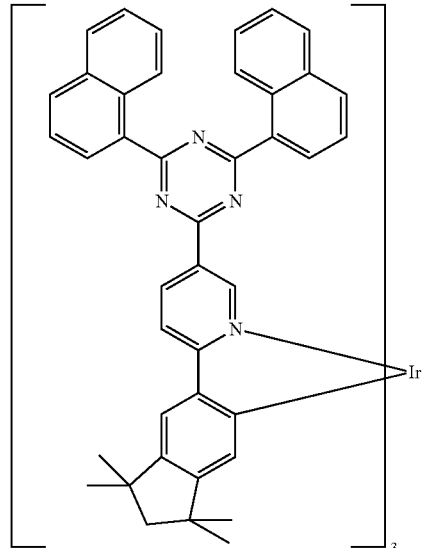 |
| Variant | A | A |
| Reaction medium | — | — |
| Melting aid | Hydroquinone | Hydroquinone |
| Reaction temp. | 265° C. | 275° C. |
| Reaction time | 24 h | 24 h |
| Suspension medium | EtOH | EtOH |
| Extractant | Ethyl acetate | Chlorobenzene |
| Yield | 11% | 5% |

| Ex. | Ir(L105)₃ | Ir(L106)₃ |
|---|---|---|
| Ligand L | L105 | L106 |
| Ir complex | 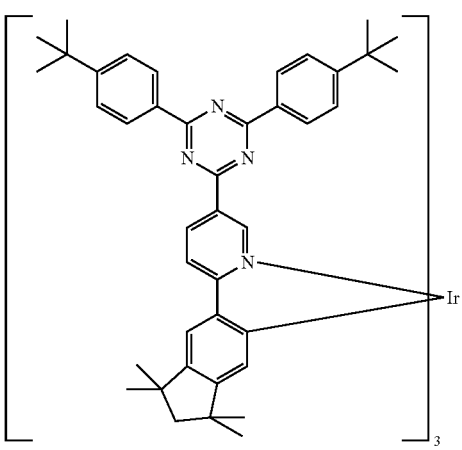 | 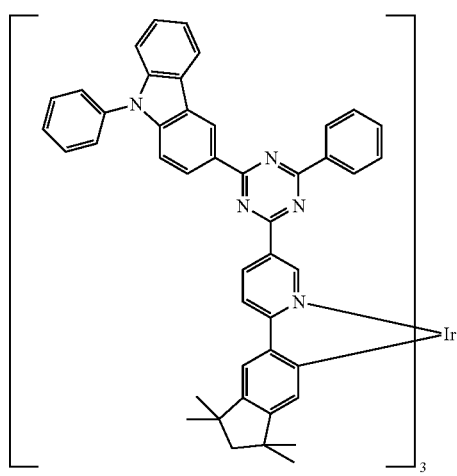 |
| Variant | A | A |
| Reaction medium | — | — |
| Melting aid | Hydroquinone | 1-Naphthol |
| Reaction temp. | 270° C. | 270° C. |
| Reaction time | 24 h | 24 h |
| Suspension medium | EtOH | EtOH |
| Extractant | Ethyl acetate | Ethyl acetate |
| Yield | 12% | 14% |

-continued

| Ex. | Ir(L107)₃ | Ir(L108)₃ |
| --- | --- | --- |
| Ligand L | L107 | L108 |
| Ir complex | | |
| Variant | A | A |
| Reaction medium | — | — |
| Melting aid | 1-Naphthol | Hydroquinone |
| Reaction temp. | 270° C. | 265° C. |
| Reaction time | 24 h | 24 h |
| Suspension medium | EtOH | EtOH |
| Extractant | Ethyl acetate | Toluene |
| Yield | 13% | 11% |

| Ex. | Ir(L109)₃ | Ir(L110)₃ |
| --- | --- | --- |
| Ligand L | L109 | L110 |
| Ir complex | | |
| Variant | A | A |
| Reaction medium | — | — |
| Melting aid | Hydroquinone | 1-Naphthol |
| Reaction temp. | 270° C. | 270° C. |
| Reaction time | 24 h | 24 h |
| Suspension medium | EtOH | EtOH |
| Extractant | Ethyl acetate | p-Xylene |
| Yield | 9% | 5% |

| Ex. | Ir(L111)₃ | Ir(L112)₃ |
|---|---|---|
| Ligand L | L111 | L112 |
| Ir complex | 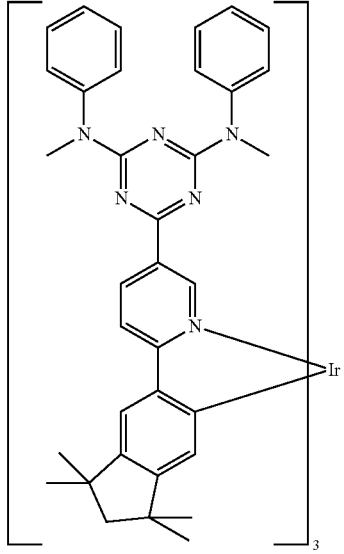 | 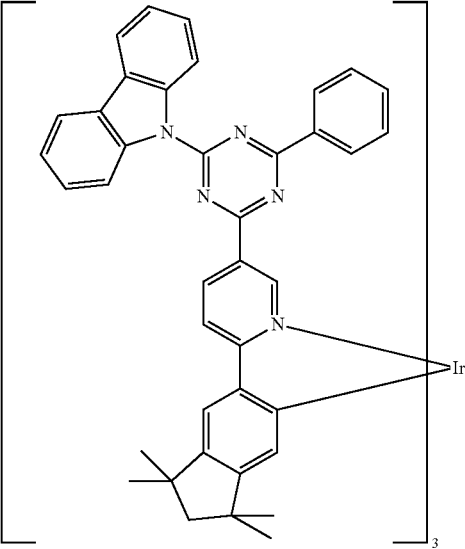 |
| Variant | A | A |
| Reaction medium | — | — |
| Melting aid | 1-Naphthol | Hydroquinone |
| Reaction temp. | 270° C. | 265° C. |
| Reaction time | 24 h | 24 h |
| Suspension medium | EtOH | EtOH |
| Extractant | Toluene | Ethyl acetate |
| Yield | 4% | 8% |

| Ex. | Ir(L113)₃ | Ir(L114)₃ |
|---|---|---|
| Ligand L | L113 | L114 |
| Ir complex | 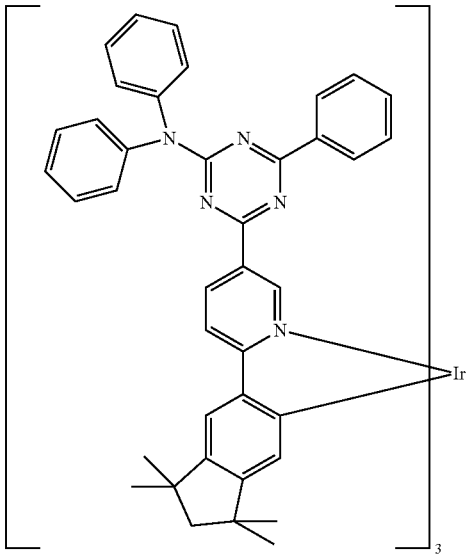 | 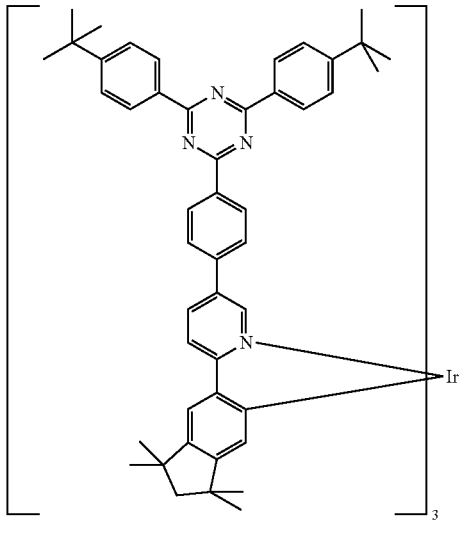 |
| Variant | A | A |
| Reaction medium | — | — |
| Melting aid | Hydroquinone | Hydroquinone |
| Reaction temp. | 265° C. | 270° C. |
| Reaction time | 24 h | 24 h |
| Suspension medium | EtOH | EtOH |
| Extractant | Ethyl acetate | Ethyl acetate |
| Yield | 10% | 4% |

-continued

| Ex. | Ir(L115)₃ | Ir(L116)₃ |
|---|---|---|
| Ligand L | L115 | L116 |
| Ir complex | 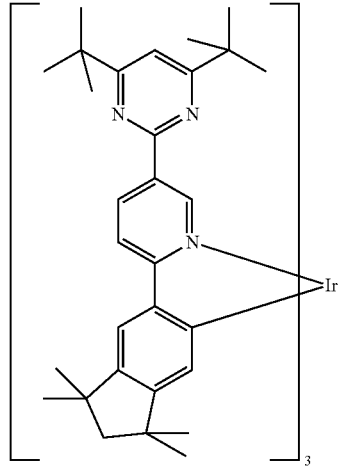 | 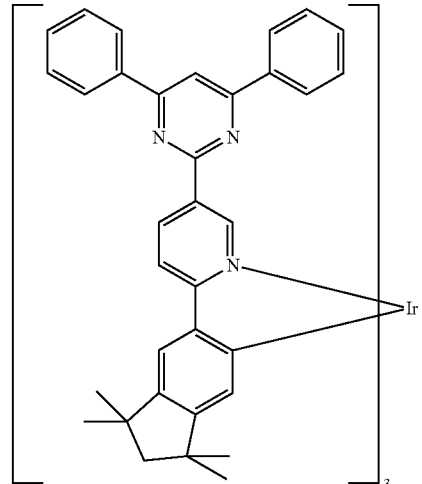 |
| Variant | A | A |
| Reaction medium | — | — |
| Melting aid | — | Hydroquinone |
| Reaction temp. | 280° C. | 275° C. |
| Reaction time | 24 h | 24 h |
| Suspension medium | EtOH | EtOH |
| Extractant | Ethyl acetate | Toluene |
| Yield | 2% | 3% |
| Ex. | Ir(L117)₃ | Ir(L118)₃ |
| Ligand L | L117 | L118 |
| Ir complex | 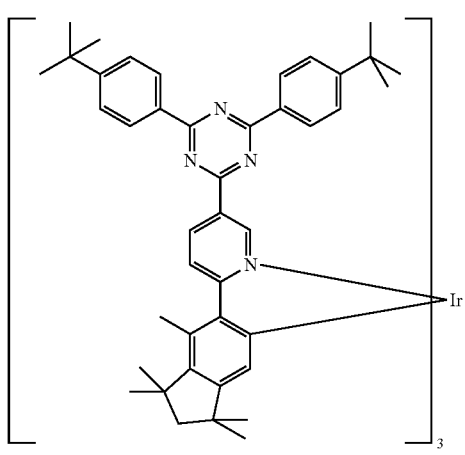 | 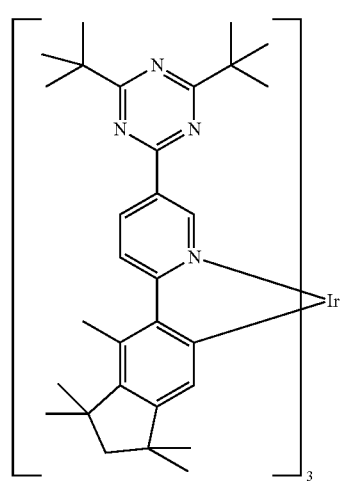 |
| Variant | A | A |
| Reaction medium | — | — |
| Melting aid | Hydroquinone | — |
| Reaction temp. | 270° C. | 280° C. |
| Reaction time | 24 h | 24 h |
| Suspension medium | EtOH | EtOH |
| Extractant | Ethyl acetate | Ethyl acetate |
| Yield | 12% | 9% |

-continued

| Ex. | Ir(L119)₃ | Ir(L120)₃ |
|---|---|---|
| Ligand L | L119 | L120 |
| Ir complex | (structure) | (structure) |
| Variant | A | A |
| Reaction medium | — | — |
| Melting aid | Hydroquinone | 1-Naphthol |
| Reaction temp. | 270° C. | 270° C. |
| Reaction time | 24 h | 24 h |
| Suspension medium | EtOH | EtOH |
| Extractant | Ethyl acetate | Ethyl acetate |
| Yield | 7% | 10% |

| Ex. | Ir(L121)₃ | Ir(L122)₃ |
|---|---|---|
| Ligand L | L121 | L122 |
| Ir complex | (structure) | (structure) |
| Variant | A | A |
| Reaction medium | — | — |
| Melting aid | Hydroquinone | — |
| Reaction temp. | 270° C. | 280° C. |
| Reaction time | 24 h | 24 h |
| Suspension medium | EtOH | EtOH |
| Extractant | Ethyl acetate | Ethyl acetate |
| Yield | 11% | 10% |

| Ex. | Ir(L123)₃ | Ir(L124)₃ |
|---|---|---|
| Ligand L | L123 | L124 |
| Ir complex | 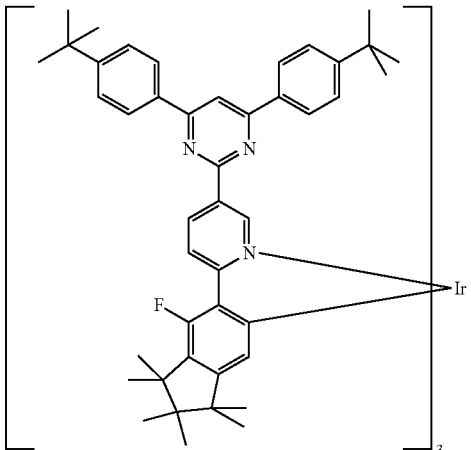 | 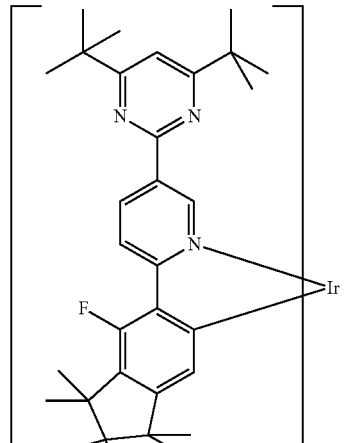 |
| Variant | A | A |
| Reaction medium | — | — |
| Melting aid | Hydroquinone | — |
| Reaction temp. | 270° C. | 280° C. |
| Reaction time | 24 h | 24 h |
| Suspension medium | EtOH | EtOH |
| Extractant | Ethyl acetate | Ethyl acetate |
| Yield | 7% | 8% |

| Ex. | Ir(L125)₃ | Ir(L126)₃ |
|---|---|---|
| Ligand L | L125 | L126 |
| Ir complex | 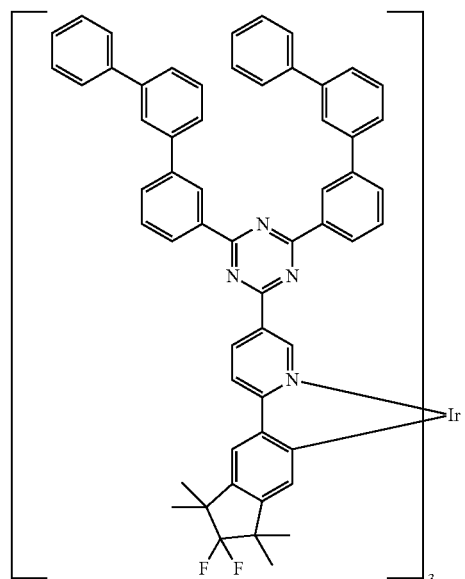 | 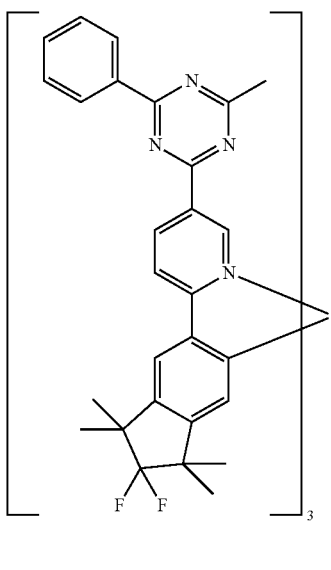 |
| Variant | A | A |
| Reaction medium | — | — |
| Melting aid | Hydroquinone | — |
| Reaction temp. | 270° C. | 270° C. |
| Reaction time | 24 h | 36 h |
| Suspension medium | EtOH | EtOH |
| Extractant | Ethyl acetate | p-Xylene |
| Yield | 8% | 5% |

-continued

| Ex. | Ir(L127)₃ | Ir(L128)₃ |
|---|---|---|
| Ligand L | L127 | L128 |
| Ir complex | 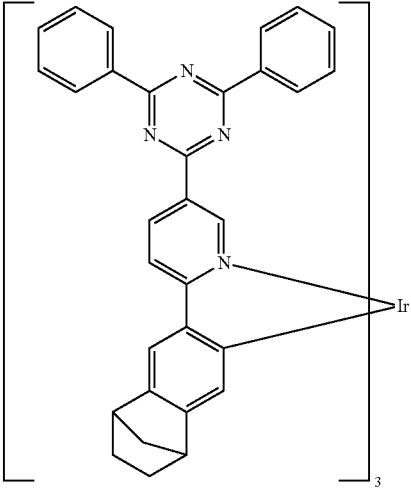 | 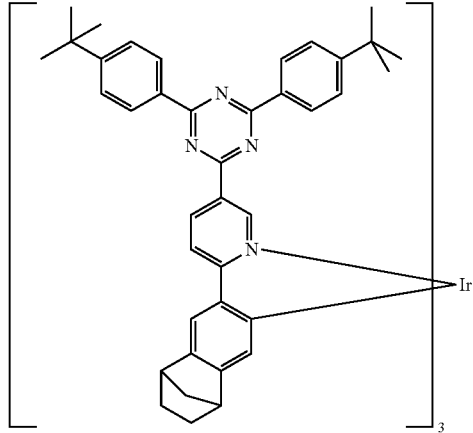 |
| Variant | A | A |
| Reaction medium | — | — |
| Melting aid | Hydroquinone | Hydroquinone |
| Reaction temp. | 275° C. | 270° C. |
| Reaction time | 24 h | 24 h |
| Suspension medium | EtOH | EtOH |
| Extractant | Toluene | Ethyl acetate |
| Yield | 5% | 9% |

| Ex. | Ir(L129)₃ | Ir(L130)₃ |
|---|---|---|
| Ligand L | L129 | L130 |
| Ir complex | 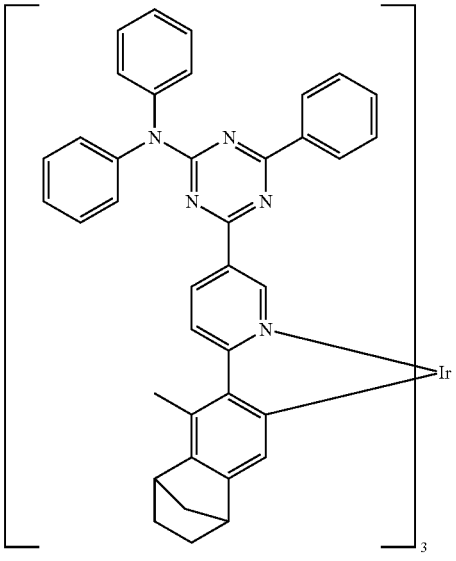 | 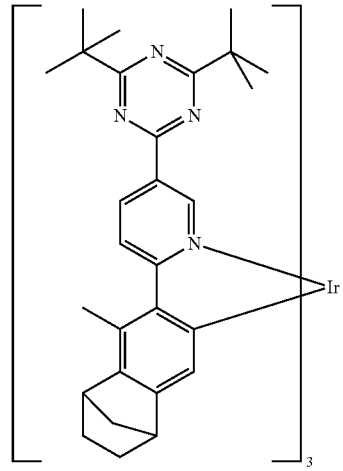 |
| Variant | A | D |
| Reaction medium | — | — |
| Melting aid | Hydroquinone | — |
| Reaction temp. | 265° C. | 280° C. |
| Reaction time | 24 h | 24 h |
| Suspension medium | EtOH | EtOH |
| Extractant | Ethyl acetate | Ethyl acetate |
| Yield | 7% | 5% |

| Ex. | Ir(L131)₃ | Ir(L132)₃ |
|---|---|---|
| Ligand L | L131 | L132 |
| Ir complex | | |
| Variant | A | A |
| Reaction medium | — | — |
| Melting aid | Hydroquinone | — |
| Reaction temp. | 270° C. | 280° C. |
| Reaction time | 24 h | 24 h |
| Suspension medium | EtOH | EtOH |
| Extractant | Toluene | Ethyl acetate |
| Yield | 13% | 4% |
| Ex. | Ir(L133)₃ | Ir(L134)₃ |
| Ligand L | L133 | L134 |
| Ir complex | | |
| Variant | A | A |
| Reaction medium | — | — |
| Melting aid | Hydroquinone | Hydroquinone |
| Reaction temp. | 275° C. | 270° C. |
| Reaction time | 24 h | 24 h |
| Suspension medium | EtOH | EtOH |
| Extractant | Toluene | Toluene |
| Yield | 7% | 10% |

-continued
| Ex. | Ir(L135)₃ | Ir(L136)₃ |
|---|---|---|
| Ligand L | L135 | L136 |
| Ir complex | 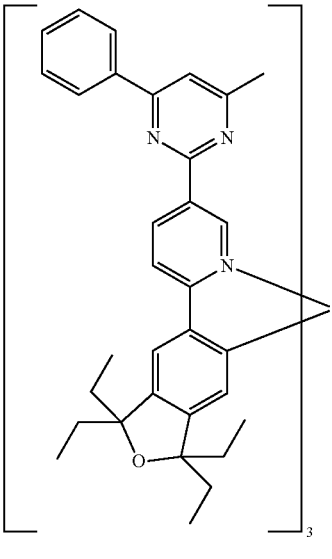 | 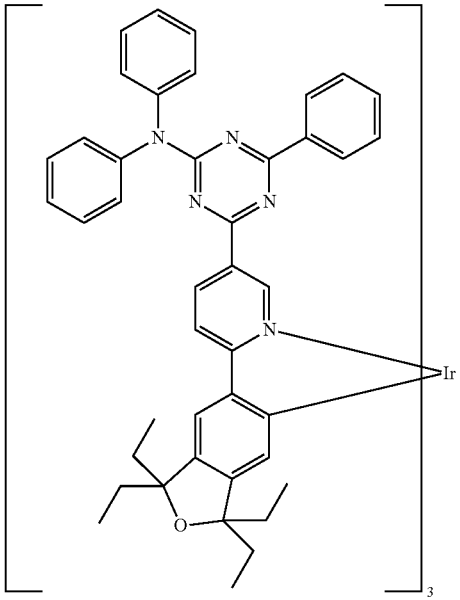 |
| Variant | A | A |
| Reaction medium | — | — |
| Melting aid | — | Hydroquinone |
| Reaction temp. | 270° C. | 265° C. |
| Reaction time | 36 h | 24 h |
| Suspension medium | EtOH | EtOH |
| Extractant | p-Xylene | Ethyl acetate |
| Yield | 13% | 10% |
| Ex. | Ir(L137)₃ | Ir(L138)₃ |
| Ligand L | L141 | L142 |
| Ir complex | 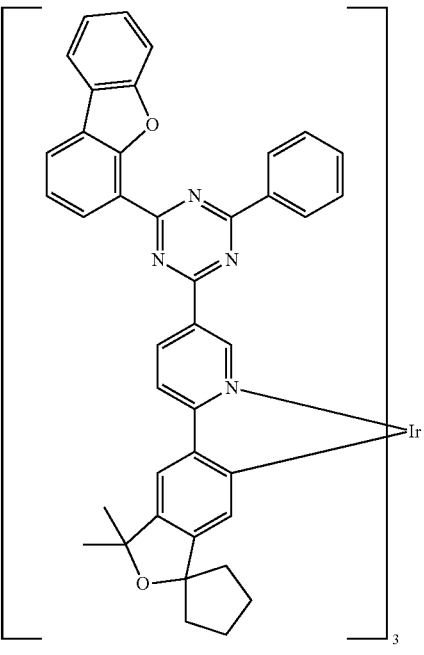 | 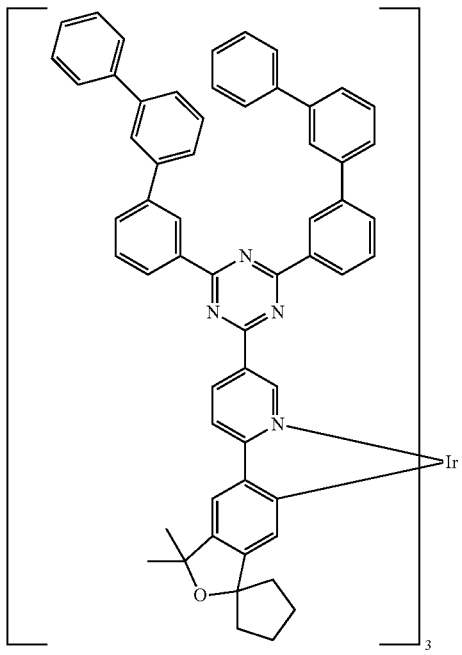 |
| Variant | A | A |
| Reaction medium | — | — |

-continued

| | | |
|---|---|---|
| Melting aid | Hydroquinone | Hydroquinone |
| Reaction temp. | 265° C. | 270° C. |
| Reaction time | 24 h | 24 h |
| Suspension medium | EtOH | EtOH |
| Extractant | Ethyl acetate | Ethyl acetate |
| Yield | 12% | 14% |

| Ex. | Ir(L139)₃ | Ir(L140)₃ |
|---|---|---|
| Ligand L | L143 | L144 |
| Ir complex | | |
| Variant | A | A |
| Reaction medium | — | — |
| Melting aid | Hydroquinone | — |
| Reaction temp. | 265° C. | 260° C. |
| Reaction time | 24 h | 24 h |
| Suspension medium | EtOH | EtOH |
| Extractant | Ethyl acetate | Ethyl acetate |
| Yield | 3% | 3% |

| Ex. | Ir(L141)₃ | Ir(L142)₃ |
|---|---|---|
| Ligand L | L137 | L138 |
| Ir complex | | |
| Variant | A | A |
| Reaction medium | — | — |
| Melting aid | Hydroquinone | Diphenyl ether |

| | | |
|---|---|---|
| Reaction temp. | 265° C. | 250° C. |
| Reaction time | 24 h | 48 h |
| Suspension medium | EtOH | EtOH |
| Extractant | Ethyl acetate | Ethyl acetate |
| Yield | 12% | 4% |

| Ex. | Ir(L143)₃ | Ir(L144)₃ |
|---|---|---|
| Ligand L | L139 | L140 |
| Ir complex | | |

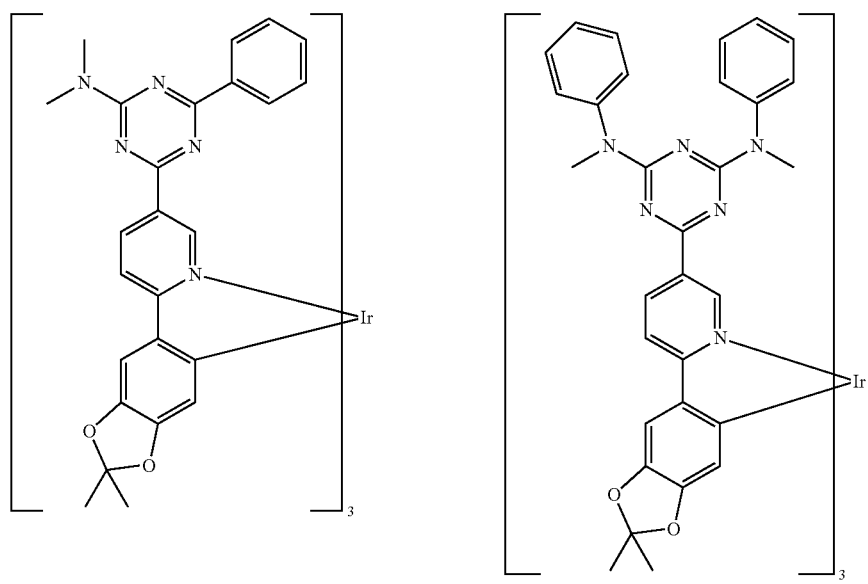

| | | |
|---|---|---|
| Variant | A | A |
| Reaction medium | — | — |
| Melting aid | 1-Naphthol | 1-Naphthol |
| Reaction temp. | 265° C. | 275° C. |
| Reaction time | 24 h | 24 h |
| Suspension medium | EtOH | EtOH |
| Extractant | Toluene | Toluene |
| Yield | 8% | 7% |

| Ex. | Ir(L145)₃ | Ir(L146)₃ |
|---|---|---|
| Ligand L | L145 | L146 |
| Ir complex | | |

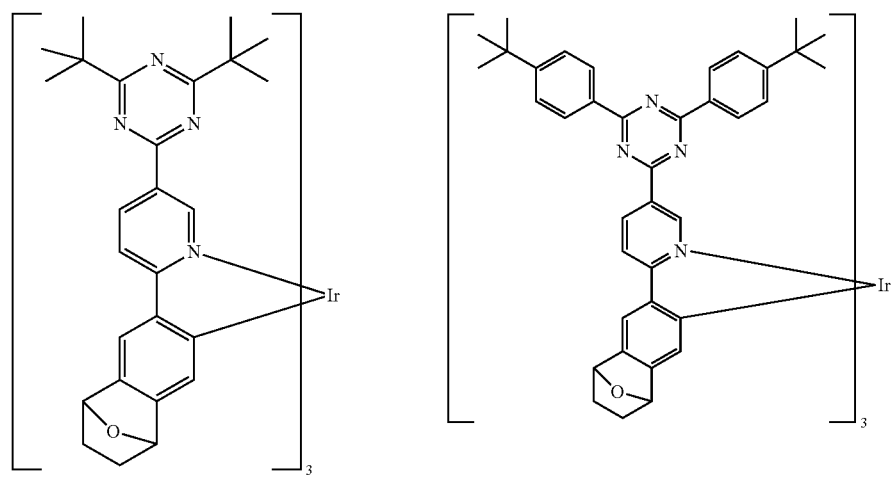

| | | |
|---|---|---|
| Variant | A | A |
| Reaction medium | — | — |
| Melting aid | — | Hydroquinone |
| Reaction temp. | 260° C. | 270° C. |
| Reaction time | 24 h | 24 h |

-continued

| Suspension medium | EtOH | EtOH |
|---|---|---|
| Extractant | Ethyl acetate | Ethyl acetate |
| Yield | 7% | 11% |

| Ex. | Ir(L147)₃ | Ir(L148)₃ |
|---|---|---|
| Ligand L | L147 | L148 |
| Ir complex | 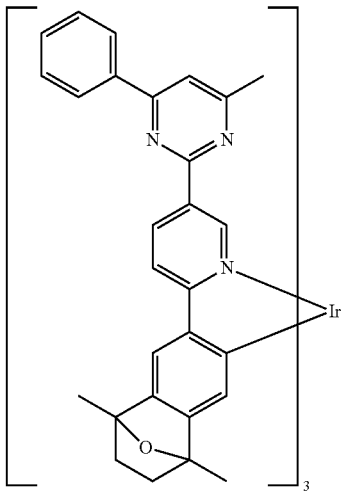 | 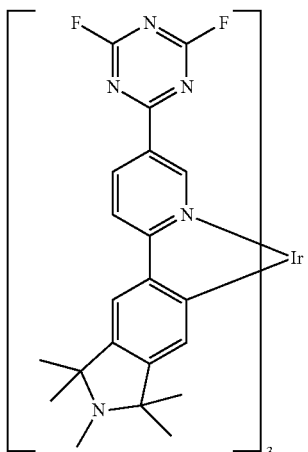 |
| Variant | A | A |
| Reaction medium | — | — |
| Melting aid | Diphenyl ether | Hydroquinone |
| Reaction temp. | 270° C. | 275° C. |
| Reaction time | 24 h | 24 h |
| Suspension medium | EtOH | EtOH |
| Extractant | p-Xylene | Chlorobenzene |
| Yield | 4% | 2% |

| Ex. | Ir(L149)₃ | Ir(L150)₃ |
|---|---|---|
| Ligand L | L149 | L150 |
| Ir complex | 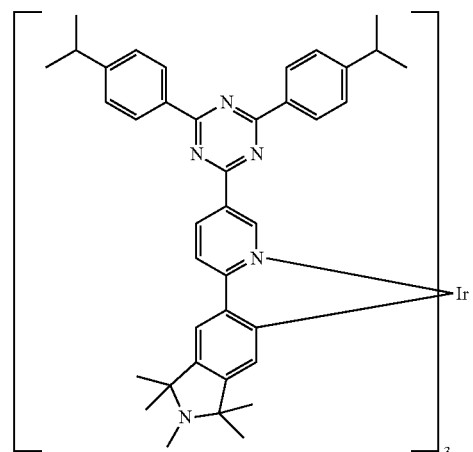 | 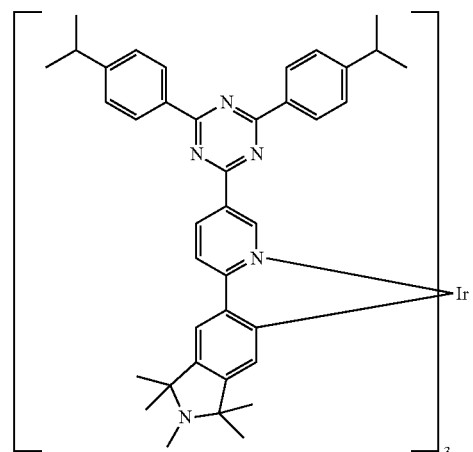 |
| Variant | A | A |
| Reaction medium | — | — |
| Melting aid | Hydroquinone | Hydroquinone |
| Reaction temp. | 265° C. | 265° C. |
| Reaction time | 24 h | 24 h |
| Suspension medium | EtOH | EtOH |
| Extractant | Chlorobenzene | Ethyl acetate |
| Yield | 5% | 13% |

| Ex. | Ir(L151)₃ | Ir(L152)₃ |
|---|---|---|
| Ligand L | L151 | L152 |
| Ir complex | | |
| Variant | A | A |
| Reaction medium | — | — |
| Melting aid | Hydroquinone | Hydroquinone |
| Reaction temp. | 275° C. | 275° C. |
| Reaction time | 24 h | 24 h |
| Suspension medium | EtOH | EtOH |
| Extractant | Ethyl acetate | Ethyl acetate |
| Yield | 4% | 2% |

| Ex. | Ir(L153)₃ | Ir(L154)₃ |
|---|---|---|
| Ligand L | L153 | L154 |
| Ir complex | | |
| Variant | A | A |
| Reaction medium | — | — |
| Melting aid | — | Hydroquinone |
| Reaction temp. | 260° C. | 265° C. |
| Reaction time | 24 h | 24 h |
| Suspension medium | EtOH | EtOH |
| Extractant | Ethyl acetate | Ethyl acetate |
| Yield | 5% | 13% |

-continued

| Ex. | Ir(L155)₃ | Ir(L156)₃ |
|---|---|---|
| Ligand L | L155 | L156 |
| Ir complex | | |
| Variant | A | A |
| Reaction medium | — | — |
| Melting aid | — | Hydroquinone |
| Reaction temp. | 260° C. | 265° C. |
| Reaction time | 24 h | 24 h |
| Suspension medium | EtOH | EtOH |
| Extractant | Ethyl acetate | Ethyl acetate |
| Yield | 4% | 14% |

| Ex. | Ir(L157)₃ | Ir(L158)₃ |
|---|---|---|
| Ligand L | L157 | L158 |
| Ir complex | | |
| Variant | A | A |
| Reaction medium | — | — |
| Melting aid | Hydroquinone | Diphenyl ether |
| Reaction temp. | 265° C. | 270° C. |
| Reaction time | 24 h | 24 h |
| Suspension medium | EtOH | EtOH |
| Extractant | Ethyl acetate | p-Xylene |
| Yield | 11% | 6% |

| Ex. | Ir(L159)$_3$ | Ir(L160)$_3$ |
| --- | --- | --- |
| Ligand L | L159 | L160 |
| Ir complex | 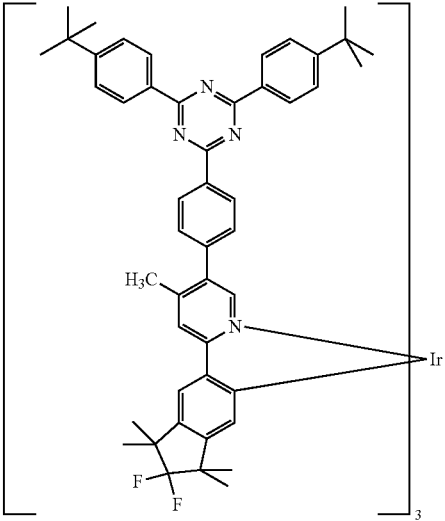 | 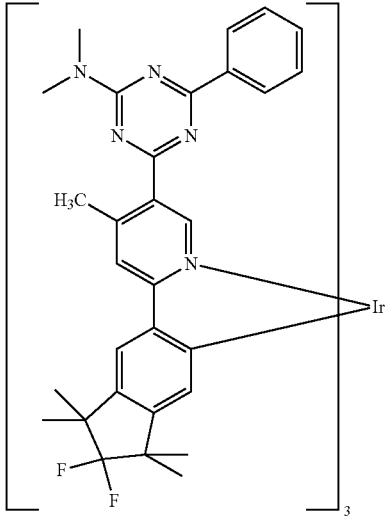 |
| Variant | A | A |
| Reaction medium | — | — |
| Melting aid | Diphenyl ether | Hydroquinone |
| Reaction temp. | 250° C. | 265° C. |
| Reaction time | 48 h | 24 h |
| Suspension medium | EtOH | EtOH |
| Extractant | Ethyl acetate | Toluene |
| Yield | 2% | 4% |

| Ex. | Ir(L161)$_3$ | Ir(L162)$_3$ |
| --- | --- | --- |
| Ligand L | L161 | L162 |
| Ir complex | 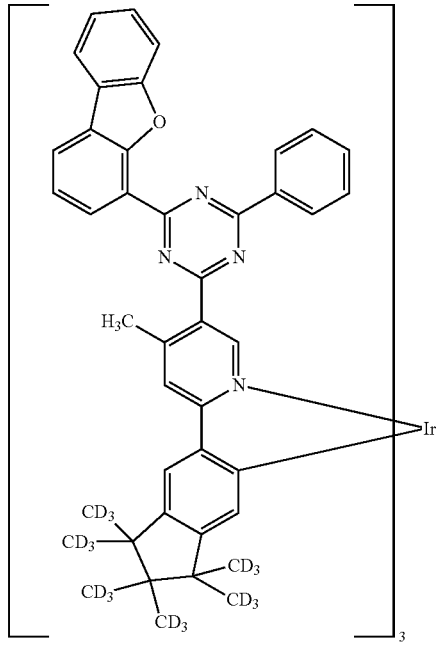 | 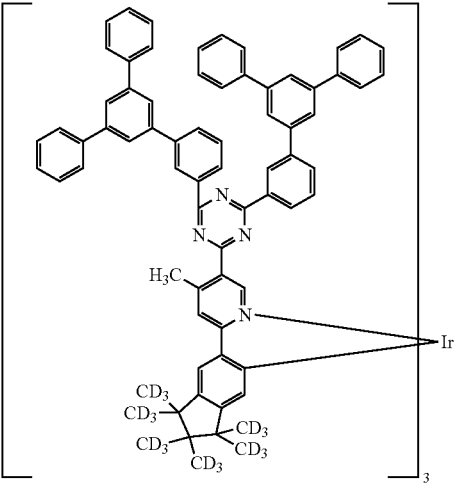 |
| Variant | A | A |
| Reaction medium | — | — |
| Melting aid | Hydroquinone | 1-Naphthol |
| Reaction temp. | 270° C. | 270° C. |
| Reaction time | 24 h | 24 h |
| Suspension medium | EtOH | EtOH |

-continued

| | | |
|---|---|---|
| Extractant | Ethyl acetate | Ethyl acetate |
| Yield | 4% | 14% |
| Ex. | Ir(L163)₃ | Ir(L164)₃ |
| Ligand L | L163 | L164 |
| Ir complex | (structure) | (structure) |
| Variant | A | A |
| Reaction medium | — | — |
| Melting aid | 1-Naphthol | Hydroquinone |
| Reaction temp. | 270° C. | 270° C. |
| Reaction time | 24 h | 24 h |
| Suspension medium | EtOH | EtOH |
| Extractant | Toluene | Ethyl acetate |
| Yield | 9% | 11% |
| Ex. | Ir(L165)₃ | Ir(L166)₃ |
| Ligand L | L165 | L166 |
| Ir complex | (structure) | (structure) |
| Variant | A | A |
| Reaction medium | — | — |

-continued

| | | |
|---|---|---|
| Melting aid | 1-Naphthol | Hydroquinone |
| Reaction temp. | 265° C. | 265° C. |
| Reaction time | 36 h | 24 h |
| Suspension medium | EtOH | EtOH |
| Extractant | Chlorobenzene | Ethyl acetate |
| Yield | 3% | 11% |

| Ex. | Ir(L167)₃ | Ir(L168)₃ |
|---|---|---|
| Ligand L | L167 | L168 |
| Ir complex | | |

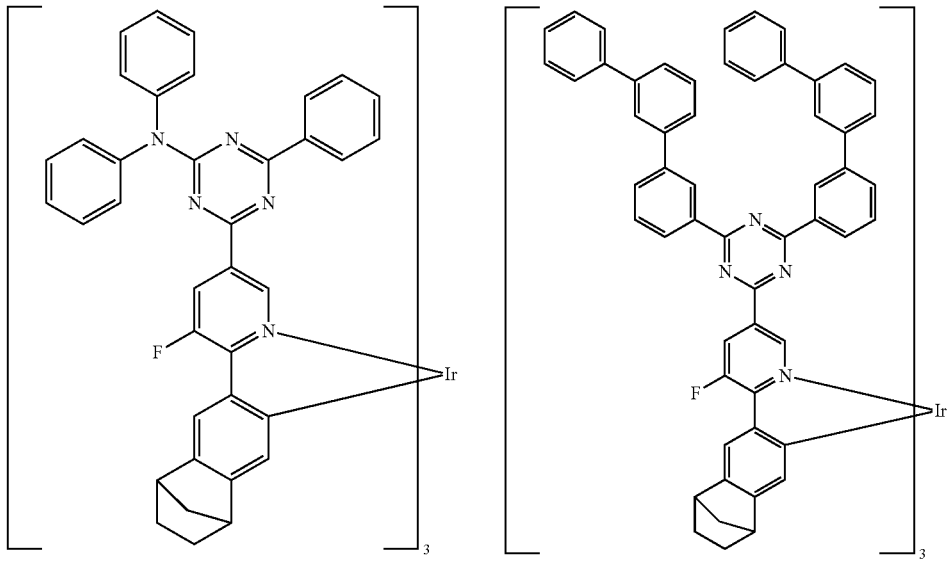

| Variant | A | A |
|---|---|---|
| Reaction medium | — | — |
| Melting aid | Hydroquinone | Hydroquinone |
| Reaction temp. | 265° C. | 270° C. |
| Reaction time | 24 h | 24 h |
| Suspension medium | EtOH | EtOH |
| Extractant | Ethyl acetate | Ethyl acetate |
| Yield | 9% | 10% |

| Ex. | Ir(L169)₃ | Ir(L170)₃ |
|---|---|---|
| Ligand L | L169 | L170 |
| Ir complex | | |

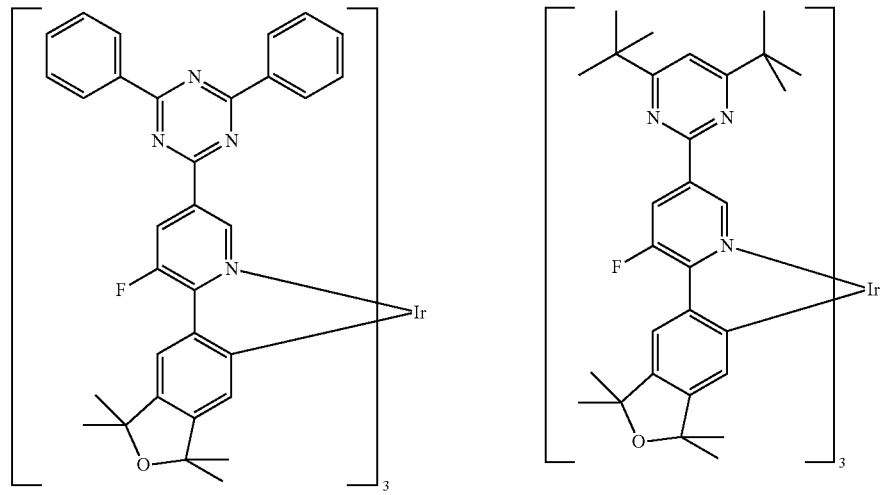

| Variant | A | A |
|---|---|---|
| Reaction medium | — | — |
| Melting aid | Hydroquinone | |

| | | |
|---|---|---|
| Reaction temp. | 275° C. | 260° C. |
| Reaction time | 24 h | 24 h |
| Suspension medium | EtOH | EtOH |
| Extractant | Chlorobenzene | Ethyl acetate |
| Yield | 12% | 3% |
| Ex. | Ir(L171)₃ | Ir(L172)₃ |
| Ligand L | L171 | L172 |
| Ir complex | 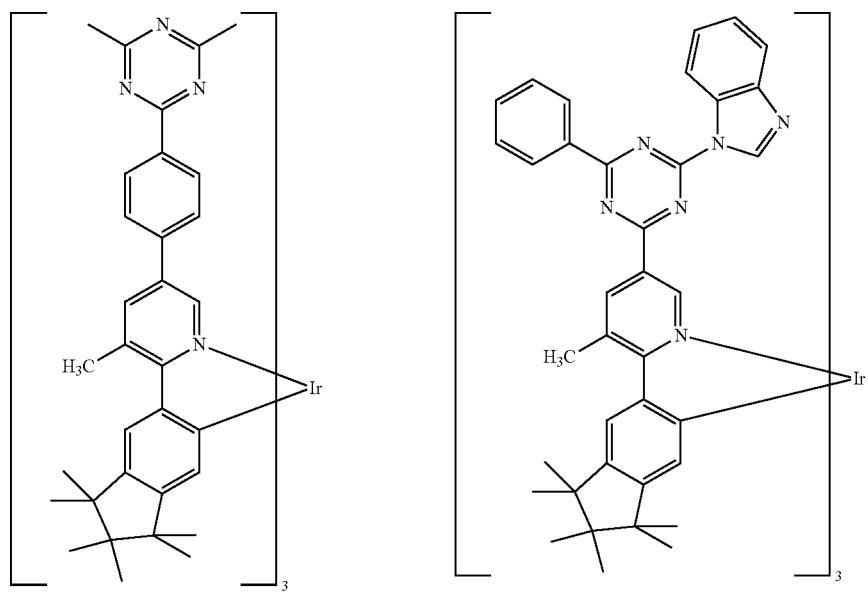 | |
| Variant | A | A |
| Reaction medium | — | — |
| Melting aid | Diphenyl ether | 1-Naphthol |
| Reaction temp. | 250° C. | 265° C. |
| Reaction time | 72 h | 36 h |
| Suspension medium | EtOH | EtOH |
| Extractant | Chlorobenzene | Chlorobenzene |
| Yield | 1% | 4% |
| Ex. | Ir(L173)₃ | Ir(L174)₃ |
| Ligand L | L173 | L174 |
| Ir complex | 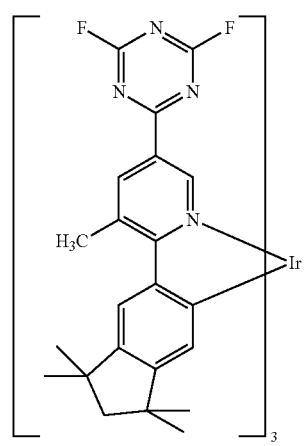 | 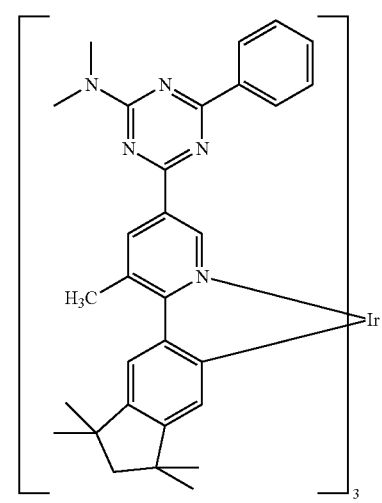 |
| Variant | A | A |
| Reaction medium | — | — |

-continued

| | | |
|---|---|---|
| Melting aid | Hydroquinone | Hydroquinone |
| Reaction temp. | 265° C. | 265° C. |
| Reaction time | 24 h | 24 h |
| Suspension medium | EtOH | EtOH |
| Extractant | Chloro-benzene | Toluene |
| Yield | 4% | 7% |

| Ex. | Ir(L175)₃ | Ir(L176)₃ |
|---|---|---|
| Ligand L | L175 | L176 |
| Ir complex | | |

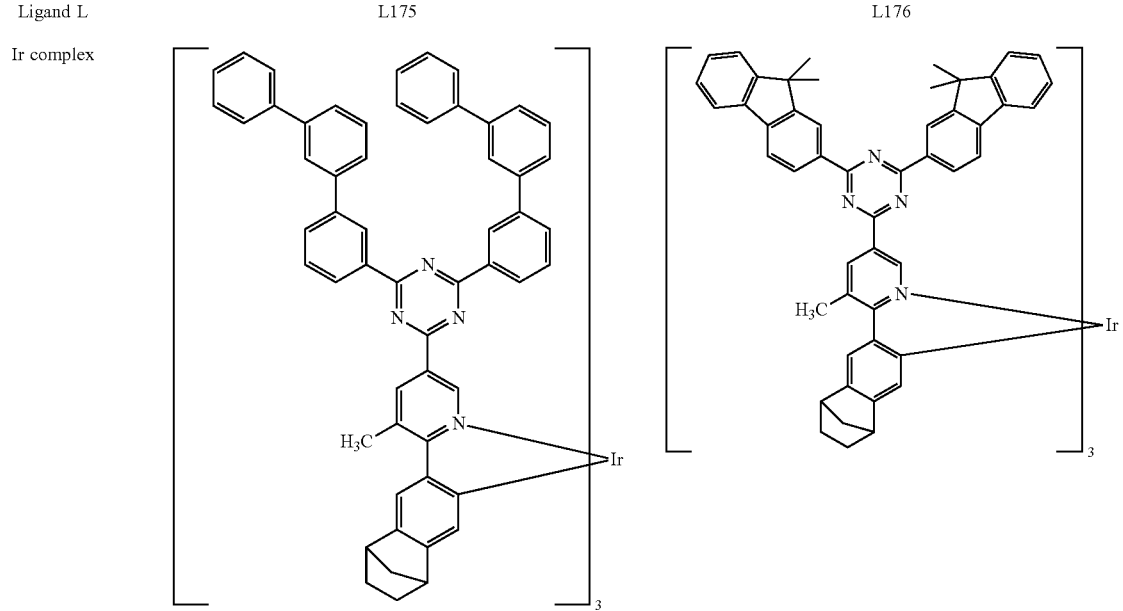

| | | |
|---|---|---|
| Variant | A | A |
| Reaction medium | — | — |
| Melting aid | Hydroquinone | Hydroquinone |
| Reaction temp. | 270° C. | 270° C. |
| Reaction time | 24 h | 24 h |
| Suspension medium | EtOH | EtOH |
| Extractant | Ethyl acetate | Toluene |
| Yield | 10% | 12% |

| Ex. | Ir(L177)₃ | Ir(L178)₃ |
|---|---|---|
| Ligand L | L177 | L178 |
| Ir complex | | |

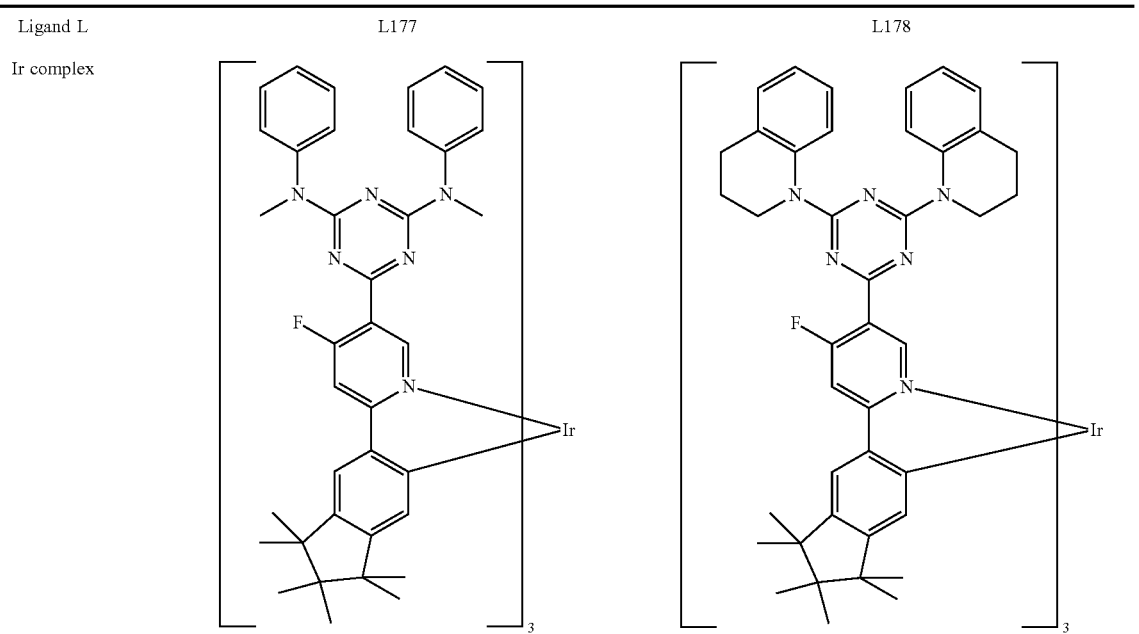

| Variant | A | A |
|---|---|---|
| Reaction medium | — | — |
| Melting aid | Diphenyl ether | 1-Naphthol |
| Reaction temp. | 270° C. | 265° C. |
| Reaction time | 24 h | 24 h |
| Suspension medium | EtOH | EtOH |
| Extractant | p-Xylene | Toluene |
| Yield | 3% | 7% |

| Ex. | Ir(L179)$_3$ | Ir(L180)$_3$ |
|---|---|---|
| Ligand L | L179 | L180 |

Ir complex

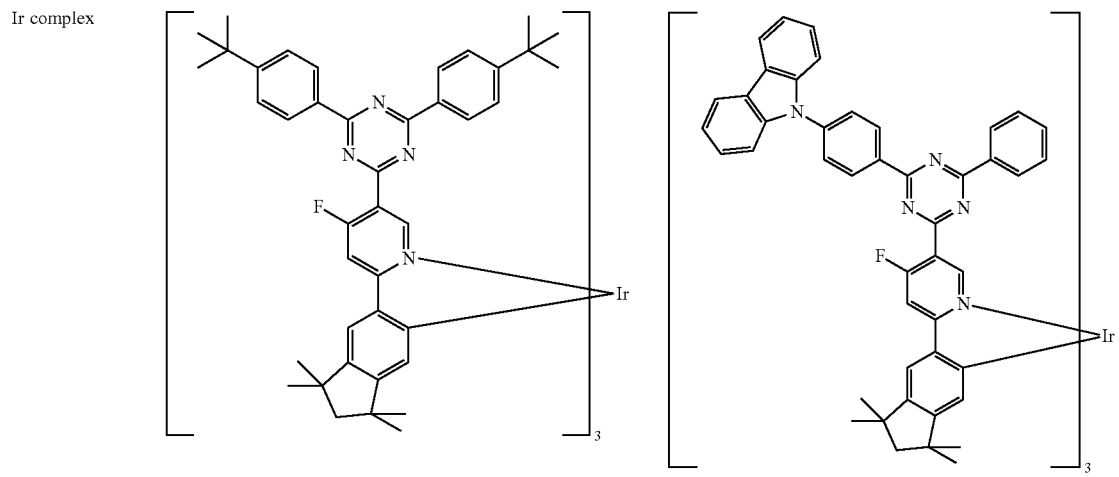

| Variant | A | A |
|---|---|---|
| Reaction medium | — | — |
| Melting aid | Hydroquinone | Hydroquinone |
| Reaction temp. | 265° C. | 275° C. |
| Reaction time | 24 h | 24 h |
| Suspension medium | EtOH | EtOH |
| Extractant | Ethyl acetate | Ethyl acetate |
| Yield | 12% | 9% |

| Ex. | Ir(L181)$_3$ | Ir(L182)$_3$ |
|---|---|---|
| Ligand L | L181 | L182 |

Ir complex

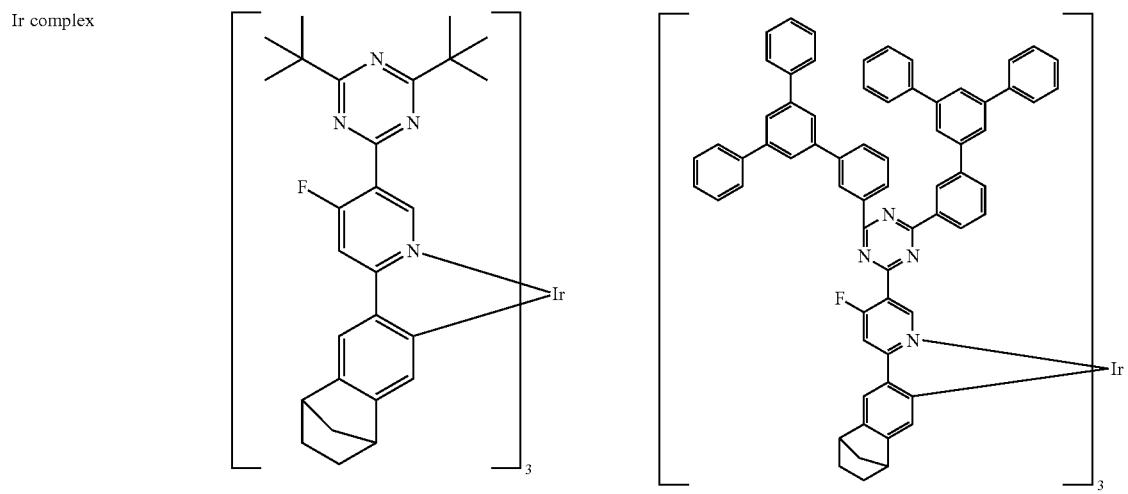

| Variant | A | A |
|---|---|---|
| Reaction medium | — | — |
| Melting aid | — | 1-Naphthol |
| Reaction temp. | 260° C. | 270° C. |

-continued

| | | |
|---|---|---|
| Reaction time | 24 h | 24 h |
| Suspension medium | EtOH | EtOH |
| Extractant | Ethyl acetate | Ethyl acetate |
| Yield | 6% | 4% |

| Ex. | Ir(L183)₃ | Ir(L184)₃ |
|---|---|---|
| Ligand L | L183 | L184 |
| Ir complex | 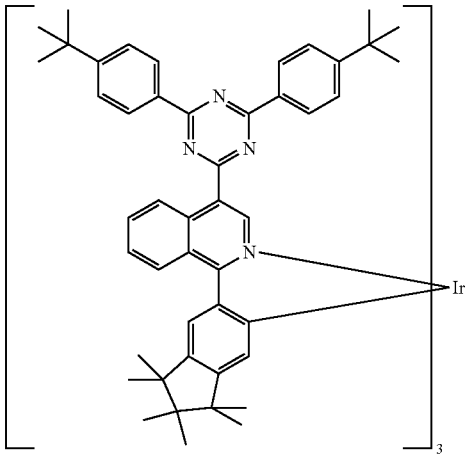 | 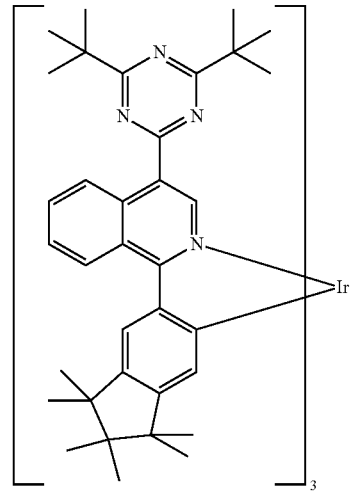 |
| Variant | A | A |
| Reaction medium | — | — |
| Melting aid | Hydroquinone | Hydroquinone |
| Reaction temp. | 265° C. | 275° C. |
| Reaction time | 24 h | 24 h |
| Suspension medium | EtOH | EtOH |
| Extractant | Ethyl acetate | Ethyl acetate |
| Yield | 3% | 2% |

| Ex. | Ir(L185)₃ | Ir(L186)₃ |
|---|---|---|
| Ligand L | L185 | L186 |
| Ir complex | 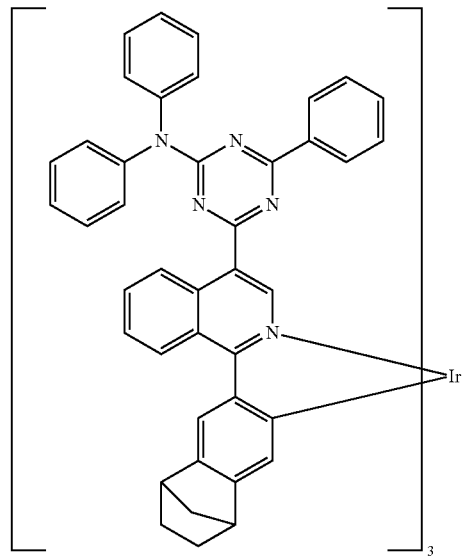 | 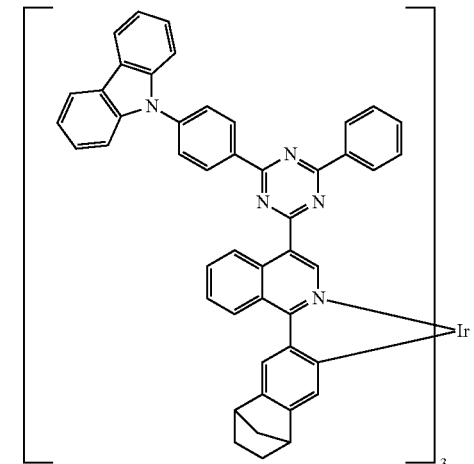 |
| Variant | A | A |
| Reaction medium | — | — |
| Melting aid | Hydroquinone | Hydroquinone |
| Reaction temp. | 275° C. | 275° C. |
| Reaction time | 24 h | 36 h |
| Suspension medium | EtOH | EtOH |

-continued

| | | |
|---|---|---|
| Extractant | Toluene | Toluene |
| Yield | 4% | 4% |

| Ex. | Ir(L187)₃ | Ir(L188)₃ |
|---|---|---|
| Ligand L | L187 | L188 |
| Ir complex | | |
| Variant | A | A |
| Reaction medium | — | — |
| Melting aid | Hydroquinone | Hydroquinone |
| Reaction temp. | 265° C. | 265° C. |
| Reaction time | 24 h | 24 h |
| Suspension medium | EtOH | EtOH |
| Extractant | Ethyl acetate | Toluene |
| Yield | 1% | 2% |

| Ex. | Ir(L189)₃ | Ir(L190)₃ |
|---|---|---|
| Ligand L | L189 | L190 |
| Ir complex | | |
| Variant | A | A |
| Reaction medium | — | — |
| Melting aid | Hydroquinone | — |
| Reaction temp. | 275° C. | 260° C. |
| Reaction time | 24 h | 24 h |

| | | |
|---|---|---|
| Suspension medium | EtOH | EtOH |
| Extractant | Toluene | Chlorobenzene |
| Yield | 3% | 1% |
| Ex. | Ir(L191)$_3$ | Ir(L192)$_3$ |
| Ligand L | L191 | L192 |
| Ir complex | 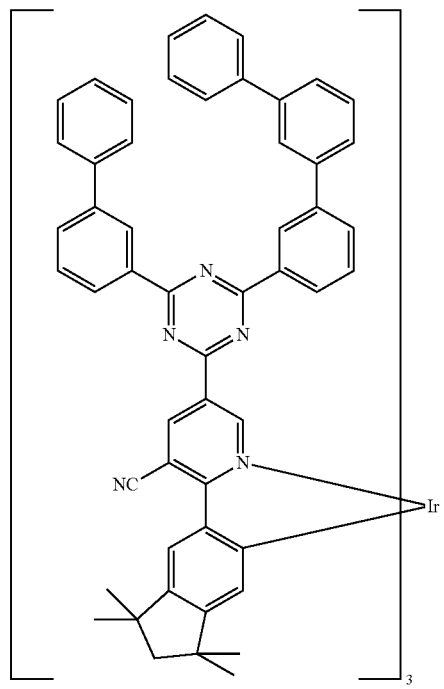 | 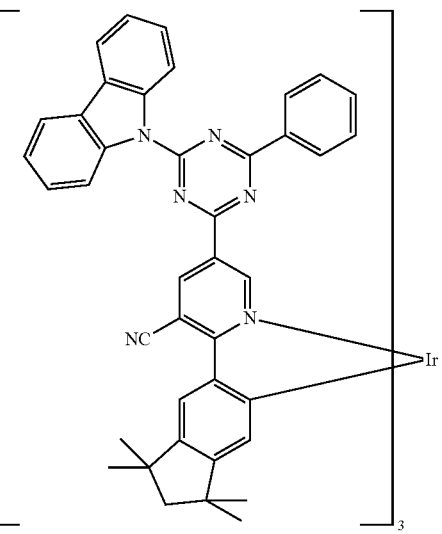 |
| Variant | A | A |
| Reaction medium | — | — |
| Melting aid | Hydroquinone | Hydroquinone |
| Reaction temp. | 270° C. | 275° C. |
| Reaction time | 24 h | 24 h |
| Suspension medium | EtOH | EtOH |
| Extractant | Ethyl acetate | Ethyl acetate |
| Yield | 7% | 5% |
| Ex. | Ir(L193)$_3$ | Ir(L194)$_3$ |
| Ligand L | L193 | L194 |
| Ir complex | 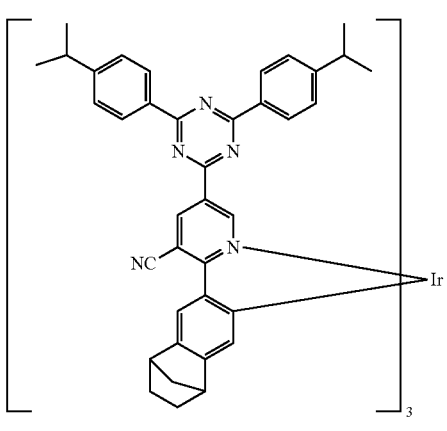 | 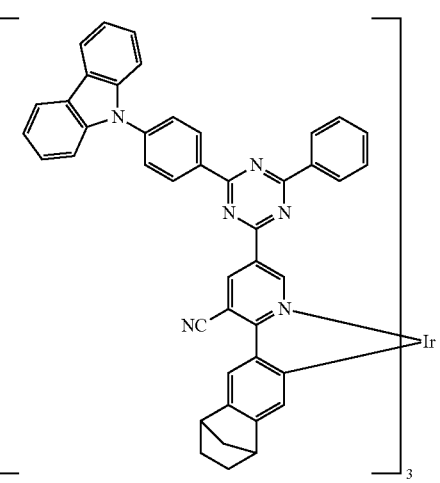 |

-continued

| | | |
|---|---|---|
| Variant | A | A |
| Reaction medium | — | — |
| Melting aid | Hydroquinone | Hydroquinone |
| Reaction temp. | 265° C. | 275° C. |
| Reaction time | 24 h | 24 h |
| Suspension medium | EtOH | EtOH |
| Extractant | Ethyl acetate | Ethyl acetate |
| Yield | 4% | 7% |

| Ex. | Ir(L195)₃ | Ir(L196)₃ |
|---|---|---|
| Ligand L | L195 | L196 |
| Ir complex | | |

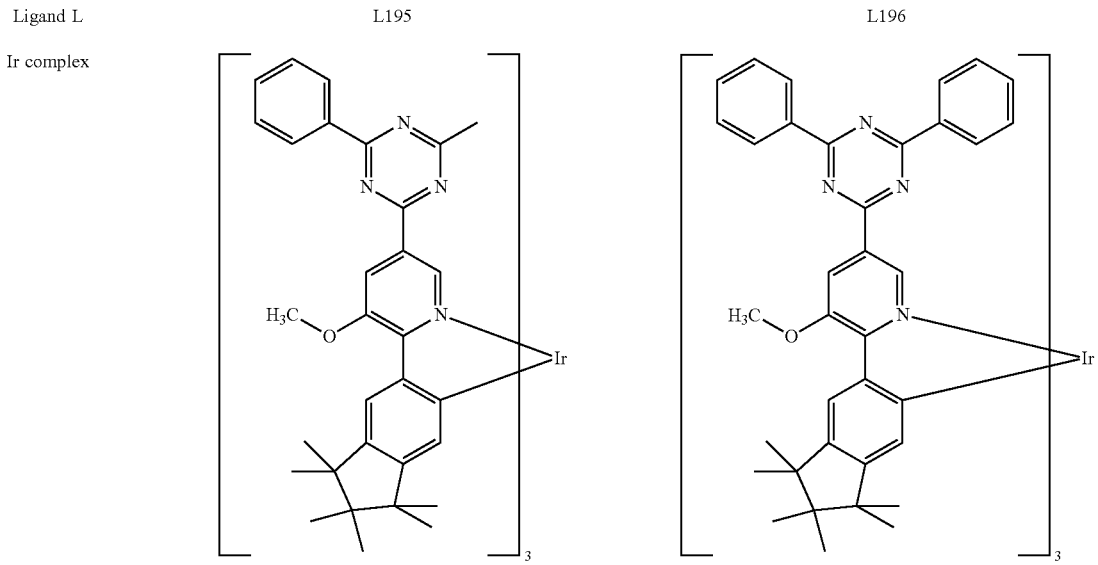

| | | |
|---|---|---|
| Variant | A | A |
| Reaction medium | — | — |
| Melting aid | Diphenyl ether | Hydroquinone |
| Reaction temp. | 270° C. | 275° C. |
| Reaction time | 24 h | 24 h |
| Suspension medium | EtOH | EtOH |
| Extractant | p-Xylene | Chlorobenzene |
| Yield | 4% | 1% |

| Ex. | Ir(L197)₃ | Ir(L198)₃ |
|---|---|---|
| Ligand L | L197 | L198 |
| Ir complex | | |

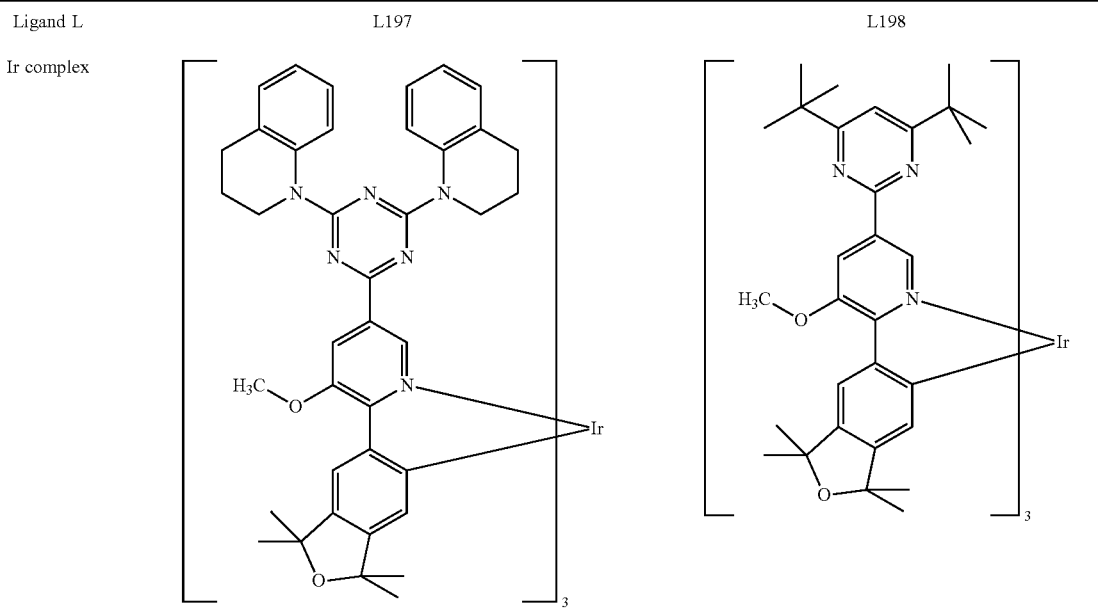

-continued

| | | |
|---|---|---|
| Variant | A | A |
| Reaction medium | — | — |
| Melting aid | 1-Naphthol | — |
| Reaction temp. | 265° C. | 260° C. |
| Reaction time | 24 h | 24 h |
| Suspension medium | EtOH | EtOH |
| Extractant | Toluene | Ethyl acetate |
| Yield | 7% | 2% |
| Ex. | Ir(L199)$_3$ | Ir(L200)$_3$ |
| Ligand L | L199 | L200 |
| Ir complex | | |
| Variant | D | A |
| Reaction medium | — | — |
| Melting aid | — | — |
| Reaction temp. | 265° C. | 260° C. |
| Reaction time | 24 h | 24 h |
| Suspension medium | EtOH | EtOH |
| Extractant | Toluene | Chlorobenzene |
| Yield | 4% | 3% |
| Ex. | Ir(L201)$_3$ | Ir(L202)$_3$ |
| Ligand L | L201 | L202 |
| Ir complex | | |

-continued

| | 405 | 406 |
|---|---|---|
| Variant | A | A |
| Reaction medium | — | — |
| Melting aid | Hydroquinone | Hydroquinone |
| Reaction temp. | 270° C. | 265° C. |
| Reaction time | 48 h | 24 h |
| Suspension medium | EtOH | EtOH |
| Extractant | Ethyl acetate | Ethyl acetate |
| Yield | 3% | 9% |
| Ex. | Ir(L203)$_3$ | Ir(L204)$_3$ |
| Ligand L | L203 | L204 |
| Ir complex | ![structure] | ![structure] |
| Variant | A | A |
| Reaction medium | — | — |
| Melting aid | Hydroquinone | Hydroquinone |
| Reaction temp. | 275° C. | 275° C. |
| Reaction time | 24 h | 24 h |
| Suspension medium | EtOH | EtOH |
| Extractant | Toluene | Toluene |
| Yield | 10% | 5% |

-continued

| Ex. | Ir(L205)₃ | Ir(L206)₃ |
|---|---|---|
| Ligand L | L205 | L206 |
| Ir complex | 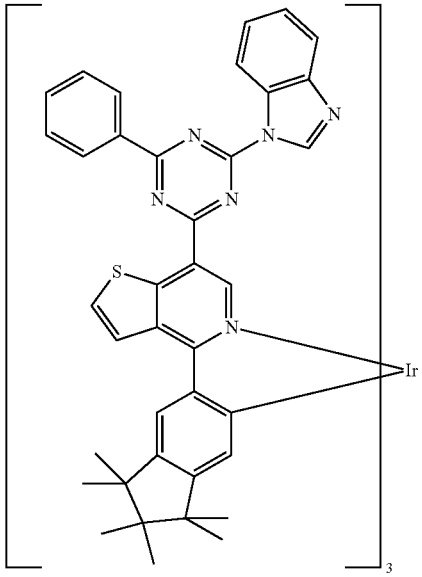 | 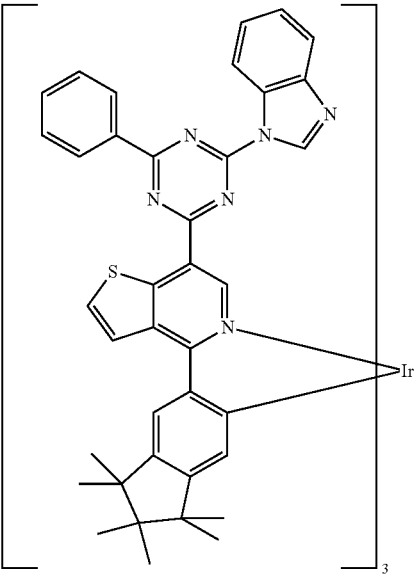 |
| Variant | A | A |
| Reaction medium | — | — |
| Melting aid | Hydroquinone | Hydroquinone |
| Reaction temp. | 275° C. | 275° C. |
| Reaction time | 24 h | 24 h |
| Suspension medium | EtOH | EtOH |
| Extractant | p-Dichloro-benzene | p-Dichloro-benzene |
| Yield | 3% | 5% |

| Ex. | Ir(L207)₃ | Ir(L208)₃ |
|---|---|---|
| Ligand L | L207 | L208 |
| Ir complex | 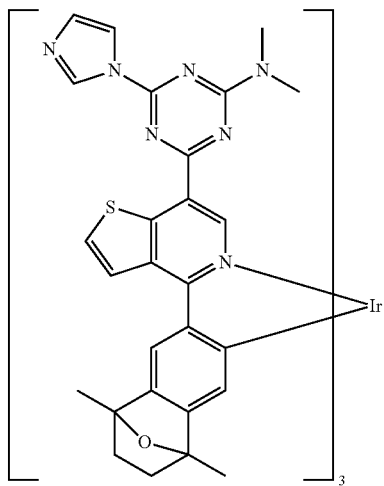 | 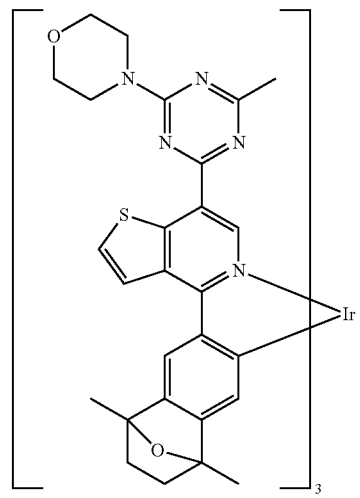 |
| Variant | A | A |
| Reaction medium | — | — |
| Melting aid | Hydroquinone | Hydroquinone |
| Reaction temp. | 285° C. | 265° C. |
| Reaction time | 48 h | 48 h |
| Suspension medium | EtOH | EtOH |
| Extractant | p-Dichloro-benzene | p-Xylene |
| Yield | 4% | 4% |

| Ex. | Ir(L209)₃ | Ir(L210)₃ |
|---|---|---|
| Ligand L | L209 | L210 |
| Ir complex | 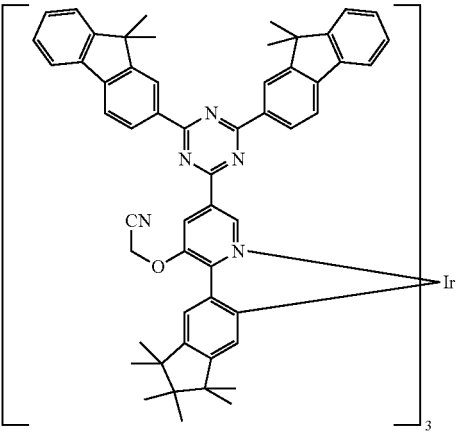 | 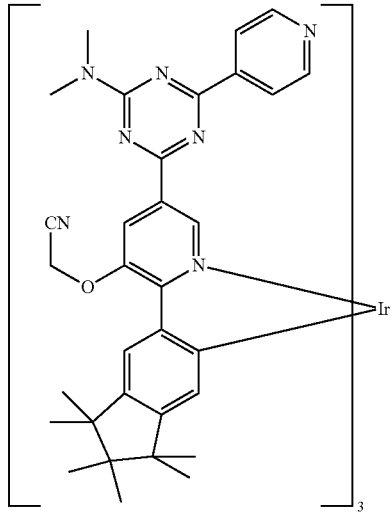 |
| Variant | A | A |
| Reaction medium | — | — |
| Melting aid | Hydroquinone | Hydroquinone |
| Reaction temp. | 275° C. | 265° C. |
| Reaction time | 24 h | 48 h |
| Suspension medium | EtOH | EtOH |
| Extractant | Toluene | p-Xylene |
| Yield | 10% | 8% |

| Ex. | Ir(L211)₃ | Ir(L212)₃ |
|---|---|---|
| Ligand L | L211 | L212 |
| Ir complex | 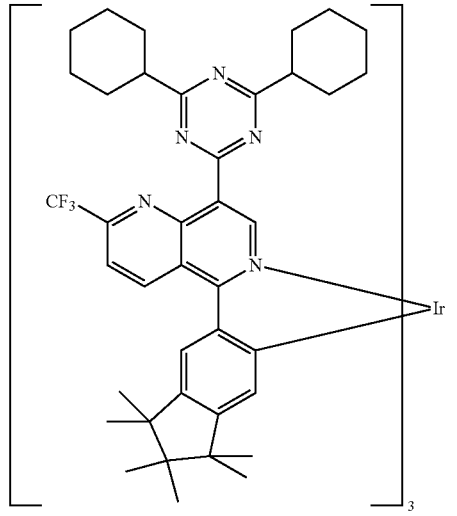 | 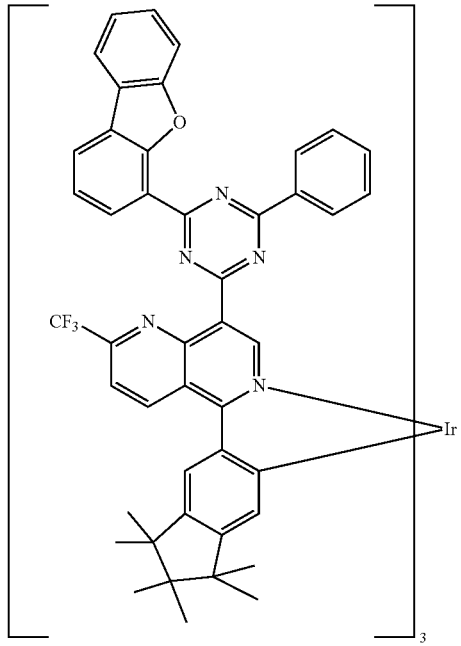 |
| Variant | A | A |
| Reaction medium | — | — |
| Melting aid | Hydroquinone | Hydroquinone |
| Reaction temp. | 275° C. | 270° C. |
| Reaction time | 48 h | 24 h |
| Suspension medium | EtOH | EtOH |

-continued

| | | |
|---|---|---|
| Extractant | Ethyl acetate | Ethyl acetate |
| Yield | 4% | 7% |
| Ex. | Ir(L213)₃ | Ir(L214)₃ |
| Ligand L | L213 | L214 |
| Ir complex | | |
| Variant | A | A |
| Reaction medium | — | — |
| Melting aid | Hydroquinone | Hydroquinone |
| Reaction temp. | 270° C. | 275° C. |
| Reaction time | 24 h | 48 h |
| Suspension medium | EtOH | EtOH |
| Extractant | Ethyl acetate | Ethyl acetate |
| Yield | 4% | 8% |
| Ex. | Ir(L215)₃ | Ir(L216)₃ |
| Ligand L | L215 | L216 |
| Ir complex | | |
| Variant | A | A |
| Reaction medium | — | — |
| Melting aid | Hydroquinone | Hydroquinone |
| Reaction temp. | 270° C. | 285° C. |
| Reaction time | 24 h | 24 h |
| Suspension medium | EtOH | EtOH |

-continued

| | | |
|---|---|---|
| Extractant | Ethyl acetate | p-Dichloro-benzene |
| Yield | 5% | 3% |

| Ex. | Ir(L217)$_3$ | Ir(L218)$_3$ |
|---|---|---|
| Ligand L | L217 | L218 |
| Ir complex | | |
| Variant | A | D |
| Reaction medium | — | — |
| Melting aid | — | — |
| Reaction temp. | 260° C. | 270° C. |
| Reaction time | 24 h | 48 h |
| Suspension medium | EtOH | EtOH |
| Extractant | Ethyl acetate | Ethyl acetate |
| Yield | 4% | 2% |

| Ex. | Ir(L219)$_3$ | Ir(L220)$_3$ |
|---|---|---|
| Ligand L | L219 | L220 |
| Ir complex | | |
| Variant | A | A |
| Reaction medium | — | — |
| Melting aid | Hydroquinone | Hydroquinone |
| Reaction temp. | 265° C. | 275° C. |
| Reaction time | 24 h | 24 h |

| | | |
|---|---|---|
| Suspension medium | EtOH | EtOH |
| Extractant | Ethyl acetate | Ethyl acetate |
| Yield | 10% | 12% |

| Ex. | Ir(L221)₃ | Ir(L222)₃ |
|---|---|---|
| Ligand L | L221 | L222 |
| Ir complex | 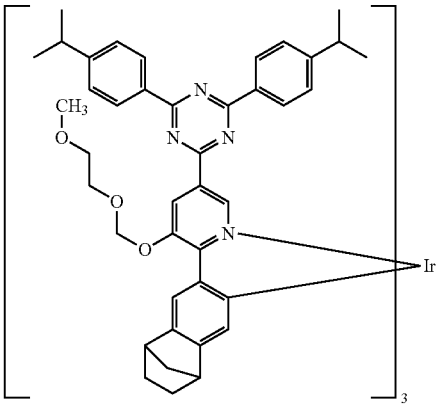 | 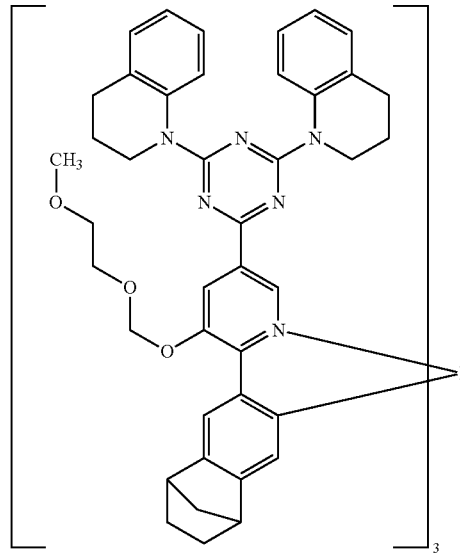 |
| Variant | A | A |
| Reaction medium | — | — |
| Melting aid | Hydroquinone | 1-Naphthol |
| Reaction temp. | 265° C. | 265° C. |
| Reaction time | 24 h | 24 h |
| Suspension medium | EtOH | EtOH |
| Extractant | Ethyl acetate | Toluene |
| Yield | 9% | 5% |

| | Ex. | Ir(L223)₃ |
|---|---|---|
| | Ligand L | L223 |
| | Ir complex | 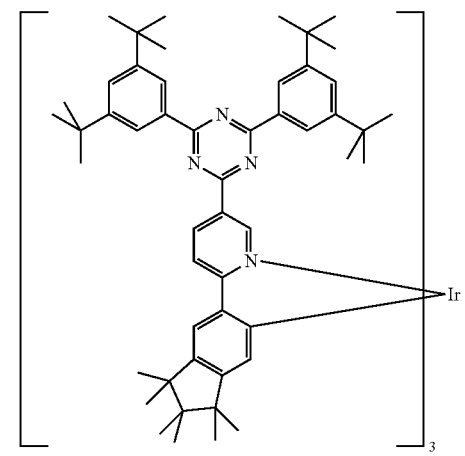 |
| | Variant | A |
| | Reaction medium | — |
| | Melting aid | — |
| | Reaction temp. | 275° C. |
| | Reaction time | 24 h |
| | Suspension medium | EtOH |
| | Extractant | Toluene |
| | Yield | 9% |

Variant E:

Step 1: Ortho-Metallation of a Brominated Ligand

A mixture of 10 mmol of trisacetylacetonatoiridium(II) [15635-87-7] and 40-60 mmol (preferably 40 mmol) of the brominated ligand 81, optionally 1-10 g—typically 3 g—of an inert high-boiling additive as melting aid or solvent, for example hexadecane, m-terphenyl, triphenylene, bisphenyl ether, 3-phenoxytoluene, 1,2-, 1,3-, 1,4-bisphenoxybenzene, triphenylphosphine oxide, sulfolane, 18-crown-6, triethylene glycol, glycerol, polyethylene glycols, phenol, 1-naphthol, hydroquinone, etc., and a glass-clad magnetic stirrer bar are melted into a thick-walled 50 ml glass ampoule in vacuo ($10^{-5}$ mbar). The ampoule is heated at the temperature indicated for the time indicated, with the molten mixture being stirred with the aid of a magnetic stirrer. In order to prevent sublimation of the ligands at colder points of the ampoule, the entire ampoule must have the temperature indicated. Alternatively, the synthesis can be carried out in a stirred autoclave with glass insert. After cooling (NOTE: the ampoules are usually under pressure!), the ampoule is opened, and the sinter cake is stirred with 100 g of glass beads (diameter 3 mm) in 100 ml of a suspension medium (the suspension medium is selected so that the ligand is readily soluble therein, but the metal complex has poor solubility therein, typical suspension media are methanol, ethanol, dichloromethane, acetone. THF, ethyl acetate, toluene, etc.) for 3 h while being mechanically digested. The fine suspension is decanted off from the glass beads, and the solid is filtered off with suction, rinsed with 50 ml of the suspension medium and dried in vacuo. The dry solid is placed in a continuous hot extractor on an aluminum oxide bed (aluminium oxide, basic activity grade 1) with a depth of 3-5 cm and then extracted with an extractant (amount initially introduced about 500 ml, the extractant is selected so that the complex is readily soluble therein at elevated temperature and has poor solubility therein at low temperature, particularly suitable extractants are hydrocarbons, such as toluene, xylenes, mesitylene, naphthalene, o-dichlorobenzene halogenated aliphatic hydrocarbons are generally unsuitable since they may halogenate or decompose the complexes). When the extraction is complete, the extractant is evaporated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, with the aluminium oxide bed being omitted from the 2nd extraction onwards. When a purity of 99.5-99.9% has been reached, the metal complex is heated or chromatographed. The heating is carried out in a high vacuum (p about $10^{-6}$ mbar) in the temperature range from about 200-300° C. Complexes which are readily soluble in organic solvents can alternatively also be chromatographed on silica gel.

If chiral ligands are employed, the derived fac metal complexes are obtained in the form of a diastereomer mixture. The enantiomers Λ,Δ in point group C3 generally have significantly lower solubility in the extractant than the enantiomers in point group C1, which consequently accumulate in the mother liquor. Separation of the C3 diastereomers from the C1 diastereomers by this method is frequently possible. In addition, the diasteromers can also be separated by chromatography. If ligands in point group C1 are employed in enantiomerically pure form, a diastereomer pair AA in point group C3 is formed. The diastereomers can be separated by crystallisation or chromatography and thus obtained as enantiomerically pure compounds.

| Ex. | Ligand S | Ir complex Diastereomer | Variant<br>Reaction medium<br>Melting aid<br>Reaction temp.<br>Reaction time<br>Suspension medium<br>Extractant | Yield |
|---|---|---|---|---|
| Ir(S1)₃ | S1 | 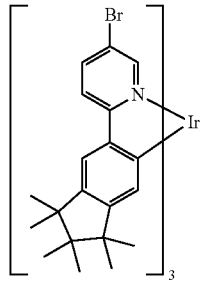 | A<br>—<br>—<br>270° C.<br>24 h<br>EtOH<br>Toluene | 15% |

Step 2: Borylation

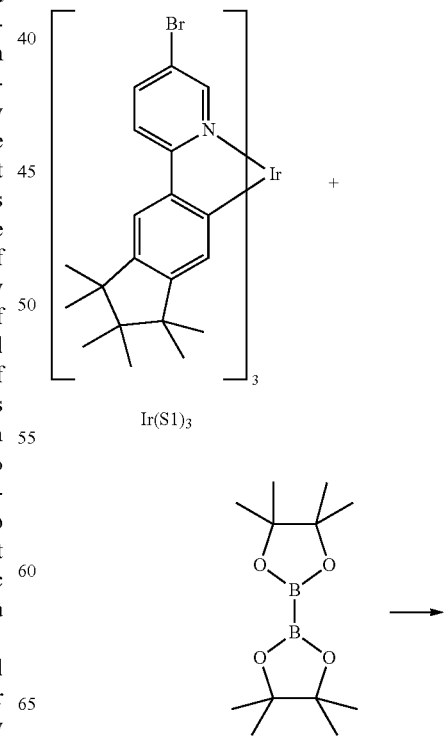

Ir(S1)₃

-continued

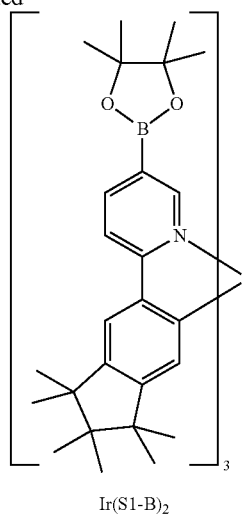

Ir(S1-B)₂

300 ml of 1,4-dioxane and 300 ml of toluene are added to a mixture of 12 mmol of Ir(S1)₃, 40 mmol of bis(pinacolato) diborane [73183-34-3], 214 mmol of potassium acetate [127-08-2] and 602 μmol of 1,1-bis(di-phenylphosphino) ferrocenepalladium(II) dichloride, and the mixture is boiled under reflux for 20 h. The reaction solution is filtered through Celite, evaporated to dryness in a rotary evaporator and employed in the next step without further purification.

Step 3: Suzuki Coupling

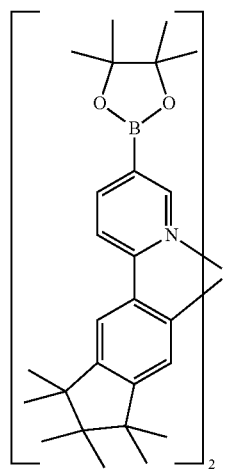

Ir(S1-8)₃

+

-continued

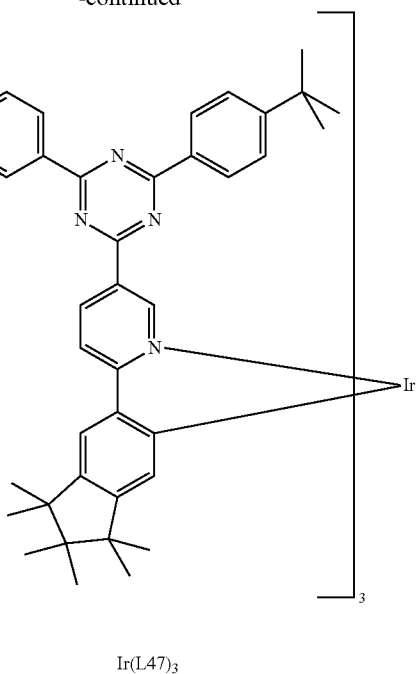

Ir(L47)₃

15.6 g (41 mmol) of the synthone [253158-13-3], 180 mg (0.8 mmol) of palladium(II) acetate, 485 mg (1.6 mmol) of tri-o-tolylphosphine and 14.5 g (60 mmol) of potassium phosphate are added to 16 g (11.4 mmol) of the complex Ir(S1-B)₃ from step 2, and 500 ml of toluene, 250 ml of deionised water and 250 ml of 1,4-dioxane are added. The reaction mixture is heated under reflux for 72 h. After cooling, the mixture is filtered through Celite, and the solvents are removed in vacuo. The residue is purified as described in Variant A.

Examples of synthones which can be used:

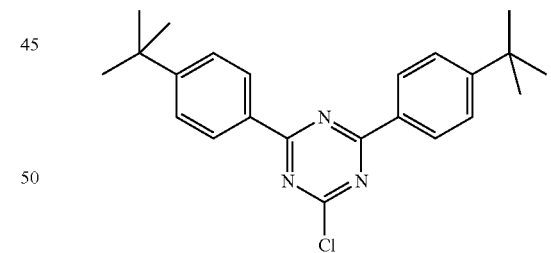

253158-13-3

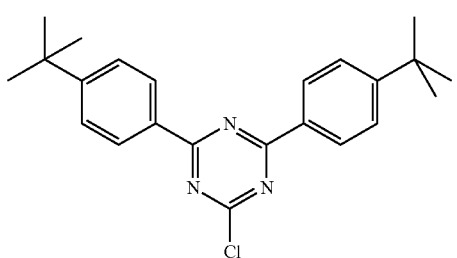

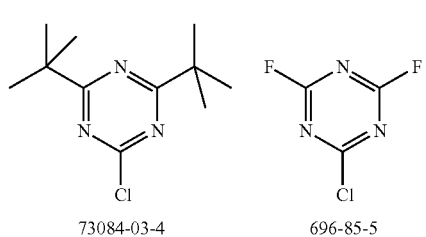

73084-03-4          696-85-5

-continued
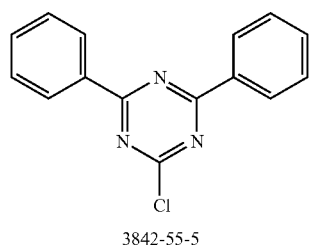
3842-55-5
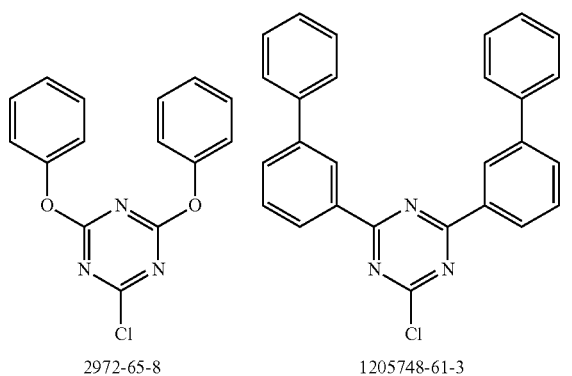
2972-65-8     1205748-61-3
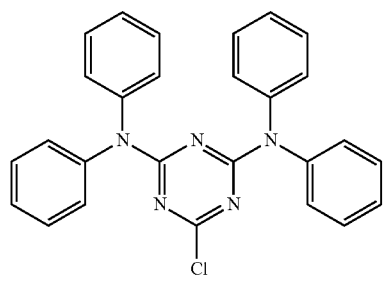
83820-01-3
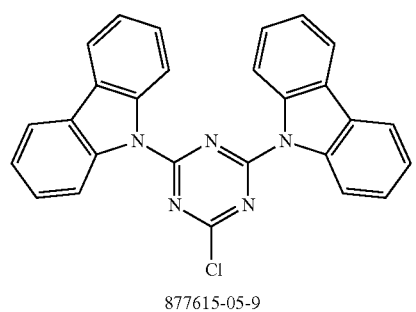
877615-05-9
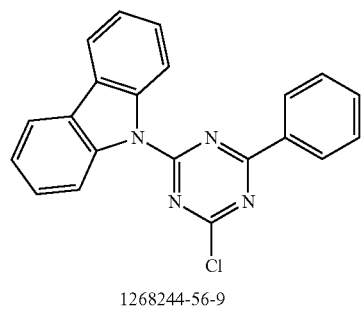
1268244-56-9
-continued
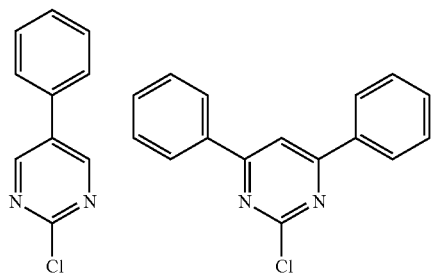
22536-62-5     2915-16-4
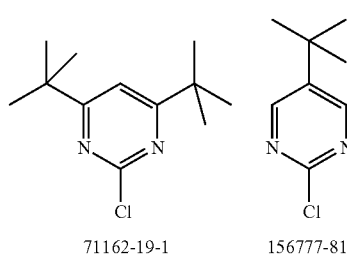
71162-19-1     156777-81-0
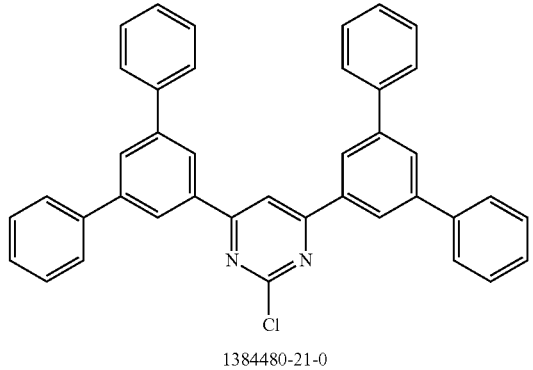
1384480-21-0
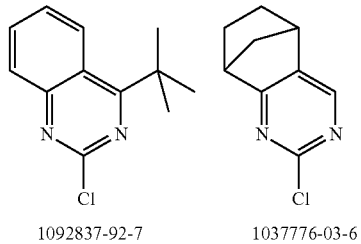
1092837-92-7     1037776-03-6
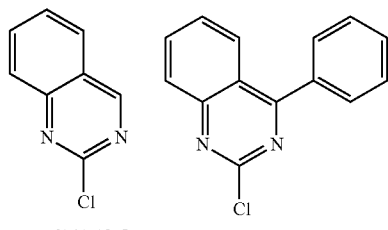
6141-13-5     529874-83-7
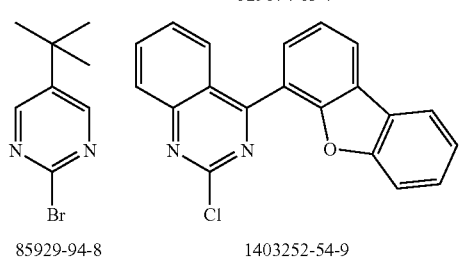
85929-94-8     1403252-54-9

423
-continued
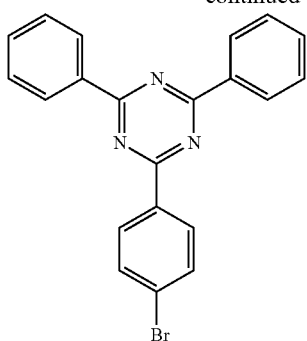
23449-08-3
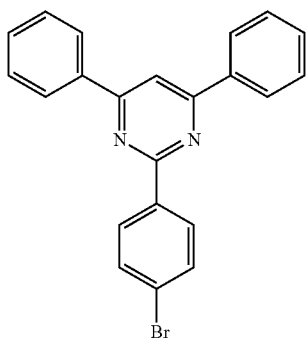
457613-56-8
424
-continued
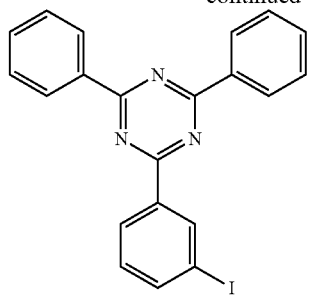
1476799-05-9
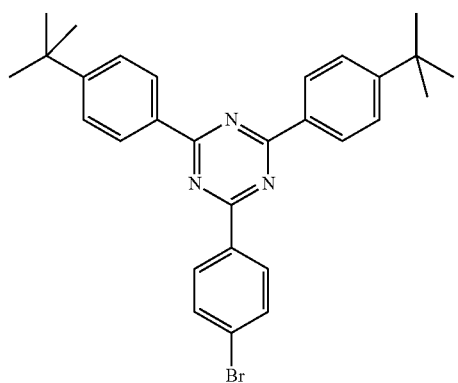
927898-18-8

| Ex. | Ir(L47)₃ | Ir(L15)₃ | Ir(L5)₃ | Ir(L17)₃ |
|---|---|---|---|---|
| Synthone CAS No. | 253158-13-3 | 73084-03-4 | 696-85-5 | 3842-55-5 |
| Ir complex | 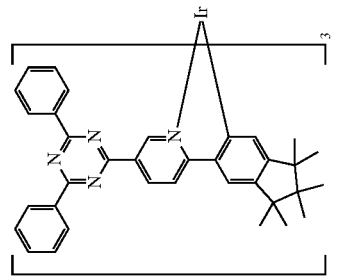 | 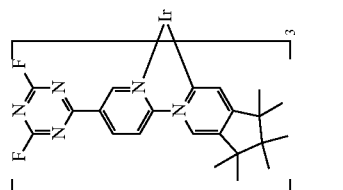 | 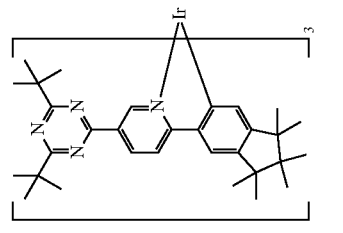 | 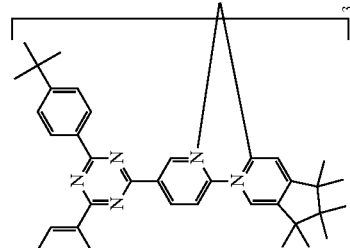 |
| Variant | A | A | A | A |
| Reaction medium | — | — | — | — |
| Melting aid | Hydroquinone | Hydroquinone | Hydroquinone | Hydroquinone |
| Reaction temp. | 250° C. | 250° C. | 250° C. | 250° C. |
| Reaction time | 48 h | 48 h | 48 h | 48 h |
| Suspension medium | EtOH | EtOH | EtOH | EtOH |
| Extractant | Ethyl acetate | Ethyl acetate | Ethyl acetate | Ethyl acetate |
| Yield | 79% | 67% | 71% | 80% |

-continued

| Ex. | Ir(L34)₃ | Ir(L74)₃ | Ir(L80)₃ | Ir(L79)₃ |
|---|---|---|---|---|
| Synthone CAS No. | 2972-65-8 | 1205748-61-3 | 83820-01-3 | 877615-05-9 |
| Ir complex | | | | |
| Variant | A | A | A | A |
| Reaction medium | — | — | — | — |
| Melting aid | Hydroquinone | Hydroquinone | Hydroquinone | Hydroquinone |
| Reaction temp. | 250° C. | 250° C. | 250° C. | 250° C. |
| Reaction time | 48 h | 48 h | 48 h | 48 h |
| Suspension medium | EtOH | EtOH | EtOH | EtOH |
| Extractant | Ethyl acetate | Ethyl acetate | Ethyl acetate | Ethyl acetate |
| Yield | 67% | 71% | 63% | 70% |

-continued

| Ex. | Ir(L67)₃ | Ir(L1000)₃ | Ir(L95)₃ | Ir(L93)₃ |
|---|---|---|---|---|
| Synthone CAS No. | 1268244-56-9 | 22536-62-5 | 2915-16-4 | 71162-19-1 |
| Ir complex | | | | |
| Variant | A | A | A | A |
| Reaction medium | — | — | — | — |
| Melting aid | Hydroquinone | Hydroquinone | Hydroquinone | Hydroquinone |
| Reaction temp. | 250° C. | 250° C. | 250° C. | 250° C. |
| Reaction time | 48 h | 48 h | 48 h | 48 h |
| Suspension medium | EtOH | EtOH | EtOH | EtOH |
| Extractant | Ethyl acetate | Ethyl acetate | Ethyl acetate | Ethyl acetate |
| Yield | 65% | 67% | 73% | 81% |

-continued

| Ex. | Ir(L1001)₃ | Ir(L1002)₃ | Ir(L1003)₃ | Ir(L1004)₃ |
|---|---|---|---|---|
| Synthone CAS No. | 156777-81-0 | 1384480-21-0 | 1092837-92-7 | 1037776-03-6 |
| Ir complex | | | | |
| Variant | A | A | A | A |
| Reaction medium | — | — | — | — |
| Melting aid | Hydroquinone | Hydroquinone | Hydroquinone | Hydroquinone |
| Reaction temp. | 250° C. | 250° C. | 250° C. | 250° C. |
| Reaction time | 48 h | 48 h | 48 h | 48 h |
| Suspension medium | EtOH | EtOH | EtOH | EtOH |
| Extractant | Ethyl acetate | Ethyl acetate | Ethyl acetate | Ethyl acetate |
| Yield | 73% | 74% | 79% | 73% |

-continued
| Ex. | Ir(L1005)₃ | Ir(L1006)₃ | Ir(L1007)₃ | Ir(L1008)₃ |
|---|---|---|---|---|
| Synthone CAS No. | 6141-13-5 | 529874-83-7 | 85929-94-8 | 1403252-54-9 |
| Ir complex | 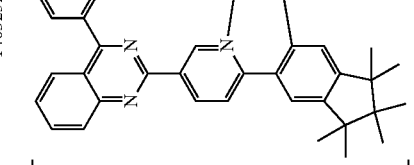 | 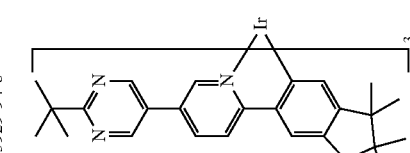 |  | 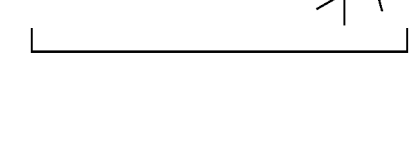 |
| Variant | A | A | A | A |
| Reaction medium | — | — | — | — |
| Melting aid | Hydroquinone | Hydroquinone | Hydroquinone | Hydroquinone |
| Reaction temp. | 250° C. | 250° C. | 250° C. | 250° C. |
| Reaction time | 48 h | 48 h | 48 h | 48 h |
| Suspension medium | EtOH | EtOH | EtOH | EtOH |
| Extractant | Ethyl acetate | Ethyl acetate | Ethyl acetate | Ethyl acetate |
| Yield | 71% | 75% | 72% | 73% |

-continued

| Ex. | Ir(L1009)₃ | Ir(L1010)₃ | Ir(L1011)₃ | Ir(L1012)₃ |
|---|---|---|---|---|
| Synthone CAS No. | 23449-08-3 | 457613-56-8 | 1476799-05-9 | 927898-18-8 |
| Ir complex | | | | |
| Variant | A | A | A | A |
| Reaction medium | — | — | — | — |
| Melting aid | Hydroquinone | Hydroquinone | Hydroquinone | Hydroquinone |
| Reaction temp. | 250° C. | 250° C. | 250° C. | 250° C. |
| Reaction time | 48 h | 48 h | 48 h | 48 h |
| Suspension medium | EtOH | EtOH | EtOH | EtOH |
| Extractant | Ethyl acetate | Ethyl acetate | Ethyl acetate | Ethyl acetate |
| Yield | 67% | 72% | 75% | 72% |

2) Heteroleptic Iridium Complexes:

Variant A:

Step 1:

See Variant D, step 1

Step 2:

The crude chloro dimer of the formula $[Ir(L)_2Cl]_2$ obtained in this way is suspended in a mixture of 75 ml of 2-ethoxyethanol and 25 ml of water, and 13 mmol of the co-ligand CL or of the co-ligand compound CL and 15 mmol of sodium carbonate are added. After 20 h under reflux, a further 75 ml of water are added dropwise, the mixture is cooled, and the solid is filtered off with suction, washed three times with 50 ml of water each time and three times with 50 ml of methanol each time and dried in vacuo. The dry solid is placed in a continuous hot extractor on an aluminium oxide bed (aluminium oxide, basic activity grade 1) with a depth of 3-5 cm and then extracted with the extractant indicated (amount initially introduced about 500 ml, the extractant is selected so that the complex is readily soluble therein at elevated temperature and has poor solubility therein at low temperature, particularly suitable extractants are hydrocarbons, such as toluene, xylenes, mesitylene, naphthalene, o-dichlorobenzene, tetrahydrofuran, dichloromethane, 1,2-dichloroethane, 1,1,2,2-tetrachloroethane, chloroform, carbon tetrachloride). When the extraction is complete, the extractant is evaporated to a few milliliters in vacuo. Metal complexes which have excessively good solubility in the extractant are brought to crystallisation by dropwise addition of 200 ml of methanol. The sold of the suspensions obtained in this way is filtered off with suction, washed once with methanol and dried. After drying, the purity of the metal complex is determined by means of NMR and/or HPLC. If the purity is below 99.5%, the hot-extraction step is repeated. When a purity of 99.5-99.9% has been reached, the metal complex is heated or sublimed. Besides the hot-extraction process for the purification, the purification can also be carried out by chromatography on silica gel or aluminium oxide. The heating is carried out in a high vacuum (p about $10^{-6}$ mbar) in the temperature range from about 200-300'C. The sublimation is carried out in a high vacuum (p about $10^{-6}$ mbar) in the temperature range from about 300-400° C., where the sublimation is preferably carried out in the form of a fractional sublimation.

| Ex. | Ligand L | Co-ligand CL | Ir complex Reaction temperature/ reaction time/suspension medium/extractant/heated or sublimed | Yield |
|---|---|---|---|---|
| Ir(L47)$_2$(CL1) | L47 | 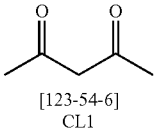[123-54-6] CL1 | 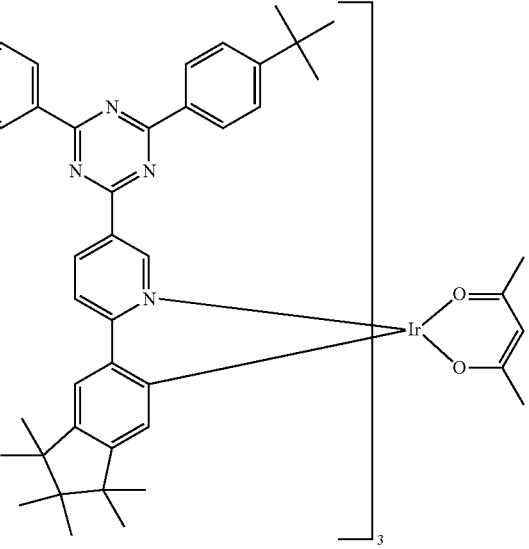 270° C./60 h/methanol/ toluene/heated | 28% |

Variant B:

200 ml of 2-ethoxyethanol are added to a mixture of 10 mmol of iridium bis(methanol) bis[CL]trifluoromethanesulfonate, 10 mmol of ligand L and 12 mmol of lutidine [108-48-5], and the mixture is stirred at 100° C. for 72 h. The solvent is removed in vacuo, and the residue is purified by column chromatography.

| Ex. | Ligand L | Iridium precursor Ir(CL)$_2$(OMe)$_2$$^+$ CF$_3$SO$_3$$^-$ | Ir complex | Yield |
|---|---|---|---|---|
| Ir(CL2)$_2$(L47) | L47 | 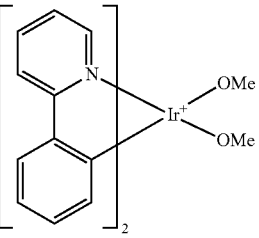 [1215692-14-0] | 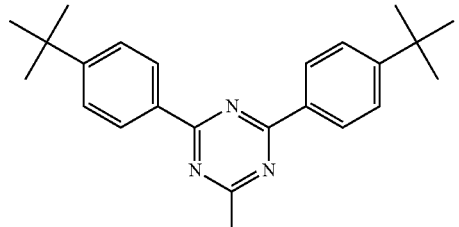 | 18% |
| Ir(CL3)$_2$(L47) | L47 | 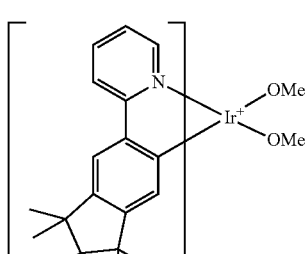 Synthesis see WO 2014/023377 | 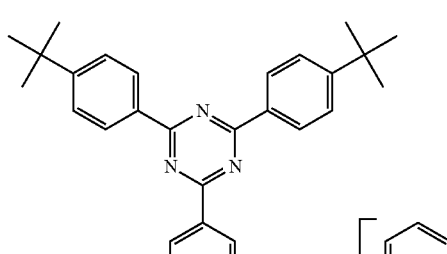 | 16% |

DEVICE EXAMPLES

Example 1: Photoluminescence in Solution

The complexes according to the invention can be dissolved in toluene. The characteristic data of photoluminescence spectra of toluene solutions of the complexes from Table 1 are shown in Table 2. Solutions having a concentration of about 1 mg/ml are used here, and the optical excitation is carried out at the local absorption maximum (at about 450 nm).

TABLE 1

Structures in photoluminescence of investigated complexes according to the invention and associated comparative complexes (the numbers in square brackets indicate the corresponding CAS numbers; the synthesis of complexes without CAS numbers is described in the enclosed patents)

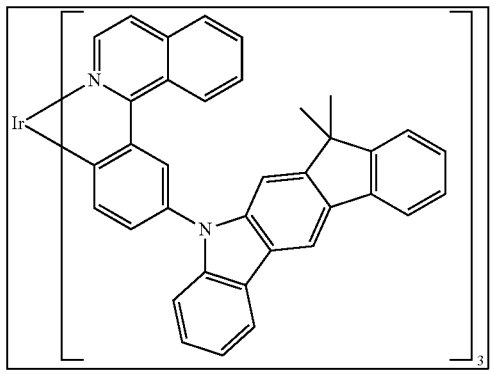

[1346011-00-4]
Ref1

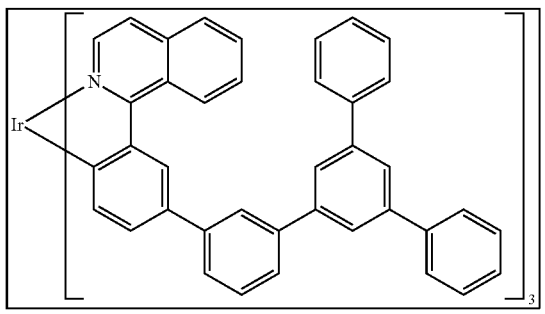

WO 2011/032626
Ref2

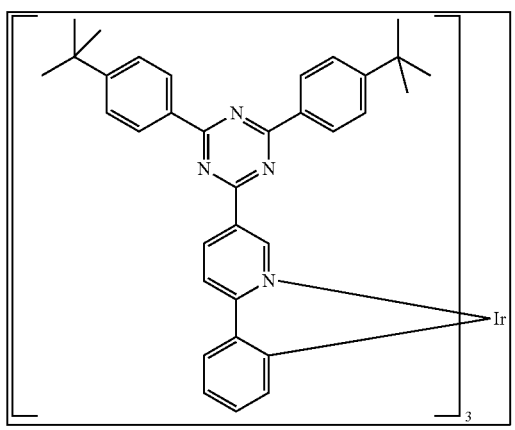

WO 2008/78800
Ref3

TABLE 1-continued

Structures in photoluminescence of investigated complexes according to the invention and associated comparative complexes (the numbers in square brackets indicate the corresponding CAS numbers; the synthesis of complexes without CAS numbers is described in the enclosed patents)

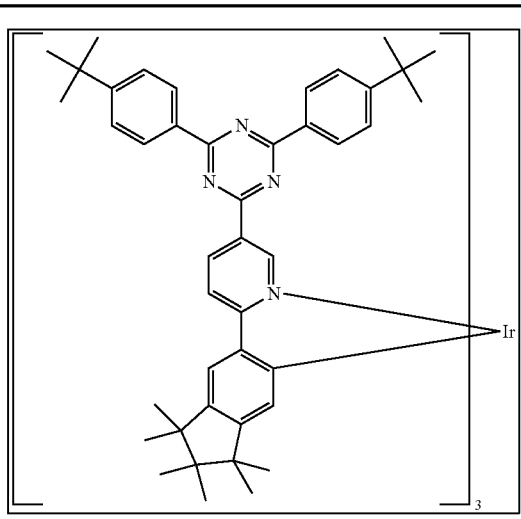

Ir(L47)$_3$

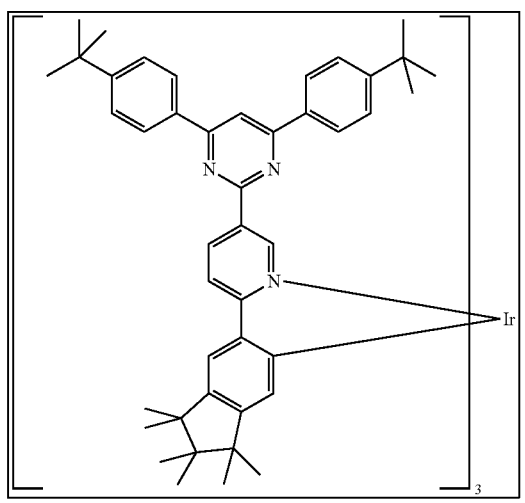

Ir(L96)$_3$

TABLE 1-continued
Structures in photoluminescence of investigated complexes according to the invention and associated comparative complexes (the numbers in square brackets indicate the corresponding CAS numbers; the synthesis of complexes without CAS numbers is described in the enclosed patents)
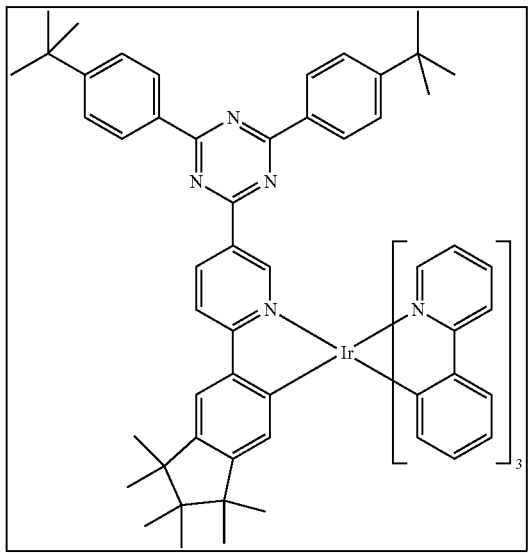
Ir(CL2)₂(L47)
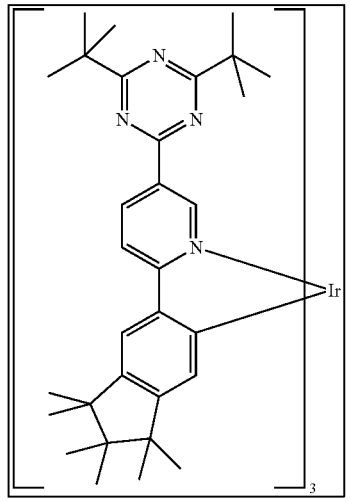
Ir(L15)₃
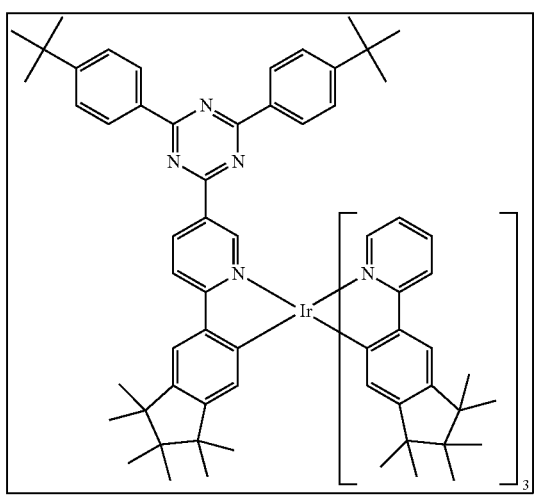
Ir(CL3)₂(L47)
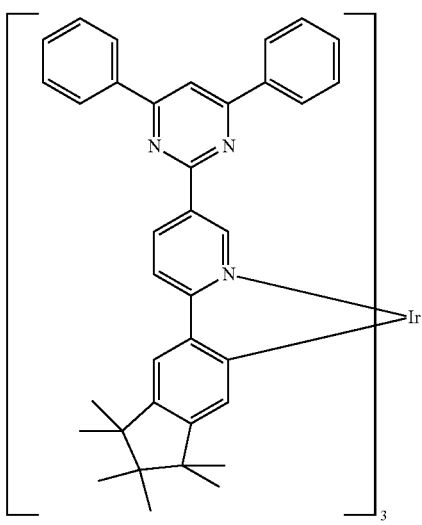
Ir(L95)₃

TABLE 1-continued
Structures in photoluminescence of investigated complexes according to the invention and associated comparative complexes (the numbers in square brackets indicate the corresponding CAS numbers; the synthesis of complexes without CAS numbers is described in the enclosed patents)
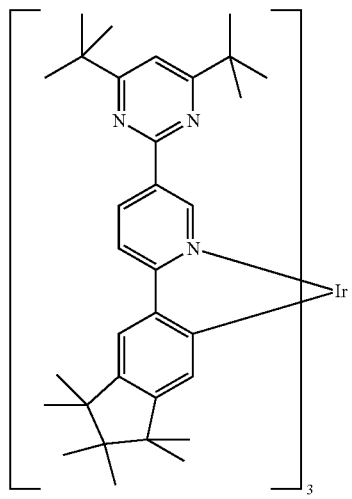
Ir(L93)₃
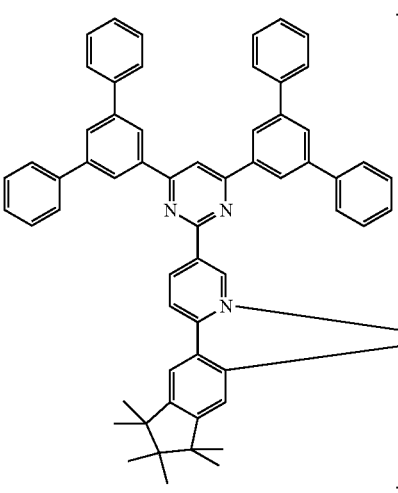
Ir(L1002)₃
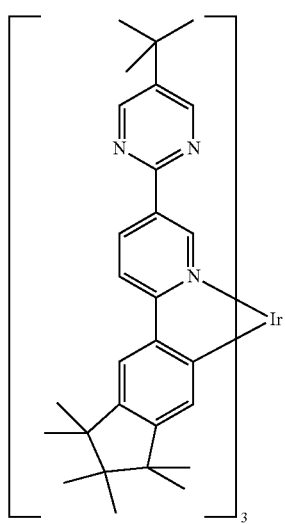
Ir(L1001)₃
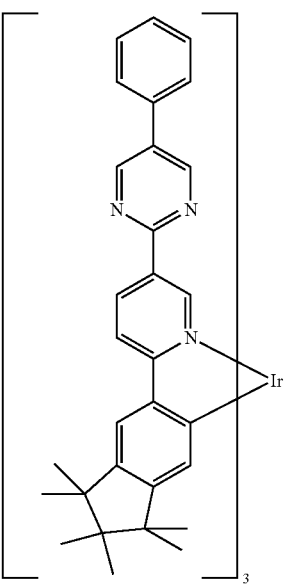
Ir(L1000)₃

TABLE 1-continued
Structures in photoluminescence of investigated complexes according to the invention and associated comparative complexes (the numbers in square brackets indicate the corresponding CAS numbers; the synthesis of complexes without CAS numbers is described in the enclosed patents)
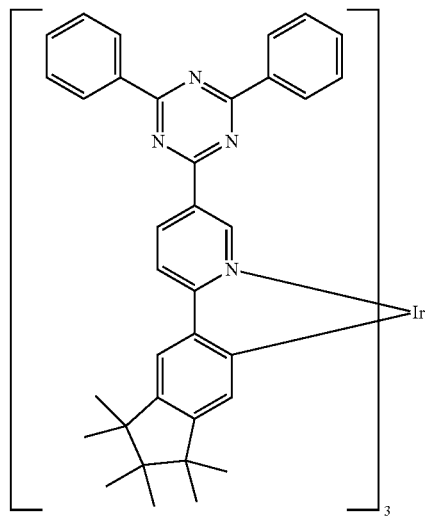
Ir(L17)$_3$
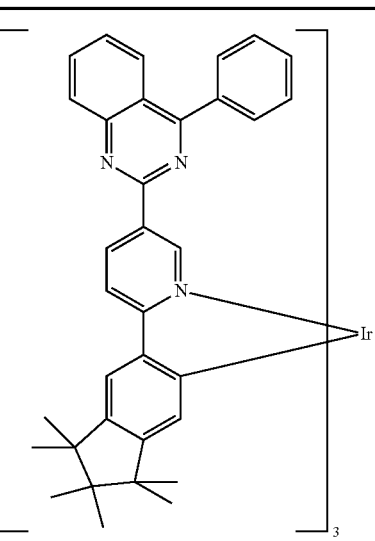
Ir(L1006)$_3$
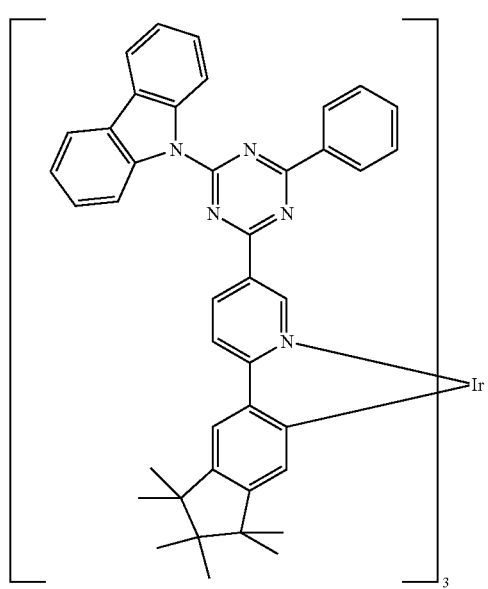
Ir(L67)$_3$
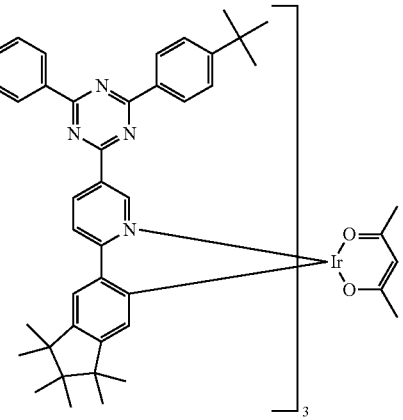
Ir(L47)$_2$(CL1)

TABLE 1-continued
Structures in photoluminescence of investigated complexes according to the invention and associated comparative complexes (the numbers in square brackets indicate the corresponding CAS numbers; the synthesis of complexes without CAS numbers is described in the enclosed patents)
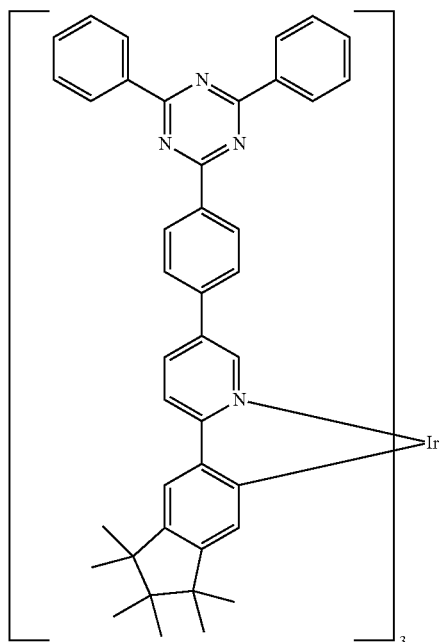
Ir(L1009)₃
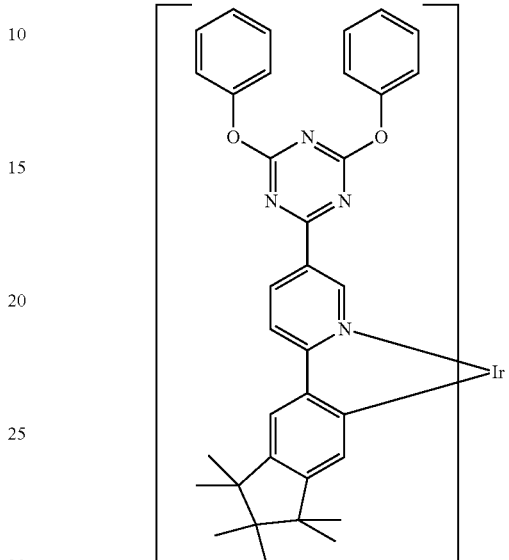
Ir(34)₃
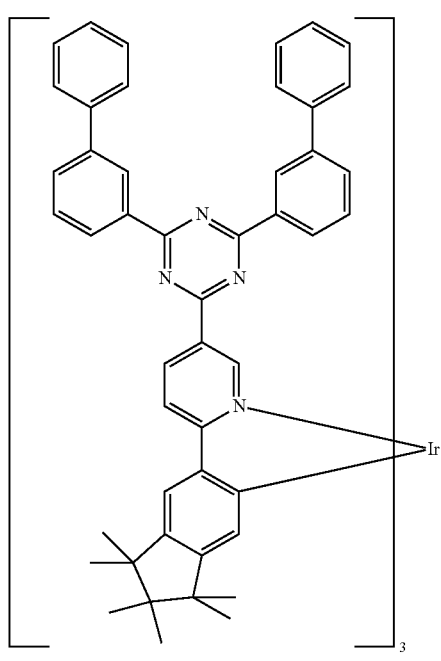
Ir(74)₃
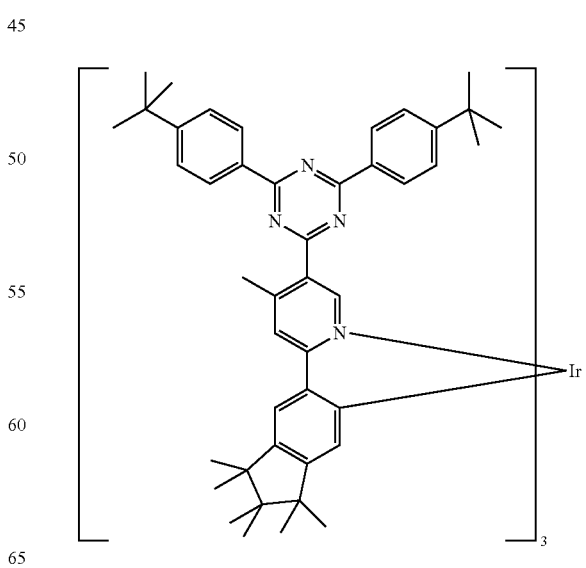
Ir(L166)₃

TABLE 1-continued

Structures in photoluminescence of investigated complexes according to the invention and associated comparative complexes (the numbers in square brackets indicate the corresponding CAS numbers; the synthesis of complexes without CAS numbers is described in the enclosed patents)

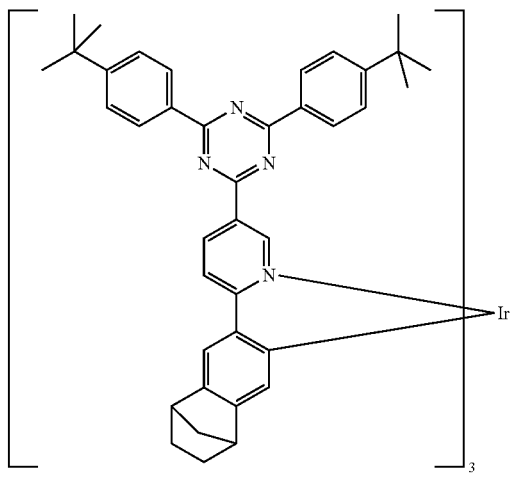

Ir(L128)₃

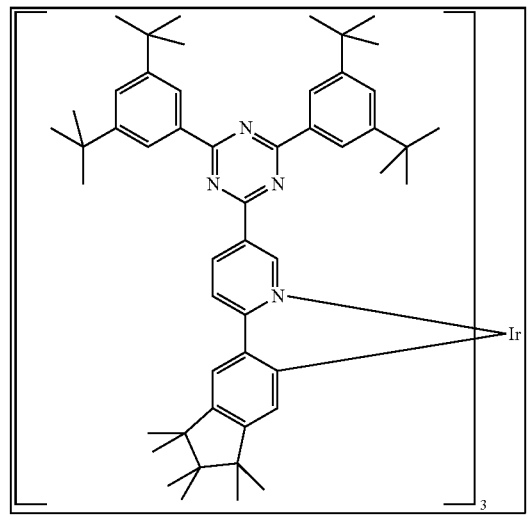

Ir(L223)₃

TABLE 2

Photoluminescence characteristic data

| Emitter | Emission max. (nm) | FWHM (nm) | PLQE (%) |
|---|---|---|---|
| Ref1 | 618 | 83 | 67 |
| Ref2 | 621 | 82 | 69 |
| Ir(L47)₃ | 619 | 48 | 80 |
| Ir(L96)₃ | 586 | 43 | 88 |
| Ir(CL2)₂(L47) | 622 | 79 | 72 |
| Ir(CL3)₂(L47) | 635 | 86 | 61 |
| Ref3 | 596 | 65 | 82 |
| Ir(L15)₃ | 602 | 49 | 83 |
| Ir(L100)₃ | 609 | 49 | 80 |
| Ir(L95)₃ | 592 | 47 | 87 |
| Ir(L93)₃ | 567 | 45 | 87 |
| Ir(L1001)₃ | 565 | 46 | 83 |
| Ir(L1002)₃ | 594 | 48 | 86 |
| Ir(1000)₃ | 574 | 50 | 86 |
| Ir(L17)₃ | 624 | 47 | 81 |
| Ir(L67)₃ | 633 | 53 | 76 |
| Ir(L1006)₃ | 623 | 52 | 78 |
| Ir(L47)₂(CL1) | 622 | 49 | 81 |
| Ir(L1009)₃ | 604 | 55 | 77 |
| Ir(74)₃ | 623 | 48 | 80 |
| Ir(L34)₃ | 607 | 51 | 85 |
| Ir(L128)₃ | 619 | 47 | 81 |
| Ir(L166)₃ | 617 | 64 | 84 |
| Ir(L223)₃ | 608 | 60 | 85 |

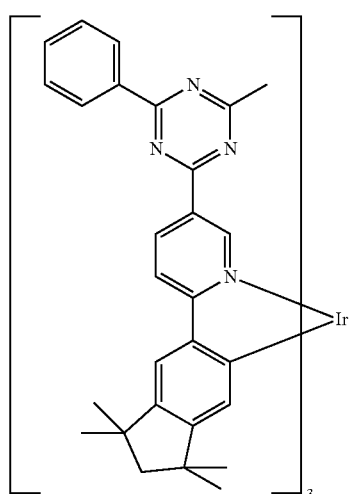

Ir(L100)₃

Example 2: Production of the OLEDs

The complexes according to the invention can be processed from solution and lead to OLEDs which are significantly simpler to produce than vacuum-processed OLEDs, but nevertheless have good properties. The production of completely solution-based OLEDs has already been described many times in the literature, for example in WO 2004/037887. The production of vacuum-based OLEDs has likewise already been described many times, inter alia in WO 2004/058911. In the examples discussed below, layers applied on a solution basis and layers applied on a vacuum basis are combined within an OLED, so that the processing up to and including the emission layer is carried out from solution and the processing in the subsequent layers (hole-blocking layer and electron-transport layer) is carried out from vacuum. The general processes described previously are for this purpose adapted to the circumstances described here (layer-thickness variation, materials) and combined as follows. The general structure is as follows: substrate/ITO (50 nm)-hole-injection layer (HIL)/hole-transport layer (HTL)/emission layer (EML)/hole-blocking layer (HBL)/electron-transport layer (ETL)/cathode (aluminium, 100 nm). The substrates used are glass plates which are coated with structured ITO (indium tin oxide) in a thickness of 50 nm. For better processing, these are coated with PEDOT:PSS (poly(3,4-ethylenedioxy-2,5-thiophene): polystyrenesulfonate, purchased from Heraeus Precious Metals GmbH & Co. KG, Germany). PEDOT:PSS is applied by spin coating from water in air and subsequently dried by heating at 180° C. in air for 10 minutes in order to remove residual water. The interlayer and the emission layer are applied to these coated glass plates. The hole-transport layer used is crosslinkable. Use is made of a polymer of the structures depicted below, which can be synthesised in accordance with WO 2010/097155 or WO 2013/156130:

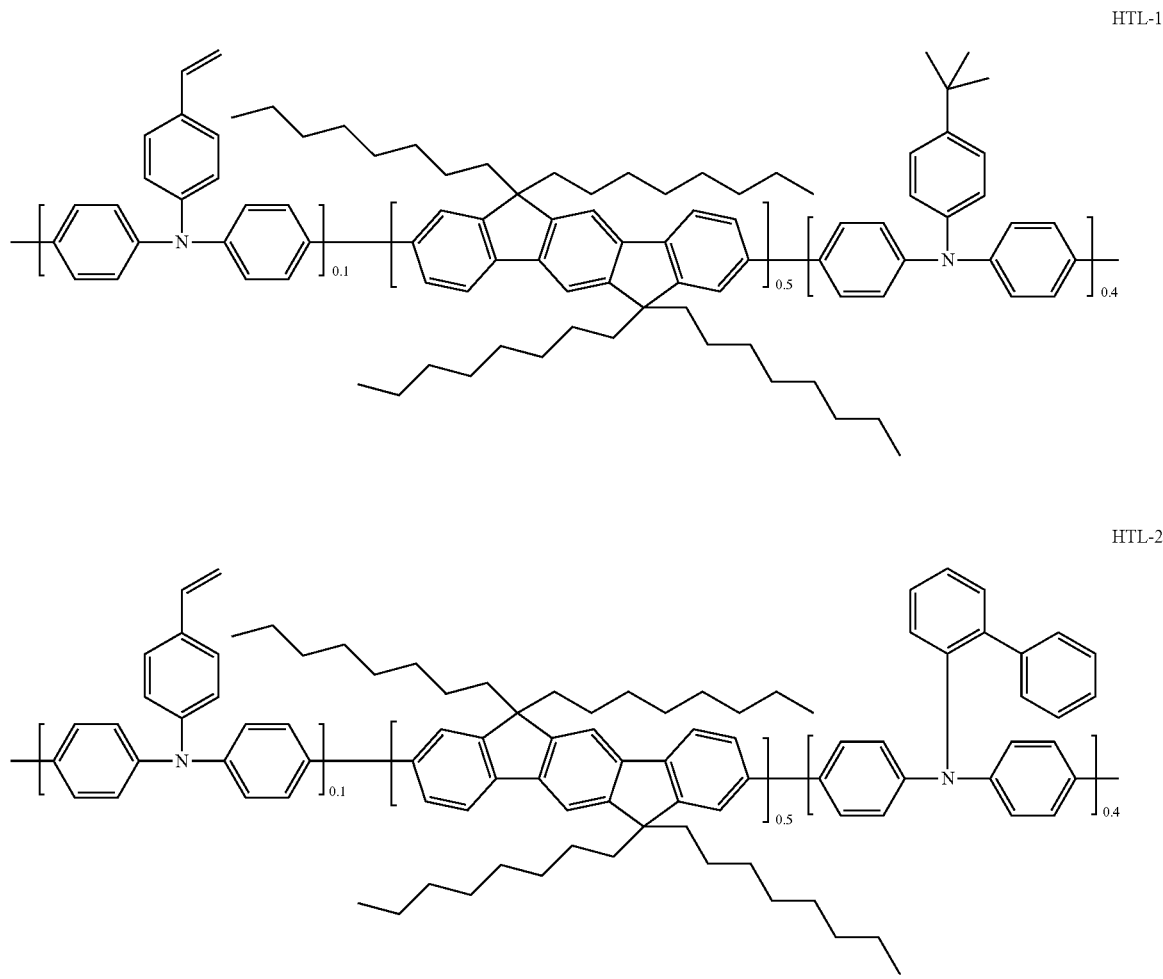

The hole-transport polymer is dissolved in toluene. The typical solids content of such solutions is about 5 g/l if, as here, the typical layer thickness of 20 nm for a device is to be achieved by means of spin coating. The layers are applied by spin coating in an inert-gas atmosphere, in the present case argon, and dried by heating at 180° C. for 60 minutes.

The emission layer is always composed of at least one matrix material (host material) and an emitting dopant (emitter). Mixtures of a plurality of matrix materials and co-dopants may furthermore occur. An expression such as TMM-A (92%):dopant (8%) here means that material TMM-A is present in the emission layer in a proportion by weight of 92% and the dopant is present in the emission layer in a proportion by weight of 8%. The mixture for the emission layer is dissolved in toluene or optionally chlorobenzene. The typical solids content of such solutions is about 18 g/l if, as here, the typical layer thickness of 60 nm for a device s to be achieved by means of spin coating. The layers are applied by spin coating in an inert-gas atmosphere, in the present case argon, and dried by heating at 160° C. for 10 minutes. The materials used in the present case are shown in Table 3.

TABLE 3
EML materials used
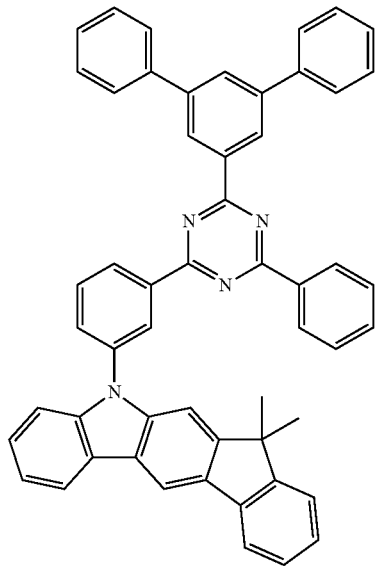 [SMILES: CC1(C)c2ccccc2-c2cc3c4ccccc4n(-c4cccc(-c5nc(-c6ccccc6)nc(-c6cc(-c7ccccc7)cc(-c7ccccc7)c6)n5)c4)c3cc21]
A-1
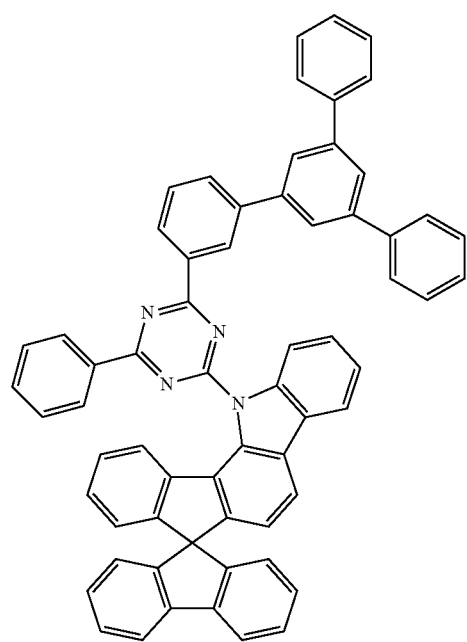 [SMILES: c1ccc(-c2cc(-c3ccccc3)cc(-c3cccc(-c4nc(-c5ccccc5)nc(-n5c6ccccc6c6ccc7c(c65)-c5ccccc5C75c6ccccc6-c6ccccc65)n4)c3)c2)cc1]
A-2

TABLE 3-continued
EML materials used
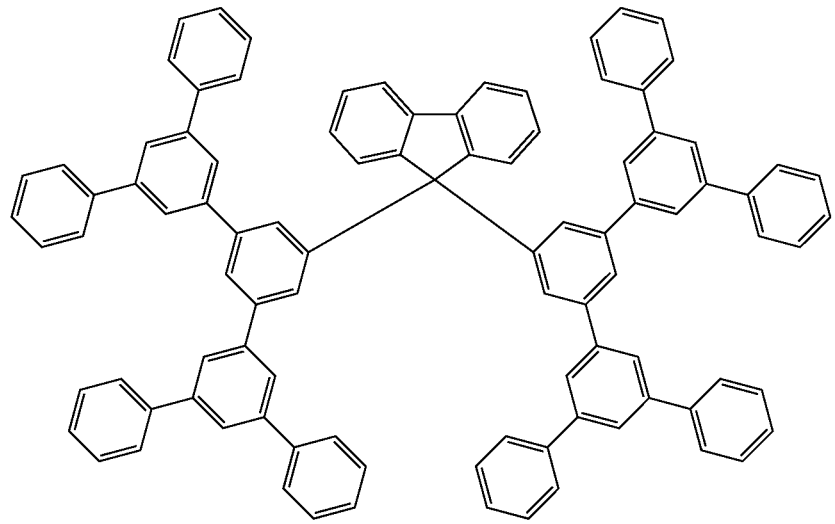 [SMILES: c1ccc(-c2cc(-c3ccccc3)cc(-c3cc(-c4cc(-c5ccccc5)cc(-c5ccccc5)c4)cc(C4(c5cc(-c6cc(-c7ccccc7)cc(-c7ccccc7)c6)cc(-c6cc(-c7ccccc7)cc(-c7ccccc7)c6)c5)c5ccccc5-c5ccccc54)c3)c2)cc1]
B1
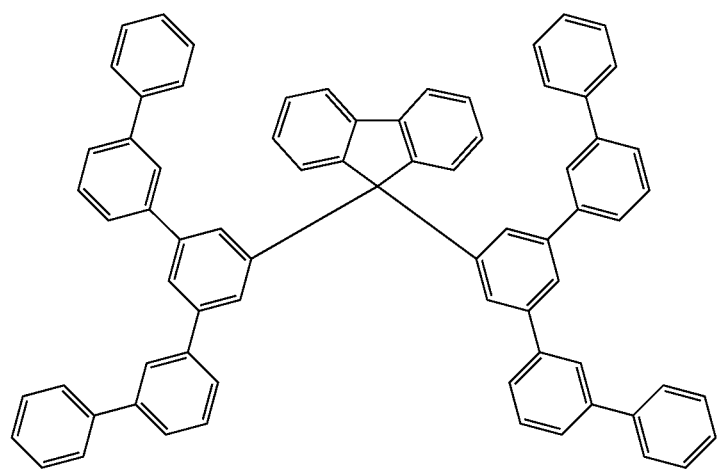 [SMILES: c1ccc(-c2cccc(-c3cc(-c4cccc(-c5ccccc5)c4)cc(C4(c5cc(-c6cccc(-c7ccccc7)c6)cc(-c6cccc(-c7ccccc7)c6)c5)c5ccccc5-c5ccccc54)c3)c2)cc1]
B2
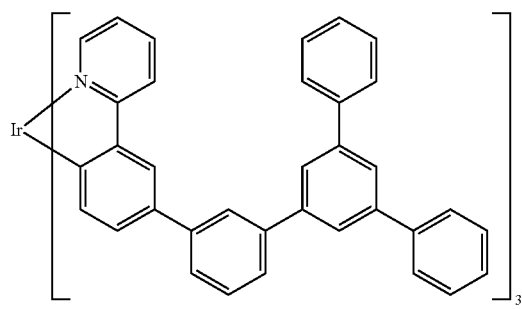
C-1

TABLE 3-continued

EML materials used

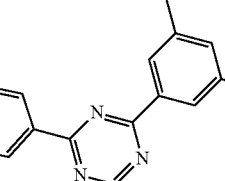

C-2

The materials for the hole-blocking layer and electron-transport layer are applied by thermal vapour deposition in a vacuum chamber. The electron-transport layer here may, for example, consist of more than one material, which are admixed with one another in a certain proportion by volume by co-evaporation. An expression such as ETM1:ETM2 (50%:50%) here means that materials ETM1 and ETM2 are present in the layer in a proportion by volume of 50% each. The materials used in the present case are shown in Table 4.

TABLE 4

HBL and ETL materials used

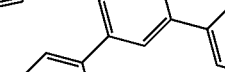

ETM1

ETM2

The cathode is formed by the thermal evaporation of a 100 nm aluminium layer. The OLEDs are characterised by standard methods. For this purpose, the electroluminescence spectra, current/voltage/luminous density characteristic lines (IUL characteristic lines) assuming Lambert emission characteristics, and the (operating) lifetime are determined. The IUL characteristic lines are used to determine characteristic numbers, such as the operating voltage (in V) and the efficiency (cd/A) at a certain luminance. The electroluminescence spectra are measured at a luminous density of 1000 cd/m$^2$, and the CIE 1931 x and y colour coordinates are calculated therefrom. The EML mixtures and structures of the OLED components investigated are depicted in Table 5 and Table 6. The associated results are found in Table 7.

TABLE 5

EML mixtures of the OLED components investigated

| Ex. | Matrix A Material | % | Co-matrix B Material | % | Co-dopant C Material | % | Dopant D Material | % |
|---|---|---|---|---|---|---|---|---|
| V-1 | A-1 | 30 | B-1 | 34 | C-1 | 30 | Ref2 | 6 |
| V-2 | A-2 | 30 | B-2 | 34 | C-1 | 30 | Ref2 | 6 |
| E-1 | A-2 | 30 | B-1 | 34 | C-1 | 30 | Ir(L96)$_3$ | 6 |
| E-2 | A-2 | 30 | B-2 | 34 | C-1 | 30 | Ir(L47)$_3$ | 6 |
| V-3 | A-2 | 39 | B-2 | 45 | C-2 | 10 | Ref1 | 6 |
| E-3 | A-2 | 39 | B-2 | 45 | C-2 | 10 | Ir(L47)$_3$ | 6 |
| V-4 | A-2 | 40 | B-2 | 45 | — | — | Ref1 | 15 |
| E-4 | A-2 | 40 | B-2 | 45 | — | — | Ir(L47)$_3$ | 15 |
| V-5 | A-1 | 40 | B-1 | 54 | — | — | Ref2 | 6 |
| E-5 | A-2 | 40 | B-1 | 54 | — | — | Ir(L96)$_3$ | 6 |
| V-6 | A-2 | 40 | B-2 | 55 | — | — | Ref3 | 5 |
| E-6 | A-2 | 40 | B-2 | 55 | — | — | Ir(L47)$_3$ | 5 |
| V-7 | A-2 | 30 | B-2 | 36 | C-1 | 30 | Ref3 | 4 |
| E-7 | A-2 | 30 | B-2 | 36 | C-1 | 30 | Ir(L47)$_3$ | 4 |
| E-8 | A-2 | 20 | B-2 | 70 | — | — | Ir(L15)$_3$ | 10 |
| E-9 | A-2 | 30 | B-2 | 49 | C-1 | 15 | Ir(L15)$_3$ | 6 |
| E-10 | A-2 | 39 | B-2 | 45 | C-1 | 10 | Ir(L93)$_3$ | 6 |
| E-11 | A-2 | 30 | B-2 | 49 | C-2 | 15 | Ir(L1001)$_3$ | 6 |
| E-12 | A-2 | 30 | B-1 | 34 | C-1 | 30 | Ir(L1002)$_3$ | 6 |
| E-13 | A-2 | 30 | B-2 | 36 | C-1 | 30 | Ir(L67)$_3$ | 4 |
| E-14 | A-2 | 40 | B-2 | 56 | — | — | Ir(L1006)$_3$ | 4 |
| E-15 | A-2 | 20 | B-2 | 70 | — | — | Ir(L47)$_2$(CL1) | 10 |
| E-16 | A-1 | 30 | B-1 | 34 | C-1 | 30 | Ir(L74)$_3$ | 6 |
| E-17 | A-2 | 30 | B-2 | 34 | C-1 | 30 | Ir(L166)$_3$ | 6 |
| E-18 | A-2 | 30 | B-2 | 49 | C-1 | 15 | Ir(L128)$_3$ | 6 |
| E-19 | A-2 | 39 | B-2 | 45 | C-1 | 10 | Ir(L100)$_3$ | 6 |
| E-20 | A-2 | 40 | B-2 | 45 | — | — | Ir(L223)$_3$ | 15 |

TABLE 6

Structure of the OLED components investigated

| Ex. | HIL (thickness) | HTL (thickness) | EML thickness | HBL (thickness) | ETL (thickness) |
|---|---|---|---|---|---|
| V-1 | PEDOT (60 nm) | HTL1 (20 nm) | 60 nm | ETM-1 (10 nm) | ETM-1(50%): ETM-2 (50%) (40 nm) |
| V-2 | PEDOT (60 nm) | HTL2 (20 nm) | 60 nm | ETM-1 (10 nm) | ETM-1(50%): ETM-2 (50%) (40 nm) |
| E-1 | PEDOT (60 nm) | HTL2 (20 nm) | 60 nm | ETM-1 (10 nm) | ETM-1(50%): ETM-2 (50%) (40 nm) |

TABLE 6-continued

Structure of the OLED components investigated

| Ex. | HIL (thickness) | HTL (thickness) | EML thickness | HBL (thickness) | ETL (thickness) |
|---|---|---|---|---|---|
| E-2 | PEDOT (60 nm) | HTL2 (20 nm) | 60 nm | ETM-1 (10 nm) | ETM-1(50%): ETM-2 (50%) (40 nm) |
| V-3 | PEDOT (60 nm) | HTL2 (20 nm) | 60 nm | ETM-1 (10 nm) | ETM-1(50%): ETM-2 (50%) (40 nm) |
| E-3 | PEDOT (60 nm) | HTL2 (20 nm) | 60 nm | ETM-1 (10 nm) | ETM-1(50%): ETM-2 (50%) (40 nm) |
| V-4 | PEDOT (60 nm) | HTL2 (20 nm) | 60 nm | ETM-1 (10 nm) | ETM-1(50%): ETM-2 (50%) (40 nm) |
| E-4 | PEDOT (60 nm) | HTL2 (20 nm) | 60 nm | ETM-1 (10 nm) | ETM-1(50%): ETM-2 (50%) (40 nm) |
| V-5 | PEDOT (80 nm) | HTL1 (20 nm) | 60 nm | ETM-1 (10 nm) | ETM-1(50%): ETM-2 (50%) (40 nm) |
| E-5 | PEDOT (60 nm) | HTL2 (20 nm) | 60 nm | ETM-1 (10 nm) | ETM-1(50%): ETM-2 (50%) (40 nm) |
| V-6 | PEDOT (60 nm) | HTL2 (20 nm) | 60 nm | ETM-1 (10 nm) | ETM-1(50%): ETM-2 (50%) (40 nm) |
| E-6 | PEDOT (60 nm) | HTL2 (20 nm) | 60 nm | ETM-1 (10 nm) | ETM-1(50%): ETM-2 (50%) (40 nm) |
| V-7 | PEDOT (60 nm) | HTL2 (20 nm) | 60 nm | ETM-1 (10 nm) | ETM-1(50%): ETM-2 (50%) (40 nm) |
| E-7 | PEDOT (60 nm) | HTL2 (20 nm) | 60 nm | ETM-1 (10 nm) | ETM-1(50%): ETM-2 (50%) (40 nm) |
| E-8 | PEDOT (60 nm) | HTL2 (20 nm) | 60 nm | ETM-1 (10 nm) | ETM-1(50%): ETM-2 (50%) (40 nm) |
| E-9 | PEDOT (60 nm) | HTL2 (20 nm) | 60 nm | ETM-1 (10 nm) | ETM-1(50%): ETM-2 (50%) (40 nm) |
| E-10 | PEDOT (60 nm) | HTL1 (20 nm) | 60 nm | ETM-1 (10 nm) | ETM-1(50%): ETM-2 (50%) (40 nm) |
| E-11 | PEDOT (60 nm) | HTL2 (20 nm) | 60 nm | ETM-1 (10 nm) | ETM-1(50%): ETM-2 (50%) (40 nm) |
| E-12 | PEDOT (60 nm) | HTL2 (20 nm) | 60 nm | ETM-1 (10 nm) | ETM-1(50%): ETM-2 (50%) (40 nm) |
| E-13 | PEDOT (60 nm) | HTL2 (20 nm) | 60 nm | ETM-1 (10 nm) | ETM-1(50%): ETM-2 (50%) (40 nm) |
| E-14 | PEDOT (60 nm) | HTL2 (20 nm) | 60 nm | ETM-1 (10 nm) | ETM-1(50%): ETM-2 (50%) (40 nm) |
| E-15 | PEDOT (60 nm) | HTL2 (20 nm) | 60 nm | ETM-1 (10 nm) | ETM-1(50%): ETM-2 (50%) (40 nm) |
| E-16 | PEDOT (60 nm) | HTL1 (20 nm) | 60 nm | ETM-1 (10 nm) | ETM-1(50%): ETM-2 (50%) (40 nm) |
| E-17 | PEDOT (60 nm) | HTL2 (20 nm) | 60 nm | ETM-1 (10 nm) | ETM-1(50%): ETM-2 (50%) (40 nm) |
| E-18 | PEDOT (60 nm) | HTL2 (20 nm) | 60 nm | ETM-1 (10 nm) | ETM-1(50%): ETM-2 (50%) (40 nm) |
| E-19 | PEDOT (60 nm) | HTL2 (20 nm) | 60 nm | ETM-1 (10 nm) | ETM-1(50%): ETM-2 (50%) (40 nm) |
| E-20 | PEDOT (60 nm) | HTL2 (20 nm) | 60 nm | ETM-1 (10 nm) | ETM-1(50%): ETM-2 (50%) (40 nm) |

TABLE 7

Results of solution-processed OLEDs
(measured at a luminance of 1000 cd/m$^2$)

| Ex. | EffL [cd/A] | U [V] | CIE x | CIE y |
|---|---|---|---|---|
| V-1 | 13.1 | 5.7 | 0.66 | 0.34 |
| V-2 | 12.7 | 6.6 | 0.65 | 0.35 |
| E-1 | 36.7 | 7.4 | 0.58 | 0.42 |
| E-2 | 17.1 | 6.7 | 0.66 | 0.34 |
| V-3 | 12.9 | 6.8 | 0.65 | 0.34 |
| E-3 | 16.8 | 6.5 | 0.66 | 0.34 |
| V-4 | 10.3 | 6.5 | 0.68 | 0.32 |
| E-4 | 13.5 | 6.2 | 0.68 | 0.32 |
| V-5 | 8.1 | 6.8 | 0.68 | 0.32 |
| E-5 | 21.8 | 7.1 | 0.59 | 0.41 |
| V-6 | 15.0 | 6.7 | 0.62 | 0.38 |
| E-6 | 13.1 | 6.4 | 0.67 | 0.33 |
| V-7 | 26.9 | 6.6 | 0.61 | 0.39 |
| E-7 | 18.7 | 6.5 | 0.65 | 0.35 |

TABLE 7-continued

Results of solution-processed OLEDs
(measured at a luminance of 1000 cd/m$^2$)

| Ex. | EffL [cd/A] | U [V] | CIE x | CIE y |
|---|---|---|---|---|
| E-8 | 15.4 | 8.2 | 0.65 | 0.35 |
| E-9 | 26.0 | 6.7 | 0.63 | 0.37 |
| E-10 | 49.2 | 6.3 | 0.46 | 0.53 |
| E-11 | 50.8 | 6.2 | 0.46 | 0.53 |
| E-12 | 34.4 | 7.3 | 0.60 | 0.40 |
| E-13 | 8.1 | 7.7 | 0.69 | 0.30 |
| E-14 | 9.2 | 7.6 | 0.69 | 0.31 |
| E-15 | 8.5 | 7.6 | 0.69 | 0.31 |
| E-16 | 14.5 | 6.9 | 0.67 | 0.33 |
| E-17 | 17.5 | 7.3 | 0.66 | 0.34 |
| E-18 | 16.9 | 6.8 | 0.66 | 0.34 |
| E-19 | 21.1 | 6.6 | 0.65 | 0.35 |
| E-20 | 17.0 | 6.7 | 0.66 | 0.34 |

The invention claimed is:

1. A compound of formula (1):

$$[Ir(L)_n(L')_m] \qquad (1)$$

wherein the compound comprises a moiety Ir(L)$_n$ of formula (2):

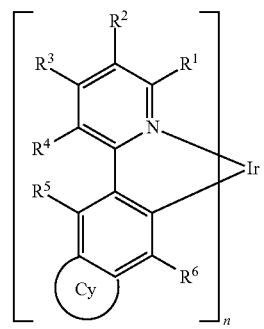

formula (2)

wherein
one of the radicals R$^2$ and R$^3$ is a group of formula —(Ar)$_p$-HetAr and the other of the radicals R$^2$ and R$^3$ has the same meaning as defined for R, R$^1$, R$^4$, R$^5$, and R$^6$;
HetAr is a group of formula (3)

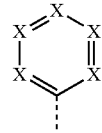

formula (3)

wherein the dashed bond indicates the bond to Ar or, for p=0, the bond to the pyridine group of the ligand;
X is on each occurrence, identically or differently, CR or N, with the proviso that at least one and at most three groups X are N;
Ar is on each occurrence, identically or differently, an aromatic or heteroaromatic ring system having 5 to 30 aromatic ring atoms, which are optionally substituted by one or more radicals R;

p is on each occurrence, identically or differently, 0 or 1;
Cy is on each occurrence, identically or differently, a group of formula (4), (5), (6), (7), (8), (9), or (10),

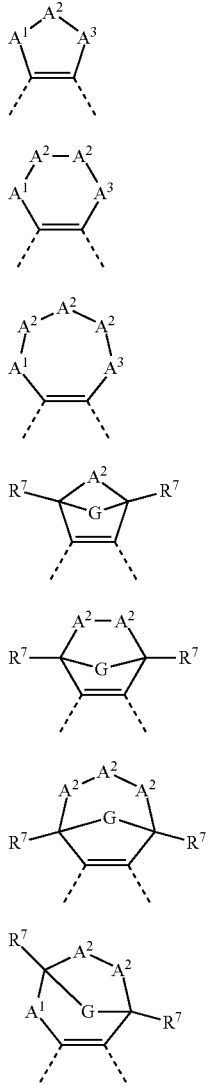

wherein the dashed bonds indicate the linking of the two carbon atoms in the ligand and:
$A^1$ and $A^3$ are, identically or differently on each occurrence, $C(R^8)_2$, O, S, $NR^8$, or C(=O);
$A^2$ is $C(R^7)_2$, O, S, $NR^8$, or C(=O);
G is an alkylene group having 1, 2, or 3 C atoms, which is optionally substituted by one or more radicals $R^9$, —$CR^9$=$CR^9$—, or an ortho-linked arylene or heteroarylene group having 5 to 14 aromatic ring atoms, which is optionally substituted by one or more radicals $R^9$;
with the proviso that no two heteroatoms in these groups are bonded directly to one another and no two groups C=O are bonded directly to one another;
R, $R^1$, $R^4$, $R^5$, $R^6$, $R^7$
are on each occurrence, identically or differently, H, D, F, Cl, Br, I, $N(R^9)_2$, CN, $Si(R^9)_3$, $B(OR^9)_2$, C(=O)$R^9$, a straight-chain alkyl, alkoxy, or thioalkoxy group having 1 to 40 C atoms or a straight-chain alkenyl or alkynyl group having 2 to 40 C atoms or a branched or cyclic alkyl, alkenyl, alkynyl, alkoxy, or thioalkoxy group having 3 to 40 C atoms, each of which is optionally substituted by one or more radicals $R^9$, wherein one or more non-adjacent $CH_2$ groups are optionally replaced by $R^9C$=$CR^9$, $Si(R^9)_2$, C=O, $NR^9$, O, S, or $CONR^9$ and wherein one or more H atoms are optionally replaced by D, F, or CN, an aromatic or heteroaromatic ring system having 5 to 60 aromatic ring atoms, which is optionally substituted by one or more radicals $R^9$, an aryloxy or heteroaryloxy group having 5 to 60 aromatic ring atoms, which is optionally substituted by one or more radicals $R^9$, or a diarylamino group, diheteroarylamino group, or arylheteroarylamino group having 10 to 40 aromatic ring atoms, which are optionally substituted by one or more radicals $R^9$; wherein two adjacent radicals R optionally define an aliphatic, aromatic, or heteroaromatic ring system with one another, and wherein the radicals $R^4$ and R optionally define an aliphatic, aromatic, or heteroaromatic ring system with one another; and wherein the radicals $R^3$ and $R^4$ optionally define an aliphatic, aromatic, or heteroaromatic ring system with one another if the group $R^2$ is a group of formula —$(Ar)_p$-HetAr;
$R^8$ is, identically or differently on each occurrence, F, a straight-chain alkyl or alkoxy group having 1 to 10 C atoms, a branched or cyclic alkyl or alkoxy group having 3 to 10 C atoms, each of which is optionally substituted by one or more radicals $R^9$, wherein one or more non-adjacent $CH_2$ groups are optionally replaced by $R^9C$=$CR^9$, C≡C, $Si(R^9)_2$, C=O, $NR^9$, O, S, or $CONR^9$ and wherein one or more H atoms may be replaced by D or F, an aromatic or heteroaromatic ring system having 5 to 24 aromatic ring atoms, which is optionally substituted by one or more radicals $R^9$, an aryloxy or heteroaryloxy group having 5 to 24 aromatic ring atoms, which is optionally substituted by one or more radicals $R^9$, or an aralkyl or heteroaralkyl group having 5 to 24 aromatic ring atoms, which are optionally substituted by one or more radicals $R^9$; and wherein two radicals $R^8$ bonded to the same carbon atom optionally define an aliphatic or aromatic ring system with one another and thus form a spiro system; and wherein $R^8$ optionally defines an aliphatic ring system with an adjacent radical $R^7$;
$R^9$ is on each occurrence, identically or differently, H, D, F, or an aliphatic, aromatic, and/or heteroaromatic organic radical having 1 to 20 C atoms, wherein one or more H atoms are optionally replaced by D or F; and wherein two or more substituents $R^9$ optionally define an aliphatic or aromatic ring system with one another;
L' is, identically or differently on each occurrence, a mono- or bidentate ligand;
n is 1, 2, or 3; and
m is 0, 1, 2, 3, or 4.
2. The compound of claim 1, wherein n=3 or n=2 and m=1, wherein L' is a monoanionic bidentate ligand which coordinates to the iridium via one carbon atom and one nitrogen atom, one carbon atom and one oxygen atom, two oxygen atoms, two nitrogen atoms, or one oxygen atom and one nitrogen atom, or n=1 and m=2 and L' is, identically or differently on each occurrence, a monoanionic bidentate ligand which coordinates to the iridium via one carbon atom and one nitrogen atom or one carbon atom and one oxygen atom.

3. The compound of claim 1, wherein p=0 or p=1 and Ar is selected, identically or differently on each occurrence, from the groups consisting of an aromatic or heteroaromatic ring system having 6 to 18 aromatic ring atoms, which are optionally substituted by one or more radicals R.

4. The compound of claim 1, wherein HetAr is selected from the group consisting of formulae (3-1) through (3-10):

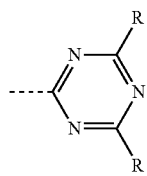
formula (3-1)

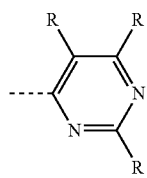
formula (3-2)

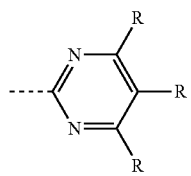
formula (3-3)

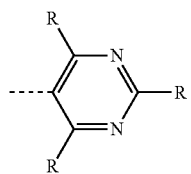
formula (3-4)

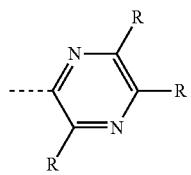
formula (3-5)

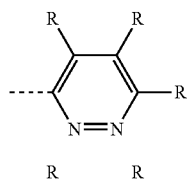
formula (3-6)

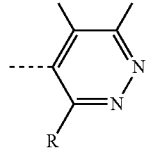
formula (3-7)

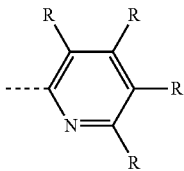
formula (3-8)

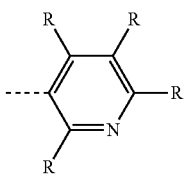
formula (3-9)

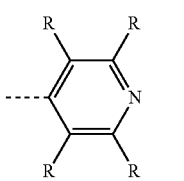
formula (3-10)

wherein the dashed bond represents the bond to Ar or, when p=0, to the pyridine ring.

5. The compound of claim 1, wherein R is, identically or differently on each occurrence, H or an aromatic or heteroaromatic ring system having 6 to 24 aromatic ring atoms, which are optionally substituted by one or more radicals $R^9$.

6. The compound of claim 1, wherein Cy is selected from the group consisting of the structures of formulae (4-A) to (4-F), (5-A) to (5-F), (6-A) to (6-E), (7-A) to (7-C), (8-A), (9-A), and (10-A)

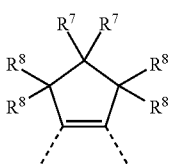
(4-A)

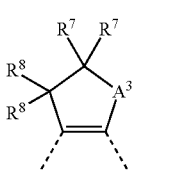
(4-B)

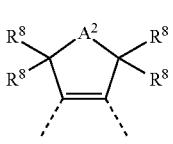
(4-C)

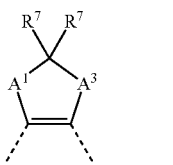
(4-D)

-continued
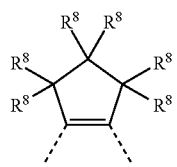 (4-E)
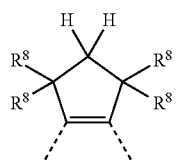 (4-F)
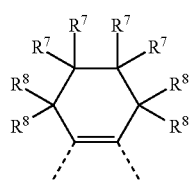 (5-A)
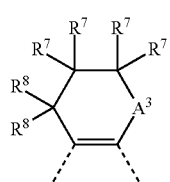 (5-B)
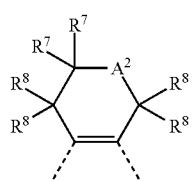 (5-C)
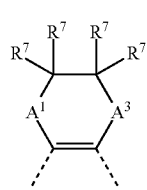 (5-D)
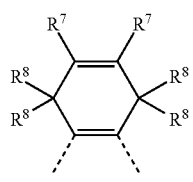 (5-E)
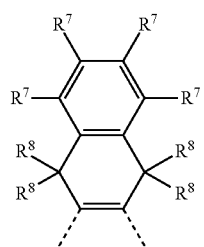 (5-F)
-continued
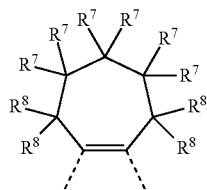 (6-A)
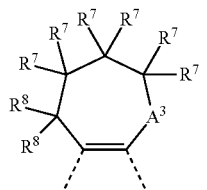 (6-B)
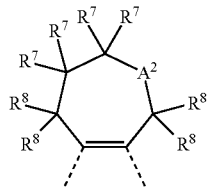 (6-C)
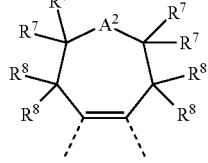 (6-D)
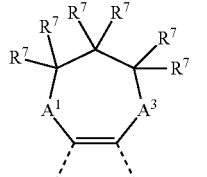 (6-E)
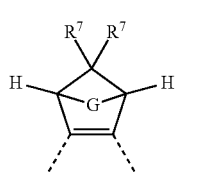 (7-A)
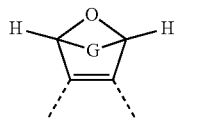 (7-B)
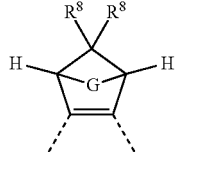 (7-C)
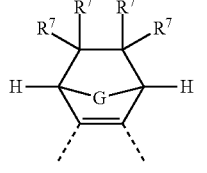 (8-A)

-continued

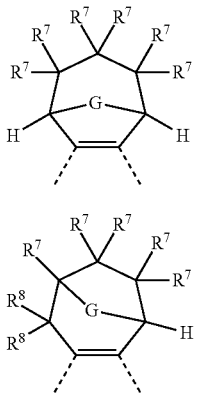

(9-A)

(10-A)

wherein $A^1$, $A^2$, and $A^3$ are, identically or differently on each occurrence, 0 or $NR^8$.

7. The compound of claim 1, wherein $R^8$ is, identically or differently on each occurrence, F, a straight-chain alkyl group having 1 to 10 C atoms or a branched or cyclic alkyl group having 3 to 10 C atoms, wherein one or more non-adjacent $CH_2$ groups are optionally replaced by $R^9C{=}CR^9$ and one or more H atoms are optionally replaced by D or F, an aromatic or heteroaromatic ring system having 5 to 14 aromatic ring atoms, which is optionally substituted by one or more radicals $R^9$; and wherein two radicals $R^8$ bonded to the same carbon atom optionally define an aliphatic or aromatic ring system with one another and thus form a spiro system; and wherein $R^8$ optionally defines an aliphatic ring system with an adjacent radical $R^7$.

8. The compound of claim 1, wherein $R^1$ to $R^6$, which are not $-(Ar)_p$-HetAr, are selected on each occurrence, identically or differently, from the group consisting of H, D, F, $N(R^9)_2$, CN, $Si(R^9)_3$, $C({=}O)R^9$, a straight-chain alkyl group having 1 to 10 C atoms or an alkenyl group having 2 to 10 C atoms or a branched or cyclic alkyl group having 3 to 10 C atoms, each of which is optionally substituted by one or more radicals $R^9$, wherein one or more H atoms are optionally replaced by D or F, or an aromatic or heteroaromatic ring system having 5 to 24 aromatic ring atoms, which is optionally substituted by one or more radicals $R^9$; and wherein the radicals $R^4$ and $R^5$ optionally define an aliphatic or aromatic ring system with one another.

9. The compound of claim 1, wherein all substituents $R^1$ to $R^6$ which are not a group $-(Ar)_p$-HetAr are H.

10. A process for preparing the compound of claim 1 comprising reacting the free ligands L and optionally L' with an iridium compound.

11. The compound of claim 1, wherein the compound is a compound of formula (44):

(44)

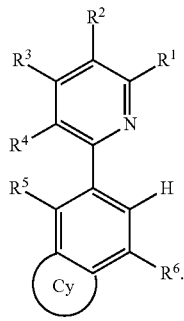

12. A formulation comprising at least one compound of claim 1 and at least one solvent and/or a further organic or inorganic compound.

13. An electronic device comprising at least one compound of claim 1.

14. The electronic device of claim 13, wherein the electronic device is an organic electroluminescent device, wherein the compound is employed as an emitting compound in one or more emitting layers.

15. An electronic device comprising at least one compound of claim 11.

16. The electronic device of claim 15, wherein the electronic device is an organic electroluminescent device, wherein the compound is employed in an emitting layer or in a hole-blocking layer or in an electron-transport layer.

* * * * *